(12) United States Patent
Brinkmann et al.

(10) Patent No.: US 12,180,279 B2
(45) Date of Patent: Dec. 31, 2024

(54) METHOD FOR IN VIVO GENERATION OF MULTISPECIFIC ANTIBODIES FROM MONOSPECIFIC ANTIBODIES

(71) Applicant: Hoffmann-La Roche Inc., Little Falls, NJ (US)

(72) Inventors: Ulrich Brinkmann, Penzberg (DE); Klaus Mayer, Penzberg (DE); Steffen Dickopf, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 40 days.

(21) Appl. No.: 16/860,406

(22) Filed: Apr. 28, 2020

(65) Prior Publication Data

US 2020/0255522 A1 Aug. 13, 2020

Related U.S. Application Data

(63) Continuation of application No. PCT/EP2018/079523, filed on Oct. 29, 2018.

(30) Foreign Application Priority Data

Oct. 30, 2017 (EP) ...................................... 17199086

(51) Int. Cl.
  *C07K 16/28* (2006.01)
  *C07K 16/46* (2006.01)
  *A61K 39/00* (2006.01)

(52) U.S. Cl.
  CPC ........ *C07K 16/2809* (2013.01); *C07K 16/468* (2013.01); *A61K 2039/505* (2013.01); *C07K 2317/24* (2013.01); *C07K 2317/31* (2013.01); *C07K 2317/526* (2013.01); *C07K 2317/55* (2013.01); *C07K 2317/569* (2013.01)

(58) Field of Classification Search
  CPC .............. C07K 16/2809; C07K 16/468; C07K 2317/24; C07K 2317/31; C07K 2317/526; C07K 2317/55; C07K 2317/569; A61K 2039/505
  See application file for complete search history.

(56) References Cited

U.S. PATENT DOCUMENTS

| | | |
|---|---|---|
| 5,500,362 A | 3/1996 | Robinson et al. |
| 5,624,821 A | 4/1997 | Winter et al. |
| 5,648,260 A | 7/1997 | Winter et al. |
| 5,821,337 A | 10/1998 | Carter et al. |
| 6,194,551 B1 | 2/2001 | Idusogie et al. |
| 6,737,056 B1 | 5/2004 | Presta |
| 7,183,076 B2 | 2/2007 | Arathoon et al. |
| 7,332,581 B2 | 2/2008 | Presta et al. |
| 7,371,826 B2 | 5/2008 | Presta et al. |
| 7,951,917 B1 | 5/2011 | Arathoon et al. |
| 8,076,459 B2 | 12/2011 | Hofmeister et al. |
| 8,592,562 B2 | 11/2013 | Kannan et al. |
| 8,642,745 B2 | 2/2014 | Arathoon et al. |
| 8,765,412 B2 | 7/2014 | Arathoon et al. |
| 9,409,989 B2 | 8/2016 | Arathoon et al. |
| 9,670,269 B2 | 6/2017 | Igawa et al. |
| 9,688,762 B2 | 6/2017 | Igawa et al. |
| 9,914,776 B2 | 3/2018 | Ast et al. |
| 10,011,858 B2 | 7/2018 | Igawa et al. |
| 10,611,840 B2 | 4/2020 | Ast et al. |
| 10,611,841 B2 | 4/2020 | Ast et al. |
| 10,633,457 B2 * | 4/2020 | Brinkmann ............ A61P 19/08 |
| 10,934,344 B2 | 3/2021 | Igawa et al. |
| 11,117,965 B2 | 9/2021 | Ast et al. |
| 11,124,576 B2 | 9/2021 | Igawa et al. |
| 11,155,639 B2 | 10/2021 | Kim et al. |
| 11,168,344 B2 | 11/2021 | Igawa et al. |
| 11,332,533 B2 | 5/2022 | Igawa et al. |
| 2005/0014934 A1 | 1/2005 | Hinton et al. |
| 2010/0286374 A1* | 11/2010 | Kannan ................... A61P 37/04 435/69.6 |
| 2014/0024111 A1 | 1/2014 | Kannan et al. |
| 2019/0382484 A1 | 12/2019 | Igawa et al. |
| 2022/0267822 A1 | 8/2022 | Igawa et al. |
| 2022/0403027 A1 | 12/2022 | Ast et al. |

FOREIGN PATENT DOCUMENTS

| | | |
|---|---|---|
| CN | 106459191 A | 2/2017 |
| EP | 1536005 A1 | 6/2005 |
| EP | 1693386 A1 | 8/2006 |
| EP | 1870459 A1 | 12/2007 |
| JP | 2016-093175 A | 5/2016 |
| WO | 93/11162 A1 | 6/1993 |

(Continued)

OTHER PUBLICATIONS

Lum et al, Biodrugs 2011: 25(6): 365-379. (Year: 2011).*
Anthony, J., et al., "Production of stable anti-digoxin Fv in *Escherichia coli*" Mol Immunol 29(10):1237-1247 (Oct. 1, 1992).
Banaszek, A., et al., "Dual Antigen-Restricted Complementation of a Trispecific Antibody Construct for Targeted Immunotheraphy of Blood Cancer" Abstract (T-10) Eighth Fabisch-Symposium fotr Cancer Research and Molecular Cell Biology, Berlin, Germany, pp. 1-6 ( Mar. 21-23, 2012).
Banaszek, A.,, "Dual Antigen-Restricted Complementation of a Two-Part Trispecific Antibody for Targeted Immunotherapy of Blood Cancer" Julius-Maximilians Universitat—Würzburg, Germany (Ph.D Dissertation),:1-142 (Sep. 20, 2013) https://d-nb.info/1110027168/34.

(Continued)

*Primary Examiner* — Meera Natarajan
*Assistant Examiner* — Cheom-Gil Cheong
(74) *Attorney, Agent, or Firm* — Genentech, Inc.

(57) ABSTRACT

Herein is reported a method for the generation of multispecific antibodies directly on the cell-surface at the site of action by a half-antibody exchange reaction between two 2/3-IgGs or two 2/3-BiFabs destabilized in one half by asymmetric perturbing mutations fostering the generation of correctly assembled full length bi- or multispecific antibodies. The method is performed in the absence hinge region disulfide bonds in the starting 2/3-IgGs or 2/3-BiFabs.

18 Claims, 51 Drawing Sheets

Specification includes a Sequence Listing.

(56) References Cited

FOREIGN PATENT DOCUMENTS

| | | |
|---|---|---|
| WO | 94/09131 A1 | 4/1994 |
| WO | 94/29351 A2 | 12/1994 |
| WO | 96/27011 A1 | 9/1996 |
| WO | 98/050431 A2 | 11/1998 |
| WO | 99/051642 A1 | 10/1999 |
| WO | 2004/056312 A2 | 7/2004 |
| WO | 2005/062916 A2 | 12/2004 |
| WO | 2005/000898 A2 | 1/2005 |
| WO | 2005/100402 A1 | 10/2005 |
| WO | 2006/029879 A2 | 3/2006 |
| WO | 2006/047340 A2 | 5/2006 |
| WO | 2007/062466 A1 | 6/2007 |
| WO | 2007/110205 A2 | 10/2007 |
| WO | 2007/147901 A1 | 12/2007 |
| WO | 2008/119353 A1 | 10/2008 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 2010/129304 A3 | 11/2010 |
| WO | 2010/151792 A1 | 12/2010 |
| WO | 2011/090754 A1 | 7/2011 |
| WO | 2011/090762 A1 | 7/2011 |
| WO | 2011/131746 A2 | 10/2011 |
| WO | 2011/133886 A2 | 10/2011 |
| WO | 2011/143545 A1 | 11/2011 |
| WO | 2012/025530 A1 | 3/2012 |
| WO | 2012/058768 A1 | 5/2012 |
| WO | 2013/060867 A2 | 5/2013 |
| WO | 2013/096291 A2 | 6/2013 |
| WO | 2013/157954 A1 | 10/2013 |
| WO | 2014/081955 A1 | 5/2014 |
| WO | 2015/189249 A1 | 12/2015 |
| WO | 2016/087416 A1 | 6/2016 |
| WO | 2016/087650 A1 | 6/2016 |
| WO | 2017/191101 A1 | 11/2017 |
| WO | 2019/077092 A1 | 4/2019 |

OTHER PUBLICATIONS

Brinkmann, U., et al., "The making of bispecific antibodies" MABS 9(2):182-212 (Jan. 10, 2017).

European Medicines Agency [EMA], "Blincyto—Annex I-Summary of Product Characteristics-" (Amgen; EMEA/H/C/003731—II/0047/G),:1-56 (Dec. 7, 2015).

Glockshuber, R., et al., "A comparison of strategies to stabilize immunoglobulin Fv-fragments" ACS Biochemistry 29(6):1362-1367 (Feb. 13, 1990).

Hamel, P.A., et al., "Relative noncovalent association constant between immunoglobulin H and L chains is unrelated to their expression or antigen-binding activity" J Immunol 139(9):3012-3020 (Nov. 1, 1987).

Hochman, J., et al., "An active antibody fragment (Fv) composed of the variable portions of heavy and light chains" ACS Biochemistry 12(6):1130-1135 (Mar. 13, 1973).

Hochman, J., et al., "Folding and interaction of subunits at the antibody combining site" ACS Biochemistry 15(12):2706-2710 (Jun. 15, 1976).

Horne, C., et al., "Noncovalent association of heavy and light chains of human immunoglobulins. III. Specific interactions between VH and VL" J Immunol 129(2):660-664 (Aug. 1, 1982).

Hu, S., et al., "Minibody: a novel engineered anti-carcinoembryonic antigen antibody fragment (single-chain Fv-CH3) which exhibits rapid, high-level targeting of xenografts" Cancer Res 56(13):3055-3061 (Jul. 1, 1996).

"International Preliminary Report on Patentability—PCT/EP2018/079523": pp. 1-16 (Jan. 23, 2020).

"International Search Report /Written Opinon—PCT/EP2018/079523": pp. 1-16 (Dec. 17, 2018).

Jaehde, U., et al., "Dosis-Individualisierung in der Krebs-Chemotherapie: Zytostatika maßgeschneidert dosieren [Individualized dosage of cytostatics. Dose individualization in cancer chemotherapy]" Pharm Unserer Zeit (German w/Eng. Transl.), 35(2):150-156 (Feb. 21, 2006).

Jordan, G., et al., "Evaluation of the potential use of hybrid LC-MS/MS for active drug quantification applying the 'free analyte QC concept" Bioanalysis 9(21):1705-1717 (Sep. 27, 2017).

Julius-Maximilians Universitat, "Annex I—Basis for Calculation-Chart":1-2 (Dec. 3, 2018).

Julius-Maximilians Universitat, "Chart: The bispecific antibodies of Harris": 1 (Dec. 3, 2018).

Julius-Maximilians Universitat, "Chart-Kalkulation Css aus Dosisangaben":1 (Dec. 3, 2018).

Julius-Maximilians Universitat, "Overview of Antibody Formats—Chart": 1 (Dec. 3, 2018).

Julius-Maximilians Universitat, "Predicted Non-associated variable domain fractions at different concentrations": 1 (Dec. 3, 2018).

Julius-Maximilians Universitat, "Supplemental Data Chart":1-4 (Dec. 3, 2018).

Julius-Maximilians Universitat, "Vossius & Partner Response to EP Rule 161&162 Communication,"; : 1-8 (Mar. 2, 2015).

Julius-Maximilians Universitat, "European Patent Application No. 12151125.7 entitled: 'Dual Antigen-Induced bipartite functional Complementation' filed Jan. 13, 2012":1-76.

Manakas, A., et al., "Demibodies for Highly Specific Cell Detection and Killing" Poster (#209) 42nd Lorne Conference on Protein Structure and Function, Lorne, NSW-Australia, pp. 1 (Feb. 5-9, 2017).

Masuda, K, et al., "Loss or down-regulation of HLA class I expression at the allelic level in freshly isolated leukemic blasts" Cancer Sci 98(1):102-108 (Nov. 3, 2006).

Mayer, K., et al., "TriFabs—Trivalent IgG-Shaped Bispecific Antibody Derivatives: Design, Generation, Characterization and Application for Targeted Payload Delivery" Int J Mol Sci 16(12):27497-27507 (Nov. 15, 2015).

Polymenis, M., et al., "Domain interactions and antigen binding of recombinant anti-Z-DNA antibody variable domains. The role of heavy and light chains measured by surface plasmon resonance" J Immunol 154(5):2198-2208 (Mar. 1, 1995).

Rothlisberger, D., et al., "Domain interactions in the Fab fragment: a comparative evaluation of the single-chain Fv and Fab format engineered with variable domains of different stability" J Mol Biol 347(4):773-789 (Apr. 8, 2005).

Shu, L., et al., "Secretion of a single-gene-encoded immunoglobulin from myeloma cells" PNAS 90(17):7995-7999 (Sep. 1, 1993).

Ueda, H., et al., "Open sandwich ELISA: a novel immunoassay based on the interchain interaction of antibody variable region" Nat Biotechnol 14(13):1714-1718 (Dec. 1, 1996).

Wang, X.B. et al., "A new recombinant single chain trispecific antibody recruits T lymphocytes to kill CEA (carcinoma embryonic antigen) positive tumor cells in vitro efficiently" J Biochemistry 135(4):555-565 (Apr. 1, 2004).

Ward, E., et al., "Binding activities of a repertoire of single immunoglobulin variable domains secreted from *Escherichia coli*" Nature 341(6242):544-546 (Oct. 12, 1989).

Angal, S., et al., "A single amino acid substitution abolishes the heterogeneity of chimeric mouse/human (IgG4) antibody" Molec Immunol 30(1):105-108 (Jan. 1, 1993).

Atwell, S., et al., "Stable Heterodimers from Remodeling the Domain Interface of a Homodimer using a Phage Display Library" J Mol Biol 270(1):26-35 (Jul. 4, 1997).

Bruggemann, M., et al., "Comparison of the effector functions of human immunoglobulins using a matched set of chimeric antibodies" J Exp Med 166(5):1351-1361 (Nov. 1, 1987).

Carter, P. et al., "Knobs-into-holes provides a rational design strategy for engineering antibody C H 3 domains for heavy chain heterodimerization" IMMUNOTECHNOLOGY 2(1):73-73 (Feb. 1, 1996).

Clynes, R., et al., "Fc receptors are required in passive and active immunity to melanoma" PNAS 95(2):652-656 (Jan. 20, 1998).

(56) References Cited

OTHER PUBLICATIONS

Cragg, M., et al., "Antibody Specificity Controls in Vivo Effector Mechanisms of Anti-CD20 Regents" BLOOD 103(7):2738-2743 (Apr. 1, 2004).

Cragg, M., et al., "Complement-mediated lysis by anti-CD20 mAb correlates with segregation into lipid rafts" BLOOD 101(3):1045-1052 (Feb. 1, 2003).

DeNardis, C., et al., "A new approach for generating bispecific antibodies based on a common light chain format and the stable architecture of human immunoglobulin G1" J Biol Chem 292(35):14706-14717 (Jun. 27, 2017).

Duncan, A., et al., "The Binding Site for C1q on IgG" NATURE 332(6166):738-740 (Apr. 21, 1988).

Elliott, J., et al., "Antiparallel Conformation of Knob and Hole Aglycosylated Half-Antibody Homodimers Is Mediated by a CH2-CH3 Hydrophobic Interaction" J Mol Biol 426(9):1947-1957 (May 1, 2014).

Gazzano-Santoro, H., et al., "A non-radioactive complement-dependent cytotoxicity assay for anti-CD20 monoclonal antibody" J Immunol Methods 202(2):163-171 (Mar. 28, 1997).

Gunasekaran, K. et al., "Enhancing Antibody Fc Heterodimer Formation through Electrostatic Steering Effects: Applications to Bi-Specific Molecules and Monovalent IgG" J Biol Chem 285(25):19637-19646 (Jun. 18, 2010).

Guyer, R., et al., "Immunoglobulin binding by mouse intestinal epithelial cell receptors" J Immunol 117(2):587-593 (Aug. 1, 1976).

Hellstrom, I. et al., "Antitumor effects of L6, an IgG2a antibody that reacts with most human carcinomas" PNAS 83(18):7059-7063 (Sep. 1, 1986).

Hellström, I. et al., "Strong antitumor activities of IgG3 antibodies to a human melanoma-associated ganglioside" PNAS 82(5):1499-1502 (Mar. 1, 1985).

Idusogie, E.E., et al., "Mapping of the C1q Binding Site on Rituxan, A Chimeric Antibody with a Human IgG1 Fc" J Immunol 164(8):4178-4184 (Apr. 15, 2000).

"International Preliminary Report on Patentability—PCT/EP2018/078675":pp. 1-21 (Sep. 17, 2019).

"International Search Report—PCT/EP2018/078675":pp. 1-17 (Dec. 6, 2018).

Kim, J., et al., "Localization of the site of the murine IgG1 molecule that is involved in binding to the murine intestinal Fc receptor" Eur J Immunol 24(10):2429-2434 (Oct. 1, 1994).

Kostelny, S., et al., "Formation of a bispecific antibody by the use of leucine zippers" J Immunol 148(5):1547-1553 (Mar. 1, 1992).

Labrijn, A.F., et al., "Efficient generation of stable bispecific IgG1 by controlled Fab-arm exchange" PNAS USA 110(13):5145-5150 (Mar. 26, 2013).

Liu, Z., et al., "A Novel Antibody Engineering Strategy for Making Monovalent Bispecific Heterodimeric IgG Antibodies by Electrostatic Steering Mechanism" J Biol Chem 290(12):7535-7562 (Mar. 20, 2015).

Merchant, A., et al., "An efficient route to human bispecific IgG" Nat Biotechnol 16(7):677-681 (Jul. 1, 1998).

Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).

Pokala, N., et al., "Energy Functions for Protein Design: Adjustment with Protein-Protein Complex Affinities, Models for the Unfolded State, and Negative Design of Solubility and Specificity" J Mol Biol 347(1):203-227 (Mar. 18, 2005).

Ravetch, J., et al., "Fc receptors" Annu Rev Immunol 9:457-492 (Apr. 1, 1991).

Ridgway, J., et al., "Knobs-into-holes' engineering of antibody CH3 domains for heavy chain heterodimerization" Protein Eng 9(7):617-621 (Jul. 1, 1996).

Rispens, T., et al., "Dynamics of Inter-heavy Chain Interactions in Human Immunoglobulin G (IgG) Subclasses Studied by Kinetic Fab Arm Exchange" J Biol Chem 289(9):6098-6109 (Feb. 28, 2014).

Schaefer, W., et al., "Immunoglobulin domain crossover as a generic approach for the production of bispecific IgG antibodies" PNAS USA 108(27):11187-11192 (Jul. 5, 2011).

Segal, D.M., et al., "Bispecific antibodies in cancer therapy" Curr Opin Immunol 11(5):558-562 (Oct. 1, 1999).

Shields, R., et al., "High Resolution Mapping of the Binding Site on Human IgG1 for FcγRI, FcγRII, FcγRIII, and FcRn and Design of IgG1 Variants with Improved Binding to the FcγR" J Biol Chem 276(9):6591-6604 (Mar. 2, 2001).

* cited by examiner

Figure 13

Figure 26
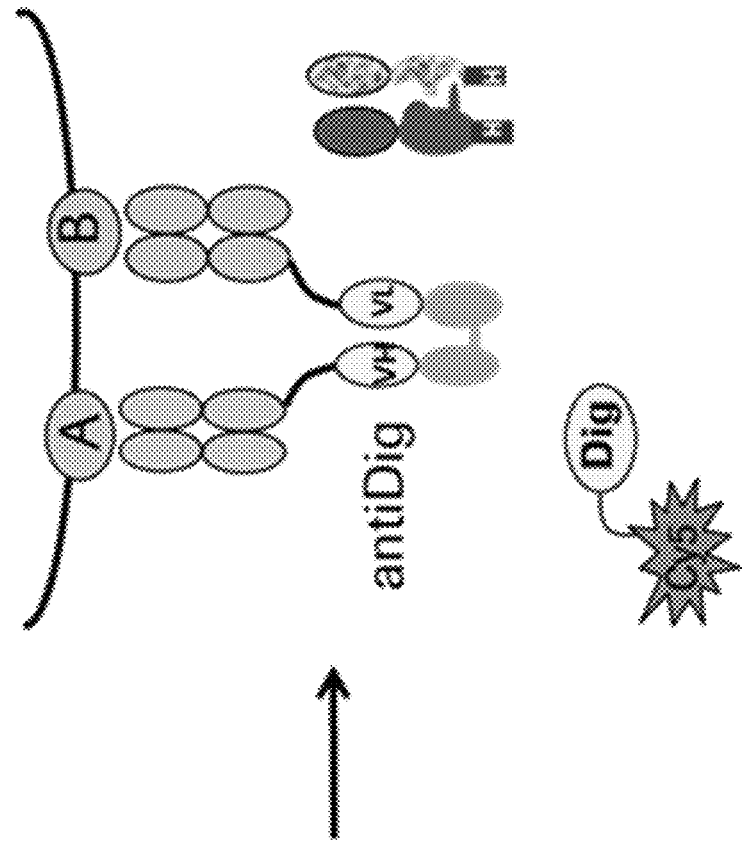
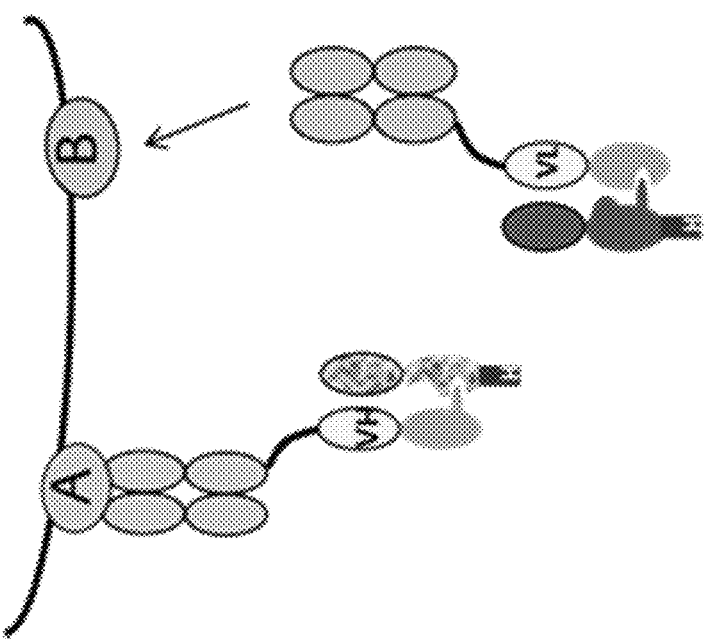

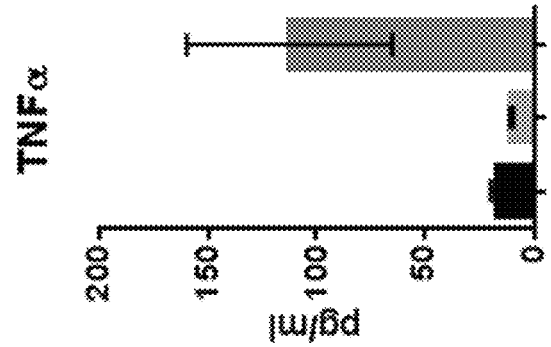
Figure 32A Figure 32B Figure 32C Figure 32D
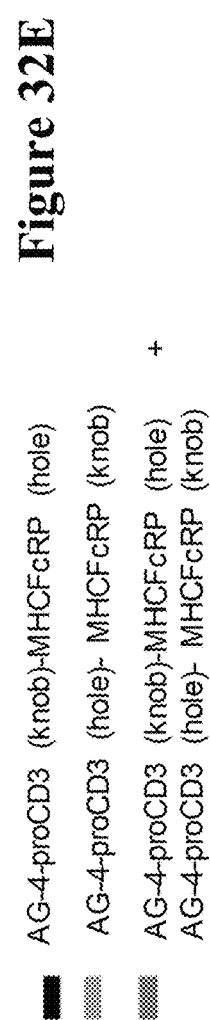
Figure 32E

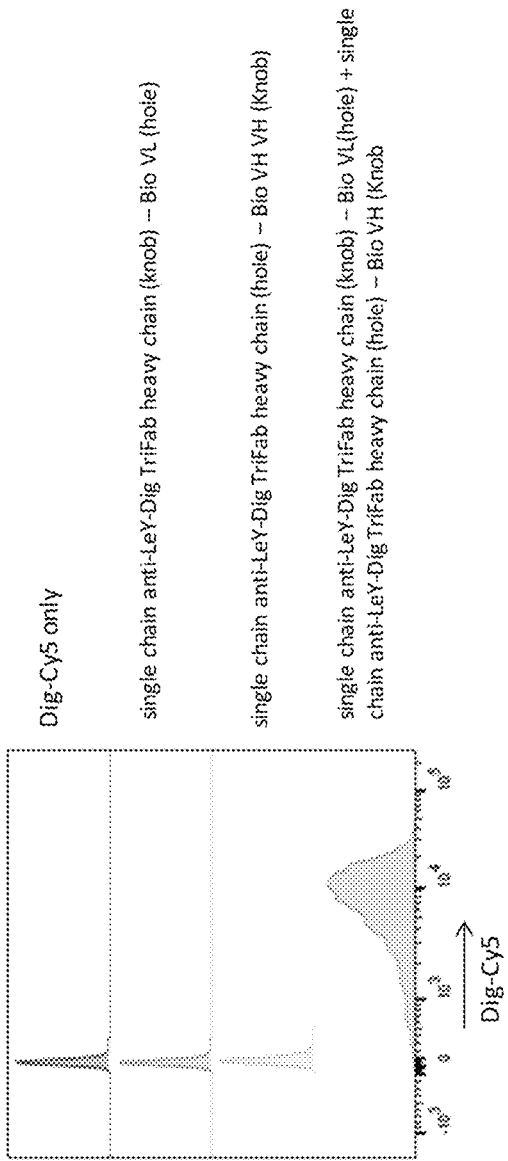 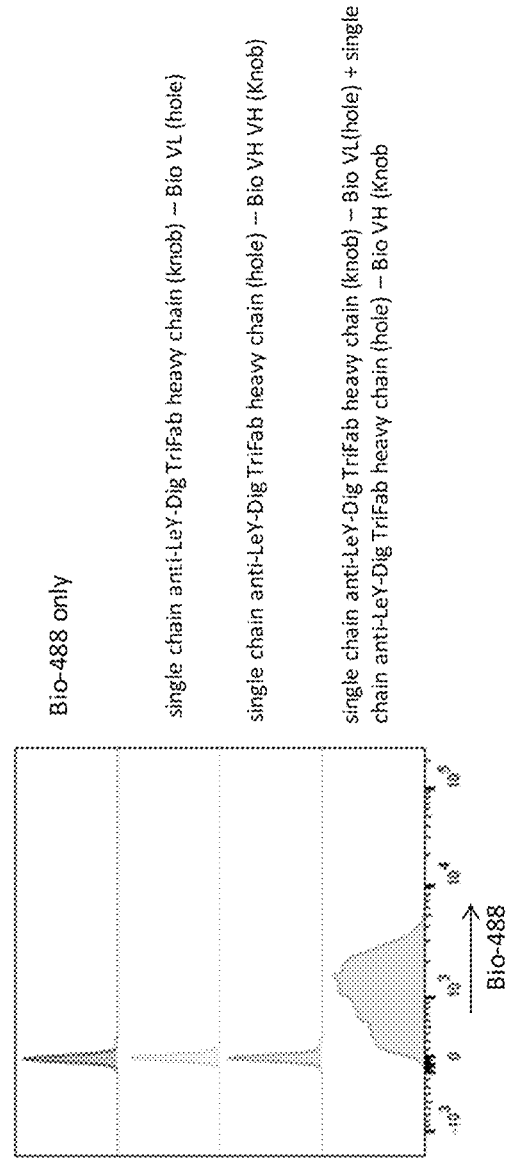
Figure 36A
Figure 36B

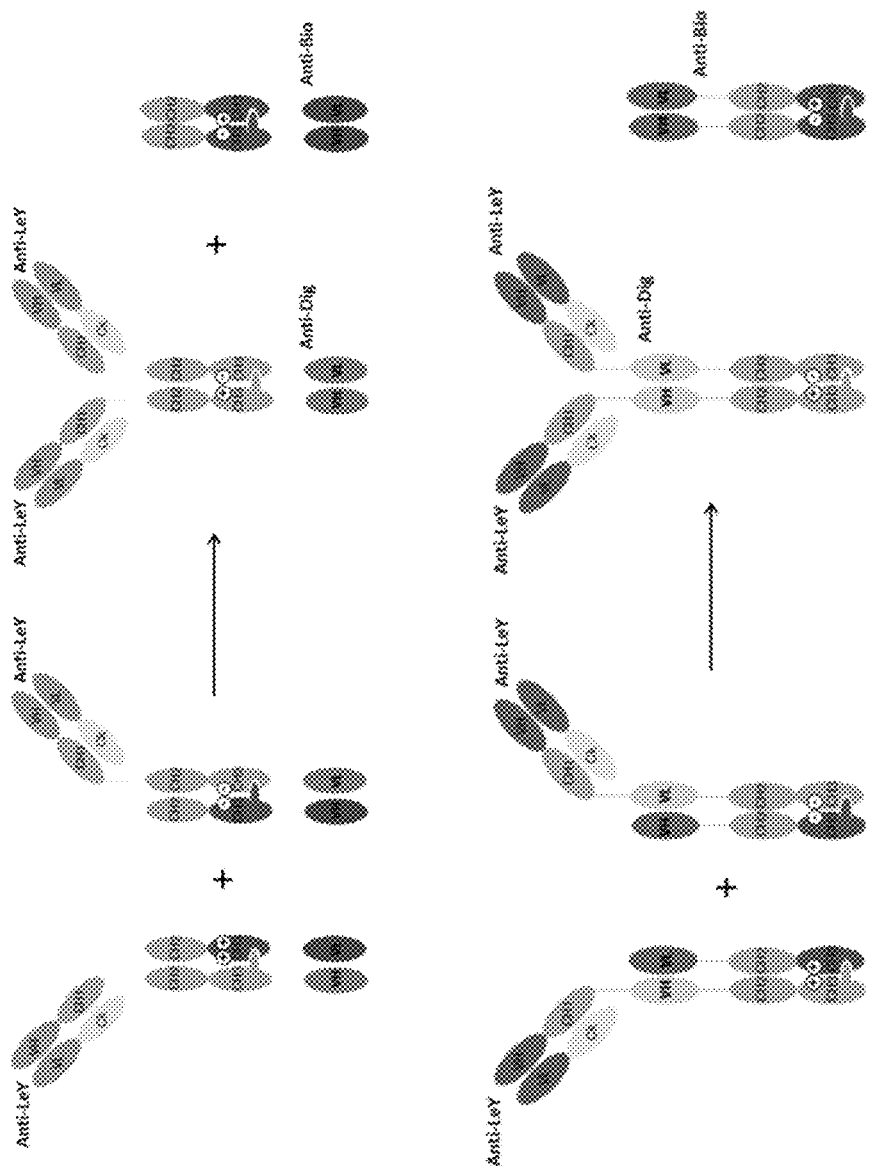
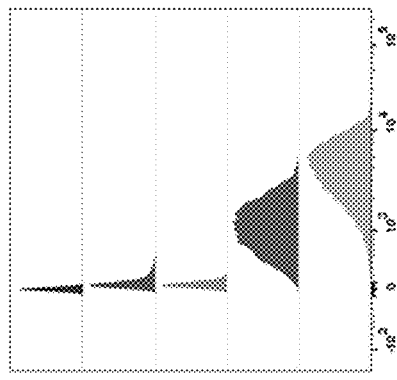
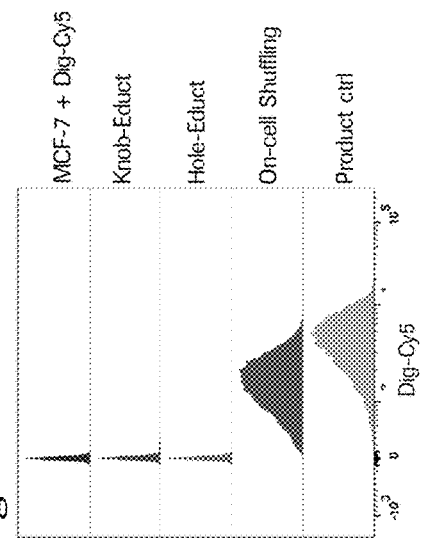
Figure 46A
Figure 46B

Figure 47
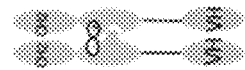
<CD-AG-2>
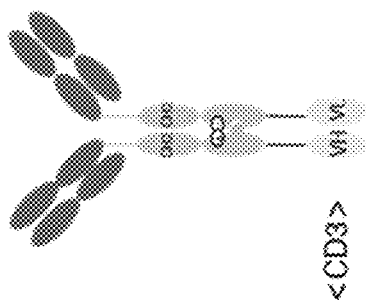
<CD3>
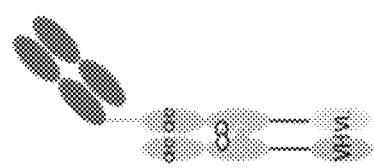
+
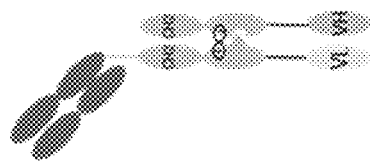

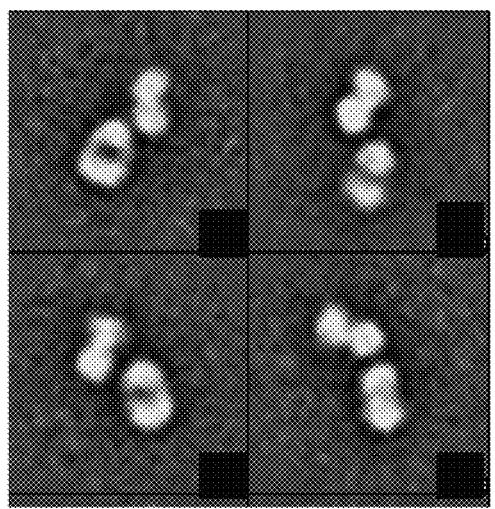
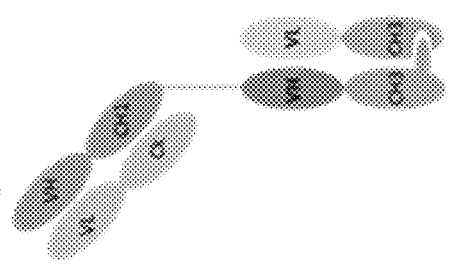
Figure 49B
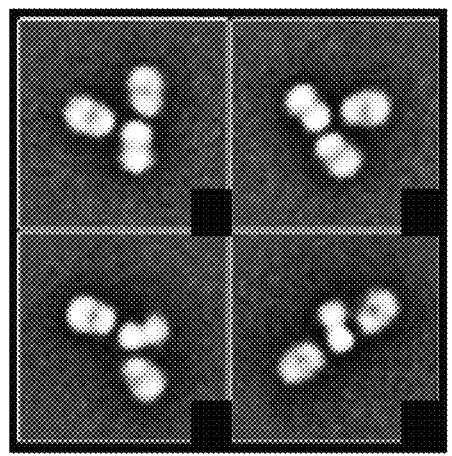
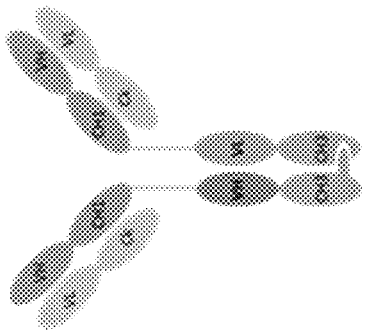
Figure 49C
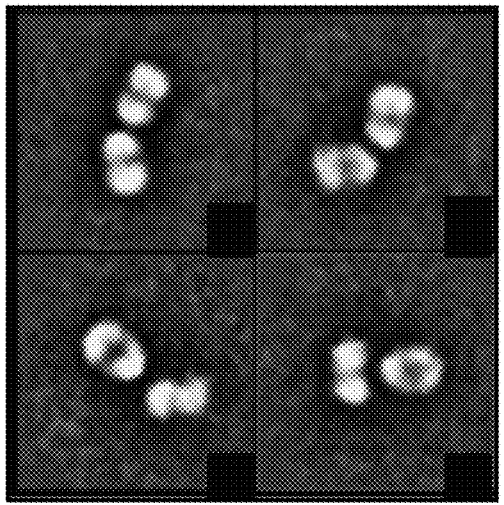
Figure 49A

SEQUENCE LISTING

<160> NUMBER OF SEQ ID NOS: 104

<210> SEQ ID NO 1
<211> LENGTH: 225
<212> TYPE: PRT
<213> ORGANISM: Homo sapiens

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
        210                 215                 220

Pro
225

<210> SEQ ID NO 2
<211> LENGTH: 324
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 3
<211> LENGTH: 375

<212> TYPE: PRT
<213> ORGANISM: Homo sapiens

<400> SEQUENCE: 3

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro
    370                 375
```

<210> SEQ ID NO 4

```
<211> LENGTH: 227
<212> TYPE: PRT
<213> ORGANISM: Homo sapiens

<400> SEQUENCE: 4

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu
225

<210> SEQ ID NO 5
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 5

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 6
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

-continued

```
                210                 215                 220
Pro
225

<210> SEQ ID NO 7
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with S354C, T366W mutations

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 8
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 8

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
             100                 105                 110
Glu Lys Thr Ile Ser Lys Ala Lys Gly Gln Pro Arg Glu Pro Gln Val
         115                 120                 125
Cys Thr Leu Pro Pro Ser Arg Asp Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                 165                 170                 175
Val Leu Asp Ser Asp Gly Ser Phe Phe Leu Val Ser Lys Leu Thr Val
             180                 185                 190
Asp Lys Ser Arg Trp Gln Gln Gly Asn Val Phe Ser Cys Ser Val Met
         195                 200                 205
His Glu Ala Leu His Asn His Tyr Thr Gln Lys Ser Leu Ser Leu Ser
210                 215                 220
Pro
225
```

<210> SEQ ID NO 9
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a L234A, L235A and S354C, T366W mutations

<400> SEQUENCE: 9

```
Asp Lys Thr His Thr Cys Pro Pro Cys Pro Ala Pro Glu Ala Ala Gly
  1               5                  10                  15
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
             100                 105                 110
Glu Lys Thr Ile Ser Lys Ala Lys Gly Gln Pro Arg Glu Pro Gln Val
         115                 120                 125
Tyr Thr Leu Pro Pro Cys Arg Asp Glu Leu Thr Lys Asn Gln Val Ser
130                 135                 140
Leu Trp Cys Leu Val Lys Gly Phe Tyr Pro Ser Asp Ile Ala Val Glu
145                 150                 155                 160
```

-continued

```
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro
225

<210> SEQ ID NO 10
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 10

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro
225

<210> SEQ ID NO 11
<211> LENGTH: 225
<212> TYPE: PRT
<213> ORGANISM: Artificial Sequence
<220> FEATURE:
<223> OTHER INFORMATION: human IgG1 Fc-region derived Fc-region
``` polypeptide with L234A, L235A mutations and P329G mutation

<400> SEQUENCE: 11

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225
```

<210> SEQ ID NO 12
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro
225

<210> SEQ ID NO 13
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220
```

Pro
225

<210> SEQ ID NO 14
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 14

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 15
<211> LENGTH: 225
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

```
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Cys Arg Asp Glu Leu Thr Lys Asn Gln Val Ser
            130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro
225

<210> SEQ ID NO 16
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 16

Glu Ser Lys Tyr Gly Pro Pro Cys Pro Pro Cys Pro Ala Pro Glu Phe
 1               5                  10                  15
Glu Gly Gly Pro Ser Val Phe Leu Phe Pro Pro Lys Pro Lys Asp Thr
                 20                  25                  30
Leu Met Ile Ser Arg Thr Pro Glu Val Thr Cys Val Val Val Asp Val
            35                  40                  45
Ser Gln Glu Asp Pro Glu Val Gln Phe Asn Trp Tyr Val Asp Gly Val
 50                  55                  60
Glu Val His Asn Ala Lys Thr Lys Pro Arg Glu Glu Gln Phe Asn Ser
 65                  70                  75                  80
Thr Tyr Arg Val Val Ser Val Leu Thr Val Leu His Gln Asp Trp Leu
                 85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
```

```
Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 17
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 17

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 18
<211> LENGTH: 227
<212> TYPE: PRT
<213> ORGANISM: Artificial Sequence
<220> FEATURE:
<223> OTHER INFORMATION: human IgG4 Fc-region derived Fc-region
``` polypeptide with S354C, T366W mutations

<400> SEQUENCE: 18

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 19
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 19

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser

```
            100                 105                 110
Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 20
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 20

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

Leu Ser Leu
225

<210> SEQ ID NO 21
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 21

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 22
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 22

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu
225

<210> SEQ ID NO 23
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 23

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Cys Thr Leu Pro Pro Ser Gln Glu Met Thr Lys Asn Gln
            130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr 165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu
225

<210> SEQ ID NO 24
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu
225

<210> SEQ ID NO 25
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and Y349C, T366S, L368A,
      Y407V mutations

<400> SEQUENCE: 25

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 26
<211> LENGTH: 227
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and S354C, T366W mutations

<400> SEQUENCE: 26

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

```
Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 27
<211> LENGTH: 103
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 28
<211> LENGTH: 107
<212> TYPE: PRT
<213> ORGANISM: Homo sapiens

<400> SEQUENCE: 28

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95
```

```
Ala Pro Ile Glu Lys Thr Ile Ser Lys Ala Lys
            100                 105

<210> SEQ ID NO 29
<211> LENGTH: 106
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 30
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X=S or P

<400> SEQUENCE: 30

Asp Lys Thr His Thr Cys Pro Xaa Cys Pro
1               5                   10

<210> SEQ ID NO 31
<211> LENGTH: 7
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X=S or P

<400> SEQUENCE: 31

His Thr Cys Pro Xaa Cys Pro
1               5

<210> SEQ ID NO 32
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X=S or P

<400> SEQUENCE: 32

Cys Pro Xaa Cys Pro
1               5
```

```
<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 105
<212> TYPE: PRT
<213> ORGANISM: Homo sapiens

<400> SEQUENCE: 34

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 35
<211> LENGTH: 240
<212> TYPE: PRT
<213> ORGANISM: Artificial Sequence
<220> FEATURE:
<223> OTHER INFORMATION: MHCFcRP-hole-D356K-His8

<400> SEQUENCE: 35

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Lys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser His His His His His His His His
225                 230                 235                 240

<210> SEQ ID NO 36
<211> LENGTH: 240
<212> TYPE: PRT
<213> ORGANISM: Artificial Sequence
<220> FEATURE:
<223> OTHER INFORMATION: MHCFcRP-hole-E357K-His8

<400> SEQUENCE: 36

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Lys Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Ser His His His His His His His His
225                 230                 235                 240
```

<210> SEQ ID NO 37
<211> LENGTH: 240
<212> TYPE: PRT
<213> ORGANISM: Artificial Sequence
<220> FEATURE:
<223> OTHER INFORMATION: MHCFcRP-knob-K370E-His8

<400> SEQUENCE: 37

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Trp Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Ser His His His His His His His His
225                 230                 235                 240
```

<210> SEQ ID NO 38
<211> LENGTH: 240
<212> TYPE: PRT
<213> ORGANISM: Artificial Sequence
<220> FEATURE:
<223> OTHER INFORMATION: MHCFcRP-knob-K439E-His8

<400> SEQUENCE: 38

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Glu Ser Leu Ser Leu Ser
    210                 215                 220

Pro Gly Lys Gly Gly Gly Ser His His His His His His
225                 230                 235                 240

<210> SEQ ID NO 39
<211> LENGTH: 214
<212> TYPE: PRT
<213> ORGANISM: Artificial Sequence
<220> FEATURE:
<223> OTHER INFORMATION: anti-bio antibody full length light chain

<400> SEQUENCE: 39

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gly Asn Ile His Asn Tyr
                 20                  25                  30

Leu Ser Trp Tyr Gln Gln Lys Pro Gly Lys Val Pro Lys Leu Leu Ile
             35                  40                  45

Tyr Ser Ala Lys Thr Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln His Phe Trp Ser Ser Ile Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 40
<211> LENGTH: 450
<212> TYPE: PRT
<213> ORGANISM: Artificial Sequence
<220> FEATURE:
<223> OTHER INFORMATION: anti-bio antibody full length heavy
      chain-knob-cys

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 41
<211> LENGTH: 450
<212> TYPE: PRT
<213> ORGANISM: Artificial Sequence
<220> FEATURE:
<223> OTHER INFORMATION: anti-bio antibody full length heavy
      chain-hole-cys

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
          195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 42
<211> LENGTH: 219
<212> TYPE: PRT
<213> ORGANISM: Artificial Sequence
<220> FEATURE:
<223> OTHER INFORMATION: anti-fluos antibody full length light chain

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

```
Thr His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 43
<211> LENGTH: 448
<212> TYPE: PRT
<213> ORGANISM: Artificial Sequence
<220> FEATURE:
<223> OTHER INFORMATION: anti-fluos antibody full length heavy chain-knob-cys

<400> SEQUENCE: 43

```
Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255
Thr Pro Glu Val Thr Cys Val Val Asp Val Ser His Glu Asp Pro
        260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Cys Arg Asp Glu Leu Thr Lys Asn Gln Val Ser Leu Trp Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 44
<211> LENGTH: 448
<212> TYPE: PRT
<213> ORGANISM: Artificial Sequence
<220> FEATURE:
<223> OTHER INFORMATION: anti-fluos antibody full length heavy
      chain-hole-cys

<400> SEQUENCE: 44

Gly Val Lys Leu Asp Glu Thr Gly Gly Gly Leu Val Gln Pro Gly Gly
1               5                   10                  15
Ala Met Lys Leu Ser Cys Val Thr Ser Gly Phe Thr Phe Gly His Tyr
            20                  25                  30
Trp Met Asn Trp Val Arg Gln Ser Pro Glu Lys Gly Leu Glu Trp Val
        35                  40                  45
Ala Gln Phe Arg Asn Lys Pro Tyr Asn Tyr Glu Thr Tyr Tyr Ser Asp
    50                  55                  60
Ser Val Lys Gly Arg Phe Thr Ile Ser Arg Asp Asp Ser Lys Ser Ser
65                  70                  75                  80
Val Tyr Leu Gln Met Asn Asn Leu Arg Val Glu Asp Thr Gly Ile Tyr
                85                  90                  95
Tyr Cys Thr Gly Ala Ser Tyr Gly Met Glu Tyr Leu Gly Gln Gly Thr
            100                 105                 110
Ser Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
                340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 45
<211> LENGTH: 214
<212> TYPE: PRT
<213> ORGANISM: Artificial Sequence
<220> FEATURE:
<223> OTHER INFORMATION: anti-dig antibody full length light chain

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
                35                  40                  45

Tyr Tyr Ser Ser Thr Leu Leu Ser Gly Val Pro Ser Arg Phe Ser Gly
        50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Ile Thr Leu Pro Pro
                    85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                    165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
        210

<210> SEQ ID NO 46
<211> LENGTH: 219
<212> TYPE: PRT
<213> ORGANISM: Artificial Sequence
<220> FEATURE:
<223> OTHER INFORMATION: anti-LeY antibody full length light chain

<400> SEQUENCE: 46

Asp Val Leu Met Thr Gln Ser Pro Leu Ser Leu Pro Val Ser Leu Gly
1               5                   10                  15
Asp Gln Ala Ser Ile Ser Cys Arg Ser Ser Gln Ile Ile Val His Ser
                20                  25                  30
Asn Gly Asn Thr Tyr Leu Glu Trp Tyr Leu Gln Lys Pro Gly Gln Ser
            35                  40                  45
Pro Lys Leu Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                    85                  90                  95
Ser His Val Pro Phe Thr Phe Gly Ser Gly Thr Lys Leu Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                    165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
```

<210> SEQ ID NO 47
<211> LENGTH: 214
<212> TYPE: PRT
<213> ORGANISM: Artificial Sequence
<220> FEATURE:
<223> OTHER INFORMATION: anti-PDGF antibody full length light chain

<400> SEQUENCE: 47

```
Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 48
<211> LENGTH: 214
<212> TYPE: PRT
<213> ORGANISM: Artificial Sequence
<220> FEATURE:
<223> OTHER INFORMATION: anti-VEGF antibody full length light chain

<400> SEQUENCE: 48

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 49
<211> LENGTH: 228
<212> TYPE: PRT
<213> ORGANISM: Artificial Sequence
<220> FEATURE:
<223> OTHER INFORMATION: anti-dig antibody VH-CH1 fragment

<400> SEQUENCE: 49

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
            35                  40                  45

Ser Ser Ile Asn Ile Gly Ala Thr Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys
225

<210> SEQ ID NO 50
<211> LENGTH: 222
<212> TYPE: PRT
<213> ORGANISM: Artificial Sequence
<220> FEATURE:
<223> OTHER INFORMATION: anti-LeY antibody VH-CH1 fragment

<400> SEQUENCE: 50

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 51
<211> LENGTH: 223
<212> TYPE: PRT
<213> ORGANISM: Artificial Sequence
<220> FEATURE:
<223> OTHER INFORMATION: anti-PDGF antibody VH-CH1 fragment

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
        210                 215                 220
```

<210> SEQ ID NO 52
<211> LENGTH: 226
<212> TYPE: PRT
<213> ORGANISM: Artificial Sequence
<220> FEATURE:
<223> OTHER INFORMATION: anti-VEGF antibody VH-CH1 fragment

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

Ser Cys
225

<210> SEQ ID NO 53
<211> LENGTH: 460
<212> TYPE: PRT
<213> ORGANISM: Artificial Sequence
<220> FEATURE:
<223> OTHER INFORMATION: anti-bio antibody full length heavy
      chain-hole-cys with C-terminal fusion

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gln Val Gln
225                 230                 235                 240

Leu Val Gln Ser Gly Ala Glu Val Lys Lys Pro Gly Ser Ser Val Lys
                245                 250                 255

Val Ser Cys Lys Ser Ser Gly Phe Asn Asn Lys Asp Thr Phe Phe Gln
            260                 265                 270

Trp Val Arg Gln Ala Pro Gly Gln Gly Leu Glu Trp Met Gly Arg Ile
        275                 280                 285

Asp Pro Ala Asn Gly Phe Thr Lys Tyr Ala Gln Lys Phe Gln Gly Arg
    290                 295                 300

Val Thr Ile Thr Ala Asp Thr Ser Thr Ser Thr Ala Tyr Met Glu Leu
305                 310                 315                 320

Ser Ser Leu Arg Ser Glu Asp Thr Ala Val Tyr Tyr Cys Ala Arg Trp
                325                 330                 335

Asp Thr Tyr Gly Ala Ala Trp Phe Ala Tyr Trp Gly Gln Gly Thr Leu

```
                340             345             350
Val Thr Val Ser Ser Ala Ser Thr Lys Gly Pro Ser Val Phe Pro Leu
            355                 360                 365

Ala Pro Ser Ser Lys Ser Thr Ser Gly Gly Thr Ala Ala Leu Gly Cys
370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
            405                 410                 415

Ser Gly Leu Tyr Ser Leu Ser Ser Val Val Thr Val Pro Ser Ser Ser
            420                 425                 430

Leu Gly Thr Gln Thr Tyr Ile Cys Asn Val Asn His Lys Pro Ser Asn
            435                 440                 445

Thr Lys Val Asp Lys Lys Val Glu Pro Lys Ser Cys
            450                 455                 460

<210> SEQ ID NO 54
<211> LENGTH: 683
<212> TYPE: PRT
<213> ORGANISM: Artificial Sequence
<220> FEATURE:
<223> OTHER INFORMATION: anti-bio antibody full length heavy
      chain-hole-cys with N- and C-terminal fusion

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
                    245                 250                 255
Ser Arg Thr Pro Glu Val Thr Cys Val Val Asp Val Ser His Glu
        260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Cys
            340                 345                 350
Thr Leu Pro Pro Ser Arg Asp Glu Leu Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Gly Gly Gly Ser Gly Gly Gly Ser Gln Val Gln Leu
    450                 455                 460
Val Gln Ser Gly Ala Glu Val Lys Lys Pro Gly Ser Ser Val Lys Val
465                 470                 475                 480
Ser Cys Lys Ser Ser Gly Phe Asn Asn Lys Asp Thr Phe Phe Gln Trp
                485                 490                 495
Val Arg Gln Ala Pro Gly Gln Gly Leu Glu Trp Met Gly Arg Ile Asp
            500                 505                 510
Pro Ala Asn Gly Phe Thr Lys Tyr Ala Gln Lys Phe Gln Gly Arg Val
        515                 520                 525
Thr Ile Thr Ala Asp Thr Ser Thr Ser Thr Ala Tyr Met Glu Leu Ser
    530                 535                 540
Ser Leu Arg Ser Glu Asp Thr Ala Val Tyr Tyr Cys Ala Arg Trp Asp
545                 550                 555                 560
Thr Tyr Gly Ala Ala Trp Phe Ala Tyr Trp Gly Gln Gly Thr Leu Val
                565                 570                 575
Thr Val Ser Ser Ala Ser Thr Lys Gly Pro Ser Val Phe Pro Leu Ala
            580                 585                 590
Pro Ser Ser Lys Ser Thr Ser Gly Gly Thr Ala Ala Leu Gly Cys Leu
        595                 600                 605
Val Lys Asp Tyr Phe Pro Glu Pro Val Thr Val Ser Trp Asn Ser Gly
    610                 615                 620
Ala Leu Thr Ser Gly Val His Thr Phe Pro Ala Val Leu Gln Ser Ser
625                 630                 635                 640
Gly Leu Tyr Ser Leu Ser Ser Val Val Thr Val Pro Ser Ser Ser Leu
                645                 650                 655
Gly Thr Gln Thr Tyr Ile Cys Asn Val Asn His Lys Pro Ser Asn Thr
```

```
                    660                 665                 670
Lys Val Asp Lys Lys Val Glu Pro Lys Ser Cys
            675                 680

<210> SEQ ID NO 55
<211> LENGTH: 458
<212> TYPE: PRT
<213> ORGANISM: Artificial Sequence
<220> FEATURE:
<223> OTHER INFORMATION: anti-fluos antibody full length heavy
      chain-hole-cys with C-terminal fusion

<400> SEQUENCE: 55

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Val Lys
225                 230                 235                 240

Leu Asp Glu Thr Gly Gly Gly Leu Val Gln Pro Gly Gly Ala Met Lys
                245                 250                 255

Leu Ser Cys Val Thr Ser Gly Phe Thr Phe Gly His Tyr Trp Met Asn
            260                 265                 270

Trp Val Arg Gln Ser Pro Glu Lys Gly Leu Glu Trp Val Ala Gln Phe
        275                 280                 285

Arg Asn Lys Pro Tyr Asn Tyr Glu Thr Tyr Tyr Ser Asp Ser Val Lys
    290                 295                 300

Gly Arg Phe Thr Ile Ser Arg Asp Asp Ser Lys Ser Ser Val Tyr Leu
305                 310                 315                 320

Gln Met Asn Asn Leu Arg Val Glu Asp Thr Gly Ile Tyr Tyr Cys Thr
                325                 330                 335
```

```
Gly Ala Ser Tyr Gly Met Glu Tyr Leu Gly Gln Gly Thr Ser Val Thr
                340                 345                 350

Val Ser Ser Ala Ser Thr Lys Gly Pro Ser Val Phe Pro Leu Ala Pro
            355                 360                 365

Ser Ser Lys Ser Thr Ser Gly Gly Thr Ala Ala Leu Gly Cys Leu Val
        370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys
    450                 455

<210> SEQ ID NO 56
<211> LENGTH: 679
<212> TYPE: PRT
<213> ORGANISM: Artificial Sequence
<220> FEATURE:
<223> OTHER INFORMATION: anti-fluos antibody full length heavy
      chain-hole-cys with N- and C-terminal fusion

<400> SEQUENCE: 56

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Cys Thr Leu
            340                 345                 350
Pro Pro Ser Arg Asp Glu Leu Thr Lys Asn Gln Val Ser Leu Ser Cys
        355                 360                 365
Ala Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Gly Ser Gly Val Lys Leu Asp Glu
    450                 455                 460
Thr Gly Gly Gly Leu Val Gln Pro Gly Gly Ala Met Lys Leu Ser Cys
465                 470                 475                 480
Val Thr Ser Gly Phe Thr Phe Gly His Tyr Trp Met Asn Trp Val Arg
                485                 490                 495
Gln Ser Pro Glu Lys Gly Leu Glu Trp Val Ala Gln Phe Arg Asn Lys
            500                 505                 510
Pro Tyr Asn Tyr Glu Thr Tyr Tyr Ser Asp Ser Val Lys Gly Arg Phe
        515                 520                 525
Thr Ile Ser Arg Asp Asp Ser Lys Ser Ser Val Tyr Leu Gln Met Asn
    530                 535                 540
Asn Leu Arg Val Glu Asp Thr Gly Ile Tyr Tyr Cys Thr Gly Ala Ser
545                 550                 555                 560
Tyr Gly Met Glu Tyr Leu Gly Gln Gly Thr Ser Val Thr Val Ser Ser
                565                 570                 575
Ala Ser Thr Lys Gly Pro Ser Val Phe Pro Leu Ala Pro Ser Ser Lys
            580                 585                 590
Ser Thr Ser Gly Gly Thr Ala Ala Leu Gly Cys Leu Val Lys Asp Tyr
        595                 600                 605
Phe Pro Glu Pro Val Thr Val Ser Trp Asn Ser Gly Ala Leu Thr Ser
    610                 615                 620
Gly Val His Thr Phe Pro Ala Val Leu Gln Ser Ser Gly Leu Tyr Ser
625                 630                 635                 640
Leu Ser Ser Val Val Thr Val Pro Ser Ser Ser Leu Gly Thr Gln Thr
                645                 650                 655
```

-continued

```
Tyr Ile Cys Asn Val Asn His Lys Pro Ser Asn Thr Lys Val Asp Lys
            660                 665                 670

Lys Val Glu Pro Lys Ser Cys
        675

<210> SEQ ID NO 57
<211> LENGTH: 450
<212> TYPE: PRT
<213> ORGANISM: Artificial Sequence
<220> FEATURE:
<223> OTHER INFORMATION: anti-bio antibody full length heavy chain-knob
      without hinge-region cysteine residues

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Ser Pro Pro Ser Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 58
<211> LENGTH: 450
<212> TYPE: PRT
<213> ORGANISM: Artificial Sequence
<220> FEATURE:
<223> OTHER INFORMATION: anti-bio antibody full length heavy chain-hole
      without hinge-cysteine residues

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
            35                  40                  45

Gly Arg Ile Asp Pro Ala Asn Gly Phe Thr Lys Tyr Ala Gln Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Ser Pro Pro Ser Pro Ala Pro Glu Leu Leu Gly Gly
```

```
                225                 230                 235                 240
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 59
<211> LENGTH: 448
<212> TYPE: PRT
<213> ORGANISM: Artificial Sequence
<220> FEATURE:
<223> OTHER INFORMATION: anti-fluos antibody full length heavy
      chain-knob without hinge-cysteine residues

<400> SEQUENCE: 59

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
            85                  90                  95

Tyr Cys Thr Gly Ala Ser Tyr Gly Met Glu Tyr Leu Gly Gln Gly Thr
            100                 105                 110

Ser Val Thr Val Ser Ser Ala Ser Thr Lys Gly Pro Ser Val Phe Pro
        115                 120                 125
```

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Ser Pro Pro Ser Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 60
<211> LENGTH: 448
<212> TYPE: PRT
<213> ORGANISM: Artificial Sequence
<220> FEATURE:
<223> OTHER INFORMATION: anti-fluos antibody full length heavy
      chain-hole without hinge-cysteine residues

<400> SEQUENCE: 60

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

```
Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Ser Pro Pro Ser Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Ser Cys
    355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445

<210> SEQ ID NO 61
<211> LENGTH: 240
```

```
<212> TYPE: PRT
<213> ORGANISM: Artificial Sequence
<220> FEATURE:
<223> OTHER INFORMATION: MHCFcRP-hole-D356K-His8 without hinge-cysteine
      residues

<400> SEQUENCE: 61

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Lys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser His His His His His His His His
225                 230                 235                 240

<210> SEQ ID NO 62
<211> LENGTH: 240
<212> TYPE: PRT
<213> ORGANISM: Artificial Sequence
<220> FEATURE:
<223> OTHER INFORMATION: MHCFcRP-hole-E357K-His8 without hinge-cysteine
      residues

<400> SEQUENCE: 62

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Lys Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser His His His His His His His His
225                 230                 235                 240

<210> SEQ ID NO 63
<211> LENGTH: 240
<212> TYPE: PRT
<213> ORGANISM: Artificial Sequence
<220> FEATURE:
<223> OTHER INFORMATION: MHCFcRP-knob-K370E-His8 without hinge-cysteine
      residues

<400> SEQUENCE: 63

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
        210                 215                 220

Pro Gly Lys Gly Gly Gly Ser His His His His His His
225                 230                 235                 240

<210> SEQ ID NO 64
<211> LENGTH: 240
<212> TYPE: PRT
<213> ORGANISM: Artificial Sequence
<220> FEATURE:
<223> OTHER INFORMATION: MHCFcRP-knob-K439E-His8 without hinge-cysteine
      residues

<400> SEQUENCE: 64

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Glu Ser Leu Ser Leu Ser
        210                 215                 220

Pro Gly Lys Gly Gly Gly Ser His His His His His His
225                 230                 235                 240

<210> SEQ ID NO 65
<211> LENGTH: 9
<212> TYPE: PRT
<213> ORGANISM: Homo sapiens

<400> SEQUENCE: 65

Asp Lys Thr His Thr Cys Pro Pro Cys
1               5

<210> SEQ ID NO 66
<211> LENGTH: 9
<212> TYPE: PRT
<213> ORGANISM: Artificial Sequence
```

```
<220> FEATURE:
<223> OTHER INFORMATION: cys-free hinge region

<400> SEQUENCE: 66

Asp Lys Thr His Thr Ser Pro Pro Ser
1               5

<210> SEQ ID NO 67
<211> LENGTH: 6
<212> TYPE: PRT
<213> ORGANISM: Artificial Sequence
<220> FEATURE:
<223> OTHER INFORMATION: hexa-histidine tag

<400> SEQUENCE: 67

His His His His His His
1               5

<210> SEQ ID NO 68
<211> LENGTH: 8
<212> TYPE: PRT
<213> ORGANISM: Artificial Sequence
<220> FEATURE:
<223> OTHER INFORMATION: octa-histidine tag

<400> SEQUENCE: 68

His His His His His His His His
1               5

<210> SEQ ID NO 69
<211> LENGTH: 4
<212> TYPE: PRT
<213> ORGANISM: Artificial Sequence
<220> FEATURE:
<223> OTHER INFORMATION: peptidic linker

<400> SEQUENCE: 69

Gly Gly Gly Ser
1

<210> SEQ ID NO 70
<211> LENGTH: 5
<212> TYPE: PRT
<213> ORGANISM: Artificial Sequence
<220> FEATURE:
<223> OTHER INFORMATION: peptidic linker

<400> SEQUENCE: 70

Gly Gly Gly Gly Ser
1               5

<210> SEQ ID NO 71
<211> LENGTH: 4
<212> TYPE: PRT
<213> ORGANISM: Artificial Sequence
<220> FEATURE:
<223> OTHER INFORMATION: peptidic linker

<400> SEQUENCE: 71

Gln Gln Gln Gly
1

<210> SEQ ID NO 72
<211> LENGTH: 5
<212> TYPE: PRT
<213> ORGANISM: Artificial Sequence
<220> FEATURE:
```

<223> OTHER INFORMATION: peptidic linker

<400> SEQUENCE: 72

Gln Gln Gln Gln Gly
1               5

<210> SEQ ID NO 73
<211> LENGTH: 4
<212> TYPE: PRT
<213> ORGANISM: Artificial Sequence
<220> FEATURE:
<223> OTHER INFORMATION: peptidic linker

<400> SEQUENCE: 73

Ser Ser Ser Gly
1

<210> SEQ ID NO 74
<211> LENGTH: 5
<212> TYPE: PRT
<213> ORGANISM: Artificial Sequence
<220> FEATURE:
<223> OTHER INFORMATION: peptidic linker

<400> SEQUENCE: 74

Ser Ser Ser Ser Gly
1               5

<210> SEQ ID NO 75
<211> LENGTH: 8
<212> TYPE: PRT
<213> ORGANISM: Artificial Sequence
<220> FEATURE:
<223> OTHER INFORMATION: peptidic linker

<400> SEQUENCE: 75

Gly Gly Gly Ser Gly Gly Gly Ser
1               5

<210> SEQ ID NO 76
<211> LENGTH: 12
<212> TYPE: PRT
<213> ORGANISM: Artificial Sequence
<220> FEATURE:
<223> OTHER INFORMATION: peptidic linker

<400> SEQUENCE: 76

Gly Gly Gly Ser Gly Gly Gly Ser Gly Gly Gly Ser
1               5                   10

<210> SEQ ID NO 77
<211> LENGTH: 16
<212> TYPE: PRT
<213> ORGANISM: Artificial Sequence
<220> FEATURE:
<223> OTHER INFORMATION: peptidic linker

<400> SEQUENCE: 77

Gly Gly Gly Ser Gly Gly Gly Ser Gly Gly Gly Ser Gly Gly Gly Ser
1               5                   10                  15

<210> SEQ ID NO 78
<211> LENGTH: 20
<212> TYPE: PRT
<213> ORGANISM: Artificial Sequence
<220> FEATURE:
<223> OTHER INFORMATION: peptidic linker

<400> SEQUENCE: 78

Gly Gly Gly Ser Gly Gly Gly Ser Gly Gly Gly Ser Gly Gly Gly Ser
1               5                   10                  15

Gly Gly Gly Ser
            20

<210> SEQ ID NO 79
<211> LENGTH: 10
<212> TYPE: PRT
<213> ORGANISM: Artificial Sequence
<220> FEATURE:
<223> OTHER INFORMATION: peptidic linker

<400> SEQUENCE: 79

Gly Gly Gly Gly Ser Gly Gly Gly Gly Ser
1               5                   10

<210> SEQ ID NO 80
<211> LENGTH: 15
<212> TYPE: PRT
<213> ORGANISM: Artificial Sequence
<220> FEATURE:
<223> OTHER INFORMATION: peptidic linker

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 20
<212> TYPE: PRT
<213> ORGANISM: Artificial Sequence
<220> FEATURE:
<223> OTHER INFORMATION: peptidic linker

<400> SEQUENCE: 81

Gly Gly Gly Gly Ser Gly Gly Gly Gly Ser Gly Gly Gly Gly Ser Gly
1               5                   10                  15

Gly Gly Gly Ser
            20

<210> SEQ ID NO 82
<211> LENGTH: 17
<212> TYPE: PRT
<213> ORGANISM: Artificial Sequence
<220> FEATURE:
<223> OTHER INFORMATION: peptidic linker

<400> SEQUENCE: 82

Gly Ser Ser Ser Ser Ser Ser Ser Ser Ser Ser Ser Ser Ser Ser Ser
1               5                   10                  15

Gly

<210> SEQ ID NO 83
<211> LENGTH: 219
<212> TYPE: PRT
<213> ORGANISM: Artificial Sequence
<220> FEATURE:
<223> OTHER INFORMATION: anti-LeY antibody full light chain

<400> SEQUENCE: 83

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 84
<211> LENGTH: 474
<212> TYPE: PRT
<213> ORGANISM: Artificial Sequence
<220> FEATURE:
<223> OTHER INFORMATION: anti-LeY-antibody heavy chain with anti-dig
      antibody variable domain as CH2 domain-knob

<400> SEQUENCE: 84

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
    210                 215                 220

Gly Gly Ser Gly Gly Gly Ser Gly Gly Gly Ser Gly Gly Gly
225                 230                 235                 240

Gly Ser Gln Val Gln Leu Val Glu Ser Gly Gly Leu Val Lys Pro
            245                 250                 255

Gly Gly Ser Leu Arg Leu Ser Cys Ala Ala Ser Gly Phe Thr Phe Ser
        260                 265                 270

Asp Tyr Ala Met Ser Trp Ile Arg Gln Ala Pro Gly Lys Gly Leu Glu
    275                 280                 285

Trp Val Ser Ser Ile Asn Ile Gly Ala Thr Tyr Ile Tyr Tyr Ala Asp
    290                 295                 300

Ser Val Lys Gly Arg Phe Thr Ile Ser Arg Asp Asn Ala Lys Asn Ser
305                 310                 315                 320

Leu Tyr Leu Gln Met Asn Ser Leu Arg Ala Glu Asp Thr Ala Val Tyr
            325                 330                 335

Tyr Cys Ala Arg Pro Gly Ser Pro Tyr Glu Tyr Asp Lys Ala Tyr Tyr
        340                 345                 350

Ser Met Ala Tyr Trp Gly Gln Gly Thr Thr Val Thr Val Ser Ser Gly
    355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 85
<211> LENGTH: 456
<212> TYPE: PRT
<213> ORGANISM: Artificial Sequence
<220> FEATURE:
<223> OTHER INFORMATION: anti-LeY-antibody heavy chain with anti-dig
      antibody variable domain as CH2 domain-hole

<400> SEQUENCE: 85

```
Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
```

```
            35                  40                  45
Ala Tyr Ile Ser Asn Asp Asp Ser Ser Ala Tyr Ser Asp Thr Val
 50                  55                  60

Lys Gly Arg Phe Thr Ile Ser Arg Asp Asn Ala Arg Asn Thr Leu Tyr
 65                  70                  75                  80

Leu Gln Met Ser Arg Leu Lys Ser Glu Asp Thr Ala Ile Tyr Tyr Cys
                 85                  90                  95

Ala Arg Gly Leu Ala Trp Gly Ala Trp Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Gly Gly
210                 215                 220

Gly Gly Ser Gly Gly Gly Gly Ser Gly Gly Gly Gly Ser Gly Gly Gly
225                 230                 235                 240

Gly Ser Asp Ile Gln Met Thr Gln Ser Pro Ser Ser Leu Ser Ala Ser
                245                 250                 255

Val Gly Asp Arg Val Thr Ile Thr Cys Arg Ala Ser Gln Asp Ile Lys
                260                 265                 270

Asn Tyr Leu Asn Trp Tyr Gln Gln Lys Pro Gly Lys Ala Pro Lys Leu
                275                 280                 285

Leu Ile Tyr Tyr Ser Ser Thr Leu Leu Ser Gly Val Pro Ser Arg Phe
290                 295                 300

Ser Gly Ser Gly Ser Gly Thr Asp Phe Thr Leu Thr Ile Ser Ser Leu
305                 310                 315                 320

Gln Pro Glu Asp Phe Ala Thr Tyr Tyr Cys Gln Gln Ser Ile Thr Leu
                325                 330                 335

Pro Pro Thr Phe Gly Gly Gly Thr Lys Val Glu Ile Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Ser Cys Ala Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
                450                 455
```

<210> SEQ ID NO 86
<211> LENGTH: 461
<212> TYPE: PRT
<213> ORGANISM: Artificial Sequence
<220> FEATURE:
<223> OTHER INFORMATION: anti-MSLN-antibody heavy chain with anti-dig
      antibody variable domain as CH2 domain-hole

<400> SEQUENCE: 86

Gln Val Lys Leu Lys Gln Ser Gly Gly Gly Leu Val Gln Pro Gly Gly
1               5                   10                  15

Ser Leu Lys Val Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Val Tyr Thr Pro Ser Leu
    50                  55                  60

Lys Asp Lys Phe Ile Met Ser Arg Asp Asn Ala Lys Asn Thr Leu Tyr
65                  70                  75                  80

Leu Gln Thr Ser Lys Val Arg Ser Ala Asp Thr Ala Leu Tyr Tyr Cys
                85                  90                  95

Ala Arg Arg Gly Ser His Tyr Tyr Gly Tyr Arg Thr Gly Tyr Phe Asp
            100                 105                 110

Val Trp Gly Ala Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Gly Gly Gly Gly Ser Gly Gly Gly Gly Ser Gly Gly Gly
225                 230                 235                 240

Gly Ser Gly Gly Gly Gly Ser Asp Ile Gln Met Thr Gln Ser Pro Ser
                245                 250                 255

Ser Leu Ser Ala Ser Val Gly Asp Arg Val Thr Ile Thr Cys Arg Ala
            260                 265                 270

Ser Gln Asp Ile Lys Asn Tyr Leu Asn Trp Tyr Gln Gln Lys Pro Gly
        275                 280                 285

Lys Ala Pro Lys Leu Leu Ile Tyr Tyr Ser Ser Thr Leu Leu Ser Gly
    290                 295                 300

Val Pro Ser Arg Phe Ser Gly Ser Gly Ser Gly Thr Asp Phe Thr Leu
305                 310                 315                 320

Thr Ile Ser Ser Leu Gln Pro Glu Asp Phe Ala Thr Tyr Tyr Cys Gln
                325                 330                 335

Gln Ser Ile Thr Leu Pro Pro Thr Phe Gly Gly Gly Thr Lys Val Glu
            340                 345                 350

Ile Lys Gly Gln Pro Arg Glu Pro Gln Val Tyr Thr Leu Pro Pro Ser

```
                355                 360                 365
Arg Asp Glu Leu Thr Lys Asn Gln Val Ser Leu Ser Cys Ala Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
        420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
        450                 455                 460

<210> SEQ ID NO 87
<211> LENGTH: 214
<212> TYPE: PRT
<213> ORGANISM: Artificial Sequence
<220> FEATURE:
<223> OTHER INFORMATION: anti-MSLN antibody light chain

<400> SEQUENCE: 87

Asp Val Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp His Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Pro Thr
                85                  90                  95

Phe Gly Gly Gly Thr Lys Leu Glu Ile Lys Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 468
<212> TYPE: PRT
<213> ORGANISM: Artificial Sequence
<220> FEATURE:
<223> OTHER INFORMATION: anti-LeY-antibody heavy chain with anti-CD3
``` antibody variable domain as CH2 domain-knob

<400> SEQUENCE: 88

```
Asp Val Lys Leu Val Glu Ser Gly Gly Gly Leu Val Gln Pro Gly
 1               5                  10                  15
Ser Leu Lys Leu Ser Cys Ala Thr Ser Gly Phe Thr Phe Ser Asp Tyr
                20                  25                  30
Tyr Met Tyr Trp Val Arg Gln Thr Pro Glu Lys Arg Leu Glu Trp Val
            35                  40                  45
Ala Tyr Ile Ser Asn Asp Asp Ser Ser Ala Ala Tyr Ser Asp Thr Val
        50                  55                  60
Lys Gly Arg Phe Thr Ile Ser Arg Asp Asn Ala Arg Asn Thr Leu Tyr
 65                  70                  75                  80
Leu Gln Met Ser Arg Leu Lys Ser Glu Asp Thr Ala Ile Tyr Tyr Cys
                85                  90                  95
Ala Arg Gly Leu Ala Trp Gly Ala Trp Phe Ala Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Gly Gly
210                 215                 220
Gly Gly Ser Gly Gly Gly Gly Ser Gly Gly Gly Gly Ser Gly Gly Gly
225                 230                 235                 240
Gly Ser Asp Ile Lys Leu Gln Gln Ser Gly Ala Glu Leu Ala Arg Pro
                245                 250                 255
Gly Ala Ser Val Lys Met Ser Cys Lys Thr Ser Gly Tyr Thr Phe Thr
            260                 265                 270
Arg Tyr Thr Met His Trp Val Lys Gln Arg Pro Gly Gln Gly Leu Glu
        275                 280                 285
Trp Ile Gly Tyr Ile Asn Pro Ser Arg Gly Tyr Thr Asn Tyr Asn Gln
290                 295                 300
Lys Phe Lys Asp Lys Ala Thr Leu Thr Thr Asp Lys Ser Ser Ser Thr
305                 310                 315                 320
Ala Tyr Met Gln Leu Ser Ser Leu Thr Ser Glu Asp Ser Ala Val Tyr
                325                 330                 335
Tyr Cys Ala Arg Tyr Tyr Asp Asp His Tyr Cys Leu Asp Tyr Trp Gly
            340                 345                 350
Gln Gly Thr Thr Leu Thr Val Ser Ser Gly Gln Pro Arg Glu Pro Gln
        355                 360                 365
Val Tyr Thr Leu Pro Pro Ser Arg Asp Glu Leu Thr Lys Asn Gln Val
        370                 375                 380
Ser Leu Trp Cys Leu Val Lys Gly Phe Tyr Pro Ser Asp Ile Ala Val
385                 390                 395                 400
```

```
Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 89
<211> LENGTH: 455
<212> TYPE: PRT
<213> ORGANISM: Artificial Sequence
<220> FEATURE:
<223> OTHER INFORMATION: anti-LeY-antibody heavy chain with anti-CD3
      antibody variable domain as CH2 domain-hole

<400> SEQUENCE: 89

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Gly Ser Gly Gly Gly
225                 230                 235                 240

Gly Ser Asp Ile Gln Leu Thr Gln Ser Pro Ala Ile Met Ser Ala Ser
                245                 250                 255

Pro Gly Glu Lys Val Thr Met Thr Cys Arg Ala Ser Ser Ser Val Ser
            260                 265                 270

Tyr Met Asn Trp Tyr Gln Gln Lys Ser Gly Thr Ser Pro Lys Arg Trp
        275                 280                 285
```

```
Ile Tyr Asp Thr Ser Lys Val Ala Ser Gly Val Pro Tyr Arg Phe Ser
            290                 295                 300

Gly Ser Gly Ser Gly Thr Ser Tyr Ser Leu Thr Ile Ser Ser Met Glu
305                 310                 315                 320

Ala Glu Asp Ala Ala Thr Tyr Tyr Cys Gln Gln Trp Ser Ser Asn Pro
                325                 330                 335

Leu Thr Phe Gly Ala Gly Thr Lys Leu Glu Leu Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 90
<211> LENGTH: 227
<212> TYPE: PRT
<213> ORGANISM: Artificial Sequence
<220> FEATURE:
<223> OTHER INFORMATION: MHCFCRP with non-binding variable domain as CH2
      domain-hole

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Gly
            20                  25                  30

Val Ala Trp Tyr Gln Gln Lys Pro Gly Lys Ala Pro Lys Leu Leu Ile
        35                  40                  45

Gly Ser Ala Ser Gly Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Ser Gly Gly Ser
                85                  90                  95

Thr Phe Gly Gln Gly Thr Lys Val Glu Ile Lys Gly Gln Pro Arg Glu
            100                 105                 110

Pro Gln Val Tyr Thr Leu Pro Pro Ser Arg Asp Lys Leu Thr Lys Asn
        115                 120                 125

Gln Val Ser Leu Ser Cys Ala Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Val Ser Lys
                165                 170                 175

Leu Thr Val Asp Lys Ser Arg Trp Gln Gln Gly Asn Val Phe Ser Cys
```

```
                        180                 185                 190
Ser Val Met His Glu Ala Leu His Asn His Tyr Thr Gln Lys Ser Leu
            195                 200                 205

Ser Leu Ser Pro Gly Lys Gly Gly Gly Ser His His His His
            210                 215                 220

His His His
225

<210> SEQ ID NO 91
<211> LENGTH: 240
<212> TYPE: PRT
<213> ORGANISM: Artificial Sequence
<220> FEATURE:
<223> OTHER INFORMATION: MHCFcRP with non-binding variable domain as CH2
      domain-knob

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ala Gly Thr
            20                  25                  30

Ala Ile His Trp Val Arg Gln Ala Pro Gly Lys Gly Leu Glu Trp Val
            35                  40                  45

Ala Ser Ile Ser Pro Gly Gly Gly Ser Thr Ala Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ser Gly Gly Ser Gly Ala Ser Ala Met Asp Tyr Trp Gly Gln
            100                 105                 110

Gly Thr Leu Val Thr Val Ser Ser Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Trp Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Gly Ser His His His His His His
225                 230                 235                 240

<210> SEQ ID NO 92
<211> LENGTH: 720
<212> TYPE: PRT
<213> ORGANISM: Artificial Sequence
<220> FEATURE:
<223> OTHER INFORMATION: single chain anti-LeY-Dig TriFab heavy chain
      (knob) - Bio VL (hole)

<400> SEQUENCE: 92

Asp Val Lys Leu Val Glu Ser Gly Gly Gly Leu Val Gln Pro Gly Gly
```

-continued

```
1               5                   10                  15
Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
            35                  40                  45

Ala Tyr Ile Ser Asn Asp Asp Ser Ser Ala Ala Tyr Ser Asp Thr Val
            50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
            85                  90                  95

Ala Arg Gly Leu Ala Trp Gly Ala Trp Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
210                 215                 220

Gly Gly Ser Gly Gly Gly Gly Ser Gly Gly Gly Gly Ser Gly Gly Gly
225                 230                 235                 240

Gly Ser Gln Val Gln Leu Val Glu Ser Gly Gly Gly Leu Val Lys Pro
            245                 250                 255

Gly Gly Ser Leu Arg Leu Ser Cys Ala Ala Ser Gly Phe Thr Phe Ser
            260                 265                 270

Asp Tyr Ala Met Ser Trp Ile Arg Gln Ala Pro Gly Lys Gly Leu Glu
            275                 280                 285

Trp Val Ser Ser Ile Asn Ile Gly Ala Thr Tyr Ile Tyr Tyr Ala Asp
            290                 295                 300

Ser Val Lys Gly Arg Phe Thr Ile Ser Arg Asp Asn Ala Lys Asn Ser
305                 310                 315                 320

Leu Tyr Leu Gln Met Asn Ser Leu Arg Ala Glu Asp Thr Ala Val Tyr
            325                 330                 335

Tyr Cys Ala Arg Pro Gly Ser Pro Tyr Glu Tyr Asp Lys Ala Tyr Tyr
            340                 345                 350

Ser Met Ala Tyr Trp Gly Gln Gly Thr Thr Val Thr Val Ser Ser Gly
            355                 360                 365

Gln Pro Arg Glu Pro Gln Val Tyr Thr Leu Pro Pro Ser Arg Asp Glu
            370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430
```

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
    450                 455                 460

Gln Lys Ser Leu Ser Leu Ser Pro Gly Lys Gly Gly Gly Gly Ser Gly
465                 470                 475                 480

Gly Gly Gly Ser Gly Gly Gly Ser Gly Gly Gly Ser Gly Gly
                485                 490                 495

Gly Gly Ser Gly Gly Gly Ser Gly Gly Asp Ile Gln Met Thr Gln
            500                 505                 510

Ser Pro Ser Ser Leu Ser Ala Ser Val Gly Asp Arg Val Thr Ile Thr
            515                 520                 525

Cys Arg Ala Ser Gly Asn Ile His Asn Tyr Leu Ser Trp Tyr Gln Gln
    530                 535                 540

Lys Pro Gly Lys Val Pro Lys Leu Leu Ile Tyr Ser Ala Lys Thr Leu
545                 550                 555                 560

Ala Asp Gly Val Pro Ser Arg Phe Ser Gly Ser Gly Ser Gly Thr Asp
                565                 570                 575

Phe Thr Leu Thr Ile Ser Ser Leu Gln Pro Glu Asp Val Ala Thr Tyr
            580                 585                 590

Tyr Cys Gln His Phe Trp Ser Ile Tyr Thr Phe Gly Gly Gly Thr
    595                 600                 605

Lys Leu Glu Ile Lys Gly Gln Pro Arg Glu Pro Gln Val Tyr Thr Leu
    610                 615                 620

Pro Pro Ser Arg Asp Lys Leu Thr Lys Asn Gln Val Ser Leu Ser Cys
625                 630                 635                 640

Ala Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Val Ser Lys Leu Thr Val Asp Lys Ser
            675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 93
<211> LENGTH: 709
<212> TYPE: PRT
<213> ORGANISM: Artificial Sequence
<220> FEATURE:
<223> OTHER INFORMATION: single chain anti-LeY-Dig TriFab heavy chain
      (hole) - Bio VH (knob)

<400> SEQUENCE: 93

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Asp Ser Ser Ala Ala Tyr Ser Asp Thr Val
    50                  55                  60

Lys Gly Arg Phe Thr Ile Ser Arg Asp Asn Ala Arg Asn Thr Leu Tyr

```
                65                  70                  75                  80
Leu Gln Met Ser Arg Leu Lys Ser Glu Asp Thr Ala Ile Tyr Tyr Cys
                        85                  90                  95

Ala Arg Gly Leu Ala Trp Gly Ala Trp Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Gly Ser Gly Gly Gly
225                 230                 235                 240

Gly Ser Asp Ile Gln Met Thr Gln Ser Pro Ser Ser Leu Ser Ala Ser
                245                 250                 255

Val Gly Asp Arg Val Thr Ile Thr Cys Arg Ala Ser Gln Asp Ile Lys
                260                 265                 270

Asn Tyr Leu Asn Trp Tyr Gln Gln Lys Pro Gly Lys Ala Pro Lys Leu
            275                 280                 285

Leu Ile Tyr Tyr Ser Ser Thr Leu Leu Ser Gly Val Pro Ser Arg Phe
        290                 295                 300

Ser Gly Ser Gly Ser Gly Thr Asp Phe Thr Leu Thr Ile Ser Ser Leu
305                 310                 315                 320

Gln Pro Glu Asp Phe Ala Thr Tyr Tyr Cys Gln Gln Ser Ile Thr Leu
                325                 330                 335

Pro Pro Thr Phe Gly Gly Thr Lys Val Glu Ile Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys Gly Gly Gly Ser Gly Gly Gly
        450                 455                 460

Gly Ser Gly Gly Gly Ser Gly Gly Gly Ser Gly Gly Gly
465                 470                 475                 480

Ser Gly Gly Gly Gly Ser Gly Gly Gln Val Gln Leu Val Gln Ser Gly
                485                 490                 495
```

```
Ala Glu Val Lys Lys Pro Gly Ser Ser Val Lys Val Ser Cys Lys Ser
            500                 505                 510
Ser Gly Phe Asn Asn Lys Asp Thr Phe Phe Gln Trp Val Arg Gln Ala
        515                 520                 525
Pro Gly Gln Gly Leu Glu Trp Met Gly Arg Ile Asp Pro Ala Asn Gly
    530                 535                 540
Phe Thr Lys Tyr Ala Gln Lys Phe Gln Gly Arg Val Thr Ile Thr Ala
545                 550                 555                 560
Asp Thr Ser Thr Ser Thr Ala Tyr Met Glu Leu Ser Ser Leu Arg Ser
                565                 570                 575
Glu Asp Thr Ala Val Tyr Tyr Cys Ala Arg Trp Asp Tyr Gly Ala
            580                 585                 590
Ala Trp Phe Ala Tyr Trp Gly Gln Gly Thr Leu Val Thr Val Ser Ser
            595                 600                 605
Gly Gln Pro Arg Glu Pro Gln Val Tyr Thr Leu Pro Pro Ser Arg Asp
        610                 615                 620
Glu Leu Thr Lys Asn Gln Val Ser Leu Trp Cys Leu Val Glu Gly Phe
625                 630                 635                 640
Tyr Pro Ser Asp Ile Ala Val Glu Trp Glu Ser Asn Gly Gln Pro Glu
                645                 650                 655
Asn Asn Tyr Lys Thr Thr Pro Pro Val Leu Asp Ser Asp Gly Ser Phe
            660                 665                 670
Phe Leu Tyr Ser Lys Leu Thr Val Asp Lys Ser Arg Trp Gln Gln Gly
        675                 680                 685
Asn Val Phe Ser Cys Ser Val Met His Glu Ala Leu His Asn His Tyr
    690                 695                 700
Thr Gln Lys Ser Leu
705

<210> SEQ ID NO 94
<211> LENGTH: 5
<212> TYPE: PRT
<213> ORGANISM: Homo sapiens

<400> SEQUENCE: 94

Asp Lys Thr His Thr
1               5

<210> SEQ ID NO 95
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X = S or P

<400> SEQUENCE: 95

Cys Pro Xaa Cys
1

<210> SEQ ID NO 96
<211> LENGTH: 6
<212> TYPE: PRT
<213> ORGANISM: Artificial Sequence
<220> FEATURE:
<223> OTHER INFORMATION: mutated hinge

<400> SEQUENCE: 96
```

His Thr Ser Pro Pro Ser
1               5

<210> SEQ ID NO 97
<211> LENGTH: 9
<212> TYPE: PRT
<213> ORGANISM: Artificial Sequence
<220> FEATURE:
<223> OTHER INFORMATION: new linker

<400> SEQUENCE: 97

Asp Lys Thr His Gly Gly Gly Gly Ser
1               5

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

His Thr Pro Ala Pro Glu
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S or P

<400> SEQUENCE: 99

His Thr Ser Pro Xaa Ser Pro
1               5

<210> SEQ ID NO 100
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Gly Gly Gly Ser Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Pro Ala Pro Ile Glu Lys Thr Ile Ser Lys Ala Lys Gly Gln Pro Arg
1               5                   10                  15

```
Glu Pro Gln Val Tyr Thr Leu Pro Cys Arg Asp Glu Leu Thr Lys
            20                  25                  30

Asn Gln Val Ser Leu Trp Cys Leu Val Lys Gly Phe Tyr Pro Ser Asp
            35                  40                  45

Ile Ala Val Glu Trp Glu Ser Asn Gly Gln Pro Glu Asn Asn Tyr Lys
50                      55                  60

Thr Thr Pro Pro Val Leu Asp Ser Asp Gly Ser Phe Phe Leu Tyr Ser
65                  70                  75                  80

Lys Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
                100                 105                 110

Leu Ser Leu Ser Pro Gly Lys
            115

<210> SEQ ID NO 102
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Pro Ala Pro Ile Glu Lys Thr Ile Ser Lys Ala Lys Gly Gln Pro Arg
1               5                   10                  15

Glu Pro Gln Val Cys Thr Leu Pro Pro Ser Arg Asp Glu Leu Thr Lys
            20                  25                  30

Asn Gln Val Ser Leu Ser Cys Ala Val Lys Gly Phe Tyr Pro Ser Asp
            35                  40                  45

Ile Ala Val Glu Trp Glu Ser Asn Gly Gln Pro Glu Asn Asn Tyr Lys
50                  55                      60

Thr Thr Pro Pro Val Leu Asp Ser Asp Gly Ser Phe Phe Leu Val Ser
65                  70                  75                  80

Lys Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
                100                 105                 110

Leu Ser Leu Ser Pro Gly Lys
            115

<210> SEQ ID NO 103
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Pro Ala Pro Ile Glu Lys Thr Ile Ser Lys Ala Lys Gly Gln Pro Arg
1               5                   10                  15

Glu Pro Gln Val Tyr Thr Leu Pro Pro Ser Arg Lys Glu Leu Thr Lys
            20                  25                  30

Asn Gln Val Ser Leu Ser Cys Ala Val Lys Gly Phe Tyr Pro Ser Asp
            35                  40                  45

Ile Ala Val Glu Trp Glu Ser Asn Gly Gln Pro Glu Asn Asn Tyr Lys
50                  55                      60
```

```
Thr Thr Pro Pro Val Leu Asp Ser Asp Gly Ser Phe Phe Leu Val Ser
 65              70                  75                  80

Lys Leu Thr Val Asp Lys Ser Arg Trp Gln Gln Gly Asn Val Phe Ser
                 85                  90                  95

Cys Ser Val Met His Glu Ala Leu His Asn His Tyr Thr Gln Lys Ser
                100                 105                 110

Leu Ser Leu Ser Pro Gly Lys
            115

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Pro Ala Pro Ile Glu Lys Thr Ile Ser Lys Ala Lys Gly Gln Pro Arg
 1               5                  10                  15

Glu Pro Gln Val Tyr Thr Leu Pro Pro Ser Arg Asp Glu Leu Thr Lys
                 20                  25                  30

Asn Gln Val Ser Leu Trp Cys Ala Val Lys Gly Phe Tyr Pro Ser Asp
                 35                  40                  45

Ile Ala Val Glu Trp Glu Ser Asn Gly Gln Pro Glu Asn Asn Tyr Lys
 50                  55                      60

Thr Thr Pro Pro Val Leu Asp Ser Asp Gly Ser Phe Phe Leu Tyr Ser
 65              70                  75                  80

Lys Leu Thr Val Asp Lys Ser Arg Trp Gln Gln Gly Asn Val Phe Ser
                 85                  90                  95

Cys Ser Val Met His Glu Ala Leu His Asn His Tyr Thr Gln Glu Ser
                100                 105                 110

Leu Ser Leu Ser Pro Gly Lys
            115
```

METHOD FOR IN VIVO GENERATION OF MULTISPECIFIC ANTIBODIES FROM MONOSPECIFIC ANTIBODIES

CROSS REFERENCE TO RELATED APPLICATIONS

This application is a continuation of International Application No. PCT/EP2018/079523, filed Oct. 29, 2018, claiming priority to European Application No. 17199086.4 filed Oct. 30, 2017, which are incorporated herein by reference in its entirety.

SEQUENCE LISTING

The application contains a Sequence Listing which has been submitted electronically in ASCII format and is hereby incorporated by reference in its entirety. Said ASCII copy, created on Jan. 18, 2023 is named P34507-US_SL.txt and is 203,299 bytes in size.

Herein is reported a method for the on-cell, in vivo assembly of multispecific, such as e.g. bispecific, antibodies using a novel half-antibody exchange method. The current method is suitable even for complete antibodies, i.e. comprising CH2-CH3 domains and having thereby effector function.

BACKGROUND OF THE INVENTION

Current state of the art methods for biochemical conversion of monospecific antibody derivatives to assembled bispecific antibodies apply (i) half-antibody complementation reactions and (ii) IgG-IgG exchange reactions.

These technologies are disclosed e.g. in WO 2015/046467, Rispens et al., J. Biol. Chem. 289 (2014) 6098-6109, U.S. Pat. No. 9,409,989, WO 2013/060867, WO 2011/131746, WO 2011/133886, WO 2011/143545, WO 2010/151792, Gunasekaran et al., J. Biol. Chem. 285 (2010) 19637-19646, WO 2009/041613, WO 2009/089004, WO 2008/119353, WO 2007/114325, U.S. Pat. Nos. 8,765,412, 8,642,745, WO 2006/047340, WO 2006/106905, WO 2005/042582, WO 2005/062916, WO 2005/000898, U.S. Pat. Nos. 7,183,076, 7,951,917, Segal, D. M., et al., Curr. Opin. Immunol. 11 (1999) 558-562, WO 98/50431, WO 98/04592, Merchant, A. M., et al., Nat. Biotechnol. 16 (1998) 677-681, WO 96/27011, Carter, P., et al., Immunotechnol. 2 (1996) 73, WO 93/11162, and Kostelny, S. A., et al., J. Immunol. 148 (1992) 1547-1553.

State of the art methods for converting monospecific antibodies or antibody derivatives to bsAbs have drawbacks, such as, e.g., limitations concerning processes for and composition of post-assembly bsAb preparations.

For example, the half-antibody technology assembles monospecific and monovalent antibody sides to bivalent IgGs. Expression of the input molecules as well as the exchange reaction by itself generates not only half-antibodies but also IgG like bivalent (monospecific) antibody derivatives. Aggregates are also present in the input material as well as in the output of the assembly reactions. Both (bivalent monospecific antibodies and aggregates) need to be either quantitatively removed from assembled bsAb via elaborate purification approaches or (as quantitative removal is hard to achieve in high throughput manner) they 'contaminate' to some degree the bsAb preparations.

The Fab-arm exchange technology, for example, assembles bispecific bivalent IgGs from monospecific bivalent IgG-derivatives. Thus, the input into the exchange reaction is bivalent i.e. avidity enabled by default. To assure complete lack of remaining bivalent monospecific input material in exchange reactions that shall be subjected to avidity or agonistic antibody screens, it would have to be assured a complete removal of any remaining bivalent input as well as of any aggregates that may form during the exchange reaction. Due to high similarity of input and bsAb, elaborate procedures for quantitative removal are necessary (very hard to achieve in high throughput), or remaining bivalent input and aggregates will contaminate to some degree the final bsAb preparations.

Labrijn, A. F., et al., disclosed efficient generation of stable bispecific IgG1 by controlled Fab-arm exchange (Proc. Natl. Acad. Sci. USA 110 (2013) 5145-5150).

WO 2014/081955 disclosed heterodimeric antibodies and methods of use.

WO 2009/089004 disclosed a method for making antibody Fc-heterodimeric molecules using electrostatic steering effects. Therein it had been disclosed that of four unique charge residue pairs involved in the domain-domain interaction (Asp356---Lys439', Glu357--Lys370', Lys392---Asp399', Asp399---Lys409') only Lys409---Asp399' is suitable for engineering as both these residues were structurally conserved as well as buried. For the other three pairs at least one of the partner is solvent exposed (% ASA>10).

WO 2018/155611 disclosed a combination of a first antigen-binding molecule and a second antigen-binding molecule that do not bind by covalent bonding, which when mixed into a liquid form heterodimers more easily than homodimers. It is disclosed therein in one embodiment that substitution by other amino acids at the cysteine residue in either one or both of position 226 and position 229 in the EU numbering system is combined with a substitution of either one or both of first CH3 and second CH3 by other amino acid residues in at least one of position 357 or position 397 in the EU numbering system.

Mayer, K., et al. (Int. J. Mol. Sci. 16 (2015) 27497-27506) disclosed TriFabs as trivalent IgG-shaped bispecific antibody derivatives, their design, generation, characterization and application for targeted payload delivery.

SUMMARY OF THE INVENTION

Herein is reported a method for the generation of multispecific antibodies by a half-antibody exchange reaction directly on the surface of target cells. This allows, amongst other things, the formation of functional binding sites from inactive pro-binding sites directly at the intended site of action. Such an on-site formation eliminates the risk of systemic side reactions.

It has been found that as starting material non-complete antibodies, such as 2/3-IgGs or 2/3-BiFabs comprising an antibody light chain, an antibody heavy chain and an antibody heavy chain fragment, wherein the heavy chain-heavy chain interaction is destabilized by an asymmetric perturbing mutation, preferably in the heavy chain fragment, and wherein no inter-heavy chain-heavy chain covalent/disulfide bonds, such as the hinge-region disulfide bonds or inter-CH3 domain disulfide bonds, are present, are advantageous. This asymmetric perturbing mutation has been found to foster on the one hand the dissociation of the starting non-complete antibodies and on the other hand the generation of correctly assembled full length bispecific antibodies. The absence of inter-heavy chain-heavy chain covalent bonds allows that the reaction can be performed in the absence of reducing agents, i.e. under in vivo or physiological conditions.

The method according to the invention is performed in the absence of reducing agents. Thus, the starting antibodies have no heavy chain-heavy chain disulfide bonds, such as e.g. hinge region disulfide bonds. Thus, the chain-exchange reaction and method according to the current invention allows for the assembly of bispecific antibodies without initial reduction making this method suitable for in vivo application. Therefore, naturally occurring intramolecular disulfide bonds between the heavy chains of the starting molecules are removed, e.g. by mutagenesis PCR. Despite lack of all intermolecular disulfide bonds between the heavy chains, the correct formation of stable, i.e. isolatable, antibodies takes place. Thus, with these starting molecules it was possible to realize an in-vivo generation of bispecific antibodies employing a reduction-free spontaneous chain-exchange reaction. Overall, the reduction-free chain exchange method according to the current invention enables an efficient generation of functional bispecific antibodies directly on the surface of cells in vivo.

Herein is reported a method for producing a (multispecific) binder/multimeric polypeptide comprising the following steps:

incubating
- a first binder (which is mono- or bispecific and heteromeric,)/multimeric polypeptide comprising a first (monomeric) polypeptide and a second (monomeric) polypeptide both comprising (in N- to C-terminal direction) an antibody variable domain (directly) followed by a human immunoglobulin (IgG1) CH3 domain,
- wherein i) the variable domain of the first polypeptide is a heavy chain variable domain and the variable domain of the second polypeptide is a light chain variable domain, or ii) the variable domain of the first polypeptide is a light chain variable domain and the variable domain of the second polypeptide is a heavy chain variable domain,
- wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation,
- wherein the first polypeptide comprises at least one functional binding site or at least a part of a binding site,
- wherein the second polypeptide comprises in the CH3 domain at least one/a first perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
- wherein the first polypeptide and the second polypeptide associate non-covalently with each other/form a non-covalent dimer/are non-covalently associated with each other/are a non-covalent dimer, (whereby the perturbing mutation in the second polypeptide results in a destabilizing interaction when the second polypeptide and the first polypeptide form a heterodimer,)

and

- a second binder (which is mono- or bispecific and heteromeric,)/multimeric polypeptide comprising a third (monomeric) polypeptide and a fourth (monomeric) polypeptide both comprising (in N- to C-terminal direction) an antibody variable domain directly followed by a human immunoglobulin (IgG1) CH3 domain,
- wherein i) the variable domain of the third polypeptide is a heavy chain variable domain and the variable domain of the fourth polypeptide is a light chain variable domain, or ii) the variable domain of the third polypeptide is a light chain variable domain and the variable domain of the fourth polypeptide is a heavy chain variable domain, whereby i) the variable domain of the fourth polypeptide is a light chain variable domain if the variable domain of the first polypeptide is a heavy chain variable domain, or ii) the variable domain of the fourth polypeptide is a heavy chain variable domain if the variable domain of the first polypeptide is a light chain variable domain,
- wherein i) the CH3 domain of the third polypeptide comprises the knob-mutation and the CH3 domain of the fourth polypeptide comprises the hole-mutations, or ii) the CH3 domain of the third polypeptide comprises the hole-mutations and the CH3 domain of the fourth polypeptide comprises the knob-mutation, whereby i) in case the first polypeptide comprises the hole-mutations the fourth polypeptide comprises the knob-mutation, or ii) in case the first polypeptide comprises the mutations knob the fourth polypeptide comprises the mutation hole,
- wherein the fourth polypeptide comprises at least one functional binding site or at least a part of a binding site,
- wherein the third polypeptide comprises in the CH3 domain at least one/a second perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T), whereby the fourth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the mutation in the third polypeptide is at a different position as the mutation in the second polypeptide,
- wherein the third polypeptide and the fourth polypeptide associate covalently or non-covalently with each other/form a covalent or non-covalent dimer/are non-covalently or covalently associated with each other/are a non-covalent or covalent dimer, (whereby the perturbing mutation in the third polypeptide results in a destabilizing interaction when the third polypeptide and the fourth polypeptide form a heterodimer,)
wherein the (first) perturbing mutation in the second polypeptide and the (second) perturbing mutation in the third polypeptide result in an attractive interaction when the second polypeptide and the third polypeptide form a heterodimer,
wherein the variable domain of the first polypeptide and the variable domain of the fourth polypeptide form a functional (antigen binding competent) binding site (pair of antibody variable domains (VH/VL pair)), and the variable domain of the second polypeptide and the variable domain of the third polypeptide form a non-functional (not antigen binding competent) pair of variable domains,
and
recovering the binder comprising the first polypeptide and the fourth polypeptide and thereby producing the (multispecific) binder/multimeric polypeptide.

In one embodiment the first to fourth polypeptide each comprise in N- to C-terminal direction i) the amino acid sequence DKTHTSPPS (SEQ ID NO: 66), ii) an antibody variable domain derived from a human IgG1 variable domain, and iii) a CH3 domain derived from a human IgG1 CH3 domain.

In one embodiment i) the first and the fourth polypeptide each further comprise a CH1 domain derived from a human IgG1 CH1 domain (a (variant) human IgG1 CH1 domain) and (independently of each other) a further (heavy chain or a light chain) variable domain, or ii) the first or the fourth polypeptide comprise a CH1 domain derived from a human IgG1 CH1 domain (a (variant) human IgG1 CH1 domain) and the respective other polypeptide comprises a domain derived from a light chain constant domain (a (variant) human kappa or lambda CL domain) and each polypeptide further comprises a further variable domain. In one embodiment the further variable domain of the first polypeptide and the further variable domain of the fourth polypeptide are a (different) heavy chain variable domain(s). In one embodiment the further variable domain of the first polypeptide is a heavy chain variable domain and the further variable domain of the fourth polypeptide is a light chain variable domain or vice versa.

In one embodiment the first and the fourth polypeptide can have the same or a different N- to C-terminal sequence and in case the first and the fourth polypeptide are the same they are selected from the following group of polypeptides comprising in N- to C-terminal direction and in case the first and the fourth polypeptide are different they are independently of each other selected from the following group of polypeptides comprising in N- to C-terminal direction i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain.

In one embodiment one of the first and the fourth polypeptide comprises in N- to C-terminal direction a second heavy chain variable domain, a first (CH1 domain derived from a) human IgG1 CH1 domain, a third heavy chain variable domain, a first light chain constant domain, a hinge region of SEQ ID NO: 66, a first heavy or light chain variable domain, and a CH3 domain derived from a human IgG1 CH3 domain, and the other of the first and the fourth polypeptide comprises in N- to C-terminal direction the second heavy chain variable domain, a (CH1 domain derived from a) human IgG1 CH1 domain, a hinge region of SEQ ID NO: 66, a first heavy or light chain variable domain, and a CH3 domain derived from a human IgG1 CH3 domain. In one embodiment the binder comprising the polypeptide comprising two heavy chain variable domains further comprises a first light chain comprising a first light chain variable domain and a second light chain constant domain (pairing with the first heavy chain variable domain) and a (domain exchanged) second light chain comprising a second light chain variable domain and a (CH1 domain derived from a) human IgG1 CH1 domain (pairing with the second heavy chain variable domain) and the other binder further comprises the first light chain.

In one embodiment one of the first and the fourth polypeptide comprises in N- to C-terminal direction a second heavy chain variable domain, a first (CH1 domain derived from a) human IgG1 CH1 domain, a second light chain variable domain, a second (CH1 domain derived from a) human IgG1 CH1 domain, a hinge region of SEQ ID NO: 66, a first heavy or light chain variable domain, and a CH3 domain derived from a human IgG1 CH3 domain, and the other of the first and the fourth polypeptide comprises in N- to C-terminal direction the second heavy chain variable domain, a (CH1 domain derived from a) human IgG1 CH1 domain, a hinge region of SEQ ID NO: 66, a first heavy or light chain variable domain, and a CH3 domain derived from a human IgG1 CH3 domain. In one embodiment the binder comprising the polypeptide comprising two variable domains further comprises a first light chain comprising a third variable light chain domain and a first light chain constant domain (pairing with the first heavy chain variable domain) and a (domain exchanged) second light chain comprising a third heavy chain variable domain and second light chain constant domain (pairing with the first light chain variable domain) and the other binder further comprises the first light chain.

In one embodiment the first and the second binder further comprise an antibody light chain.

In one embodiment the
the first binder comprises
as first polypeptide a polypeptide selected from the group of polypeptides comprising in N- to C-terminal direction
i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, comprising the knob-mutation or the hole-mutations, and as second polypeptide a polypeptide selected from the group of polypeptides comprising in N- to C-terminal direction a hinge region of SEQ ID NO: 66, a first heavy or light chain variable domain, and a CH3 domain derived from a human IgG1 CH3 domain, wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain, wherein the CH3 domain comprises the knob-mutation if the first polypeptide comprises the hole-mutations, or the hole-mutations if the first polypeptide comprises the knob-mutation, comprising a first perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate non-covalently with each other/form a non-covalent dimer, (whereby the perturbing mutation in the second polypeptide results in a destabilizing interaction when the second polypeptide and the first polypeptide form a heterodimer,)

and a third polypeptide comprising a further light chain variable domain and a light chain constant domain, wherein the third polypeptide is covalently bound to the first polypeptide by a disulfide bond, and the second binder comprises as fourth polypeptide a polypeptide selected from the group of polypeptides comprising in N- to C-terminal direction a hinge region of SEQ ID NO: 66, a first heavy or light chain variable domain, and a CH3 domain derived from a human IgG1 CH3 domain, wherein the CH3 domain comprises the mutations knob if the second polypeptide comprises the hole-mutations, or the hole-mutations if the second polypeptide comprises the mutations knob, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the fifth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv,
vii) a hinge region of SEQ ID NO: 66, a heavy or light chain variable domain, a CH3 domain derived from a human IgG1 CH3 domain, optionally a peptidic linker, and a scFab,
viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain,
ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain,
x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv,
xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab,
xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain,
xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain,
xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and
xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, wherein the CH3 domain comprises the knob-mutation if the fourth polypeptide comprises the hole-mutations, or the hole-mutations if the fourth polypeptide comprises the knob-mutation, wherein i) the variable domain of the fourth polypeptide is a heavy chain variable domain if the variable domain of the second polypeptide is a light chain variable domain, or ii) the variable domain of the fourth polypeptide is a light chain variable domain if the variable domain of the second polypeptide is a heavy chain variable domain, wherein the fourth polypeptide and the fifth polypeptide associate non-covalently with each other/form a non-covalent dimer, (whereby the perturbing mutation in the fourth polypeptide results in a destabilizing interaction when the fourth polypeptide and the fifth polypeptide form a heterodimer,)

and a sixth polypeptide comprising a light chain variable domain and a light chain constant domain, wherein the sixth polypeptide is covalently bound to the fourth polypeptide by a disulfide bond.

In one embodiment the incubation step is in the absence of a reducing agent.

In one embodiment i) the second polypeptide and the third polypeptide, or ii) the second polypeptide and the fifth polypeptide further comprise a (C-terminal) tag. In one embodiment the tag has the amino acid sequence HHHHHH (SEQ ID NO: 67) or HHHHHHHH (SEQ ID NO: 68) and the recovering is by chromatography on a metal (nickel) chelate affinity chromatography column.

In one embodiment the
the first binder comprises
as first polypeptide a polypeptide selected from the group of polypeptides comprising in N- to C-terminal direction
i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain,
ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain,
iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, comprising the knob-mutation or the hole-mutations, and as second polypeptide a polypeptide selected from the group of polypeptides comprising in N- to C-terminal direction a hinge region of SEQ ID NO: 66, a first heavy or light chain variable domain, and a CH3 domain derived from a human IgG1 CH3 domain, wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain, wherein the CH3 domain comprises the mutations knob if the first polypeptide comprises the hole-mutations, or the hole-mutations if the first polypeptide comprises the knob-mutation, comprising a first perturbing mutation selected from the group of mutations consisting of D356S, D356A, D356K, E357S, E357A, E357L, E357F, E357K, K370E, and K439E, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate non-covalently with each other/form a non-covalent, (whereby the perturbing mutation in the second polypeptide results in a destabilizing interaction when the second polypeptide and the first polypeptide form a heterodimer,)

and a third polypeptide comprising a light chain variable domain and a light chain constant domain, wherein the third polypeptide is covalently bound to the first polypeptide by a disulfide bond, and the second binder comprises as fourth polypeptide a polypeptide selected from the group of polypeptides comprising in N- to C-terminal direction a hinge region of SEQ ID NO: 66, a CH2 domain derived from a human IgG1 CH2 domain, and a CH3 domain derived from a human IgG1 CH3 domain, wherein the CH3 domain comprises the knob-mutation if the second polypeptide comprises the hole-mutations, or the hole-mutations if the second polypeptide comprises the knob-mutation, comprising a second perturbing mutation selected from the group of mutations consisting of D356S, D356A, D356K, E357S, E357A, E357L, E357F, E357K, K370E, and K439E, whereby the fifth polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the fourth polypeptide is at a different position as the perturbing mutation in the second polypeptide, and as fifth polypeptide a polypeptide selected from the group of polypeptides comprising in N- to C-terminal direction
- i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain,
- ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain,
- iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain,
- iv) a scFv, optionally a peptidic linker, a hinge region of SEQ ID NO: 66, a heavy or light chain variable domain, and a CH3 domain derived from a human IgG1 CH3 domain,
- v) a scFab, optionally a peptidic linker, a hinge region of SEQ ID NO: 66, a heavy or light chain variable domain, and a CH3 domain derived from a human IgG1 CH3 domain,
- vi) a hinge region of SEQ ID NO: 66, a heavy or light chain variable domain, a CH3 domain derived from a human IgG1 CH3 domain, optionally a peptidic linker, and a scFv,
- vii) a hinge region of SEQ ID NO: 66, a heavy or light chain variable domain, a CH3 domain derived from a human IgG1 CH3 domain, optionally a peptidic linker, and a scFab,
- viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain,
- ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain,
- x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv,
- xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab,
- xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain,
- xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain,
- xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and
- xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, comprising the mutations knob if the fourth polypeptide comprises the hole-mutations, or the hole-mutations if the fourth polypeptide comprises the knob-mutation, wherein the fourth polypeptide and the fifth polypeptide associate non-covalently with each other/form a non-covalent dimer, (whereby the perturbing mutation in the fourth polypeptide results in a destabilizing interaction when the fourth polypeptide and the fifth polypeptide form a heterodimer,)

wherein the variable domain of the first polypeptide and the variable domain of the fourth polypeptide form a functional (antigen binding competent) binding site (pair of antibody variable domains (VH/VL pair)), and the variable domain of the second polypeptide and the variable domain of the third polypeptide form a non-functional (not antigen binding competent) pair of variable domains, and a sixth polypeptide comprising a light chain variable domain and a light chain constant domain,
- wherein the sixth polypeptide is covalently bound to the fourth polypeptide by a disulfide bond.

One aspect as reported herein is a method for identifying a binder combination comprising the steps of
  producing a multitude of binders by subjecting each combination of a first binder selected from a first multitude of binders and a second binder selected from a second multitude of binders to the method according to the invention,
  measuring individually the (amount of) simultaneous binding of each binder of the produced multitude of binders to at least two antigens in an ELISA assay, and
  selecting a binder from the multitude of binders based on the result of the ELISA and thereby identifying a binder combination.

One aspect as reported herein is a multimeric polypeptide comprising a first polypeptide and a second polypeptide
  wherein both polypeptides comprise (in N- to C-terminal direction directly after each other optionally with an peptidic linker between the variable domain and the CH3 domain) the amino acid sequence DKTHTSPPS (SEQ ID NO: 66), an antibody variable domain, and a human immunoglobulin (IgG1) CH3 domain,
  wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain,
  wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation,
  wherein the first polypeptide comprises at least one functional binding site or at least a part of a binding site,
  wherein the second polypeptide comprises in the CH3 domain at least one perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
  wherein the first polypeptide and the second polypeptide associate non-covalently with each other/form a non-covalent dimer, (whereby the perturbing mutation in the second polypeptide results in a destabilizing interaction when the second polypeptide and the first polypeptide form a heterodimer),
  the variable domain of the first polypeptide and the variable domain of the second polypeptide form a functional or non-functional (not antigen binding competent) pair of variable domains.

In one embodiment the first polypeptide is a polypeptide selected from the group of polypeptides comprising in N- to C-terminal direction
  i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain,
  ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain,
  iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain,
  iv) a scFv, optionally a peptidic linker, a hinge region of SEQ ID NO: 66, a heavy or light chain variable domain, and a CH3 domain derived from a human IgG1 CH3 domain,
  v) a scFab, optionally a peptidic linker, a hinge region of SEQ ID NO: 66, a heavy or light chain variable domain, and a CH3 domain derived from a human IgG1 CH3 domain,
  vi) a hinge region of SEQ ID NO: 66, a heavy or light chain variable domain, a CH3 domain derived from a human IgG1 CH3 domain, optionally a peptidic linker, and a scFv,
  vii) a hinge region of SEQ ID NO: 66, a heavy or light chain variable domain, a CH3 domain derived from a human IgG1 CH3 domain, optionally a peptidic linker, and a scFab,
  viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1
  ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain,
  x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv,
  xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab,
  xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain,
  xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, (and comprises the knob-mutation or the hole-mutations,) and the second polypeptide is a polypeptide selected from the group of polypeptides comprising in N- to C-terminal direction a hinge region of SEQ ID NO: 66, a first heavy or light chain variable domain, a CH3 domain derived from a human IgG1 CH3 domain comprising the knob-mutation or the hole-mutations, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation.

In one embodiment the multimeric polypeptide further comprises a third polypeptide comprising a (further) light chain variable domain and a light chain constant domain, wherein the third polypeptide is covalently bound to (the CH1 domain of) the first polypeptide by a disulfide bond.

One aspect as reported herein is a composition comprising a first heterotrimeric polypeptide comprising as first polypeptide a polypeptide selected from the group of polypeptides comprising in N- to C-terminal direction i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, (comprising the knob-mutation or the hole-mutations,)

and
as second polypeptide a polypeptide selected from the group of polypeptides comprising in N- to C-terminal direction
a hinge region of SEQ ID NO: 66, a heavy or light chain variable domain, a CH3 domain derived from a human IgG1 CH3 domain,
wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain,
wherein the CH3 domain comprises the knob-mutation if the first polypeptide comprises the hole-mutations, or the hole-mutations if the first polypeptide comprises the knob-mutation, comprising a perturbing mutation selected from the group of mutations
consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
and
as third polypeptide a polypeptide comprising a further light chain variable domain and a light chain constant domain, wherein the third polypeptide is covalently bound to the first polypeptide by a disulfide bond,
and
a second heterotrimeric polypeptide comprising
as first (fourth) polypeptide a polypeptide selected from the group of polypeptide comprising in N- to C-terminal direction
a hinge region of SEQ ID NO: 66, a first heavy or light chain variable domain, and a CH3 domain derived from a human IgG1 CH3 domain,
wherein the CH3 domain comprises the knob-mutation if the second polypeptide of the first heterotrimer comprises the hole-mutations, or the hole-mutations if the second polypeptide of the first heterotrimer comprises the knob-mutation,
comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the second (fifth) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the first (fourth) polypeptide is at a different position as the perturbing mutation in the second polypeptide of the first heterotrimer,
and
as second (fifth) polypeptide a polypeptide selected from the group of polypeptides comprising in N- to C-terminal direction
i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain,
ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain,
iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain,
iv) a scFv, optionally a peptidic linker, a hinge region of SEQ ID NO: 66, a heavy or light chain variable domain, and a CH3 domain derived from a human IgG1 CH3 domain,
v) a scFab, optionally a peptidic linker, a hinge region of SEQ ID NO: 66, a heavy or light chain variable domain, and a CH3 domain derived from a human IgG1 CH3 domain,
vi) a hinge region of SEQ ID NO: 66, a heavy or light chain variable domain, a CH3 domain derived from a human IgG1 CH3 domain, optionally a peptidic linker, and a scFv,
vii) a hinge region of SEQ ID NO: 66, a heavy or light chain variable domain, a CH3 domain derived from a human IgG1 CH3 domain, optionally a peptidic linker, and a scFab,
viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, comprising the knob-mutation if the first (fourth) polypeptide comprises the hole-mutations, or the hole-mutations if the first (fourth) polypeptide comprises the knob-mutation, wherein i) the variable domain of the fifth polypeptide is a heavy chain variable domain if the variable domain of the second polypeptide is a light chain variable domain, or ii) the variable domain of the fifth polypeptide is a light chain variable domain if the variable domain of the second polypeptide is a heavy chain variable domain, and as third (sixth) polypeptide a polypeptide comprising a light chain variable domain and a light chain constant domain, wherein the sixth polypeptide is covalently bound to the first (fourth) polypeptide by a disulfide bond, wherein i) the CH3 domain of the first polypeptide of the first heterotrimer comprises the knob-mutation and the CH3 domain of the second polypeptide of the first heterotrimer comprises the hole-mutations, or ii) the CH3 domain of the first polypeptide of the first heterotrimer comprises the hole-mutations and the CH3 domain of the second polypeptide of the first heterotrimer comprises the knob-mutation, whereby i) in case the first polypeptide of the first heterotrimer comprises the hole-mutations the second polypeptide of the second heterotrimer (fifth) polypeptide comprises the knob-mutation, or ii) in case the first polypeptide of the first heterotrimer comprises the knob-mutation the second polypeptide of the second heterotrimer (fifth) polypeptide comprises the hole-mutations, wherein the second polypeptide of the first heterotrimer and the first polypeptide of the second heterotrimer (fourth) polypeptide do not comprise the perturbing mutations at the same position/comprise perturbing mutations at different positions, wherein the variable domain of the first polypeptide and the variable domain of the fifth polypeptide form a functional (antigen binding competent) binding site (pair of antibody variable domains (VH/VL pair)), and the variable domain of the second polypeptide and the variable domain of the fourth polypeptide form a non-functional (not antigen binding competent) pair of variable domains.

One aspect as reported herein is a multimeric polypeptide comprising a first polypeptide and a second polypeptide wherein both polypeptides comprise a human immunoglobulin (IgG1) CH3 domain, wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation, wherein the first polypeptide comprises at least one functional binding site or at least a part of a binding site, wherein the second polypeptide comprises in the CH3 domain at least one perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T), whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, wherein the first polypeptide and the second polypeptide associate non-covalently or covalently with each other/form a non-covalent or covalent dimer, (whereby the perturbing mutation in the second polypeptide results in a destabilizing interaction when the second polypeptide and the first polypeptide form a heterodimer).

In one embodiment the first polypeptide is a polypeptide selected from the group of polypeptides comprising in N- to C-terminal direction i) a heavy chain variable domain, a (CH1 domain derived from a) human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a (CH1 domain derived from a) human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a (CH1 domain derived from a) human IgG1 CH1 domain, and a heavy chain variable domain, iv) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second (CH1 domain derived from) a human IgG1 CH1 domain, v) a first heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a second heavy chain variable domain, vi) a heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 domain, x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, and comprises the knob-mutation or the hole-mutations, and the second polypeptide is a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain comprising the mutations knob or the hole-mutations, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation.

In one embodiment the multimeric polypeptide further comprises a third polypeptide comprising a light chain variable domain and a light chain constant domain covalently bound to the first polypeptide by a disulfide bond.

One aspect as reported herein is a composition comprising a first heterotrimeric polypeptide comprising as first polypeptide a polypeptide selected from the group of polypeptides comprising in N- to C-terminal direction i) a heavy chain variable domain, (a CH1 domain derived from) a human IgG1 CH1 domain, a hinge region of SEQ ID NO: 65 or 66, a CH2 domain derived from a human IgG1 CH2 domain, and a CH3 domain derived from a human IgG1 CH3 domain,
ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and (a CH1 domain derived from) a human IgG1 CH1 domain,
iii) a hinge region of SEQ ID NO: 65 or 66, a CH2 domain derived from a human IgG1 CH2 domain, a CH3 domain derived from a human IgG1 CH3 domain, optionally a peptidic linker, (a CH1 domain derived from) a human IgG1 CH1 domain, and a heavy chain variable domain,
iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain,
v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain, and a second heavy chain variable domain,
vi) a heavy chain variable domain, (a CH1 domain derived from) a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv,
vii) a heavy chain variable domain, (a CH1 domain derived from) a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab,
viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain,
ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1
x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain,
xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and
xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa,
comprising the knob-mutation or the hole-mutations, and
as second polypeptide a polypeptide selected from the group of polypeptides comprising in N- to C-terminal direction
a hinge region of SEQ ID NO: 65 or 66, a CH2 domain derived from a human IgG1 CH2 domain, a CH3 domain derived from a human IgG1 CH3 domain, comprising the knob-mutation if the first polypeptide comprises the hole-mutations, or the hole-mutations if the first polypeptide comprises the knob-mutation,
comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
and
as third polypeptide a polypeptide comprising a light chain variable domain and a light chain constant domain covalently bound to the first polypeptide by a disulfide bond,
and
a second heterotrimeric polypeptide comprising
as first (fourth) polypeptide a polypeptide selected from the group of polypeptide comprising in N- to C-terminal direction a hinge region of SEQ ID NO: 65 or 66, a CH2 domain derived from a human IgG1 CH2 domain, and a CH3 domain derived from a human IgG1 CH3 domain, comprising the knob-mutation if the second polypeptide of the first heterotrimer comprises the hole-mutations, or the hole-mutations if the second polypeptide of the first heterotrimer comprises the knob-mutation, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the second (fifth) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the first (fourth) polypeptide is at a different position as the perturbing mutation in the second polypeptide of the first heterotrimer, and as second (fifth) polypeptide a polypeptide selected from the group of polypeptides comprising in N- to C-terminal direction i) a heavy chain variable domain, (a CH1 domain derived from) a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and (a CH1 domain derived from) a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, (a CH1 domain derived from) a human IgG1 CH1 domain, and a heavy chain variable domain, iv) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second CH1 domain derived from a human IgG1 CH1 domain, v) a first heavy chain variable domain, a first CH1 domain derived from a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second CH1 domain derived from a human IgG1 CH1 domain, and a second heavy chain variable domain, vi) a heavy chain variable domain, (a CH1 domain derived from) a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, (a CH1 domain derived from) a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second (CH1 domain derived from a) human IgG1 CH1 domain, and a light chain variable domain, ix) a heavy chain variable domain, a first (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second (CH1 domain derived from a) human IgG1 CH1 x) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a (light chain constant domain derived from a) human IgG1 kappa or lambda light chain constant domain, xi) a first heavy chain variable domain, a (CH1 domain derived from a) human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a (light chain constant domain derived from a) human IgG1 kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain (of the same polypeptide associate and) form a functional binding site that specifically binds to a target; in one embodiment the first part of the binding domain is an antibody heavy chain Fab fragment (VH-CH1 or CH1-VH) and the second part of the binding domain is a light chain Fab fragment (VL-CL or CL-VL) or vice versa, comprising the knob-mutation if the first (fourth) polypeptide comprises the hole-mutations, or the hole-mutations if the first (fourth) polypeptide comprises the knob-mutation, and as third (sixth) polypeptide a polypeptide comprising a light chain variable domain and a light chain constant domain covalently bound to the first (fourth) polypeptide by a disulfide bond, wherein i) the CH3 domain of the first polypeptide of the first heterotrimer comprises the knob-mutation and the CH3 domain of the second polypeptide of the first heterotrimer comprises the hole-mutations, or ii) the CH3 domain of the first polypeptide of the first heterotrimer comprises the hole-mutations and the CH3 domain of the second polypeptide of the first heterotrimer comprises the knob-mutation, whereby i) in case the first polypeptide of the first heterotrimer comprises the hole-mutations the second polypeptide of the second heterotrimer (fifth) polypeptide comprises the knob-mutation, or ii) in case the first polypeptide of the first heterotrimer comprises the knob-mutation the second polypeptide of the second heterotrimer (fifth) polypeptide comprises the hole-mutations, wherein the second polypeptide of the first heterotrimer and the first polypeptide of the second heterotrimer (fourth) polypeptide do not comprise the perturbing mutations at the same position/ comprise perturbing mutations at different positions.

One aspect as reported herein is a pharmaceutical formulations comprising a 2/3-IgG without inter-heavy chain-heavy chain disulfide bonds or comprising a 2/3-BiFab without inter-heavy chain-heavy chain disulfide bonds or comprising a composition comprising two different 2/3-IgG without inter-heavy chain-heavy chain disulfide bonds or two different 2/3-BiFab without inter-heavy chain-heavy chain disulfide bonds as described herein are prepared by mixing such 2/3-IgG(s) or 2/3-BiFab(s)

One aspect as reported herein is a 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds for use as a medicament.

One aspect as reported herein is the use of a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds in the manufacture or preparation of a medicament.

One aspect as reported herein is a method for treating a disease comprising administering to an individual having a disease an effective amount of a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds.

In one embodiment the composition comprises a first heterotrimeric polypeptide, which comprises a first, a second, and a third monomeric polypeptide, and a second heterotrimeric polypeptide, which comprises a fourth, a fifth, and a sixth monomeric polypeptide (i.e. each heterotrimeric polypeptide is comprising three (non-identical) monomeric polypeptides (comprising together a total of six (non-identical) monomeric polypeptides (i.e. a first, a second, a third, a fourth, a fifth and a sixth non-identical, monomeric polypeptide))), wherein first, second, fourth and fifth (monomeric) polypeptide each comprises (in N- to C-terminal direction) (i) the amino acid sequence DKTHTSPPS (SEQ ID NO: 66), (ii) a first antibody variable domain, and (iii) a human immunoglobulin (IgG1) CH3 domain, wherein (i), (ii) and (iii) are independently of each other either directly or via a peptidic linker conjugated each other, wherein the first antibody variable domain of i) the first and the second (monomeric) polypeptide, and ii) the first and the fifth (monomeric) polypeptide, iii) the second and the fourth (monomeric) polypeptide, and iv) the fifth and the fourth (monomeric) polypeptide are a VH/VL pair (i.e. the first variable domain of the first (monomeric) polypeptide is either a heavy chain variable domain or a light chain variable domain, whereby in case it is a heavy chain variable domain the first variable domain of the second and the fifth (monomeric) polypeptide is a light chain variable domain or in case it is a light chain variable domain the first variable domain of the second and the fifth (monomeric) polypeptide is a heavy chain variable domain, and the first variable domain of the fourth (monomeric) polypeptide is a light chain variable domain in case the first variable domain of the fifth (monomeric) polypeptide is a heavy chain variable domain or it is a heavy chain variable domain in case the first variable domain of the fifth (monomeric polypeptide) is a light chain variable domain), wherein the CH3 domain of i) the first and the fifth (monomeric) polypeptide, and ii) the first and the second (monomeric) polypeptide, iii) the second and the fourth (monomeric) polypeptide, and iv) the fifth and the fourth (monomeric) polypeptide are a knob-into-hole pair (i.e. the CH3 domain of the first (monomeric) polypeptide comprises either the knob-mutation or the hole-mutations, whereby in case it comprises the knob-mutation the CH3 domain of the second and the fifth (monomeric) polypeptide comprises the hole-mutations or in case it comprises the hole-mutations the CH3 domain of the second and the fifth (monomeric) polypeptide comprise the hole mutation, and the CH3 domain of the fourth (monomeric) polypeptide comprises the knob-mutation in case the CH3 domain of the fifth (monomeric) polypeptide comprises the hole-mutations or it comprises the hole-mutations in case the CH3 domain of the fifth (monomeric polypeptide) comprises the knob-mutation), wherein the first (monomeric) polypeptide and the fifth (monomeric) polypeptide each comprise independently of each other at one or both of the N- and C-terminus independently of each other a scFv, or a scFab, or a Fab, wherein the second and the fourth (monomeric) polypeptide comprises in the CH3 domain at least one perturbing mutation (selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T), whereby the first (monomeric) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation of the second (monomeric) polypeptide, whereby the fifth (monomeric) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation of the fourth (monomeric) polypeptide, whereby the perturbing mutation in the second (monomeric) polypeptide is not at the same position in the amino acid sequence as the perturbing mutation in the fourth (monomeric) polypeptide, whereby the perturbing mutation in the second (monomeric) polypeptide and the perturbing mutation in the fourth (monomeric) polypeptide result in an attractive (charge) interaction when the second polypeptide and the fourth polypeptide form a heterodimer, whereby the perturbing mutations in the second and the fourth (monomeric) polypeptide result in repulsive (charge) interactions when the second (monomeric) polypeptide forms a heterodimer with the first (monomeric) polypeptide and the fourth (monomeric) polypeptide forms a heterodimer with the fifth (monomeric) polypeptide, respectively, wherein the first and the second (monomeric) polypeptide form a non-covalent dimer, the fourth and the fifth (monomeric) polypeptide form a non-covalent dimer, the third and the first (monomeric) polypeptide form a disulfide-linked dimer, and the sixth and the fifth (monomeric) polypeptide form a disulfide-linked dimer, wherein the third and the sixth (monomeric) polypeptide are antibody light chains.

In one embodiment the first (monomeric) polypeptide is selected from the group of polypeptides comprising in N- to C-terminal direction i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain.

In one embodiment the second (monomeric) polypeptide is selected from the group of polypeptides comprising in N- to C-terminal direction a hinge region of SEQ ID NO: 66, a heavy or light chain variable domain, a CH3 domain derived from a human IgG1 CH3 domain, wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain, wherein the CH3 domain comprises the knob-mutation if the first polypeptide comprises the hole-mutations, or the hole-mutations if the first polypeptide comprises the knob-mutation, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, and as third polypeptide a polypeptide comprising a further light chain variable domain and a light chain constant domain, wherein the third polypeptide is covalently bound to the first polypeptide by a disulfide bond.

In one embodiment the fourth (monomeric) polypeptide is selected from the group of polypeptide comprising in N- to C-terminal direction a hinge region of SEQ ID NO: 66, a first heavy or light chain variable domain, and a CH3 domain derived from a human IgG1 CH3 domain, wherein the CH3 domain comprises the knob-mutation if the second polypeptide of the first heterotrimer comprises the hole-mutations, or the hole-mutations if the second polypeptide of the first heterotrimer comprises the knob-mutation, comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the second (fifth) polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, whereby the perturbing mutation in the first (fourth) polypeptide is at a different position as the perturbing mutation in the second polypeptide of the first heterotrimer.

In one embodiment the fifth (monomeric) polypeptide is selected from the group of polypeptides comprising in N- to C-terminal direction i) a second heavy chain variable domain, (a CH1 domain derived from) a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and (a CH1 domain derived from) a human IgG1 CH1 domain, iii) a hinge region of SEQ ID NO: 66, a first heavy or light chain variable domain, a CH3 domain derived from a human IgG1 CH3 domain, optionally a peptidic linker, (a CH1 domain derived from) a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second (CH1 domain derived from a) human IgG1 CH1 domain, ix) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a third heavy chain variable domain, x) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, and a scFv, human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second (CH1 domain derived from a) human IgG1 CH1 domain, and a second light chain variable domain, xiii) a second heavy chain variable domain, a first (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second (CH1 domain derived from a) human IgG1 CH1 domain, xiv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a (light chain constant domain derived from a) human IgG1 kappa or lambda light chain constant domain, and xv) a second heavy chain variable domain, a (CH1 domain derived from a) human IgG1 CH1 domain, a hinge region of SEQ ID NO: 66, a first heavy or light chain variable domain, a CH3 domain derived from a human IgG1 CH3 domain, optionally a peptidic linker, a (light chain constant domain derived from a) human IgG1 kappa or lambda light chain constant domain, and a third heavy chain variable domain, comprising the knob-mutation if the first (fourth) polypeptide comprises the hole-mutations, or the hole-mutations if the first (fourth) polypeptide comprises the knob-mutation, wherein i) the variable domain of the fifth polypeptide is a heavy chain variable domain if the variable domain of the second polypeptide is a light chain variable domain, or ii) the variable domain of the fifth polypeptide is a light chain variable domain if the variable domain of the second polypeptide is a heavy chain variable domain.

In one embodiment the variable domain of the first polypeptide and the variable domain of the fifth polypeptide form a functional (antigen binding competent) binding site (pair of antibody variable domains (VH/VL pair)), and the variable domain of the second polypeptide and the variable domain of the fourth polypeptide form a functional or non-functional (not antigen binding competent) pair of variable domains.

One aspect of the invention is a (isolated) non-covalent complex/multimeric polypeptide comprising a first polypeptide comprising
  i) in N- to C-terminal direction a) a first antibody variable domain selected from a pair of an antibody light chain variable domain and an antibody heavy chain variable domain specifically binding to a first target, and b) a first human immunoglobulin G CH3 domain, and
  ii) a pair of an antibody light chain variable domain and an antibody heavy chain variable domain specifically binding to a second target located either N-terminal to the first antibody variable domain or C-terminal to the first CH3 domain, a second polypeptide comprising
  i) in N- to C-terminal direction a) a second antibody variable domain selected from a pair of an antibody light chain variable domain and an antibody heavy chain variable domain specifically binding to a third target, and b) a second human immunoglobulin G CH3 domain,
    wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
    and
    wherein the second CH3 domain comprises a perturbing mutation selected from the group of mutations consisting of D356K, E357K, K370E and K439E, whereby the first CH3 domain comprises
      a) the amino acid residue K at position 439 if the perturbing mutations is D356K, or
      b) the amino acid residue K at position 370 if the perturbing mutations is E357K, or
      c) the amino acid residue E at position 357 if the perturbing mutations is K370E, or
      d) the amino acid residue D at position 356 if the perturbing mutations is K439E,
    and
  ii) optionally a pair of an antibody light chain variable domain and an antibody heavy chain variable domain specifically binding to the second target or to a fourth target located either N-terminal to the second antibody variable domain or C-terminal to the second CH3 domain, the location being independent of the location of said pair of variable domains of the first polypeptide, whereby all numbering is according to Kabat EU index.

In one embodiment of all aspects the first CH3 domain and the second CH3 domain comprise amino acid mutations as disclosed herein to promote heterodimer formation, i.e. as outlined in section D) Heterodimerization herein below.

In one embodiment of all aspects the first CH3 domain and the second CH3 domain comprise further mutations to foster heterodimer formation between said first CH3 domain and said second CH3 domain and that are different from the perturbing mutation.

In one embodiment of all aspects
the first CH3 domain comprises
  a) the mutation T366W, or
  b) the mutations T366S/L368A/Y407V,
and
the second CH3 domain comprises
  a) the mutations T366S/L368A/Y407V if the first CH3 domain comprises the mutation T366W, or
  b) the mutation T366W if the first CH3 domain comprises the mutations T366S/L368A/Y407V.

One aspect of the invention is a (isolated) non-covalent complex/multimeric polypeptide comprising a first polypeptide comprising
  i) in N- to C-terminal direction a) a first antibody variable domain selected from a pair of an antibody light chain variable domain and an antibody heavy chain variable domain specifically binding to a first target, and b) a first human immunoglobulin G CH3 domain,
    wherein the first CH3 domain comprises
      a) the mutation T366W, or the mutations T366S/L368A/Y407V,
      and
      b) optionally the mutation Y349C or S354C,
    and
  ii) a pair of an antibody light chain variable domain and an antibody heavy chain variable domain specifically binding to a second target located either N-terminal to the first antibody variable domain or C-terminal to the first CH3 domain, a second polypeptide comprising
  i) in N- to C-terminal direction a) a second antibody variable domain selected from a pair of an antibody light chain variable domain and an antibody heavy chain variable domain specifically binding to a third target, and b) a second human immunoglobulin G CH3 domain, wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain, and wherein the second CH3 domain comprises
a) the mutations T366S/L368A/Y407V if the first CH3 domain comprises the mutation T366W, or
b) the mutation T366W if the first CH3 domain comprises the mutations T366S/L368A/Y407V, and wherein the second CH3 domain comprises a perturbing mutation selected from the group of mutations consisting of D356K, E357K, K370E and K439E, whereby the first CH3 domain comprises
a) the amino acid residue K at position 439 if the perturbing mutations is D356K, or
b) the amino acid residue K at position 370 if the perturbing mutations is E357K, or
c) the amino acid residue E at position 357 if the perturbing mutations is K370E, or
d) the amino acid residue D at position 356 if the perturbing mutations is K439E, and ii) optionally a pair of an antibody light chain variable domain and an antibody heavy chain variable domain specifically binding to the second target or to a fourth target located either N-terminal to the second antibody variable domain or C-terminal to the second CH3 domain, the location being independent of the location of said pair of variable domains of the first polypeptide, whereby all numbering is according to Kabat EU index.

One aspect of the invention is a (isolated) non-covalent complex/multimeric polypeptide comprising a first polypeptide comprising
i) in N- to C-terminal direction a) a first human immunoglobulin G CH3 domain, and b) a first antibody variable domain selected from a pair of an antibody light chain variable domain and an antibody heavy chain variable domain specifically binding to a first target,
and
ii) a pair of an antibody light chain variable domain and an antibody heavy chain variable domain specifically binding to a second target located either N-terminal to the first antibody CH3 domain or C-terminal to the first antibody variable, a second polypeptide comprising
i) in N- to C-terminal direction a) a second human immunoglobulin G CH3 domain and b) a second antibody variable domain selected from a pair of an antibody light chain variable domain and an antibody heavy chain variable domain specifically binding to a third target, wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain, and wherein the second CH3 domain comprises a perturbing mutation selected from the group of mutations consisting of D356K, E357K, K370E and K439E, whereby the first CH3 domain comprises
a) the amino acid residue K at position 439 if the perturbing mutations is D356K, or
b) the amino acid residue K at position 370 if the perturbing mutations is E357K, or
c) the amino acid residue E at position 357 if the perturbing mutations is K370E, or
d) the amino acid residue D at position 356 if the perturbing mutations is K439E, and ii) optionally a pair of an antibody light chain variable domain and an antibody heavy chain variable domain specifically binding to the second target or to a fourth target either N-terminal to the second CH3 domain or C-terminal to the second variable domain, the location being independent of the location of said pair of variable domains of the first polypeptide, whereby all numbering is according to Kabat EU index.

In one embodiment of all aspects the first CH3 domain and the second CH3 domain comprise amino acid mutations as disclosed herein to promote heterodimer formation, i.e. as outlined in section D) Heterodimerization herein below.

In one embodiment of all aspects the first CH3 domain and the second CH3 domain comprise further mutations to foster heterodimer formation between said first CH3 domain and said second CH3 domain and that are different from the perturbing mutation.

In one embodiment of all aspects
the first CH3 domain comprises
a) the mutation T366W, or
b) the mutations T366S/L368A/Y407V,
and
the second CH3 domain comprises
a) the mutations T366S/L368A/Y407V if the first CH3 domain comprises the mutation T366W, or
b) the mutation T366W if the first CH3 domain comprises the mutations T366S/L368A/Y407V.

One aspect of the invention is a (isolated) non-covalent complex/multimeric polypeptide comprising a first polypeptide comprising
i) in N- to C-terminal direction a) a first human immunoglobulin G CH3 domain, and b) a first antibody variable domain selected from a pair of an antibody light chain variable domain and an antibody heavy chain variable domain specifically binding to a first target,
wherein the first CH3 domain comprises
a) the mutation T366W, or the mutations T366S/L368A/Y407V,
and
b) optionally the mutation Y349C or S354C,
and
ii) a pair of an antibody light chain variable domain and an antibody heavy chain variable domain specifically binding to a second target located either N-terminal to the first antibody CH3 domain or C-terminal to the first antibody variable, a second polypeptide comprising
i) in N- to C-terminal direction a) a second human immunoglobulin G CH3 domain and b) a second antibody variable domain selected from a pair of an antibody light chain variable domain and an antibody heavy chain variable domain specifically binding to a third target,
wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
and
wherein the second CH3 domain comprises
a) the mutations T366S/L368A/Y407V if the first CH3 domain comprises the mutation T366W, or
b) the mutation T366W if the first CH3 domain comprises the mutations T366S/L368A/Y407V,
and
wherein the second CH3 domain comprises a perturbing mutation selected from the group of mutations consisting of D356K, E357K, K370E and K439E, whereby the first CH3 domain comprises
a) the amino acid residue K at position 439 if the perturbing mutations is D356K, or
b) the amino acid residue K at position 370 if the perturbing mutations is E357K, or
c) the amino acid residue E at position 357 if the perturbing mutations is K370E, or
d) the amino acid residue D at position 356 if the perturbing mutations is K439E,
ii) optionally a pair of an antibody light chain variable domain and an antibody heavy chain variable domain specifically binding to the second target or to a fourth target either N-terminal to the second CH3 domain or C-terminal to the second variable domain, the location being independent of the location of said pair of variable domains of the first polypeptide,
whereby all numbering is according to Kabat EU index.

In one embodiment of all aspects according to the invention the first polypeptide and the second polypeptide are a non-covalent dimer.

In one embodiment of all aspects according to the invention the first variable domain and the second variable domain associate/are associated and form a non-functional binding site.

In one embodiment of all aspects according to the invention the first and the second polypeptide each comprise the amino acid sequence DKTHTSPPS (SEQ ID NO: 66) or DKTHT (SEQ ID NO: 94) or GGGS (SEQ ID NO: 69) or DKTHGGGGS (SEQ ID NO: 97) N-terminal to each of the first and second variable domains in case the first CH3 domain is located C-terminal to the first variable domain, or N-terminal to each of the first and second CH3 domains in case the first variable domain is located C-terminal to the first and second CH3 domain.

In one embodiment of all aspects according to the invention the human immunoglobulin G is human IgG1 or human IgG2 or human IgG3 or human IgG4. In one embodiment of all aspects according to the invention the human immunoglobulin G is human IgG1.

In one embodiment of all aspects according to the invention the human immunoglobulin G CH3 domain is a human IgG1 CH3 domain or a human IgG2 CH3 domain or a human IgG3 CH3 domain or a human IgG4 CH3 domain.

In one embodiment of all aspects according to the invention
i) the first CH3 domain comprises the mutation T366W and the amino acid residue K at position 439,
and
the second CH3 domain comprises the perturbing mutation D356K and the mutations T366S/L368A/Y407V, or
ii) the first CH3 domain comprises the mutation T366W and the amino acid residue K at position 370,
and
the second CH3 domain comprises the perturbing mutation E357K and the mutations T366S/L368A/Y407V, or
iii) the first CH3 domain comprises the mutations T366S/L368A/Y407V and the amino acid residue E at position 357,
and
the second CH3 domain comprises the perturbing mutation K370E and the mutation T366W, or
iv) the first CH3 domain comprises the mutations T366S/L368A/Y407V and the amino acid residue D at position 356,
and
the second CH3 domain comprises the perturbing mutation K439E and the mutation T366W.

In one embodiment of all aspects according to the invention the first, second and third target are different.

In one embodiment of all aspects according to the invention the first target or the third target is human CD3.

In one embodiment of all aspects according to the invention the pair of an antibody light chain variable domain and an antibody heavy chain variable domain specifically binding to the second target is selected from the group consisting of Fv, scFc, Fab, scFab, dsscFab, CrossFab, bispecific Fab, sdAb, and VHH.

In one embodiment of all aspects according to the invention the pair of an antibody light chain variable domain and an antibody heavy chain variable domain specifically binding to the fourth target is selected independently of the pair of an antibody light variable domain and an antibody heavy chain variable domain specifically binding to the second target from the group consisting of Fv, scFc, Fab, scFab, dsscFab, CrossFab, bispecific Fab, sdAb, and VHH.

In one embodiment of all aspects of the invention the first polypeptide comprises in N- to C-terminal direction
an antibody heavy chain variable domain or an antibody light chain variable domain,
a human immunoglobulin G CH1 domain or a human antibody light chain constant domain,
optionally a further antibody heavy chain variable domain or an antibody light chain variable domain, and a further human immunoglobulin G CH1 domain or a human antibody light chain constant domain,
the amino acid sequence of SEQ ID NO: 66 or SEQ ID NO: 94 or SEQ ID NO: 69 or SEQ ID NO: 77 or SEQ ID NO: 75 or SEQ ID NO: 76 or SEQ ID NO: 79 or SEQ ID NO: 97,
the first antibody variable domain,
optionally a human immunoglobulin G CH2 domain,
the first human immunoglobulin G CH3 domain,
optionally the amino acid sequence SEQ ID NO: 69 or SEQ ID NO: 77 or SEQ ID NO: 75 or SEQ ID NO: 76 or SEQ ID NO: 79,
optionally a Fab or a domain exchanged Fab or a scFv or a scFab.

In one embodiment of all aspects of the invention the first polypeptide comprises in N- to C-terminal direction
- an antibody heavy chain variable domain or an antibody light chain variable
- a human immunoglobulin G CH1 domain or a human antibody light chain constant domain,
- optionally a further antibody heavy chain variable domain or an antibody light chain variable domain, and a further human immunoglobulin G CH1 domain or a human antibody light chain constant domain,
- the amino acid sequence of SEQ ID NO: 66 or SEQ ID NO: 94 or SEQ ID NO: 69 or SEQ ID NO: 77 or SEQ ID NO: 75 or SEQ ID NO: 76 or SEQ ID NO: 79 or SEQ ID NO: 97,
- optionally a human immunoglobulin G CH2 domain,
- the first human immunoglobulin G CH3 domain,
- the first antibody variable domain,
- optionally the amino acid sequence SEQ ID NO: 69 or SEQ ID NO: 77 or SEQ ID NO: 75 or SEQ ID NO: 76 or SEQ ID NO: 79,
- optionally a Fab or a domain exchanged Fab or a scFv or a scFab.

One aspect of the invention is a composition comprising a first multimeric polypeptide according to the invention and a second multimeric polypeptide according to the invention, wherein
the second CH3 domain of the first multimeric polypeptide comprises the mutation D356K and the second CH3 domain of the second multimeric polypeptide comprises the mutation K439E,
or
the second CH3 domain of the first multimeric polypeptide comprises the mutation E357K and the second CH3 domain of the second multimeric polypeptide comprises the mutation K370E,
and
the first antibody variable domain of the first multimeric polypeptide and the first variable domain of the second multimeric polypeptide are a pair of an antibody light chain variable domain and an antibody heavy chain variable domain that specifically bind to the first target,
and
the second antibody variable domain of the first multimeric polypeptide and the second variable domain of the second multimeric polypeptide are a pair of an antibody light chain variable domain and an antibody heavy chain variable domain that specifically bind to the third target,
and
the second and fourth target are independently of each other a cell surface antigen.

In one embodiment of all composition aspects the first CH3 domain of the first multimeric polypeptide and the second CH3 domain of the second multimeric polypeptide comprise the same mutations to foster heterodimer formation and the second CH3 domain of the first multimeric polypeptide and the first CH3 domain of the second multimeric polypeptide comprise the same mutations to foster heterodimer formation.

In one embodiment of all composition aspects the first CH3 domain of the first polypeptide comprises
a) the mutation T366W, or
b) the mutations T366S/L368A/Y407V,
and
the second CH3 domain of the first polypeptide comprises
a) the mutations T366S/L368A/Y407V if the first CH3 domain comprises the mutation T366W, or
b) the mutation T366W if the first CH3 domain comprises the mutations T366S/L368A/Y407V.

One aspect according to the current invention is a (pharmaceutical) composition comprising a first multimeric polypeptide according to the invention and a second multimeric polypeptide according to the invention,
wherein
the first CH3 domain of the first multimeric polypeptide and the second CH3 domain of the second multimeric polypeptide both comprise the mutation T366W or the mutations T366S/L368A/Y407V,
and
wherein
the second CH3 domain of the first multimeric polypeptide comprises the mutation D356K and the second CH3 domain of the second multimeric polypeptide comprises the mutation K439E, or vice versa,
or
the second CH3 domain of the first multimeric polypeptide comprises the mutation E357K and the second CH3 domain of the second multimeric polypeptide comprises the mutation K370E, or vice versa,
and
optionally wherein
the first antibody variable domain of the second multimeric polypeptide is an antibody light chain variable domain if the first antibody variable domain of the first multimeric polypeptide is an antibody heavy chain variable domain, or
the first antibody variable domain of the second multimeric polypeptide is an antibody heavy chain variable domain if the first antibody variable domain of the first multimeric polypeptide is an antibody light chain variable domain,
and
wherein
the first antibody variable domain of the first multimeric polypeptide and the first antibody variable domain of the second multimeric polypeptide are a pair of an antibody light chain variable domain and an antibody heavy chain variable domain that specifically bind to the first target,
and
the second antibody variable domain of the first multimeric polypeptide and the second antibody variable domain of the second multimeric polypeptide are a pair of an antibody light chain variable domain and an antibody heavy chain variable domain that specifically bind to the third target,
and
wherein
the second and fourth target are independently of each other a cell surface antigen.

In one embodiment of all aspects according to the invention the first target or the third target is human CD3.

One aspect of the invention is the multimeric polypeptide or the (pharmaceutical) composition according to the invention for use as a medicament.

One aspect as reported herein is a method of treatment comprising the administration of a multimeric polypeptide or a (pharmaceutical) composition according to the invention to a patient in need of such treatment.

DETAILED DESCRIPTION OF THE INVENTION

The invention is based, at least in part, on the finding that multispecific antibodies can be obtained by a half-antibody exchange reaction using as starting material non-complete antibodies, such as 2/3-IgGs or 2/3-BiFabs comprising an antibody light chain, an antibody heavy chain and an antibody heavy chain fragment, wherein the heavy chain-heavy chain interaction is destabilized by an asymmetric perturbing mutation, preferably in the heavy chain fragment, wherein the perturbing mutation fosters on the one hand the dissociation of the starting non-complete antibodies and promotes on the other hand the generation of correctly assembled full length bi-/multispecific antibodies. It has further been found that by using such starting compounds if the inter-heavy chain-heavy chain disulfide bonds are removed from the starting non-complete antibodies the method of the invention can even be performed in the absence of reducing agents (the generation of the starting material as well as the exchange reaction and the production of multispecific antibodies still work efficiently).

In more detail, the invention is based, at least in part, on the finding that multispecific antibodies in combination with on-cell activation of binding sites can be obtained by a half-antibody exchange reaction using as starting material non-complete, i.e. not bispecifically binding, antibodies. The starting molecules each comprise a pair of antibody CH3 domains associated with each other and forming a dimer/multimer, a pair of an antibody heavy chain variable domain and an antibody light chain variable domain that do not form a functional binding, site as well as at least one functional binding site for in vivo cell surface targeting. Thus, said pair of CH3 domains can be part of larger molecules, such as a pair of antibody heavy chains, a pair of fusion polypeptides, etc. The pair of CH3 domains with the modifications as outlined herein define the minimal structural elements required for the exchange reaction according to the current invention. In the non-complete starting antibodies the CH3 domains still associate with each other (resulting in the formation of a dimer or multimer), but the attraction between said pair of CH3 domains is reduced, i.e. destabilized, by an asymmetric perturbing (charge) mutation present only in one of the CH3 domains. The respective other CH3 domain still has the wild-type residues at the positions interaction with the mutated position as in an associated wild-type CH3 domain pair. Said perturbing mutation fosters the dissociation of the starting non-complete antibodies and promotes the generation of correctly assembled complete bispecific antibodies only in case a second/further, better matching complementary non-complete antibody is present. It has been found that the destabilized starting materials can be isolated from cell culture supernatants despite i) the presence of the destabilizing mutation between the CH3 domains; and ii) the absence of disulfide bonds between the two CH3 domain comprising polypeptides of the starting non-complete bispecific antibodies.

The invention is based, at least in part, on the further finding that by using starting compounds as outlined above the exchange reaction and formation of complete and functional bispecific antibodies is taking place in the absence of reducing agents, i.e. can be performed in vivo. That is, disulfide bonds between the CH3 domain containing polypeptides of the starting molecules are not required. Thus, hinge region disulfide bonds as well as other heavy chain-heavy chain disulfide bonds can be removed from the starting non-complete antibodies.

I. DEFINITIONS

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, hinge, CH2 and CH3, which is herein further clarified by referring to "numbering according to Kabat EU index" in this case).

The CH3 domains in the heavy chains of an antibody can be altered by the "knob-into-holes" technology, which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of these two CH3 domains and thereby of the polypeptide comprising them. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield. But this is absent in the molecules of the current invention.

The mutation T366W in the CH3 domain (of an antibody heavy chain) is denoted as "knob-mutation" or "mutation knob" and the mutations T366S, L368A, Y407V in the CH3 domain (of an antibody heavy chain) are denoted as "hole-mutations" or "mutations hole" (numbering according to Kabat EU index). An additional inter-chain disulfide bridge between the CH3 domains can also be used (Merchant, A. M., et al., Nature Biotech. 16 (1998) 677-681) e.g. by introducing a S354C mutation into the CH3 domain of the heavy chain with the "knob-mutation" (denotes as "knob-cys-mutations" or "mutations knob-cys") and by introducing a Y349C mutation into the CH3 domain of the heavy chain with the "hole-mutations" (denotes as "hole-cys-mutations" or "mutations hole-cys") (numbering according to Kabat EU index). But this is absent in the molecules of the current invention.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a". "an", and "the" include plural reference unless the context clearly dictates otherwise. Thus, for example, reference to "a cell" includes a plurality of such cells and equivalents thereof known to those skilled in the art, and so forth. As well, the terms "a" (or "an"). "one or more" and "at least one" can be used interchangeably herein. It is also to be noted that the terms "comprising", "including", and "having" can be used interchangeably.

The term "MHCFcRP" denotes a mutated heavy chain Fc-region polypeptide comprising at least an immunoglobulin constant domain 3 (CH3) comprising either the knob-mutation or the hole-mutations and at least one perturbing (i.e. destabilizing) mutation, which is introducing one (i.e. a single and/or additional) repulsive charge with respect to the wild-type sequence. That is, when the MHCFcRP is paired with a second CH3-domain containing polypeptide the second CH3-domain comprises the human immunoglobulin wild-type amino acid residue(s) in its amino acid sequence at the amino acid position(s) interacting (in a wild-type immunoglobulin) with the amino acid residue at the perturbing mutation. In one embodiment the perturbing mutation is selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T (numbering according to Kabat EU index). In one preferred embodiment the perturbing mutations is selected from the group of mutations consisting of D356K, E357K, K370E, and K439E.

The term "BiFab" denotes a molecule comprising two pairs of $V_1$-$C_1$/$V_2$-$C_2$ wherein V denotes an antibody variable domain and C denotes an antibody constant domain, which are associated with each other. For example, the pairs can be $VH_1$-CH1/$VL_1$-CL and $VH_2$-$CH3_1$/$VL_2$-$CH3_2$. Likewise, the term "TriFab" denotes a molecule comprising three pairs of $V_1$-$C_1$/$V_2$-$C_2$ wherein V denotes an antibody variable domain and C denotes an antibody constant domain, which are associated with each other. For example, the pairs can be $VH_1$-CH1/$VL_1$-CL, $VH_2$-CH1/$VL_2$-CL, and $VH_3$-$CH3_1$/$VL_3$-$CH3_2$.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "amino acid substitution" or "amino acid mutation" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "antibody-dependent cellular cytotoxicity (ADCC)" is a function mediated by Fc receptor binding and refers to lysis of target cells mediated by an antibody Fc-region in the presence of effector cells. ADCC is measured in one embodiment by the treatment of a preparation of target expressing erythroid cells (e.g. K562 cells expressing recombinant target) with an Fc-region comprising polypeptide as reported herein in the presence of effector cells such as freshly isolated PBMC (peripheral blood mononuclear cells) or purified effector cells from buffy coats, like monocytes or NK (natural killer) cells. Target cells are labeled with Cr-51 and subsequently incubated with the polypeptide as reported herein. The labeled cells are incubated with effector cells and the supernatant is analyzed for released Cr-51. Controls include the incubation of the target endothelial cells with effector cells but without the polypeptide as reported herein. The capacity of the polypeptide to induce the initial steps mediating ADCC is investigated by measuring the binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

The term "CH1 domain" denotes the part of an antibody heavy chain polypeptide that extends approximately from EU position 118 to EU position 215 (EU numbering system). In one embodiment a CH1 domain comprises the amino acid sequence of (SEQ ID NO: 27)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSC.

The term "CH2 domain" denotes the part of an antibody heavy chain polypeptide that extends approximately from EU position 231 to EU position 340 (EU numbering system according to Kabat). In one embodiment a CH2 domain comprises the amino acid sequence of APELLGGPSV FLFPPKPKDT LMISRTPEVT CVWDVSHEDP EVKFNWYVDG VEVHNAKTKP REEQESTYRW SVLTVLHQDW LNGKEYKCKV SNKALPAPIE KTISKAK (SEQ ID NO: 28). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain comprises the amino acid sequence of GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPG (SEQ ID NO: 29).

The term "comprising" also includes the term "consisting of".

The term "complement-dependent cytotoxicity (CDC)" refers to lysis of cells induced by the Fc-region of an antibody as reported herein in the presence of complement. CDC is measured in one embodiment by the treatment of target expressing human endothelial cells with a polypeptide as reported herein in the presence of complement. The cells are in one embodiment labeled with calcein. CDC is found if the polypeptide induces lysis of 20% or more of the target cells at a concentration of 30 µg/ml. Binding to the complement factor C1q can be measured in an ELISA. In such an assay in principle an ELISA plate is coated with concentration ranges of the polypeptide, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate]).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies as reported herein are used to delay development of a disease or to slow the progression of a disease.

"Effector functions" refer to those biological activities attributable to the Fc-region of an antibody, which vary with the antibody class from which it is derived. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) presenting the Fc-region, via antibody-dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG type Fc-regions are referred to as FcγR. Fc receptor binding is described e.g. in Ravetch, J. V. and Kinet. J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; Gessner, J. E., et al., Ann. Hematol. 76 (1998) 231-248.

Cross-linking of receptors for the Fc-region of IgG type antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

- FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by 103-fold and eliminated the human monocyte response to antibody-sensitized red blood cells (Armour, K. L., et al., Eur. J. Immunol. 29 (1999) 2613-2624).
- FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).
- FcγRIII (CD16) binds IgG with medium to low affinity and exists as two types. FcγRIIIA is found on NK cells, macrophages, eosinophils and some monocytes and T-cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "hinge region" denotes the part of an antibody heavy chain polypeptide that joins in a wild-type antibody heavy chain the CH1 domain and the CH2 domain, e. g. from about position 221 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. The hinge region normally has the amino acid sequence DKTHTCPXCP (SEQ ID NO: 30), wherein X is either S or P. or HTCPXCP (SEQ ID NO: 31), wherein X is either S or P, or CPXCP (SEQ ID NO: 32), wherein X is either S or P.

In one embodiment the hinge region has no internal disulfide bonds. This is achieved by substituting the cysteine residues in the sequence of SEQ ID NO: 32 (and likewise in SEQ ID NO: 30 and 31) by serine residues or by deleting the CPXC stretch (SEQ ID NO: 95) from the hinge region of SEQ ID NO: 30, 31 or 32.

The term "peptidic linker" denotes a linker of natural and/or synthetic origin. A peptidic linker consists of a linear chain of amino acids wherein the 20 naturally occurring amino acids are the monomeric building blocks which are connected by peptide bonds. The chain has a length of from 1 to 50 amino acid residues, preferred between 1 and 28 amino acid residues, especially preferred between 3 and 25 amino acid residues. The peptidic linker may contain repetitive amino acid sequences or sequences of naturally occurring polypeptides. The peptidic linker has the function to ensure that the domains of a fusion polypeptide can perform their biological activity by allowing the domains to fold correctly and to be presented properly. Preferably the peptidic linker is a "synthetic peptidic linker" that is designated to be rich in glycine, glutamine, and/or serine residues. These residues are arranged e.g. in small repetitive units of up to five amino acids, such as GGGS (SEQ ID NO: 69), GGGGS (SEQ ID NO: 70), QQQG (SEQ ID NO: 71), QQQQG (SEQ ID NO: 72), SSSG (SEQ ID NO: 73) or SSSSG (SEQ ID NO: 74). This small repetitive unit may be repeated for two to five times to form a multimeric unit, such as e.g. (GGGS)2 (SEQ ID NO: 75), (GGGS)3 (SEQ ID NO: 76), (GGGS)4 (SEQ ID NO: 77), (GGGS)5 (SEQ ID NO: 78), (GGGGS)2 (SEQ ID NO: 79), (GGGGS)3 (SEQ ID NO: 80), or (GGGGS)4 (SEQ ID NO: 81). In one embodiment the peptidic linker is selected from the group of linkers of SEQ ID NO: 69 to 82. In one embodiment each of the peptidic linkers is selected independently of each other from the group of linkers consisting of SEQ ID NO: 69 to 82. In one preferred embodiment the peptidic linker/each peptidic linker is selected (independently of each other) from the group of linkers consisting of SEQ ID NO: 75 to 81. At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 82). All peptidic linkers can be encoded by a nucleic acid molecule and therefore can be recombinantly expressed. As the linkers are themselves peptides, the antifusogenic peptide is connected to the linker via a peptide bond that is formed between two amino acids.

An "antibody fragment" refers to a molecule other than an intact antibody that comprises a portion of an intact antibody that binds the antigen to which the intact antibody binds. Examples of antibody fragments include but are not limited to Fv, scFv, Fab, scFab, Fab', Fab'-SH, F(ab')2; diabodies; linear antibodies; single-chain antibody molecules (e.g. scFv); and multispecific antibodies formed from antibody fragments. For a review of certain antibody fragments, see Hudson, P. J. et al., Nat. Med. 9 (2003) 129-134. For a review of scFv fragments, sec. e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571, 894 and 5,587,458.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g. *E. coli* or phage).

The term "antibody fragment" also includes a "Dual Acting Fab" or "DAF" comprising an antigen binding site that binds to two different antigens (see, US 2008/0069820, for example).

A "monospecific antibody" denotes an antibody that has a single binding specificity for one antigen. Monospecific antibodies can be prepared as full-length antibodies or antibody fragments (e.g. F(ab')2) or combinations thereof (e.g. full length antibody plus additional scFv or Fab fragments).

A "multispecific antibody" denotes an antibody that has binding specificities for at least two different epitopes on the same antigen or two different antigens. Multispecific antibodies can be prepared as full-length antibodies or antibody fragments (e.g. F(ab')2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1). One multispecific antibody is a bispecific antibody. Multi-specific antibodies may also be made by engineering electrostatic steering effects for making antibody Fc-heterodimeric molecules (WO 2009/089004).

The term "binding to" denotes the binding of a binding site to its target, such as e.g. of an antibody binding site comprising an antibody heavy chain variable domain and an antibody light chain variable domain to the respective antigen. This binding can be determined using, for example, a BIAcore® assay (GE Healthcare, Uppsala, Sweden). That is the term "binding (to an antigen)" denotes the binding of an antibody in an in vitro assay. In one embodiment binding is determined in a binding assay in which the antibody is bound to a surface and binding of the antigen to the antibody is measured by Surface Plasmon Resonance (SPR). Binding means e.g. a binding affinity ($K_D$) of $10^{-8}$ M or less, in some embodiments of $10^{-13}$ to $10^{-8}$ M, in some embodiments of $10^{-13}$ to $10^{-9}$ M. The term "binding" also includes the term "specifically binding".

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

For example, in one possible embodiment of the BIAcore® assay the antigen is bound to a surface and binding of the antibody binding site is measured by surface plasmon resonance (SPR). The affinity of the binding is defined by the terms ka (association constant: rate constant for the association to form a complex), kd (dissociation constant; rate constant for the dissociation of the complex), and KD (kd/ka). Alternatively, the binding signal of a SPR sensorgram can be compared directly to the response signal of a reference, with respect to the resonance signal height and the dissociation behaviors.

The term "binding site" denotes any proteinaceous entity that shows binding specificity to a target. This can be, e.g., a receptor, a receptor ligand, an anticalin, an affibody, an antibody, etc. Thus, the term "binding site" as used herein denotes a polypeptide that can specifically bind to or can be specifically bound by a second polypeptide. In one embodiment the binding site is selected from the group of polypeptides consisting of an antibody heavy chain variable domain, an antibody light chain variable domain, a pair of an antibody heavy chain and an antibody light chain variable domains, a receptor or functional fragment thereof, a receptor ligand or a functional fragment thereof, an enzyme or its substrate.

In case of an antibody the binding site comprises at least three HVRs (e.g. in case of a VHH) or six HVRs (e.g. in case of a naturally occurring, i.e. native, antibody). Generally, the amino acid residues of an antibody that are responsible for antigen binding are forming the binding site. These residues are normally contained in a pair of an antibody heavy chain variable domain and a cognate antibody light chain variable domain. The antigen-binding site of an antibody comprises amino acid residues from the "hypervariable regions" or "HVRs". "Framework" or "FR" regions are those variable domain regions other than the hypervariable region residues as herein defined. Therefore, the light and heavy chain variable domains of an antibody comprise from N- to C-terminus the regions FR1, HVR1/CDR1, FR2, HVR2/CDR2, FR3, HVR3/CDR3, and FR4 (immunoglobulin framework). Especially, the HVR3/CDR3 region of the heavy chain variable domain is the region, which contributes most to antigen binding and defines the binding specificity of an antibody. A "functional binding site" is capable of specifically binding to its target. The term "specifically binding to" denotes the binding of a binding site to its target in an in vitro assay, in one embodiment in a binding assay. Such binding assay can be any assay as long the binding event can be detected. For example, an assay in which the antibody is bound to a surface and binding of the antigen(s) to the antibody is measured by Surface Plasmon Resonance (SPR). Alternatively, a bridging ELISA can be used. Binding means a binding affinity from antibody (binder) to its target ($K_D$) of $10^{-8}$ M or less, in some embodiments of $10^{-13}$ to $10^{-8}$ M, in some embodiments of $10^{-13}$ to $10^{-9}$ M.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "Fc-region" denotes the C-terminal region of an immunoglobulin heavy chain that contains at least a part of the hinge region, the CH2 domain and the CH3 domain. In one embodiment, a human IgG heavy chain Fc-region extends from Asp221, or from Cys226, or from Pro230, to the carboxyl-terminus of the heavy chain. However, the C-terminal lysine (Lys447) of the Fc-region may or may not be present. The Fc-region is composed of two heavy chain Fc-region polypeptides, which can be covalently linked to each other via the hinge region cysteine residues forming inter-chain disulfide bonds.

The multimeric polypeptides/binders as reported herein may comprise a complete Fc-region, in one embodiment an Fc-region derived from human origin but without the hinge region cysteine residues. In one embodiment the Fc-region comprises all parts of the human constant region but without the hinge region cysteine residues. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogic, E. E., et al., J. Immunol. 164 (2000) 4178-4184; Hezarch, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A and optionally P329G (numbering according to EU index of Kabat).

The term "full length antibody" denotes an antibody having a structure substantially similar to a native antibody structure. A full length antibody comprises two full length antibody light chains each comprising a light chain variable domain and a light chain constant domain, and two full length antibody heavy chains each comprising a heavy chain variable domain, a first constant domain, a hinge region, a second constant domain and a third constant domain. A full length antibody may comprise further domains, such as e.g. additional scFv or a scFab conjugated to one or more of the chains of the full length antibody. These conjugates are also encompassed by the term full length antibody.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "derived from" denotes that a variant amino acid sequence is obtained from a parent amino acid sequence by introducing alterations/mutations at at least one position. Thus a derived amino acid sequence differs from the corresponding parent amino acid sequence at at least one corresponding position. In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise, a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

In one embodiment one or both heavy chain Fc-region polypeptide(s) are derived from an Fc-region polypeptide of SEQ ID NO: 01 and have at least one amino acid mutation or deletion compared to the Fc-region polypeptide of SEQ ID NO: 01. In one embodiment the Fc-region polypeptide comprises/has from about one to about ten amino acid mutations or deletions, and in one embodiment from about one to about five amino acid mutations or deletions. In one embodiment the Fc-region polypeptide has at least about 80% homology with a human Fc-region polypeptide of SEQ ID NO: 01. In one embodiment the Fc-region polypeptide has least about 90% homology with a human Fc-region polypeptide of SEQ ID NO: 01. In one embodiment the Fc-region polypeptide has at least about 95% homology with a human Fc-region polypeptide of SEQ ID NO: 01.

The Fc-region polypeptide derived from a human Fc-region polypeptide of SEQ ID NO: 01, or 02 or 03, or 04 is further defined by the amino acid alterations that are contained. Thus, for example, the term P329G denotes an Fc-region polypeptide derived human Fc-region polypeptide with the mutation of proline to glycine at amino acid position 329 relative to the human Fc-region polypeptide of SEQ ID NO: 01, or 02, or 03, or 04.

A human IgG1 Fc-region polypeptide comprises the following amino acid sequence:

(SEQ ID NO: 01)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFS

CSVMHEALHNHYTQKSLSLSP.

The following Fc-regions are variants derived from the wild-type human IgG1 Fc-region.

A human IgG1 Fc-region derived Fc-region polypeptide with the mutations L234A, L235A comprises the following amino acid sequence:

(SEQ ID NO: 05)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with Y349C, T366S, L368A and Y407V mutations comprises the following amino acid sequence:

(SEQ ID NO: 06)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVCTLPPSRDELTKNQVSLSCAVKGFY

PSDIAVEWESNGQPENNYKTTPPVLDSDGSFFLVSKLTVDKSRWQQGNVFS

CSVMHEALHNHYTQKSLSLSP.

A human IgG1 Fc-region derived Fc-region polypeptide with S354C, T366W mutations comprises the following amino acid sequence:

(SEQ ID NO: 07)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPCRDELTKNQVSLWCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with L234A, L235A mutations and Y349C, T366S, L368A, Y407V mutations comprises the following amino acid sequence:

(SEQ ID NO: 08)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVCTLPPSRDELTKNQVSLSCAVKGFY

PSDIAVEWESNGQPENNYKTTPPVLDSDGSFFLVSKLTVDKSRWQQGNVFS

CSVMHEALHNHYTQKSLSLSP.

A human IgG1 Fc-region derived Fc-region polypeptide with a L234A, L235A and S354C, T366W mutations comprises the following amino acid sequence:

(SEQ ID NO: 09)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPCRDELTKNQVSLWCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with a P329G mutation comprises the following amino acid sequence:

(SEQ ID NO: 10)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with L234A, L235A mutations and P329G mutation comprises the following amino acid sequence:

(SEQ ID NO: 11)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with a P329G mutation and Y349C, T366S, L368A, Y407V mutations comprises the following amino acid sequence:

(SEQ ID NO: 12)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVCTLPPSRDELTKNQVSLSCAVKGFY

PSDIAVEWESNGQPENNYKTTPPVLDSDGSFFLVSKLTVDKSRWQQGNVFS

CSVMHEALHNHYTQKSLSLSP.

A human IgG1 Fc-region derived Fc-region polypeptide with a P329G mutation and S354C, T366W mutation comprises the following amino acid sequence:

(SEQ ID NO: 13)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVYTLPPCRDELTKNQVSLWCLVKGFY

PSDIAVEWESNGQPENNYKTTPPVLDSDGSFFLYSKLTVDKSRWQQGNVFS

CSVMHEALHNHYTQKSLSLSP.

A human IgG1 Fc-region derived Fc-region polypeptide with L234A, L235A, P329G and Y349C, T366S, L368A, Y407V mutations comprises the following amino acid sequence:

(SEQ ID NO: 14)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVCTLPPSRDELTKNQVSLSCAVKGFY

PSDIAVEWESNGQPENNYKTTPPVLDSDGSFFLVSKLTVDKSRWQQGNVFS

CSVMHEALHNHYTQKSLSLSP.

A human IgG1 Fc-region derived Fc-region polypeptide with L234A, L235A, P329G mutations and S354C, T366W mutations comprises the following amino acid sequence:

(SEQ ID NO: 15)
DKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALGAPIEKTISKAKGQPREPQVYTLPPCRDELTKNQVSLWCLVKGFY

PSDIAVEWESNGQPENNYKTTPPVLDSDGSFFLYSKLTVDKSRWQQGNVFS

CSVMHEALHNHYTQKSLSLSP.

A human IgG4 Fc-region polypeptide comprises the following amino acid sequence:

(SEQ ID NO: 04)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNV

FSCSVMHEALHNHYTQKSLSLSL.

The following Fc-regions are variants derived from the wild-type human IgG4 Fc-region.

A human IgG4 Fc-region derived Fc-region polypeptide with S228P and L235E mutations comprises the following amino acid sequence:

(SEQ ID NO: 16)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with S228P, L235E mutations and P329G mutation comprises the following amino acid sequence:

(SEQ ID NO: 17)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVYTLPPSQEEMTKNQVSLTCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with S354C, T366W mutations comprises the following amino acid sequence:

(SEQ ID NO: 18)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVYTLPPCQEEMTKNQVSLWCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with Y349C, T366S, L368A, Y407V mutations comprises the following amino acid sequence:

(SEQ ID NO: 19)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVCTLPPSQEEMTKNQVSLSCAVKG

FYPSDIAVEWESNGQPENNYKTTPPVLDSDGSFFLVSRLTVDKSRWQEGNV

FSCSVMHEALHNHYTQKSLSLSL.

A human IgG4 Fc-region derived Fc-region polypeptide with a S228P, L235E and S354C, T366W mutations comprises the following amino acid sequence:

(SEQ ID NO: 20)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVYTLPPCQEEMTKNQVSLWCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with a S228P, L235E and Y349C, T366S, L368A, Y407V mutations comprises the following amino acid sequence:

(SEQ ID NO: 21)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLPSSIEKTISKAKGQPREPQVCTLPPSQEEMTKNQVSLSCAVKG

FYPSDIAVEWESNGQPENNYKTTPPVLDSDGSFFLVSRLTVDKSRWQEGNV

FSCSVMHEALHNHYTQKSLSLSL.

A human IgG4 Fc-region derived Fc-region polypeptide with a P329G mutation comprises the following amino acid sequence:

(SEQ ID NO: 22)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVYTLPPSQEEMTKNQVSLTCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with a P329G and Y349C, T366S, L368A, Y407V mutations comprises the following amino acid sequence:

(SEQ ID NO: 23)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVCTLPPSQEEMTKNQVSLSCAVKG

FYPSDIAVEWESNGQPENNYKTTPPVLDSDGSFFLVSRLTVDKSRWQEGNV

FSCSVMHEALHNHYTQKSLSLSL.

A human IgG4 Fc-region derived Fc-region polypeptide with a P329G and S354C, T366W mutations comprises the following amino acid sequence:

(SEQ ID NO: 24)
ESKYGPPCPSCPAPEFLGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVYTLPPCQEEMTKNQVSLWCLVKG

FYPSDIAVEWESNGQPENNYKTTPPVLDSDGSFFLYSRLTVDKSRWQEGNV

FSCSVMHEALHNHYTQKSLSLSL.

A human IgG4 Fc-region derived Fc-region polypeptide with a S228P, L235E, P329G and Y349C, T366S, L368A, Y407V mutations comprises the following amino acid sequence:

(SEQ ID NO: 25)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVCTLPPSQEEMTKNQVSLSCAVKG

FYPSDIAVEWESNGQPENNYKTTPPVLDSDGSFFLVSRLTVDKSRWQEGNV

FSCSVMHEALHNHYTQKSLSLSL.

A human IgG4 Fc-region derived Fc-region polypeptide with a S228P, L235E, P329G and S354C, T366W mutations comprises the following amino acid sequence:

(SEQ ID NO: 26)
ESKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEYK

CKVSNKGLGSSIEKTISKAKGQPREPQVYTLPPCQEEMTKNQVSLWCLVKG

FYPSDIAVEWESNGQPENNYKTTPPVLDSDGSFFLYSRLTVDKSRWQEGNV

FSCSVMHEALHNHYTQKSLSLSL.

A "humanized" antibody refers to an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the heavy chain variable domain VH (H1, H2, H3), and three in the light chain variable domain VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "light chain" denotes the shorter polypeptide chains of native IgG antibodies. The light chain of an antibody may be assigned to one of two types, called kappa (κ) and lambda (2), based on the amino acid sequence of its constant domain. See SEQ ID NO: 33 for a human kappa light chain constant domain and SEQ ID NO: 34 for a human lambda light chain constant domain.

The term "paratope" refers to that part of a given antibody molecule that is required for specific binding between a target and a binding site. A paratope may be continuous, i.e. formed by adjacent amino acid residues present in the binding site, or discontinuous, i.e. formed by amino acid residues that are at sequentially different positions in the primary sequence, such as in the amino acid sequence of the HVRs/CDRs, but in close proximity in the three-dimensional structure, which the binding site adopts.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis, CE-SDS) or chromatographic (e.g., size exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (2), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "recombinant antibody", as used herein, denotes all antibodies (chimeric, humanized and human) that are prepared, expressed, created or isolated by recombinant means. This includes antibodies isolated from a host cell such as a NS0, HEK, BHK or CHO cell or antibodies expressed using a recombinant expression plasmid transfected into a host cell.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "trivalent". The trispecific antibodies as reported herein as reported herein are in one preferred embodiment "trivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "variant" denotes molecules which have an amino acid sequence that differs from the amino acid sequence of a parent molecule. Typically, such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent domain or Fc-region. In one embodiment the variant has an amino acid sequence that has from about 75% to less than 100% amino acid sequence identity with the amino acid sequence of the parent domain or Fc-region, especially from about 80% to less than 100%, especially from about 85% to less than 100%, especially from about 90% to less than 100%, and especially from about 95% to less than 100%. In one embodiment the parent domain or Fc-region and the variant domain or Fc-region differ by one (a single), two or three amino acid residue(s).

The term "domain crossover" as used herein denotes that in a pair of an antibody heavy chain VH-CH1 fragment and its corresponding cognate antibody light chain, i.e. in an antibody binding arm (i.e. in the Fab fragment), the domain sequence deviates from the natural sequence in that at least one heavy chain domain is substituted by its corresponding light chain domain and vice versa. There are three general types of domain crossovers, (i) the crossover of the CH1 and the CL domains, which leads to domain crossover light chain with a VL-CH1 domain sequence and a domain crossover heavy chain fragment with a VH-CL domain sequence (or a full length antibody heavy chain with a VH-CL-hinge-CH2-CH3 domain sequence), (ii) the domain crossover of the VH and the VL domains, which leads to domain crossover light chain with a VH-CL domain sequence and a domain crossover heavy chain fragment with a VL-CH1 domain sequence, and (iii) the domain crossover of the complete light chain (VL-CL) and the complete VH-CH1 heavy chain fragment ("Fab crossover"), which leads to a domain crossover light chain with a VH-CH1 domain sequence and a domain crossover heavy chain fragment with a VL-CL domain sequence (all aforementioned domain sequences are indicated in N-terminal to C-terminal direction).

As used herein the term "replaced by each other" with respect to corresponding heavy and light chain domains refers to the aforementioned domain crossovers. As such, when CH1 and CL domains are "replaced by each other" it is referred to the domain crossover mentioned under item (i) and the resulting heavy and light chain domain sequence. Accordingly, when VH and VL are "replaced by each other" it is referred to the domain crossover mentioned under item (ii); and when the CH1 and CL domains are "replaced by each other" and the VH1 and VL domains are "replaced by each other" it is referred to the domain crossover mentioned under item (iii). Bispecific antibodies including domain crossovers are reported, e.g. in WO 2009/080251. WO 2009/080252, WO 2009/080253, WO 2009/080254 and Schaefer. W. et al, Proc. Natl. Acad. Sci USA 108 (2011) 11187-11192.

Multispecific antibody produced with a method as reported herein can also comprises Fab fragments including a domain crossover of the CH1 and the CL domains as mentioned under item (i) above, or a domain crossover of the VH and the VL domains as mentioned under item (ii) above. The Fab fragments specifically binding to the same antigen(s) are constructed to be of the same domain sequence. Hence, in case more than one Fab fragment with a domain crossover is contained in the multispecific antibody, said Fab fragment(s) specifically bind to the same antigen.

II. GENERATION OF BI-/MULTISPECIFIC ANTIBODIES BY EXCHANGE REACTION ACCORDING TO THE INVENTION

A) Method to Convert Monospecific Monovalent IgG Derivatives to Bispecific Bivalent IgG's The exchange method as outlined in the following can achieve the conversion of monospecific (monovalent) antibodies or antibody fragments to bivalent bispecific antibodies (bsAbs) or of already multispecific antibodies to higher order multispecific antibodies, such as e.g. bispecific antibodies in tri- or tetraspecific antibodies.

Two non-functional half antibodies (i.e. only monospecific for the cell target) are used as starting material. Exemplarily, 2/3-IgGs can be used. 2/3-IgGs are composed of a heavy chain with the first set of knob-into-hole (KiH) mutations, a light chain complementary thereto, as well as an Fc-region, which is made complementary to the Fc-region of the heavy chain by the respective complementary second set of knob-into-hole-mutations. The complementary Fc-region can be, e.g., an Fc-region heavy chain fragment or a second heavy chain (optionally with no binding specificity). To further foster correct assembly of the desired bi-(multi-)specific antibody the complementary Fc-region comprises besides the second complementary set of KiH mutations an additional perturbing (destabilizing) repulsive charge mutation. Additionally, the complementary Fc-region may comprise an affinity tag (e.g. a His6 (SEQ ID NO: 67) or C-tag) for efficient removal of non-desired educts and side-products after its production. The second non-functional monospecific antibody comprises a complementary perturbing mutation. These two perturbing mutations turn into attractive mutations once the antibody-halves exchange with each other, e.g. upon interaction while being bound on the cell surface.

The on-cell exchange reaction/method that can be performed with the multimeric molecules according to the current invention comprises the following step
bringing a first (starting) multimeric polypeptide, which comprises a first polypeptide and a second polypeptide, and a second (starting) multimeric polypeptide, which comprises a third polypeptide and a fourth polypeptide, in proximity on the surface of a cell to crosswise exchange the second and the third polypeptide to form a third multimeric polypeptide (comprising the first and the fourth polypeptide) and a fourth multimeric polypeptide (comprising the second and the third polypeptide), wherein i) the second polypeptide comprises a (first perturbing) mutation resulting in a destabilization of the first multimeric polypeptide compared to a (multimeric) polypeptide identical to said first multimeric polypeptide except for said mutation in the second polypeptide, ii) the third polypeptide comprises a (second perturbing) mutation resulting in a destabilization of the second multimeric polypeptide compared to a multimeric polypeptide identical to said second (multimeric) polypeptide except for said mutation in the third polypeptide, iii) the (first perturbing) mutation in the second polypeptide and the (second perturbing) mutation in the third polypeptide result in a stabilization of the third (exchanged) multimeric polypeptide comprising said second polypeptide and said third polypeptide compared to the first (starting) multimeric polypeptide and/or to the second (starting) multimeric polypeptide, iv) the fourth (exchanged) multimeric polypeptide is more stable compared to the first (starting) multimeric polypeptide and/or the second (starting) multimeric polypeptide, v) the first multimeric polypeptide and the second multimeric polypeptide each comprise only a part of one or two new binding sites that are not functional, i.e. that cannot bind to its target, and vi) the third and/or the fourth multimeric polypeptide comprise the one or two new binding sites in functional form, i.e. in a form that allows specific binding to its respective target, whereby the one or two new functional binding sites have been generated/activated by the exchange of the second and third polypeptide between the first multimeric polypeptide and the second multimeric polypeptide, i.e. by bringing the non-functional parts of said one or two new binding sites together to form one or two new functional binding sites.

Thus, the current invention is based, at least in part, on the finding that adding a single (one-sided, not paired) destabilizing (perturbing) mutation in a (hetero-)multimeric polypeptide is sufficient to foster polypeptide chain exchange with a second (hetero-)multimeric polypeptide comprising also one single (one-sided, not paired) destabilizing (perturbing) mutation as both resulting newly formed exchanged (hetero-)multimeric polypeptides have improved stability compared to the starting (hetero-)multimeric polypeptides (i.e. lower CH3-CH3 binding free energy) as the destabilizing mutations turn into attractive mutations upon exchange and recombination. The only proviso that has to be followed is that the destabilizing (perturbing) mutations are introduced at positions that interact with each other once the respective polypeptides associate with each other.

This methodology can be applied to any (hetero-)multimeric polypeptide fulfilling the criteria as outlined above.

Nevertheless, the method according to the current invention is especially useful in the pharmaceutical area.

From the art different methods for the generation of (hetero-)multimeric polypeptides are known. Any of these methods can be used as long as the mutations required for the formation of the starting (hetero-)multimeric polypeptides do not interfere or overlap with the (perturbing) destabilizing mutations needed for the exchange reaction according to the current invention.

Turning back to the pharmaceutical area antibodies are the most widely used class of binders. Antibodies dimerize via interactions in their constant region, especially between the CH3 domains of the heavy chains.

Thus, the current invention is based, at least in part, on the finding that for performing the method according to the current invention the introduction of a single destabilizing mutations in one CH3 domain of a pair of CH3 domains is sufficient. In more detail, it has been found that the introduction of a first destabilizing mutation at position 357 in only one CH3 domain of the first starting (hetero-)multimeric polypeptide and a second destabilizing mutation at position 370 in only one CH3 domain of the second starting polypeptide fosters upon spatial approach between the two starting (hetero-)multimeric polypeptides the spontaneous exchange of polypeptide chains between these starting polypeptides. One of the resulting exchanged polypeptides comprises the CH3 domain pair with the mutations at positions 357 and 370, respectively, which result in a stabilization of the exchanged (hetero-)multimer. The like can be achieved with the mutations at positions 356 and 439. The numbering of all positions is according to the EU index of Kabat. One preferred pair of mutations is E357K and K370E. Another preferred pair of mutations is D356K and K439E. The method according to the current invention can be applied to any IgG subclass, i.e. IgG1, IgG2, IgG3 and IgG4, as the residues in question are highly conserved. In one preferred embodiment the CH3 domain is of the IgG1 subclass.

The invention is based, at least in part, on the finding that the polypeptide chains of the starting (hetero-)multimeric polypeptides do not need to be covalently linked to each other, e.g. via disulfide bonds, to allow the formation and isolation of the starting (hetero-)multimeric polypeptides. In more detail, as the starting polypeptides are already heterodimers these will comprise further mutations for heterodimerization. It has been found that these mutations are sufficient to stabilize the starting heterodimers even in the presence of specific destabilizing (perturbing) single one-sided mutation. Thereby the need for a covalent linkage of the chains in the starting (hetero-)multimeric polypeptides is no longer given. Thus, in one embodiment, in case of hinge region containing starting (hetero-)multimeric polypeptides these hinge regions either comprises the mutations C226S and C229S or a deletion of the entire CPXC (SEQ ID NO: 95) sequence (numbering according to Kabat EU index).

By the omission of disulfide bonds between the Fc-region comprising chains of the (hetero-)multimeric starting polypeptides no reducing agent is required to initiate the exchange reaction. This allows the exchange reaction to take place under mild in vivo conditions. Additionally, other disulfide bonds may be present in the starting (hetero-)multimeric polypeptides, such as e.g. in a Fab fragment, as long as these do not interfere with the exchange reaction (covalently bind the CH3 domain comprising polypeptides together).

The invention is based, at least in part, on the finding that exchanged (hetero-)multimeric polypeptides, e.g. those comprising only functional and the targeting binding sites, can further be stabilized by the formation of disulfide bonds only after the exchange reaction. For example, mutations well established for the formation of (hetero-)multimeric antibodies are the knobs-into-holes mutations. These exist in two variants: without and with additional disulfide bond. Thus, one alternative starting (hetero-)multimeric polypeptide comprises the knobs-into-holes mutations for the formation of the starting (hetero-)multimeric polypeptides, and provides the knobs-into-holes cysteine residue only in the polypeptide chain that harbors the targeting binding site(s). Thereby only in the exchanged (hetero-)multimeric polypeptide, which comprises both targeting binding sites, both cysteine residues required for the formation of a disulfide bond at the corresponding matching positions are present. Thus, only in said exchanged product a disulfide bond is formed. This results in a further stabilization of the target exchanged (hetero-)multimeric polypeptide preventing dissociation and/or back-reaction.

The term "(hetero-)multimeric" as used herein denotes a polypeptide comprising at least two polypeptide chains that are not identical in amino acid sequences either in part or completely and that fulfill the requirements of the invention. The term also encompasses polypeptides comprising three or more polypeptide chains as long as at least two of them are (hetero-)multimeric according to the invention. Thus, the term "multimeric" denotes a polypeptide comprising at least three polypeptide chains whereof at least two are (hetero-) multimeric and fulfill the requirements of the invention.

The term "perturbing mutation" denotes a mutation that results in the destabilization of a (hetero)dimeric polypeptide. This destabilization is generally achieved by changing the charge of an amino acid residue, such e.g. by exchanging a positively charged amino acid residue with a negatively charged amino acid residue, or vice versa. Such an exchange results in like charges at interacting positions of the CH3-CH3 domain interface and, thus, in charge repulsion. One preferred pair of mutations is E357K and K370E. Another preferred pair of mutations is D356K and K439E. Additionally, the method according to the current invention can be applied to any IgG subclass, i.e. IgG1. IgG2, IgG3 and IgG4, as the residues in question are highly conserved. In one preferred embodiment the CH3 domain is of the IgG1 subclass.

A method to assess the effect of the CH3 domain mutation on dimer stability is disclosed in WO 2009/089004 (incorporated herein by reference). Therein it is outlined how EGAD software can be used to estimate the CH3-CH3 domain binding free energy (see also Pokala, N. and Handel, T. M., J. Mol. Biol. 347 (2005) 203-227, incorporated herein by reference in its entirety):

EGAD can be used to roughly compare the binding free energy of various mutations made at the CH3 domain interface. The binding free energy of a mutant is defined as $\Delta\Delta Gmut=\mu$ ($\Delta Gmut-\Delta Gwt$) (mut=mutant, wt=wild-type). Where, $\mu(=0.1$, in general) is the scaling factor used to normalize the predicted changes in binding affinity to have a slope of 1 when comparing with the experimental energies. The free energy of dissociation ($\Delta G$) is defined as the energy difference between the complex ($\Delta Gbound$) and free states ($\Delta Gfree$).

The invention is in the following exemplified with specific, exemplary starting materials, i.e. 2/3-IgGs. This is presented as an exemplification of the general underlying concept and shall not be construed as a limitation of the invention. The true scope of the invention is set forth in the claims.

FIG. 1 shows the design and modular composition of 2/3-IgGs used as exemplary starting compounds in the methods according to the current invention. 2/3-IgGs are composed of three individual chains: one light chain (normally a full length light chain comprising a light chain variable domain and a light chain constant domain), one heavy chain (normally a full length heavy chain comprising a heavy chain variable domain and all heavy chain constant domains including a hinge region with or without cysteine residues), and one complementary heavy chain Fc-region polypeptide (normally a heavy chain Fc-region fragment comprising at least a part of a hinge and CH2-CH3, the hinge region is without cysteine residues). The variable domains of the light chain and the heavy chain form a functional binding site, i.e. a VH/VL-pair.

The design and modular composition of 2/3-BiFabs that can also be used as exemplary starting compounds in the methods according to the current invention is alike. 2/3-BiFabs are composed of three individual chains: one light chain (normally a full length light chain comprising a light chain variable domain and a light chain constant domain), one heavy chain (normally a variant full length heavy chain comprising a first heavy chain variable domain, a CH1 domain, a second variable domain and a CH3 domain including a hinge region with our without cysteine residues), and one complementary heavy chain polypeptide (normally a heavy chain fragment comprising hinge-variable domain-CH3, the hinge region with or without cysteine residues). The variable domains of the light chain and the first variable domain of the heavy chain form a functional binding site, i.e. a VH/VL-pair, and the second variable domain of the heavy chain and the variable domain of the complementary heavy chain Fc-region polypeptide also form a VH/VL-pair, which is normally non-functional, i.e. not-binding competent.

The heavy chain (normally of the human IgG1 subclass) contains either i) the knob-mutation or the hole-mutations (the mutation T366W in the CH3 domain of an antibody heavy chain is denoted as "knob-mutation" and the mutations T366S. L368A, and Y407V in the CH3 domain of an antibody heavy chain are denoted as "hole-mutations" (numbering according to Kabat EU index)), or ii) the knob-cys-mutations or the hole-cys-mutations (the mutations T366W and S354C in the CH3 domain of an antibody heavy chain is denoted as "knob-cys-mutations" and the mutations T366S, L368A. Y407V, Y349C in the CH3 domain of an antibody heavy chain are denoted as "hole-cys-mutations"; the inverted setting is likewise possible: T366W/Y349C and T366S/L368A/Y407V/S354C (numbering according to Kabat EU index)) in the CH3 domain to enable the formation of knob-into-hole Fc-region heterodimers.

The complementary heavy chain Fc-region polypeptide or the complementary heavy chain polypeptide can also be denoted as a 'dummy-Fc' or 'dummy-HC', i.e. an IgG1 derivative that lacks VH and CH1, starts at the N-terminus with the hinge region sequence (or a fragment thereof) followed either by a CH2 domain or a variable domain followed by a CH3 domain and optionally comprises a purification tag, e.g. His6 (SEQ ID NO: 67) or His8 (SEQ ID NO: 68) or C-tag, at its C-terminus. In addition, this complementary polypeptide contains in its CH3 domain either the knob-mutation or the hole-mutations depending on the mutations in the heavy chain. In addition to the knob-mutation or the hole-mutations comprises the complementary polypeptide at least one perturbing (i.e. destabilizing) mutation introducing one (i.e. a single additional) or more repulsive charge(s) with respect to the wild-type sequence. For example, the mutation D356K or E357K, respectively, in combination with the mutation K370E or K439E, respectively (see FIG. 2). Such a mutated heavy chain Fc-region polypeptide is denoted as MHCFcRP in the following.

The heavy chain and the MHCFcRP can form two types of heterodimers depending on the distribution of the knob-into-hole-mutations therein:
  i) heavy chain-knob:: MHCFcRP-hole, and
  ii) heavy chain-hole:: MHCFcRP-knob.

Thus, the 2/3-IgGs and 2/3-BiFabs are heterodimers with associated light chain, i.e. heterotrimers. These are, however, somewhat 'flawed' as the charge mutation in the MHCFcRP is without matching counterpart in the heavy chain and, if present in the heavy chain, the MHCFcRP's charge perturbing mutation is without matching heavy chain counterpart(s).

2/3-IgGs are monovalent, non-dimerising/aggregating, one-armed antibody derivatives that can be expressed and purified to similar yields as normal IgGs (see FIG. 3). This assures monovalency of the starting material. If a bivalent 2/3-IgG would be used this could be monospecific as well as bispecific.

The polypeptides that make up those flawed 2/3-IgGs, however, are capable to rearrange to bispecific antibodies as shown in FIG. 4.

The exchange reaction between the two starting molecules is driven by better complementarity of the KiH (knobs-into-holes) heavy chains (H-chains) to each other (no charge repulsion and optionally formation of a disulfide bond if free cysteine residues are present) as well as by better complementarity of the two MHCFcRPs to each other. In the reaction the Fc-region complexes of the two starting molecules dissociate and exchange polypeptides to form two more favorable complexes. This drives the reaction as follows:

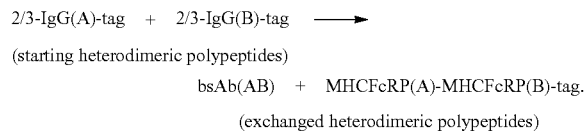

2/3-IgG(A)-tag + 2/3-IgG(B)-tag ⟶
(starting heterodimeric polypeptides)
           bsAb(AB) + MHCFcRP(A)-MHCFcRP(B)-tag.
(exchanged heterodimeric polypeptides)

In the example as depicted in FIG. 4 the heavy chain (knob-cys) of starting 2/3-IgG A and the heavy chain (hole-cys) of starting 2/3-IgG B form a matching bispecific antibody heterotetramer (2×HC+2×LC).

As hinge-region-disulfide-bond-free 2/3-IgGs are used in this on-cell/in vivo situation, no reduction step is required. The chain rearrangement occurs spontaneously.

The same applies to 2/3-BiFabs.

See examples 1 to 5.

B) Method to Convert Mono- and/or Bivalent Mono- or Bispecific IgG Derivatives to Bi-, Tri- or Tetravalent Bi-, Tri- or Tetraspecific Antibodies With the method according to the current invention it is not only possible to combine different binding specificities but also at the same time to produce these combinations within different formats and with differing valencies. This is achieved by expanding the starting materials used in the method as outlined in the previous section.

For example, starting from 2/3-IgGs as outlined in the previous section, the MHCFcRP is maintained unchanged, but the heavy chain is used in different formats. Such formats can be, e.g., chains that have either one binding site at the C-terminus or at the N-terminus or two binding sites (one at the N-terminus and one at the C-terminus) (see FIGS. 9 and 10 for examples).

In This example, different starting formats (e.g. with an N-terminal binding site, a C-terminal binding site, or N- and C-terminal binding sites) are combined with each other in the method according to the invention allowing the generation of different antibody formats that have different valencies, different geometries and different three-dimensional arrangement/positions of the individual binding sites (9 in the current example, see FIG. 11).

For generation of the multispecific antibodies the exchange driving principle (conversion of flawed input molecules to matching output-molecules) is not changed. The MHCFcRPs are also retained. Thus, only the heavy chain is changed.

For example, FIGS. 1 and 9-10 show three different starting molecules (2/3-IgG with N-terminal, C-terminal, and N- and C-terminal binding site(s)) that have been combined with each other in the exchange reaction, i.e. in the method according to the current invention, to result in nine different bispecific formats. These differ in valencies, geometries and positions of the individual binding sites.

Without being bound by this theory it is assumed that exchange reactions based on temporary separation of flawed heteromultimers of two different 2/3-IgGs or 2/3-BiFabs should result in products that contain preferentially matching Fc-region heterodimers.

The exchange therefore converts the 2/3-IgGs to four-chain IgGs (in different formats), as well as corresponding Fc-region heterodimer.

If hinge-region disulfide bonds are present in vitro, the exchange reactions are initiated by a reduction step to break the inter-chain hinge region disulfide bonds, which can be omitted in the on-cell/in vivo situation without hinge-region disulfide bonds. Chain rearrangement occurs spontaneously. See Examples 6 and 7.

C) Reaction without Fc-Fc Inter-Chain Disulfide Bonds and without Reduction Step Heavy chain inter-chain disulfide bonds stabilize antibodies and define the flexibility of the Fab arms that are connected to the hinge. Exchange approaches of hinge-region comprising starting antibodies require the reduction of these disulfides before or during the exchange reaction as well as removal of the reducing agents upon completion of the exchange reaction (see Examples 3 and 7).

Thus, herein is reported an exchange reaction of starting molecules that have a hinge region but do not have inter-chain disulfide bonds.

To exemplify this 2/3-IgGs as well as 2/3-BiFabs in which all disulfide bonds in the Fc-region have been eliminated have been produced. It has been found that such disulfide-depleted 2/3-molecules can be produced and purified in an effective manner even without these inter-chain disulfide bonds (see e.g. FIGS. 15 and 20). When using such disulfide-bond-depleted 2/3-molecules as starting molecules the method according to the current invention is possible to be exerted in vivo as the reduction step is no longer necessary making these molecules especially suitable for on cell exchange reaction and in vivo application. The multispecific antibodies produced from these disulfide-bond-depleted 2/3-IgGs and 2/3-BiFabs are functional and stable, held together by non-covalent Fc-Fc interactions without inter-chain disulfides (see FIGS. 15 and 16).

Thus, elimination of Fc-Fc inter-chain disulfides, thus, allows for corresponding Fc-region mismatch driven exchange reactions without the need for reduction and re-oxidation, i.e. under physiological conditions. This facilitates preparation and (high-throughput) screening procedures. This also enables domain-exchange reactions to occur under physiological conditions, including on the surface of living cells.

See Example 8.

In one embodiment the hinge region is disulfide-bond-free. The disulfide-bond-free hinge region comprises serine residues in place of the cysteine residues in the sequence of SEQ ID NO: 32.

Beside the removal of the disulfide bonds in addition the hinge region can be shortened. By using such modified hinge regions bispecific antibodies can be obtained that provide for different distances between the individual binding sites (see FIG. 51). Thus, in one embodiment the hinge region has the amino acid sequence of SEQ ID NO: 31 (HTCPXCP, X=S or P), or SEQ ID NO: 99 (HTSPXSP, X=S or P), or SEQ ID NO: 98 (HTPAPE; CPXC of SEQ ID NO: 31 has been deleted (SEQ ID NO: 95)) or DKTHGGGGS (SEQ ID NO: 97).

III. THE METHOD ACCORDING TO THE INVENTION

Herein is reported a method for the on-cell assembly/half-antibody exchange of two differentially targeted antibody-prodrug derivatives to generate a new functionality, preferably one that has therapeutic effect, at the site of indented action directly ion the cell's surface.

The method according to the invention is in the following exemplified with specific, exemplary starting materials, i.e. 2/3-IgGs and 2/3-BiFabs. This is presented solely as an exemplification of the general underlying concept and shall not be construed as a limitation of the invention. The true scope of the invention is set forth in the claims.

A) On-Cell Conversion of Monovalent Monospecific Antibodies to Bivalent IgGs

Monovalent antibodies can display reduced binding competence to cell surfaces compared to bivalent antibodies. Without being bound by this theory it is assumed that the reason for that is a bivalency-induced enhancement of apparent affinity to cell surfaces, i.e. an avidity effect. Avidity-enhanced binding and/or retention on cell surfaces can be achieved by binding the same antigen/epitope with two binding sites/two arms of an antibody. In this monospecific setting, bivalent binding can increase binding specificity to cells carrying large amounts of cognate antigen (increased probability that both arms bind) compared to cells with low antigen density (reduced probability that both arms bind).

Avidity-enhanced binding and/or retention on cell surfaces can also be achieved by binding two different antigens with different binding sites/different arms of a bispecific antibody. Without being bound by this theory it is assumed that in this bispecific setting, bivalent binding results in an increased binding specificity to cells that present and/or express both antigens (both binding sites/both arms bind) compared to cells that present and/or express only one of the antigens (only one binding site/one arm can bind).

State of the art technologies to address avidity-mediated improvement of binding apply preformed bsAbs that recognize two targets. To achieve specificity, it is necessary to have rather low affinity of each monovalent arm to avoid that sufficient binding strength in a monovalent manner overrides the avidity effect. If that prerequisite is fulfilled, bsAbs can bind with increased specificity to cells that present and/or express both antigens.

One drawback of currently available avidity-driven binding improvement concepts is that the density of both antigens on cell surfaces may not be an essential prerequisite for binding of preformed bsAbs per se (as long as both are present and accessible). Antigen densities may just determine the amount of bsAb that binds to cells that express antigens.

Entities with very high potency (and/or potential toxicity issues) carry therefore risks of binding to—and affecting—cells presenting/expressing high as well as low levels of both target antigens. For example, bsAbs with inherent or added cytotoxic functionalities may not only affect tumor cells that display high antigen levels, but also non-target normal cells with low antigen levels.

The method as reported herein wherein the bispecific antibody is formed by on-cell conversion of monovalent, monospecific antibodies can be applied to address the above outlined problems as the exchange reaction requires physical interaction of two monospecific exchange partners. The probability of such an interaction is concentration dependent, i.e. there is a low probability to interact and exchange at low concentrations and higher probability to interact and exchange at increased concentrations. Thus, for example, separate (consecutive) application of monospecific antibodies with different specificities leads to increased accumulation (with low affinity) of both monospecific components on cells that display larger amounts of both antigens. In consequence, such cells will not only accumulate increased concentrations of the individual antibodies, but also convert them much more effective to bsAbs. Those bsAbs in turn are retained on target cells due to avid binding by their two binding sites to cell surface antigens while non-exchanged precursors antibodies will dissociate.

B) Generation of BiFabs with Prodrug Functionality and On-Cell Conversion to Functional TriFabs The driving force of the exchange reaction reported herein is the conversion of two input molecules with "flawed" CH3-interface into two products with matching CH3-interface. The design that specifies these CH3-interfaces lies in the composition of the MHCFcRPs. The MHCFcRPs comprise a CH2 domain and a CH3 domain. All mutations that contribute to the special composition of the MHCFcRPs, however, are positioned in the CH3 domain. It is, thus, possible to replace the CH2 domains of the MHCFcRPs as well as those of the associated heavy chain with other, different domains. Those must still allow (or even support) heavy chain-MHCFcRP heterodimerization to generate "flawed" molecules.

The possibility to replace the CH2 domains of IgG like molecules with other heterodimerization-enabling domains has been shown in the TriFab format (see WO 2016/087416; FIG. 18). TriFabs display bispecific functionalities due to an exchange of the CH2 domains to a VH and a VL, respectively. The Fc-like 'stem-region' of such molecules is held together by intact KiH CH3 domains. Because KiH CH3 domains are compatible with the modified CH3 domains of MHCFcRPs, those may also enable the generation of MHCFcRP containing 2/3-BiFab analogues with exchange-enabling features.

TriFabs harbor a functional Fv instead of the CH2 domains of an Fc-region because one CH2 domain is replaced with a VH domain and the other with a complementary VL domain. 2/3-BiFab derivatives contain MHCFcRPs with irrelevant, i.e. non-cognate, VH or VL domains (at the former CH2 position), i.e. these do not bind to a target. 2/3-BiFabs retain one functional monovalent binding arm and yet contain one half of the 3rd binding site in the stem region (see FIG. 18). Exchange reaction of two complementary 2/3-BiFab molecules reconstitutes not only the TriFab format but leads also to re-constitution of the additional 3rd binding functionality at the 'stem-position'

(CH2 replacement). The exchange reaction therefore converts two 2/3-BiFab prodrugs to fully functional TriFabs.

Elimination of Fc-Fc inter-chain disulfide bonds (hinge region and CH3 domain) as described above for 2/3-IgGs enables MHCFcRP driven exchange reactions without the need for controlled reduction and re-oxidation. It is, thus, possible for the exchange reaction of such molecules to take place under physiological conditions, especially including conditions at which the individual (monospecific) entities are bound to target cell surfaces. Applying the same principle, 2/3-BiFabs accumulate on target cells upon binding of their functional Fab arms/functional binding site. If two complementary 2/3-BiFabs (both carrying binding-inactive but yet each other complementing stem-Fvs) bind to the surface of the same cell, chain exchange reactions occur directly on the surface of said cells. This exchange generates on-cell/in situ/in vivo, i.e. directly on the cell surface at the intended site of action, a fully functional TriFab with at least dual or even triple specificity directly on the cell surface, i.e. at the site of action. The 2/3-BiFab derived prodrug activation principle generates binding functionalities only on the surface of cells that express one or more target antigens in sufficient densities. This enables the generation of functionalities (incl. those of very high potency and/or potential PK or toxicity issues) only on desired cells.

With the method of the invention it is possible to use low affine monospecific binders to generate directly on the cell a high affine avidity binder and at the same time activate a therapeutic binding site.

IV. MULTISPECIFIC MOLECULES FOR USE IN THE METHOD ACCORDING TO THE INVENTION

A) Multimeric Polypeptides

Multimeric polypeptides to be used in the on-cell exchange reaction/method according to the current invention are defined by
  comprising a first polypeptide and a second polypeptide, wherein each comprises an immunoglobulin CH3 domain and a non-functional part of a binding site, whereby this non-functional part of a binding site is located either N-terminal or C-terminal to the CH3 domain in both polypeptides; and at least one of the polypeptides comprises a functional binding site specifically binding to a cell surface target, preferably to a non-internalizing cell surface target,
  comprising a (perturbing) mutation in only one of the CH3 domains resulting in the destabilization of the multimeric polypeptide compared to a (multimeric) polypeptide identical to said destabilized multimeric polypeptide except for said mutation in the second polypeptide,
  comprising mutations for the formation of a heterodimer, and
  the absence of disulfide-bonds between said first and second polypeptide.

Thus, the current invention is based, at least in part, on the finding that adding a single (one-sided, not paired) destabilizing (perturbing) mutation in a (hetero-)multimeric polypeptide is sufficient to foster polypeptide chain exchange with a second (hetero-)multimeric polypeptide comprising also one single (one-sided, not paired) destabilizing (perturbing) mutation as both resulting newly formed exchanged (hetero-)multimeric polypeptides have improved stability compared to the starting (hetero-)multimeric polypeptides (i.e. lower CH3-CH3 binding free energy) as the destabilizing mutations turn into attractive mutations upon exchange and recombination. The only proviso that has to be followed is that the destabilizing (perturbing) mutations are introduced at positions that interact with each other once the respective polypeptides associate with each other.

This methodology can be applied to any (hetero-)multimeric polypeptide fulfilling the criteria as outlined above.

Thus, the multimeric polypeptide to be used in the method according to the invention can comprise further domains or polypeptides.

The multimeric polypeptide according to the invention in one embodiment comprises in the first and the second polypeptide in addition an immunoglobulin CH2 domain either (directly) N-terminal or (directly) C-terminal to the CH3 domain. In one preferred embodiment the additional immunoglobulin CH2 domain is N-terminal to the CH3 domain.

In one embodiment, the multimeric polypeptide comprises a hinge region and the mutations C226S and C229S or a hinge region without the CPXC (SEQ ID NO: 95) sequence (numbering according to Kabat EU index) or no hinge region.

From the art different methods for the generation of (hetero-)multimeric polypeptides are known. Any of these methods can be used as long as the mutations required for the formation of the starting (hetero-)multimeric polypeptides do not interfere or overlap with the (perturbing) destabilizing mutations needed for the exchange reaction according to the current invention.

Thus, the current invention is based, at least in part, on the finding that for performing the method according to the current invention the introduction of a single destabilizing mutations in one CH3 domain of a pair of CH3 domains is sufficient. In more detail, it has been found that the introduction of a first destabilizing mutation at position 357 in only one CH3 domain of the first starting (hetero-)multimeric polypeptide and a second destabilizing mutation at position 370 in only one CH3 domain of the second starting polypeptide fosters upon spatial approach between the two starting (hetero-)multimeric polypeptides the spontaneous exchange of polypeptide chains between these starting polypeptides. One of the resulting exchanged polypeptides comprises the CH3 domain pair with the mutations at positions 357 and 370, respectively, which result in a stabilization of the exchanged (hetero-)multimer. The like can be achieved with the mutations at positions 356 and 439. The numbering of all positions is according to the EU index of Kabat. One preferred pair of mutations is E357K and K370E. Another preferred pair of mutations is D356K and K439E. The method according to the current invention can be applied to any IgG subclass, i.e. IgG1, IgG2, IgG3 and IgG4, as the residues in question are highly conserved. In one preferred embodiment the CH3 domain is of the IgG1 subclass.

In one embodiment the multimeric polypeptide comprises
  a first polypeptide comprising
    i) in N- to C-terminal direction a) a first antibody variable domain selected from a pair of an antibody light and heavy chain variable domain specifically binding to a first target, and b) a first human immunoglobulin G CH3 domain,
      wherein the first CH3 domain comprises
        a) the mutation T366W, or
        b) the mutations T366S/L368A/Y407V,
      and
    ii) a pair of an antibody light and heavy chain variable domain specifically binding to a second target either N-terminal to the first antibody variable domain or C-terminal to the first CH3 domain, a second polypeptide comprising
  i) in N- to C-terminal direction a) a second antibody variable domain selected from a pair of an antibody light and heavy chain variable domain specifically binding to a third target, and b) a second human immunoglobulin G CH3 domain,
    wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
    and
    wherein the second CH3 domain comprises
      a) the mutations T366S/L368A/Y407V if the first CH3 domain comprises the mutation T366W, or
      b) the mutation T366W if the first CH3 domain comprises the mutations T366S/L368A/Y407V,
    and
    wherein the second CH3 domain comprises a perturbing mutation selected from the group of mutations consisting of D356K, E357K, K370E and K439E, whereby the first CH3 domain comprises
      a) the amino acid residue K at position 439 if the perturbing mutations is D356K, or
      b) the amino acid residue K at position 370 if the perturbing mutations is E357K, or
      c) the amino acid residue E at position 357 if the perturbing mutations is K370E, or
      d) the amino acid residue D at position 356 if the perturbing mutations is K439E,
    and
  ii) optionally a pair of an antibody light and heavy chain variable domain specifically binding to the second or a fourth target either N-terminal to the second antibody variable domain or C-terminal to the second CH3 domain,
whereby all numbering is according to Kabat EU index.

In one embodiment the multimeric polypeptide comprises
a first polypeptide comprising
  i) in N- to C-terminal direction a) a first human immunoglobulin G CH3 domain, and b) a first antibody variable domain selected from a pair of an antibody light and heavy chain variable domain specifically binding to a first target,
    wherein the first CH3 domain comprises
      a) the mutation T366W, or
      b) the mutations T366S/L368A/Y407V,
    and
  ii) a pair of an antibody light and heavy chain variable domain specifically binding to a second target either N-terminal to the first CH3 domain or C-terminal to the first variable domain,
a second polypeptide comprising
  i) in N- to C-terminal direction a) a second human immunoglobulin G CH3 domain and b) a second antibody variable domain selected from a pair of an antibody light and heavy chain variable domain specifically binding to a third target,
    wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
    and
    wherein the second CH3 domain comprises
      a) the mutations T366S/L368A/Y407V if the first CH3 domain comprises the mutation T366W, or
      b) the mutation T366W if the first CH3 domain comprises the mutations T366S/L368A/Y407V,
    and
    wherein the second CH3 domain comprises a perturbing mutation selected from the group of mutations consisting of D356K, E357K, K370E and K439E, whereby the first CH3 domain comprises
      a) the amino acid residue K at position 439 if the perturbing mutations is D356K, or
      b) the amino acid residue K at position 370 if the perturbing mutations is E357K, or
      c) the amino acid residue E at position 357 if the perturbing mutations is K370E, or
      d) the amino acid residue D at position 356 if the perturbing mutations is K439E,
    and
  ii) optionally a pair of an antibody light and heavy chain variable domain specifically binding to the second or a fourth target either N-terminal to the second CH3 domain or C-terminal to the second variable domain,
whereby all numbering is according to Kabat EU index.

In one embodiment of all aspects of the invention the first polypeptide and the second polypeptide are a non-covalent dimer.

In one embodiment of all aspects of the invention the first variable domain and the second variable domain form a non-functional binding site.

In one embodiment of all aspects of the invention the first and the second polypeptide each comprise the amino acid sequence DKTHTSPPS (SEQ ID NO: 66) or DKTHT (SEQ ID NO: 94) or GGGS (SEQ ID NO: 69) or DKTHGGGGS (SEQ ID NO: 97) N-terminal to the first and second variable domain.

In one embodiment of all aspects of the invention
  i) the first CH3 domain comprises the mutation T366W and the amino acid residue K at position 439,
    and
    the second CH3 domain comprises the perturbing mutation D356K and the mutations T366S/L368A/Y407V, or
  i) the first CH3 domain comprises the mutation and the amino acid residue K at position 370,
    and
    the second CH3 domain comprises the perturbing mutation E357K and the mutations T366S/L368A/Y407V, or
  iii) the first CH3 domain comprises the mutations T366S/L368A/Y407V and the amino acid residue E at position 357,
    and
    the second CH3 domain comprises the perturbing mutation K370E and the mutation T366W, or
  iv) the first CH3 domain comprises the mutations T366S/L368A/Y407V and the amino acid residue D at position 356,
    and
    the second CH3 domain comprises the perturbing mutation K439E and the mutation T366W.

In one embodiment of all aspects of the invention the first, second and third target are different.

In one embodiment of all aspects of the invention the first target or the third target is human CD3.

In one embodiment of all aspects the second and if present the fourth target are the same or different and both are located on the surface of the same (target) cell.

In one embodiment of all aspects of the invention the pair of an antibody light and heavy chain variable domain specifically binding to the second target is selected from the group consisting of Fv, scFc, Fab, scFab, dsscFab, CrossFab, bispecific Fab, sdAb, and VHH.

In one embodiment of all aspects of the invention the pair of an antibody light and heavy chain variable domain specifically binding to the fourth target is selected independently of the pair of an antibody light and heavy chain variable domain specifically binding to the second target from the group consisting of Fv, scFc, Fab, scFab, dsscFab, CrossFab, bispecific Fab, sdAb, and VHH.

In one embodiment of all aspects of the invention the first and the second polypeptide further comprises an immunoglobulin G CH2 domain N-terminal to the CH3 domain.

In one embodiment of all aspects of the invention the human immunoglobulin G is human IgG1 or human IgG2 or IgG3 or human IgG4.

B) Compositions for Use in the Methods According to the Invention

The on-cell exchange reaction/method that can be performed with a composition comprising two multimeric molecules according to the current invention which comprises the following step bringing a first (starting) multimeric polypeptide, which comprises a first polypeptide and a second polypeptide, and a second (starting) multimeric polypeptide, which comprises a third polypeptide and a fourth polypeptide, in proximity on the surface of a cell to crosswise exchange the second and the third polypeptide to form a third multimeric polypeptide and a fourth multimeric polypeptide, wherein i) the second polypeptide comprises a (first perturbing) mutation resulting in a destabilization of the first multimeric polypeptide compared to a (multimeric) polypeptide identical to said first multimeric polypeptide except for said mutation in the second polypeptide, ii) the third polypeptide comprises a (second perturbing) mutation resulting in a destabilization of the second multimeric polypeptide compared to a multimeric polypeptide identical to said second (multimeric) polypeptide except for said mutation in the third polypeptide, iii) the (first perturbing) mutation in the second polypeptide and the (second perturbing) mutation in the third polypeptide result in a stabilization of the third (exchanged) multimeric polypeptide comprising said second polypeptide and said third polypeptide compared to the first (starting) multimeric polypeptide and/or to the second (starting) multimeric polypeptide, iv) the fourth (exchanged) multimeric polypeptide is stabilized compared to the first (starting) multimeric polypeptide and/or the second (starting) multimeric polypeptide, v) the first multimeric polypeptide and the second multimeric polypeptide each comprise only a part of one or two new binding sites that are not functional, i.e. that cannot bind to its target, and vi) the third and/or the fourth multimeric polypeptide comprise the one or two new binding sites in functional form, i.e. in a form that allows specific binding to its respective target, which have been generated/activated by the exchange of polypeptide between the first multimeric polypeptide and the second multimeric polypeptide, i.e. by bringing the non-functional parts of said one or two new binding sites together to form one or two new functional binding sites.

One aspect of the invention is a composition comprising a first multimeric polypeptide according to the invention and a second multimeric polypeptide according to the invention, wherein the first CH3 domain of the first multimeric polypeptide and the second CH3 domain of the second multimeric polypeptide comprise the mutation T366W or the mutations T366S/L368A/Y407V, and the second CH3 domain of the first multimeric polypeptide comprises the mutation D356K and the second CH3 domain of the second multimeric polypeptide comprises the mutation K439E, or the second CH3 domain of the first multimeric polypeptide comprises the mutation E357K and the second CH3 domain of the second multimeric polypeptide comprises the mutation K370E, and the first antibody variable domain of the first multimeric polypeptide and the first antibody variable domain of the second multimeric polypeptide are a pair of an antibody light chain variable domain and an antibody heavy chain variable domain that specifically bind to the first target, and the second antibody variable domain of the first multimeric polypeptide and the second antibody variable domain of the second multimeric polypeptide are a pair of an antibody light chain variable domain and an antibody heavy chain variable domain that specifically bind to the third target, and the second and fourth target are independently of each other a cell surface antigen.

In one embodiment of all aspects of the invention the first and/or the third target is human CD3.

In one embodiment of all aspects of the invention the composition is a pharmaceutical composition and further comprises a pharmaceutically acceptable excipient.

In one embodiment of all aspects of the invention the composition is for use as a medicament.

C) Fc-Region Variants

In certain embodiments, one or more further amino acid modifications may be introduced into the Fc-region of a multimeric polypeptide according to the invention provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates multimeric polypeptide according to the invention variant that possesses some but not all effector functions, which make it a desirable candidate for applications in which the half-life in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multimeric polypeptide according to the invention lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g., Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg. M. S. et al., Blood 101 (2003) 1045-1052; and Cragg. M. S. and M. J. Glennic, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Multimeric polypeptide according to the invention comprising Fc-regions with reduced effector function include those with substitution of one or more of Fc-region residues 238, 265, 269, 270, 297, 327 and 329 (U.S. Pat. No. 6,737,056). Such Fc-region mutants include Fc-region mutants with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain multimeric polypeptide according to the invention comprise Fc-region variants with improved or diminished binding to FcRs (see, e.g., U.S. Pat. No. 6,737,056; WO 2004/056312, and Shields, R. L. et al., J. Biol. Chem. 276 (2001) 6591-6604).

In certain embodiments, a multimeric polypeptide according to the invention comprises an Fc-region variant with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

In one embodiment of all aspects the multimeric polypeptide according to the invention comprises (all positions according to EU index of Kabat)
  i) an Fc-region of the human IgG1 subclass with the mutations P329G, L234A and L235A in both Fc-region polypeptides, or
  ii) an Fc-region of the human IgG4 subclass with the mutations P329G, S228P and L235E in both Fc-region polypeptides, or
  iii) an Fc-region of the human IgG1 subclass with the mutations P329G, L234A, L235A, I253A, H310A, and H435A in both Fc-region polypeptides, or with the mutations P329G, L234A, L235A, H310A, H433A, and Y436A in both Fc-region polypeptides, or
  iv) a heterodimeric Fc-region of the human IgG1 subclass whereof both Fc-region polypeptides comprise the mutations P329G, L234A and L235A and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
    or
  v) a heterodimeric Fc-region of the human IgG4 subclass whereof both Fc-region polypeptides comprise the mutations P329G, S228P and L235E and
    a) one Fc-region polypeptide comprises the mutation T366W, and the other Fc-region polypeptide comprises the mutations T366S, L368A and Y407V, or
    b) one Fc-region polypeptide comprises the mutations T366W and Y349C, and the other Fc-region polypeptide comprises the mutations T366S, L368A, Y407V, and S354C, or
    c) one Fc-region polypeptide comprises the mutations T366W and S354C, and the other Fc-region polypeptide comprises the mutations T366S, L368A, Y407V and Y349C,
    or
  vi) a combination of one of i), ii), and iii) with one of iv), and v).

In one embodiment of all aspects as reported herein, a multimeric polypeptide according to the invention comprising a CH3 domain, comprises an additional C-terminal glycine-lysine dipeptide (G446 and K447, numbering according to Kabat EU index). In one embodiment of all aspects as reported herein, a multimeric polypeptide according to the invention comprising a CH3 domain comprises an additional C-terminal glycine residue (G446, numbering according to Kabat EU index).

The multimeric polypeptide according to the invention comprises in one embodiment an Fc-region characterized by being of human subclass IgG1 with mutations PVA236, L234A/L235A, and/or GLPSS331 (numbering according to EU index of Kabat), or of subclass IgG4. In a further embodiment, the multimeric polypeptide according to the invention is characterized by comprising an Fc-region being of any IgG class, in one embodiment being of the IgG1 or IgG4 subclass, containing at least one mutation in E233, L234, L235, G236, D270, N297, E318, K320, K322, A327, A330, P331 and/or P329 (numbering according to EU index of Kabat). It is further in one embodiment that the multimeric polypeptide according to the invention comprises an Fc-region of the human IgG4 subclass which contains the mutation S228P, or the mutations S228P and L235E (Angal, S., et al., Mol. Immunol. 30 (1993) 105-108) (numbering according to EU index of Kabat).

The C-terminus of the Fc-region polypeptides comprised in the multimeric polypeptide according to the invention can be a complete C-terminus ending with the amino acid residues PGK. The C-terminus can be a shortened C-terminus in which one or two of the C-terminal amino acid residues have been removed. In one preferred embodiment the C-terminus is a shortened C-terminus ending with the amino acid residues PG.

D) Heterodimerization

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference.

Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain heterodimerizes with another heavy chain comprising the CH3 domain, which is engineered in a complementary manner. For this embodiment, the CH3 domain of the first heavy chain Fc-region polypeptide and the CH3 domain of the second heavy chain Fc-region polypeptide are engineered in a complementary manner by amino acid substitutions, such that the first heavy chain Fc-region polypeptide and the second heavy chain Fc-region polypeptide heterodimerize, whereas the first heavy chain Fc-region polypeptide and the second heavy chain Fc-region polypeptide do no longer homodimerize (e.g. for steric reasons).

The different approaches for supporting heavy chain heterodimerization known in the art, that were cited and included above, are contemplated as different alternatives used in providing the heterodimeric/multimeric polypeptides (e.g. 2/3-IgGs) as reported herein.

The CH3 domains of the multimeric polypeptide according to the invention can be altered by the "knob-into-holes" technology which is described in detail with several examples in e.g. WO 96/027011. Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chain Fc-region polypeptides containing these two CH3 domains. Each of the two CH3 domains (of the two heavy chain Fc-region polypeptides) can be the "knob", while the other is the "hole". A disulfide bridge can be additionally introduced to further stabilize the heterodimers (Merchant, A. M., et al., Nature Biotech. 16 (1998) 677-681; Atwell, S., et al., J. Mol. Biol. 270 (1997) 26-35) and increase the yield in the exchange reaction according to the current invention.

In one preferred embodiment the multimeric polypeptide according to the invention comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into one of the CH3 domains of the knobs chains and a E356C mutation or a S354C mutation into one of the CH3 domain of the hole chains (in the exchange reaction according to the current invention two multimers are used as starting materials on only one of the CH3 domains of said multimers comprises the additional cysteine residue so that only in the exchanged product the additional disulfide bond is formed). Thus in a another preferred embodiment, the multimeric polypeptide according to the invention comprises the Y349C and T366W mutations in one of the CH3 domains of the first multimer and the E356C, T366S, L368A and Y407V mutations the respective complementary CH3 domain of the second multimer; or the multimeric polypeptide according to the invention comprises the Y349C and T366W mutations in one of the CH3 domains of the first multimer and the S354C, T366S, L368A and Y407V mutations in the respective complementary CH3 domain of the second multimer (the additional Y349C mutation in one CH3 domain and the additional E356C or S354C mutation in the corresponding CH3 domain forming a interchain disulfide bridge) (numbering according to Kabat EU index).

But also other knobs-in-holes technologies as described in EP 1 870 459 A1, can be used alternatively or additionally. In one embodiment the multimeric polypeptide according to the invention comprises the R409D and K370E mutations in the CH3 domain of the "knobs chain" and the D399K and E357K mutations in the CH3 domain of the "hole-chain" (numbering according to Kabat EU index).

In one embodiment the multimeric polypeptide according to the invention comprises a T366W mutation in the CH3 domain of the "knobs chain" and the T366S. L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multimeric polypeptide according to the invention comprises the Y349C and T366W mutations in one of the CH3 domains and the S354C, T366S, L368A and Y407V mutations in the complementary CH3 domain, or the multimeric polypeptide according to the invention comprises the Y349C and T366W mutations in one of the CH3 domains and the S354C, T366S. L368A and Y407V mutations in the complementary CH3 domain and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multimeric polypeptide according to the invention to enforce heterodimerization are known in the art. These technologies, especially the ones described in WO 96/27011, WO 98/050431, EP 1870459, WO 2007/110205, WO 2007/

147901, WO 2009/089004, WO 2010/129304, WO 2011/ 90754, WO 2011/143545, WO 2012/058768, WO 2013/ 157954 and WO 2013/096291 are contemplated herein as alternatives to the "knob-into-hole technology" in combination with a multimeric polypeptide according to the invention.

In one embodiment of a multimeric polypeptide according to the invention the approach described in EP 1 870 459 A1 is used to support heterodimerization of the first heavy chain and the second heavy chain of the multimeric polypeptide according to the invention. This approach is based on the introduction of charged amino acids with opposite charges at specific amino acid positions in the CH3/CH3-domain-interface between both, the first and the second heavy chain.

Accordingly, this embodiment relates to a multimeric polypeptide according to the invention, wherein in the tertiary structure of the multimer the CH3 domain of the first heavy chain Fc-region polypeptide and the CH3 domain of the second heavy chain Fc-region polypeptide form an interface that is located between the respective CH3 domains, wherein the respective amino acid sequences of the CH3 domain of the first heavy chain Fc-region polypeptide and the CH3 domain of the second heavy chain Fc-region polypeptide each comprise a set of amino acids that is located within said interface in the tertiary structure of the multimeric polypeptide according to the invention, wherein from the set of amino acids that is located in the interface in the CH3 domain of one heavy chain Fc-region polypeptide a first amino acid is substituted by a positively charged amino acid and from the set of amino acids that is located in the interface in the CH3 domain of the other heavy chain Fc-region polypeptide a second amino acid is substituted by a negatively charged amino acid. The multimeric polypeptide according to this embodiment is herein also referred to as "CH3(+/−)-engineered multimeric polypeptide" (wherein the abbreviation "+/−" stands for the oppositely charged amino acids that were introduced in the respective CH3 domains).

In one embodiment of said CH3(+/−)-engineered multimeric polypeptide according to the invention the positively charged amino acid is selected from K, R and H, and the negatively charged amino acid is selected from E or D.

In one embodiment of said CH3(+/−)-engineered multimeric polypeptide according to the invention the positively charged amino acid is selected from K and R, and the negatively charged amino acid is selected from E or D.

In one embodiment of said CH3(+/−)-engineered multimeric polypeptide according to the invention the positively charged amino acid is K, and the negatively charged amino acid is E.

In one embodiment of said CH3(+/−)-engineered 2/3-IgG as reported herein in the CH3 domain of one heavy chain the amino acid R at position 409 is substituted by D and the amino acid K at position 370 is substituted by E, and in the CH3 domain of the other heavy chain the amino acid D at position 399 is substituted by K and the amino acid E at position 357 is substituted by K (numbering according to Kabat EU index).

In one embodiment of a multimeric polypeptide according to the invention the approach described in WO 2013/157953 is used to support heterodimerization of the first heavy chain Fc-region polypeptide and the second heavy chain Fc-region polypeptide of the multimeric polypeptide. In one embodiment of said multimeric polypeptide according to the invention, in the CH3 domain of one heavy chain Fc-region polypeptide the amino acid T at position 366 is substituted by K, and in the CH3 domain of the other heavy chain Fc-region polypeptide the amino acid L at position 351 is substituted by D (numbering according to Kabat EU index).

In another embodiment of said multimeric polypeptide according to the invention, in the CH3 domain of one heavy chain Fc-region polypeptide the amino acid T at position 366 is substituted by K and the amino acid L at position 351 is substituted by K, and in the CH3 domain of the other heavy chain Fc-region polypeptide the amino acid L at position 351 is substituted by D (numbering according to Kabat EU index).

In another embodiment of said multimeric polypeptide according to the invention, in the CH3 domain of one heavy chain Fc-region polypeptide the amino acid T at position 366 is substituted by K and the amino acid L at position 351 is substituted by K, and in the CH3 domain of the other heavy chain Fc-region polypeptide the amino acid L at position 351 is substituted by D (numbering according to Kabat EU index). Additionally, at least one of the following substitutions is comprised in the CH3 domain of the other heavy chain Fc-region polypeptide: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multimeric polypeptide according to the invention the approach described in WO 2012/058768 is used to support heterodimerization of the first Fc-region polypeptide and the second Fc-region polypeptide of the multimeric polypeptide according to the invention. In one embodiment of said multimeric polypeptide according to the invention, in the CH3 domain of one heavy chain Fc-region polypeptide the amino acid L at position 351 is substituted by Y and the amino acid Y at position 407 is substituted by A, and in the CH3 domain of the other heavy chain Fc-region polypeptide the amino acid T at position 366 is substituted by A and the amino acid K at position 409 is substituted by F (numbering according to Kabat EU index). In another embodiment, in addition to the aforementioned substitutions, in the CH3 domain of the other heavy chain Fc-region polypeptide at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another embodiment of the multimeric polypeptide according to the invention (engineered according to WO 2012/058768), in the CH3 domain of one heavy chain Fc-region polypeptide the amino acid L at position 351 is substituted by Y and the amino acid Y at position 407 is substituted by A, and in the CH3 domain of the other heavy chain Fc-region polypeptide the amino acid T at position 366 is substituted by V and the amino acid K at position 409 is substituted by F (numbering according to Kabat EU index). In another embodiment of said multimeric polypeptide according to the invention, in the CH3 domain of one heavy chain Fc-region polypeptide the amino acid Y at position 407 is substituted by A, and in the CH3 domain of the other heavy chain Fc-region polypeptide the amino acid T at position 366 is substituted by A and the amino acid K at position 409 is substituted by F (numbering according to Kabat EU index). In said last aforementioned embodiment, in the CH3 domain of said other heavy chain Fc-region polypeptide the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multimeric polypeptide according to the invention the approach described in WO 2011/143545 is used to support heterodimerization of the first Fc-region polypeptide and the second Fc-region polypeptide of the multimeric polypeptide according to the invention. In one embodiment of said multimeric polypeptide according to the invention, amino acid modifications in the CH3 domains of both heavy chain Fc-region polypeptides are introduced at positions 368 and/or 409 (numbering according to Kabat EU index).

In one embodiment of a multimeric polypeptide according to the invention the approach described in WO 2011/090762 is used to support heterodimerization of the first Fc-region polypeptide and the second Fc-region polypeptide of the multimeric polypeptide according to the invention. WO 2011/090762 relates to amino acid modifications according to the "knob-into-hole" technology. In one embodiment of said CH3(KiH)-engineered multimeric polypeptide according to the invention, in the CH3 domain of one heavy chain Fc-region polypeptide the amino acid T at position 366 is substituted by W, and in the CH3 domain of the other heavy chain Fc-region polypeptide the amino acid Y at position 407 is substituted by A (numbering according to Kabat EU index). In another embodiment of said CH3(KiH)-engineered multimeric polypeptide according to the invention, in the CH3 domain of one heavy chain Fc-region polypeptide the amino acid T at position 366 is substituted by Y, and in the CH3 domain of the other heavy chain Fc-region polypeptide the amino acid Y at position 407 is substituted by T (numbering according to Kabat EU index).

In one embodiment of a multimeric polypeptide according to the invention, which is of IgG2 isotype, the approach described in WO 2011/090762 is used to support heterodimerization of the first heavy chain Fc-region polypeptide and the second heavy chain Fc-region polypeptide of the multimeric polypeptide according to the invention.

In one embodiment of a multimeric polypeptide according to the invention, the approach described in WO 2007/147901 is used to support heterodimerization of the first Fc-region polypeptide and the second Fc-region polypeptide of the multimeric polypeptide according to the invention. In one embodiment of said multimeric polypeptide according to the invention, in the CH3 domain of one heavy chain Fc-region polypeptide the amino acid K at position 253 is substituted by E, the amino acid D at position 282 is substituted by K and the amino acid K at position 322 is substituted by D, and in the CH3 domain of the other heavy chain Fc-region polypeptide the amino acid D at position 239 is substituted by K, the amino acid E at position 240 is substituted by K and the amino acid K at position 292 is substituted by D (numbering according to Kabat EU index).

In one embodiment of a multimeric polypeptide according to the invention, the approach described in WO 2007/110205 is used to support heterodimerization of the first polypeptide and the second polypeptide of the multimeric polypeptide according to the invention.

In one embodiment of all aspects as reported herein, the multimeric polypeptide according to the invention has a constant domain structure of an IgG type antibody. In one further embodiment of all aspects as reported herein, the multimeric polypeptide according to the invention is characterized in that said multimeric polypeptide comprises an Fc-region of human subclass IgG1, or of human subclass IgG1 with the mutations L234A and L235A and optionally P329G. In one further embodiment of all aspects as reported herein, the multimeric polypeptide according to the invention is characterized in that said multimeric polypeptide comprises an Fc-region of human subclass IgG2. In one further embodiment of all aspects as reported herein, the multimeric polypeptide according to the invention is characterized in that said multimeric polypeptide comprises an Fc-region of human subclass IgG3. In one further embodiment of all aspects as reported herein, the multimeric polypeptide according to the invention is characterized in that said multimeric polypeptide comprises an Fc-region of human subclass IgG4 or, of human subclass IgG4 with the additional mutation S228P and L235E and optionally P329G.

In one embodiment of all aspects the multimeric polypeptide according to the invention comprises a first Fc-region polypeptide and a second Fc-region polypeptide wherein
  i) the first and the second Fc-region polypeptide comprise the mutation Y436A, or
  ii) the first and the second Fc-region polypeptide comprise the mutations I253A, H310A and H435A, or
  iii) the first and the second Fc-region polypeptide comprise the mutations H310A, H433A and Y436A, or
  iv) the first and the second Fc-region polypeptide comprise the mutations L251D, L314D and L432D, or
  v) the first Fc-region polypeptide comprises the mutation Y436A and the second Fc-region polypeptide comprises
    a) the mutations I253A, H310A and H435A, or
    b) the mutations H310A, H433A and Y436A, or
    c) the mutations L251D, L314D and L432D,
  or
  vi) the first Fc-region polypeptide comprises the mutations I253A, H310A and H435A and the second Fc-region polypeptide comprises
    a) the mutations H310A, H433A and Y436A, or
    b) the mutations L251D, L314D and L432D,
  or
  vii) the first Fc-region polypeptide comprises the mutations H310A, H433A and Y436A and the second Fc-region polypeptide comprises
    a) the mutations L251D, L314D and L432D.

V. RECOMBINANT METHODS AND COMPOSITIONS

Antibodies may be produced using recombinant methods and compositions, e.g., as described in U.S. Pat. No. 4,816,567. In one embodiment, isolated nucleic acid encoding a 2/3-IgG without inter-heavy chain-heavy chain disulfide bonds or a 2/3-BiFab without inter-heavy chain-heavy chain disulfide bonds as described herein is provided. In a further embodiment, one or more vectors (e.g., expression vectors) comprising such nucleic acid are provided. In a further embodiment, a host cell comprising such nucleic acid is provided. In one embodiment, the host cell is eukaryotic, e.g. a Human Embryonic Kidney (HEK) cell, or a Chinese Hamster Ovary (CHO) cell, or a lymphoid cell (e.g., Y0, NS0, Sp2/0 cell). In one embodiment, a method of making a 2/3-IgG without inter-heavy chain-heavy chain disulfide bonds or a 2/3-BiFab without inter-heavy chain-heavy chain disulfide bonds is provided, wherein the method comprises culturing a host cell comprising a nucleic acid encoding the 2/3-IgG without inter-heavy chain-heavy chain disulfide bonds or a 2/3-BiFab without inter-heavy chain-heavy chain disulfide bonds, as provided above, under conditions suitable for expression of the antibody, and optionally recovering the 2/3-IgG without inter-heavy chain-heavy chain disulfide bonds or a 2/3-BiFab without inter-heavy chain-heavy chain disulfide bonds from the host cell (or host cell culture medium).

For recombinant production of a 2/3-IgG without inter-heavy chain-heavy chain disulfide bonds or a 2/3-BiFab without inter-heavy chain-heavy chain disulfide bonds, nucleic acid encoding a 2/3-IgG without inter-heavy chain-heavy chain disulfide bonds or a 2/3-BiFab without inter-heavy chain-heavy chain disulfide bonds, e.g., as described above, is isolated and inserted into one or more vectors for further cloning and/or expression in a host cell.

Suitable host cells for cloning or expression of 2/3-IgG without inter-heavy chain-heavy chain disulfide bonds- or a 2/3-BiFab without inter-heavy chain-heavy chain disulfide bonds-encoding vectors include prokaryotic or eukaryotic cells described herein.

For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for 2/3-IgG without inter-heavy chain-heavy chain disulfide bonds- or a 2/3-BiFab without inter-heavy chain-heavy chain disulfide bonds-encoding vectors, including fungi and yeast strains whose glycosylation pathways have been "humanized," resulting in the production of a 2/3-IgG without inter-heavy chain-heavy chain disulfide bonds or a 2/3-BiFab without inter-heavy chain-heavy chain disulfide bonds with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated 2/3-IgG without inter-heavy chain-heavy chain disulfide bonds or a glycosylated 2/3-BiFab without inter-heavy chain-heavy chain disulfide bonds are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

VI. METHODS AND COMPOSITIONS FOR DIAGNOSTICS AND DETECTION

In certain embodiments, any of the 2/3-IgG without inter-heavy chain-heavy chain disulfide bonds or the 2/3-BiFab without inter-heavy chain-heavy chain disulfide bonds provided herein are useful for detecting the presence of their targets in a biological sample. The term "detecting" as used herein encompasses quantitative or qualitative detection. In certain embodiments, a biological sample comprises a cell or tissue.

In one embodiment, a 2/3-IgG without inter-heavy chain-heavy chain disulfide bonds or a 2/3-BiFab without inter-heavy chain-heavy chain disulfide bonds for use in a method of diagnosis or detection is provided.

In certain embodiments, labeled 2/3-IgG without inter-heavy chain-heavy chain disulfide bonds or labelled 2/3-BiFab without inter-heavy chain-heavy chain disulfide bonds are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

VII. IMMUNOCONJUGATES

The invention also provides immunoconjugates comprising a 2/3-IgG without inter-heavy chain-heavy chain disulfide bonds or a 2/3-BiFab without inter-heavy chain-heavy chain disulfide bonds as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which a 2/3-IgG without inter-heavy chain-heavy chain disulfide bonds or a 2/3-BiFab without inter-heavy chain-heavy chain disulfide bonds is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and U.S. Pat. No. 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises a 2/3-IgG without inter-heavy chain-heavy chain disulfide bonds or a 2/3-BiFab without inter-heavy chain-heavy chain disulfide bonds as described herein conjugated to an enzymatically active toxin or fragment thereof, including but not limited to diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, for example, WO 93/21232 published Oct. 28, 1993.

In another embodiment, an immunoconjugate comprises a 2/3-IgG without inter-heavy chain-heavy chain disulfide bonds or a 2/3-BiFab without inter-heavy chain-heavy chain disulfide bonds as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of a 2/3-IgG without inter-heavy chain-heavy chain disulfide bonds or a 2/3-BiFab without inter-heavy chain-heavy chain disulfide bonds and a cytotoxic agent may be made using a variety of bifunctional coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Conjugates of a 2/3-IgG without inter-heavy chain-heavy chain disulfide bonds or a 2/3-BiFab without inter-heavy chain-heavy chain disulfide bonds as reported herein and one or more small molecule toxins, such as a calicheamicin, a maytansine (U.S. Pat. No. 5,208,020), a trichothene, and CC1065 are also contemplated herein. In one embodiment of the invention, the 2/3-IgG without inter-heavy chain-heavy chain disulfide bonds or the 2/3-BiFab without inter-heavy chain-heavy chain disulfide bonds is conjugated to one or more maytansine molecules (e.g. about 1 to about 10 maytansine molecules per antagonist molecule). Maytansine may, for example, be converted to May-SS-Me which may be reduced to May-SH3 and reacted with modified antagonist (Chari et al. Cancer Research 52: 127-131 (1992)) to generate a maytansinoid-antibody conjugate.

Alternatively, the 2/3-IgG without inter-heavy chain-heavy chain disulfide bonds or the 2/3-BiFab without inter-heavy chain-heavy chain disulfide bonds as reported herein is conjugated to one or more calicheamicin molecules. The calicheamicin family of antibiotics are capable of producing double-stranded DNA breaks at sub-picomolar concentrations. Structural analogues of calicheamicin which may be used include, but are not limited to, γ1 I, α2 I, α3 I, N-acetyl-γ1 I, PSAG and θI 1 (Hinman et al. Cancer Research 53: 3336-3342 (1993) and Lode et al. Cancer Research 58: 2925-2928 (1998)).

The present invention further contemplates a 2/3-IgG without inter-heavy chain-heavy chain disulfide bonds or a 2/3-BiFab without inter-heavy chain-heavy chain disulfide bonds as reported herein conjugated with a compound with nucleolytic activity (e.g. a ribonuclease or a DNA endonuclease such as a deoxyribonuclease; DNase).

Alternatively, a fusion protein comprising a 2/3-IgG without inter-heavy chain-heavy chain disulfide bonds or a 2/3-BiFab without inter-heavy chain-heavy chain disulfide bonds as reported herein and cytotoxic agent may be made, e.g. by recombinant techniques or peptide synthesis.

VIII. PHARMACEUTICAL FORMULATIONS

Pharmaceutical formulations of a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds as described herein are prepared by mixing such 2/3-IgG(s) or 2/3-BiFab(s) having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

Lyophilized formulations adapted for subcutaneous administration are described in WO 97/04801. Such lyophilized formulations may be reconstituted with a suitable diluent to a high protein concentration and the reconstituted formulation may be administered subcutaneously to the mammal to be treated herein.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration are generally sterile. Sterility may be readily accomplished, e.g., by filtration through sterile filtration membranes. In one embodiment the formulation is isotonic.

IX. THERAPEUTIC METHODS AND COMPOSITIONS

Any of the 2/3-IgG without inter-heavy chain-heavy chain disulfide bonds or of the 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds provided herein may be used in therapeutic methods.

In one aspect, a 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds for use as a medicament is provided. In certain embodiments, a 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds for use in a method of treatment is provided. An "individual" according to any of the above embodiments is preferably a human.

In a further aspect, herein is provided the use a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds in the manufacture or preparation of a medicament. An "individual" according to any of the above embodiments may be a human.

In a further aspect, herein is provided a method for treating a disease. In one embodiment, the method comprises administering to an individual having a disease an effective amount of a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds. In one such embodiment, the method further comprises administering to the individual an effective amount of at least one additional therapeutic agent, such as given below. An "individual" according to any of the above embodiments may be a human.

In a further aspect, herein are provided pharmaceutical formulations comprising any of the 2/3-IgGs without inter-heavy chain-heavy chain disulfide bonds as provided herein or of the 2/3-BiFabs without inter-heavy chain-heavy chain disulfide bonds as provided herein or of the compositions comprising two different 2/3-IgG without inter-heavy chain-heavy chain disulfide bonds or two different 2/3-BiFab without inter-heavy chain-heavy chain disulfide bonds as provided herein, e.g., for use in any of the above therapeutic methods. In one embodiment, a pharmaceutical formulation comprises any of the 2/3-IgGs without inter-heavy chain-heavy chain disulfide bonds or of the 2/3-BiFabs without inter-heavy chain-heavy chain disulfide bonds or of the compositions comprising two different 2/3-IgG without inter-heavy chain-heavy chain disulfide bonds or two different 2/3-BiFab without inter-heavy chain-heavy chain disulfide bonds provided herein and a pharmaceutically acceptable carrier. In another embodiment, a pharmaceutical formulation comprises any of the 2/3-IgG without inter-heavy chain-heavy chain disulfide bonds or of the 2/3-BiFab without inter-heavy chain-heavy chain disulfide bonds or of the compositions comprising two different 2/3-IgG without inter-heavy chain-heavy chain disulfide bonds or two different 2/3-BiFab without inter-heavy chain-heavy chain disulfide bonds provided herein and at least one additional therapeutic agent, e.g., as given below.

2/3-IgGs without inter-heavy chain-heavy chain disulfide bonds or 2/3-BiFabs without inter-heavy chain-heavy chain disulfide bonds or compositions comprising two different 2/3-IgG without inter-heavy chain-heavy chain disulfide bonds or two different 2/3-BiFab without inter-heavy chain-heavy chain disulfide bonds as reported herein can be used either alone or in combination with other agents in a therapy. For instance, a 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds as reported herein may be co-administered with at least one additional therapeutic agent.

Such combination therapies noted above encompass combined administration (where two or more therapeutic agents are included in the same or separate formulations), and separate administration, in which case, administration of the 2/3-IgG without inter-heavy chain-heavy chain disulfide bonds or of the 2/3-BiFab without inter-heavy chain-heavy chain disulfide bonds or of the composition comprising two different 2/3-IgG without inter-heavy chain-heavy chain disulfide bonds or two different 2/3-BiFab without inter-heavy chain-heavy chain disulfide bonds as reported herein can occur prior to, simultaneously, and/or following, administration of the additional therapeutic agent or agents. 2/3-IgGs without inter-heavy chain-heavy chain disulfide bonds or of 2/3-BiFabs without inter-heavy chain-heavy chain disulfide bonds or of compositions comprising two different 2/3-IgG without inter-heavy chain-heavy chain disulfide bonds or two different 2/3-BiFab without inter-heavy chain-heavy chain disulfide bonds as reported herein can also be used in combination with other interventional therapies such as, but not limited to, radiation therapy, behavioral therapy, or other therapies known in the art and appropriate for the neurological disorder to be treated or prevented.

A 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

2/3-IgGs without inter-heavy chain-heavy chain disulfide bonds or 2/3-BiFabs without inter-heavy chain-heavy chain disulfide bonds or compositions comprising two different 2/3-IgG without inter-heavy chain-heavy chain disulfide bonds or two different 2/3-BiFab without inter-heavy chain-heavy chain disulfide bonds as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The 2/3-IgG without inter-heavy chain-heavy chain disulfide bonds or the 2/3-BiFab without inter-heavy chain-heavy chain disulfide bonds or the composition comprising two different 2/3-IgG without inter-heavy chain-heavy chain disulfide bonds or two different 2/3-BiFab without inter-heavy chain-heavy chain disulfide bonds need not be, but is optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Lipid-based methods of transporting the compounds across the BBB include, but are not limited to, encapsulating the fusion construct or a compound in liposomes that are coupled to monovalent binding entity that bind to receptors on the vascular endothelium of the BBB (see e.g., US 2002/0025313), and coating the monovalent binding entity in low-density lipoprotein particles (see e.g., US 2004/0204354) or apolipoprotein E (see e.g., US 2004/0131692).

For the prevention or treatment of disease, the appropriate dosage of a 2/3-IgG without inter-heavy chain-heavy chain disulfide bonds or of a 2/3-BiFab without inter-heavy chain-heavy chain disulfide bonds or of a composition comprising two different 2/3-IgG without inter-heavy chain-heavy chain disulfide bonds or two different 2/3-BiFab without inter-heavy chain-heavy chain disulfide bonds as reported herein (when used alone or in combination with one or more other additional therapeutic agents) will depend on the type of disease to be treated, the type of 2/3-IgG without inter-heavy chain-heavy chain disulfide bonds or of 2/3-BiFab without inter-heavy chain-heavy chain disulfide bonds or of composition comprising two different 2/3-IgG without inter-heavy chain-heavy chain disulfide bonds or two different 2/3-BiFab without inter-heavy chain-heavy chain disulfide bonds, the severity and course of the disease, whether the antibody is administered for preventive or therapeutic purposes, previous therapy, the patient's clinical history and response to the antibody, and the discretion of the attending physician. The 2/3-IgG without inter-heavy chain-heavy chain disulfide bonds or the 2/3-BiFab without inter-heavy chain-heavy chain disulfide bonds or the composition comprising two different 2/3-IgG without inter-heavy chain-heavy chain disulfide bonds or two different 2/3-BiFab without inter-heavy chain-heavy chain disulfide bonds is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate as reported herein in place of or in addition to a 2/3-IgG without inter-heavy chain-heavy chain disulfide bonds or a 2/3-BiFab without inter-heavy chain-heavy chain disulfide bonds or a composition comprising two different 2/3-IgG without inter-heavy chain-heavy chain disulfide bonds or two different 2/3-BiFab without inter-heavy chain-heavy chain disulfide bonds.

The composition comprising 2/3-IgGs without inter-heavy chain-heavy chain disulfide bonds or 2/3-BiFabs without inter-heavy chain-heavy chain disulfide bonds as reported herein will be formulated, dosed, and administered in a fashion consistent with good medical practice. Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners. The therapeutically effective amount to be administered will be governed by such considerations.

As noted above, however, these suggested amounts to be administered are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

General techniques for conjugating additional therapeutic agents to antibodies are well known (see, e.g., Arnon et al., "Monoclonal Antibodies for Immunotargeting of Drugs in Cancer Therapy", in Monoclonal Antibodies and Cancer Therapy. Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62 (1982) 119-58).

X. ARTICLES OF MANUFACTURE

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition, which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as reported herein. The label or package insert indicates that the composition is used for treating the condition of choice. Moreover, the article of manufacture may comprise (a) a first container with a composition contained therein, wherein the composition comprises an antibody as reported herein; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a bispecific antibody as reported herein.

XI. SETS OF SPECIFIC EMBODIMENTS OF THE INVENTION

1$^{St}$ Set:

1. A multimeric 2/3-BiFab polypeptide comprising a first polypeptide and a second polypeptide
    wherein both polypeptides comprise the amino acid sequence DKTHTSPPS (SEQ ID NO: 66), an antibody variable domain, and a human immunoglobulin (IgG1) CH3 domain,
    wherein i) the variable domain of the first polypeptide is a heavy chain variable domain if the variable domain of the second polypeptide is a light chain variable domain, or ii) the variable domain of the first polypeptide is a light chain variable domain if the variable domain of the second polypeptide is a heavy chain variable domain,
    wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation,
    wherein the first polypeptide comprises at least one functional binding site or at least a part of a binding site,
    wherein the second polypeptide comprises in the CH3 domain at least one perturbing mutation, whereby the first polypeptide comprises the human immunoglobulin wild-type amino acid residue(s) in its amino acid sequence (CH3 domain) at the amino acid position(s) interacting in a wild-type immunoglobulin with the amino acid residue at the perturbing mutation,
    wherein the first polypeptide and the second polypeptide are a non-covalent dimer,
    wherein the variable domain of the first polypeptide and the variable domain of the second polypeptide form a non-functional binding site.

2. The multimeric 2/3-BiFab polypeptide according to embodiment 1, wherein the first polypeptide is a polypeptide selected from the group of polypeptides comprising in N- to C-terminal direction
    i) a second heavy chain variable domain, a human IgG1 CH1 domain, a hinge region of SEQ ID NO: 66, a first heavy or light chain variable domain, and a CH3 domain derived from a human IgG1 CH3 domain,
    ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain,
    iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain,
    iv) a scFv, optionally a peptidic linker, a hinge region of SEQ ID NO: 66, a heavy or light chain variable domain, and a CH3 domain derived from a human IgG1 CH3 domain,
    v) a scFab, optionally a peptidic linker, a hinge region of SEQ ID NO: 66, a heavy or light chain variable domain, and a CH3 domain derived from a human IgG1 CH3 domain,
    vi) a hinge region of SEQ ID NO: 66, a heavy or light chain variable domain, a CH3 domain derived from a human IgG1 CH3 domain, optionally a peptidic linker, and a scFv,
    vii) a hinge region of SEQ ID NO: 66, a heavy or light chain variable domain, a CH3 domain derived from a human IgG1 CH3 domain, optionally a peptidic linker, and a scFab,
    viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain,
    ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain,
    x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv,
    xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab,
    xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain,
    xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain,
    xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and
    xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain,
    and
    the second polypeptide is a polypeptide selected from the group of polypeptides comprising in N- to C-terminal direction
        a hinge region of SEQ ID NO: 66, a first heavy or light chain variable domain, a CH3 domain derived from a human IgG1 CH3 domain comprising the knob-mutation or the hole-mutations,
        wherein the CH3 domain comprises a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin wild-type amino acid residue(s) in its (CH3 domain) amino acid sequence at the amino acid position(s) interacting in a wild-type immunoglobulin (CH3 domain) with the amino acid residue at the perturbing mutation.

3. The multimeric 2/3-BiFab polypeptide according to any one of embodiments 1 to 2, wherein the multimeric polypeptide further comprises a third polypeptide comprising a further light chain variable domain and a light chain constant domain, wherein the third polypeptide is covalently bound to the first polypeptide by a disulfide bond.

4. A composition comprising
a first heterotrimeric 2/3-BiFab polypeptide comprising
  as first polypeptide a polypeptide selected from the group of polypeptides comprising in N- to C-terminal direction
    i) a second heavy chain variable domain, a human IgG1 CH1 domain, a hinge region of SEQ ID NO: 66, a first heavy or light chain variable domain, and a CH3 domain derived from a human IgG1 CH3 domain,
    ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain,
    iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain,
    iv) a scFv, optionally a peptidic linker, a hinge region of SEQ ID NO: 66, a heavy or light chain variable domain, and a CH3 domain derived from a human IgG1 CH3 domain,
    v) a scFab, optionally a peptidic linker, a hinge region of SEQ ID NO: 66, a heavy or light chain variable domain, and a CH3 domain derived from a human IgG1 CH3 domain,
    vi) a hinge region of SEQ ID NO: 66, a heavy or light chain variable domain, a CH3 domain derived from a human IgG1 CH3 domain, optionally a peptidic linker, and a scFv,
    vii) a hinge region of SEQ ID NO: 66, a heavy or light chain variable domain, a CH3 domain derived from a human IgG1 CH3 domain, optionally a peptidic linker, and a scFab,
    viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain,
    ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain,
    x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv,
    xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab,
    xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain,
    xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain,
    xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and
    xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain,
  and
  as second polypeptide a polypeptide selected from the group of polypeptides comprising in N- to C-terminal direction
    a hinge region of SEQ ID NO: 66, a heavy or light chain variable domain, a CH3 domain derived from a human IgG1 CH3 domain,
    wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain,
    wherein the CH3 domain comprises the knob-mutation if the first polypeptide comprises the hole-mutations, or the hole-mutations if the first polypeptide comprises the knob-mutation,
    wherein the CH3 domain comprises a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s)

interacting in a wild-type immunoglobulin (IgG1) with the amino acid residue at the perturbing mutation, and
as third polypeptide a polypeptide comprising a further light chain variable domain and a light chain constant domain, wherein the third polypeptide is covalently bound to the first polypeptide by a disulfide bond, and
a second heterotrimeric 2/3-BiFab polypeptide comprising
as first polypeptide a polypeptide selected from the group of polypeptide comprising in N- to C-terminal direction
a hinge region of SEQ ID NO: 66, a first heavy or light chain variable domain, and a CH3 domain derived from a human IgG1 CH3 domain,
wherein the CH3 domain comprises the knob-mutation if the second polypeptide of the first heterotrimer comprises the hole-mutations, or the hole-mutations if the second polypeptide of the first heterotrimer comprises the knob-mutation,
wherein the CH3 domain comprises a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the second polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation, and
as second polypeptide a polypeptide selected from the group of polypeptides comprising in N- to C-terminal direction
i) a second heavy chain variable domain, a human IgG1 CH1 domain, a hinge region of SEQ ID NO: 66, a first heavy or light chain variable domain, and a CH3 domain derived from a human IgG1 CH3 domain,
ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain,
iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain,
iv) a scFv, optionally a peptidic linker, a hinge region of SEQ ID NO: 66, a heavy or light chain variable domain, and a CH3 domain derived from a human IgG1 CH3 domain,
v) a scFab, optionally a peptidic linker, a hinge region of SEQ ID NO: 66, a heavy or light chain variable domain, and a CH3 domain derived from a human IgG1 CH3 domain,
vi) a hinge region of SEQ ID NO: 66, a heavy or light chain variable domain, a CH3 domain derived from a human IgG1 CH3 domain, optionally a peptidic linker, and a scFv,
vii) a hinge region of SEQ ID NO: 66, a heavy or light chain variable domain, a CH3 domain derived from a human IgG1 CH3 domain, optionally a peptidic linker, and a scFab,
viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain,
ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain,
x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv,
xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab,
xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain,
xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain,
xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human IgG1 kappa or lambda light chain constant domain, and
xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human IgG1 kappa or lambda light chain constant domain, and a third heavy chain variable domain,
comprising the knob-mutation if the first polypeptide comprises the hole-mutations, or the hole-mutations if the first polypeptide comprises the knob-mutation,
wherein i) the variable domain of the second polypeptide is a heavy chain variable domain if the variable domain of the second polypeptide of the first heterotrimer is a light chain variable domain, or ii) the variable domain of the second polypeptide is a light chain variable domain if the variable domain of the second polypeptide of the first heterotrimer is a heavy chain variable domain, and as third polypeptide a polypeptide comprising a light chain variable domain and a light chain constant domain, wherein the sixth polypeptide is covalently bound to the first polypeptide by a disulfide bond, wherein i) the CH3 domain of the first polypeptide of the first heterotrimer comprises the knob-mutation and the CH3 domain of the second polypeptide of the first heterotrimer comprises the hole-mutations, or ii) the CH3 domain of the first polypeptide of the first heterotrimer comprises the hole-mutations and the CH3 domain of the second polypeptide of the first heterotrimer comprises the knob-mutation, whereby i) in case the first polypeptide of the first heterotrimer comprises the hole-mutations the second polypeptide of the second heterotrimer polypeptide comprises the knob-mutation, or ii) in case the first polypeptide of the first heterotrimer comprises the knob-mutation the second polypeptide of the second heterotrimer polypeptide comprises the hole-mutations, wherein the second polypeptide of the first heterotrimer and the first polypeptide of the second heterotrimer polypeptide comprise perturbing mutations at different positions, wherein the variable domain of the first polypeptide of the first heterotrimer and the variable domain of the second polypeptide of the second heterotrimer form a functional binding site, and the variable domain of the second polypeptide of the first heterotrimer and the variable domain of the first polypeptide of the second heterotrimer form a non-functional pair of variable domains.

5. A multimeric 2/3-IgG polypeptide comprising a first polypeptide and a second polypeptide wherein both polypeptides comprise a human immunoglobulin CH3 domain, wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation, wherein the first polypeptide comprises at least one functional binding site or at least a part of a binding site, wherein the second polypeptide comprises in the CH3 domain at least one perturbing mutation, whereby the first polypeptide comprises the human immunoglobulin (CH3 domain) wild-type amino acid residue(s) in its amino acid sequence at the amino acid position(s) interacting in a wild-type immunoglobulin with the amino acid residue at the perturbing mutation, wherein the first polypeptide and the second polypeptide are a non-covalent or covalent dimer.

6. The multimeric 2/3-IgG polypeptide according to embodiment 5, wherein the first polypeptide is a polypeptide selected from the group of polypeptides comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, and the second polypeptide is a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain comprising the mutations knob or the hole-mutations, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin wild-type amino acid residue(s) in its amino acid sequence at the amino acid position(s) interacting in a wild-type immunoglobulin with the amino acid residue at the perturbing mutation.

7. The multimeric 2/3-IgG polypeptide according to any one of embodiments 5 or 6, wherein the multimeric polypeptide further comprises a third polypeptide comprising a light chain variable domain and a light chain constant domain, wherein the third polypeptide is covalently bound to the first polypeptide by a disulfide bond.

8. A composition comprising a first heterotrimeric 2/3-IgG polypeptide comprising as first polypeptide a polypeptide selected from the group of polypeptides comprising in N- to C-terminal direction i) a heavy chain variable domain, a human IgG1 CH1 domain, a hinge region of SEQ ID NO: 66, a CH2 domain derived from a human IgG1 CH2 domain, and a CH3 domain derived from a human IgG1 CH3 domain, ii) a hinge region of SEQ ID NO: 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a human IgG1 kappa or lambda light chain constant domain, and a second heavy chain variable domain, and xii) a first part of the binding domain, optionally a first peptidic linker, a hinge region of SEQ ID NO: 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the knob-mutation or the hole-mutations, and as second polypeptide a polypeptide selected from the group of polypeptides comprising in N- to C-terminal direction a hinge region of SEQ ID NO: 66, a CH2 domain derived from a human IgG1 CH2 domain, a CH3 domain derived from a human IgG1 CH3 domain, comprising the knob-mutation if the first polypeptide comprises the hole-mutations, or the hole-mutations if the first polypeptide comprises the knob-mutation, comprising a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation, and as third polypeptide a polypeptide comprising a light chain variable domain and a light chain constant domain covalently bound to the first polypeptide by a disulfide bond, and a second heterotrimeric 2/3-IgG polypeptide comprising as first polypeptide a polypeptide selected from the group of polypeptide comprising in N- to C-terminal direction a hinge region of SEQ ID NO: 66, a CH2 domain derived from a human IgG1 CH2 domain, and a CH3 domain derived from a human IgG1 CH3 domain, wherein the CH3 domain comprises the knob-mutation if the second polypeptide of the first heterotrimer comprises the hole-mutations, or the hole-mutations if the second polypeptide of the first heterotrimer comprises the knob-mutation, wherein the CH3 domain comprises a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the second polypeptide comprises the human immunoglobulin wild-type amino acid residue(s) in its amino acid sequence (of the CH3 domain) at the amino acid position(s) interacting in a wild-type immunoglobulin with the amino acid residue at the second perturbing mutation, and as second polypeptide a polypeptide selected from the group of polypeptides comprising in N- to C-terminal direction i) a heavy chain variable domain, a human IgG1 CH1 domain, a hinge region of SEQ ID NO: 66, a CH2 domain derived from a human IgG1 CH2 domain, and a CH3 domain derived from a human IgG1 CH3 domain, ii) a hinge region of SEQ ID NO: 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a human IgG1 kappa or lambda light chain constant domain, xi) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, comprising the knob-mutation if the first polypeptide comprises the hole-mutations, or the hole-mutations if the first polypeptide comprises the knob-mutation, and as third polypeptide a polypeptide comprising a light chain variable domain and a light chain constant domain, wherein the third polypeptide is covalently bound to the first polypeptide by a disulfide bond, wherein i) the CH3 domain of the first polypeptide of the first heterotrimer comprises the knob-mutation and the CH3 domain of the second polypeptide of the first heterotrimer comprises the hole-mutations, or ii) the CH3 domain of the first polypeptide of the first heterotrimer comprises the hole-mutations and the CH3 domain of the second polypeptide of the first heterotrimer comprises the knob-mutation, whereby i) in case the first polypeptide of the first heterotrimer comprises the hole-mutations the second polypeptide of the second heterotrimer polypeptide comprises the knob-mutation, or ii) in case the first polypeptide of the first heterotrimer comprises the knob-mutation the second polypeptide of the second heterotrimer polypeptide comprises the hole-mutations, wherein the second polypeptide of the first heterotrimer and the first polypeptide of the second heterotrimer polypeptide comprise perturbing mutations at different positions.

9. A pharmaceutical formulations comprising a 2/3-IgG according to any one of embodiments 5, 6, and 7, or comprising a 2/3-BiFab according to any one of embodiments 1, 2, and 3, or comprising a composition according to any one of embodiments 4, and 8, and optionally a pharmaceutically acceptable excipient.

10. A pharmaceutical formulations comprising a first heterotrimeric polypeptide, which comprises a first, a second, and a third monomeric polypeptide,
and
a second heterotrimeric polypeptide, which comprises a fourth, a fifth, and a sixth monomeric polypeptide,
wherein first, second, fourth and fifth monomeric polypeptide each comprises in N- to C-terminal direction
(i) the amino acid sequence DKTHTSPPS (SEQ ID NO: 66),
(ii) a first antibody variable domain, and
(iii) a human immunoglobulin (IgG1) CH3 domain, wherein (i), (ii) and (iii) are independently of each other either directly or via a peptidic linker conjugated to each other,
wherein the first antibody variable domain of i) the first and the second monomeric polypeptide, and ii) the first and the fourth monomeric polypeptide, iii) the second and the fifth monomeric polypeptide, and iv) the fourth and the fifth monomeric polypeptide are each a VH/VL pair,
wherein the CH3 domain of i) the first and the fourth monomeric polypeptide, and ii) the first and the second monomeric polypeptide, iii) the second and the fifth monomeric polypeptide, and iv) the fourth and the fifth monomeric polypeptide are each a knob-into-hole pair,
wherein the first monomeric polypeptide and the fourth monomeric polypeptide each comprise independently of each other at one or both of their N- and C-terminus independently of each other a scFv, or a scFab, or a Fab,
wherein the second and the fifth monomeric polypeptide each comprise in the CH3 domain at least one perturbing mutation, whereby the first monomeric polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation of the second monomeric polypeptide, whereby the fourth monomeric polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation of the fifth monomeric polypeptide, whereby the perturbing mutation in the second monomeric polypeptide is not at the same position in the amino acid sequence as the perturbing mutation in the fifth monomeric polypeptide, whereby the perturbing mutation in the second monomeric polypeptide and the perturbing mutation in the fifth monomeric polypeptide result in an attractive (charge) interaction when the second monomeric polypeptide and the fifth monomeric polypeptide form a heterodimer, whereby the perturbing mutations in the second and fifth monomeric polypeptide result in repulsive (charge) interactions when the second monomeric polypeptide forms a heterodimer with the first monomeric polypeptide and the fifth monomeric polypeptide forms a heterodimer with the fourth monomeric polypeptide, respectively, wherein the first and the second monomeric polypeptide are a non-covalent dimer, the fourth and the fifth monomeric polypeptide are a non-covalent dimer, the third and the first monomeric polypeptide are a disulfide-linked dimer, and the sixth and the fourth monomeric polypeptide are a disulfide-linked dimer, wherein the third and the sixth monomeric polypeptide are antibody light chains.

11. The pharmaceutical formulation according to embodiment 10, wherein the first polypeptide is selected from the group of polypeptides comprising in N- to C-terminal direction i) a second heavy chain variable domain, a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain, iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain, ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain, x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain, xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain, xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain, and the third polypeptide is a polypeptide comprising a further light chain variable domain and a light chain constant domain, wherein the third polypeptide is covalently bound to the first polypeptide by a disulfide bond.

12. The pharmaceutical formulation according to any one of embodiments 10 and 11, wherein the second polypeptide is selected from the group of polypeptides comprising in N- to C-terminal direction a hinge region of SEQ ID NO: 66, a heavy or light chain variable domain, a CH3 domain derived from a human IgG1 CH3 domain, wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain, wherein the CH3 domain comprises the knob-mutation if the first polypeptide comprises the hole-mutations, or the hole-mutations if the first polypeptide comprises the knob-mutation, wherein the CH3 domain comprises a perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the first polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation.

13. The pharmaceutical formulation according to any one of embodiments 10 to 12, wherein the fifth polypeptide is selected from the group of polypeptide comprising in N- to C-terminal direction a hinge region of SEQ ID NO: 66, a first heavy or light chain variable domain, and a CH3 domain derived from a human IgG1 CH3 domain, wherein the CH3 domain comprises the knob-mutation if the second polypeptide of the first heterotrimer comprises the hole-mutations, or the hole-mutations if the second polypeptide of the first heterotrimer comprises the knob-mutation, wherein the CH3 domain comprising a second perturbing mutation selected from the group of mutations consisting of E345R, Q347K, Y349W, Y349E, L351F, L351Y, S354E, S354V, D356S, D356A, D356K, E357S, E357A, E357L, E357F, E357K, K360S, K360E, Q362E, S364V, S364L, T366I, L368F, L368V, K370E, N390E, K392E, K392D, T394I, V397Y, D399A, D399K, S400K, D401R, F405W, Y407W, Y407L, Y407I, K409D, K409E, K409I, K439E, L441Y, Y349C, S366T, A368L, V407Y, S354C, and W366T, whereby the fifth polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation, whereby the perturbing mutation in the fifth polypeptide is at a different position as the perturbing mutation in the second polypeptide.

14. The pharmaceutical formulation according to any one of embodiments 10 to 13, wherein the fourth polypeptide is selected from the group of polypeptides comprising in N- to C-terminal direction i) a second heavy chain variable domain, a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain, iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain, ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain, x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain, xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain, xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain, comprising the knob-mutation if the first polypeptide comprises the hole-mutations, or the hole-mutations if the first polypeptide comprises the knob-mutation, wherein i) the first variable domain of the fourth polypeptide is a heavy chain variable domain if the first variable domain of the first polypeptide is a light chain variable domain, or ii) the first variable domain of the fourth polypeptide is a light chain variable domain if the first variable domain of the first polypeptide is a heavy chain variable domain, and the sixth polypeptide is a polypeptide comprising a further light chain variable domain and a light chain constant domain, wherein the sixth polypeptide is covalently bound to the fourth polypeptide by a disulfide bond.

15. The pharmaceutical formulation according to any one of embodiments 10 to 14, wherein the first variable domain of the first polypeptide and the first variable domain of the fourth polypeptide form a functional binding site, and the first variable domain of the second polypeptide and the first variable domain of the fifth polypeptide form a non-functional pair of variable domains.

$2^{nd}$ Set:

1. A multimeric polypeptide comprising
   a first polypeptide comprising in N- to C-terminal direction an antibody variable domain and a human immunoglobulin G CH3 domain,
   a second polypeptide comprising in N- to C-terminal direction an antibody variable domain and a human immunoglobulin G CH3 domain,
   wherein i) the variable domain of the first polypeptide is a heavy chain variable domain if the variable domain of the second polypeptide is a light chain variable domain, or ii) the variable domain of the first polypeptide is a light chain variable domain if the variable domain of the second polypeptide is a heavy chain variable
   wherein the second polypeptide comprises in the CH3 domain at least one perturbing mutation, whereby the first polypeptide comprises the human immunoglobulin wild-type amino acid residue(s) in its amino acid sequence (CH3 domain) at the amino acid position(s) interacting in a wild-type immunoglobulin with the amino acid residue at the perturbing mutation,
   wherein the first polypeptide and the second polypeptide are a non-covalent dimer,
   wherein the variable domain of the first polypeptide and the variable domain of the second polypeptide form a non-functional binding site, wherein the first polypeptide further comprises a functional binding site.

2. The multimeric polypeptide according to embodiments 1, wherein the first and the second polypeptide each comprise the amino acid sequence DKTHTSPPS (SEQ ID NO: 66) or DKTHT (SEQ ID NO: 94) or GGGS (SEQ ID NO: 69) or DKTHGGGGS (SEQ ID NO: 97) N-terminal to the variable domain.

3. A multimeric polypeptide comprising
   a first polypeptide comprising in N- to C-terminal direction a human immunoglobulin G CH3 domain and an antibody variable domain,
   a second polypeptide comprising in N- to C-terminal direction a human immunoglobulin G CH3 domain and an antibody variable domain,
   wherein i) the variable domain of the first polypeptide is a heavy chain variable domain if the variable domain of the second polypeptide is a light chain variable domain, or ii) the variable domain of the first polypeptide is a light chain variable domain if the variable domain of the second polypeptide is a heavy chain variable domain, wherein the second polypeptide comprises in the CH3 domain at least one perturbing mutation, whereby the first polypeptide comprises the human immunoglobulin wild-type amino acid residue(s) in its amino acid sequence (CH3 domain) at the amino acid position(s) interacting in a wild-type immunoglobulin with the amino acid residue at the perturbing mutation, wherein the first polypeptide and the second polypeptide are a non-covalent dimer, wherein the variable domain of the first polypeptide and the variable domain of the second polypeptide form a non-functional binding site, wherein the first polypeptide further comprises a functional binding site.

4. The multimeric polypeptide according to embodiment 4, wherein the first and the second polypeptide each comprise the amino acid sequence DKTHTSPPS (SEQ ID NO: 66) or GGGS (SEQ ID NO: 69) or DKTHT (SEQ ID NO: 94) or DKTHGGGS (SEQ ID NO: 97) N-terminal to the CH3 domain.

5. The multimeric polypeptide according to any one of embodiment 1 to 4, wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation.

6. The multimeric polypeptide according to any one of embodiments 1 to 5, wherein i) the CH3 domain of the first polypeptide comprises the knob-cys-mutations and the CH3 domain of the second polypeptide comprises the hole-mutations, or ii) the CH3 domain of the first polypeptide comprises the hole-cys-mutations and the CH3 domain of the second polypeptide comprises the knob-mutation.

7. The multimeric polypeptide according to any one of embodiments 1 to 6, wherein the perturbing mutations is selected from the group of mutations comprising D356K, E357K, K370E and K439E.

8. The multimeric polypeptide according to any one of embodiments 1 to 7, wherein the human immunoglobulin G CH3 domain is a human IgG1 CH3 domain or a human IgG2 CH3 domain or a human IgG3 CH3 domain or a human IgG4 CH3 domain.

9. The multimeric polypeptide according to any one of embodiments 1 to 8, wherein i) the first polypeptide comprises the knob- or knob-cys-mutations and the second polypeptide comprises the perturbing mutation D356K and the hole-mutations, or ii) the first polypeptide comprises the knob- or knob-cys-mutations and the second polypeptide comprises the perturbing mutation E357K and the hole-mutations, or iii) the first polypeptide comprises the hole- or hole-cys-mutations and the second polypeptide comprises the perturbing mutation K370E and the knob-mutation, or iv) the first polypeptide comprises the hole- or hole-cys-mutations and the second polypeptide comprises the perturbing mutation K439E and the knob-mutation.

10. The multimeric polypeptide according to any one of embodiments 1 to 9, wherein the first polypeptide is a polypeptide selected from the group of polypeptides comprising in N- to C-terminal direction i) a heavy chain variable domain, a human IgG1 CH1 domain, optionally SEQ ID NO: 66 or 69 or 94 or 97, the heavy or light chain variable domain, and the human immunoglobulin G CH3 domain, ii) optionally SEQ ID NO: 66 or 69 or 94 or 97, the heavy or light chain variable domain, the human immunoglobulin G CH3 domain, optionally a peptidic linker, a heavy chain variable domain, and a human IgG1 CH1 domain, iii) optionally SEQ ID NO: 66 or 69 or 94 or 97, the heavy or light chain variable domain, the human immunoglobulin G CH3 domain, optionally a peptidic linker, a human IgG1 CH1 domain, and a heavy chain variable domain, iv) a scFv, optionally a peptidic linker, optionally SEQ ID NO: 66 or 69 or 94 or 97, the heavy or light chain variable domain, and the human immunoglobulin G CH3 domain, v) a scFab, optionally a peptidic linker, optionally SEQ ID NO: 66 or 69 or 94 or 97, the heavy or light chain variable domain, and the human immunoglobulin G CH3 domain, vi) optionally SEQ ID NO: 66 or 69 or 94 or 97, the heavy or light chain variable domain, the human immunoglobulin G CH3 domain, optionally a peptidic linker, and a scFv, vii) optionally SEQ ID NO: 66 or 69 or 94 or 97, the heavy or light chain variable domain, the human immunoglobulin G CH3 domain, optionally a peptidic linker, and a scFab, viii) a heavy chain variable domain, a first human IgG1 CH1 domain, optionally SEQ ID NO: 66 or 69 or 94 or 97, the heavy or light chain variable domain, the human immunoglobulin G CH3 domain, optionally a peptidic linker, a heavy chain variable domain, and a second human IgG1 CH1 domain, ix) a heavy chain variable domain, a first human IgG1 CH1 domain, optionally SEQ ID NO: 66 or 69 or 94 or 97, the heavy or light chain variable domain, the human immunoglobulin G CH3 domain, optionally a peptidic linker, a second human IgG1 CH1 domain, and a heavy chain variable domain, x) a heavy chain variable domain, a human IgG1 CH1 domain, optionally SEQ ID NO: 66 or 69 or 94 or 97, the heavy or light chain variable domain, the human immunoglobulin G CH3 domain, optionally a peptidic linker, and a scFv, xi) a heavy chain variable domain, a human IgG1 CH1 domain, optionally SEQ ID NO: 66 or 69 or 94 or 97, the heavy or light chain variable domain, the human immunoglobulin G CH3 domain, optionally a peptidic linker, and a scFab, xii) a heavy chain variable domain, a first human IgG1 CH1 domain, optionally SEQ ID NO: 66 or 69 or 94 or 97, the heavy or light chain variable domain, the human immunoglobulin G CH3 domain, optionally a peptidic linker, a second human IgG1 CH1 domain, and a light chain variable domain, xiii) a heavy chain variable domain, a first human IgG1 CH1 domain, optionally SEQ ID NO: 66 or 69 or 94 or 97, the heavy or light chain variable domain, the human immunoglobulin G CH3 domain, optionally a peptidic linker, a light chain variable domain, and a second human IgG1 CH1 domain, xiv) a heavy chain variable domain, a human IgG1 CH1 domain, optionally SEQ ID NO: 66 or 69 or 94 or 97, the heavy or light chain variable domain, the human immunoglobulin G CH3 domain, optionally a peptidic linker, a heavy chain variable domain, and a human kappa or lambda light chain constant domain, XV) a heavy chain variable domain, a human IgG1 CH1 domain, optionally SEQ ID NO: 66 or 69 or 94 or 97, the heavy or light chain variable domain, the human immunoglobulin G CH3 domain, optionally a peptidic linker, a human kappa or lambda light chain constant domain, and a heavy chain variable domain, xvi) a heavy chain variable domain, a human IgG1 CH1 domain, optionally SEQ ID NO: 66 or 69 or 94 or 97, the human immunoglobulin G CH3 domain, optionally a peptidic linker, and the heavy or light chain variable domain, xvii) a light chain variable domain, a human IgG1 CH1 domain, optionally SEQ ID NO: 66 or 69 or 94 or 97, the human immunoglobulin G CH3 domain, optionally a peptidic linker, and the heavy or light chain variable domain, xviii) a light chain variable domain, a human kappa or lambda light chain constant domain, optionally SEQ ID NO: 66 or 69 or 94 or 97, the human immunoglobulin G CH3 domain, optionally a peptidic linker, and the heavy or light chain variable domain, and xiv) a heavy chain variable domain, a human kappa or lambda light chain constant domain, optionally SEQ ID NO: 66 or 69 or 94 or 97, the human immunoglobulin G CH3 domain, optionally a peptidic linker, and the heavy or light chain variable domain, and the second polypeptide is a polypeptide selected from the group of polypeptides comprising in N- to C-terminal direction i) optionally SEQ ID NO: 66 or 69 or 94 or 97, the heavy or light chain variable domain, the human immunoglobulin G CH3 domain, or ii) optionally SEQ ID NO: 66 or 69 or 94 or 97, the human immunoglobulin G CH3 domain and the heavy or light chain variable domain, wherein the CH3 domain comprises a perturbing mutation selected from the group of mutations consisting of D356K, E357K, K370E, and K439E, whereby the first polypeptide comprises the human immunoglobulin wild-type amino acid residue(s) in its (CH3 domain) amino acid sequence at the amino acid position(s) interacting in a wild-type immunoglobulin (CH3 domain) with the amino acid residue at the perturbing mutation.

11. The multimeric polypeptide according to any one of embodiments 1 to 10, wherein the multimeric polypeptide further comprises a third polypeptide comprising a light chain variable domain and a light chain constant domain, wherein the third polypeptide is covalently bound to the first polypeptide by a disulfide bond.

12. A composition comprising a first multimeric polypeptide according to any one of embodiments 1 to 11, and a second multimeric polypeptide according to any one of embodiments 1 to 11, wherein i) in the first multimeric polypeptide the perturbing mutation is D356K and in the second multimeric polypeptide the perturbing mutation is K439E, or ii) in the first multimeric polypeptide the perturbing mutation is E357K and in the second multimeric polypeptide the perturbing mutation is K370E.

13. A multimeric comprising a first polypeptide and a second polypeptide wherein both polypeptides comprise a human immunoglobulin CH3 domain, wherein i) the CH3 domain of the first polypeptide comprises the knob-mutation and the CH3 domain of the second polypeptide comprises the hole-mutations, or ii) the CH3 domain of the first polypeptide comprises the hole-mutations and the CH3 domain of the second polypeptide comprises the knob-mutation, wherein the first polypeptide comprises at least one functional binding site or at least a part of a binding site, wherein the second polypeptide comprises in the CH3 domain at least one perturbing mutation, whereby the first polypeptide comprises the human immunoglobulin (CH3 domain) wild-type amino acid residue(s) in its amino acid sequence at the amino acid position(s) interacting in a wild-type immunoglobulin with the amino acid residue at the perturbing mutation, wherein the first polypeptide and the second polypeptide are a non-covalent or covalent dimer.

14. The multimeric polypeptide according to embodiment 13, wherein the first polypeptide is a polypeptide selected from the group of polypeptides comprising in N- to C-terminal direction i) a heavy chain variable domain, a human IgG1 CH1 domain, a hinge region of SEQ ID NO: 65 or 66, a CH2 domain derived from a human IgG1 CH2 domain, and a CH3 domain derived from a human IgG1 CH3 domain, ii) a hinge region of SEQ ID NO: 65 or 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 65 or 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 65 or 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and xii) a first part of the binding domain, optionally a first peptidic linker, a hinge region of SEQ ID NO: 65 or 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target, and the second polypeptide is a polypeptide selected from the group of polypeptides comprising in N- to C-terminal direction a hinge region of SEQ ID NO: 65 or 66, a CH2 domain derived from a human IgG1 CH2 domain, a CH3 domain derived from a human IgG1 CH3 domain comprising the mutations knob or the hole-mutations, comprising a perturbing mutation selected from the group of mutations consisting of D356K, E357K, K370E, and K439E, whereby the first polypeptide comprises the human immunoglobulin wild-type amino acid residue(s) in its amino acid sequence at the amino acid position(s) interacting in a wild-type immunoglobulin with the amino acid residue at the perturbing mutation.

15. The multimeric polypeptide according to any one of embodiments 13 or 14, wherein the multimeric polypeptide further comprises a third polypeptide comprising a light chain variable domain and a light chain constant domain, wherein the third polypeptide is covalently bound to the first polypeptide by a disulfide bond.

16. A composition comprising
a first multimeric polypeptide comprising
as first polypeptide a polypeptide selected from the group of polypeptides comprising in N- to C-terminal direction
i) a heavy chain variable domain, a human IgG1 CH1 domain, a hinge region of SEQ ID NO: 66, a CH2 domain derived from a human IgG1 CH2 domain, and a CH3 domain derived from a human IgG1 CH3 domain, ii) a hinge region of SEQ ID NO: 66, a CH2 domain derived from a human IgG1 CH2 domain, a CH3 domain derived from a human IgG1 CH3 domain, optionally a peptidic linker, a heavy chain variable domain, and a human IgG1 CH1 domain, iii) a hinge region of SEQ ID NO: 66, a CH2 domain derived from a human IgG1 CH2 domain, a CH3 domain derived from a human IgG1 CH3 domain, optionally a peptidic linker, a human IgG1 CH1 domain, and a heavy chain variable domain, iv) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a second human IgG1 CH1 domain, v) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a second heavy chain variable domain, vi) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFv, vii) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFab, viii) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a light chain variable domain, ix) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a light chain variable domain, and a second human IgG1 CH1 domain, x) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a human kappa or lambda light chain constant domain, xi) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a human IgG1 kappa or lambda light chain constant domain, and a second heavy chain variable domain, and xii) a first part of the binding domain, optionally a first peptidic linker, a hinge region of SEQ ID NO: 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target,
comprising the knob-mutation or the hole-mutations,
and
as second polypeptide a polypeptide selected from the group of polypeptides comprising in N- to C-terminal direction
  a hinge region of SEQ ID NO: 66, a CH2 domain derived from a human IgG1 CH2 domain, a CH3 domain derived from a human IgG1 CH3 domain,
  comprising the knob-mutation if the first polypeptide comprises the hole-mutations, or the hole-mutations if the first polypeptide comprises the knob-mutation,
  comprising a perturbing mutation selected from the group of mutations consisting of D356K, E357K, K370E, and K439E, whereby the first polypeptide comprises the human immunoglobulin (IgG1) wild-type amino acid residue(s) in its amino acid sequence at the amino acid position(s) interacting in a wild-type immunoglobulin (IgG1) with the amino acid residue at the perturbing mutation,
and
as third polypeptide a polypeptide comprising a light chain variable domain and a light chain constant domain covalently bound to the first polypeptide by a disulfide bond,
and
a second multimeric polypeptide comprising
as first polypeptide a polypeptide selected from the group of polypeptide comprising in N- to C-terminal direction
  a hinge region of SEQ ID NO: 66, a CH2 domain derived from a human IgG1 CH2 domain, and a CH3 domain derived from a human IgG1 CH3 domain,
  wherein the CH3 domain comprises the knob-mutation if the second polypeptide of the first heterotrimer comprises the hole-mutations, or the hole-mutations if the second polypeptide of the first heterotrimer comprises the knob-mutation,
  wherein the CH3 domain comprises a second perturbing mutation selected from the group of mutations consisting of D356K, E357K, K370E, and K439E, whereby the second polypeptide comprises the human immunoglobulin wild-type amino acid residue(s) in its amino acid sequence (of the CH3 domain) at the amino acid position(s) interacting in a wild-type immunoglobulin with the amino acid residue at the second perturbing mutation,
and
as second polypeptide a polypeptide selected from the group of polypeptides comprising in N- to C-terminal direction
i) a heavy chain variable domain, a human IgG1 CH1 domain, a hinge region of SEQ ID NO: 66, a CH2 domain derived from a human IgG1 CH2 domain, and a CH3 domain derived from a human IgG1 CH3
ii) a hinge region of SEQ ID NO: 66, a CH2 domain derived from a human IgG1 CH2 domain, a CH3 domain derived from a human IgG1 CH3 domain, optionally a peptidic linker, a heavy chain variable domain, and a human IgG1 CH1 domain,
iii) a hinge region of SEQ ID NO: 66, a CH2 domain derived from a human IgG1 CH2 domain, a CH3 domain derived from a human IgG1 CH3 domain, optionally a peptidic linker, a human IgG1 CH1 domain, and a heavy chain variable domain,
iv) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a second human IgG1 CH1 domain,
v) a first heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a second heavy chain variable domain,
vi) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFv,
vii) a heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, and a scFab,
viii) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second human IgG1 CH1 domain, and a light chain variable domain,
ix) a heavy chain variable domain, a first human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a light chain variable domain, and a second human IgG1 CH1 domain,
x) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a second heavy chain variable domain, and a human IgG1 kappa or lambda light chain constant domain,
xi) a first heavy chain variable domain, a human IgG1 CH1 domain, a hinge region of SEQ ID NO: 66, a CH2 domain derived from a human IgG1 CH2 domain, a CH3 domain derived from a human IgG1 CH3 domain, optionally a peptidic linker, a human kappa or lambda light chain constant domain, and a second heavy chain variable domain, and
xii) a first part of the binding domain, optionally a first peptidic linker, a hinge region of SEQ ID NO: 66, a CH2 domain derived from a human IgG1 CH2 domain, a CH3 domain derived from a human IgG1 CH3 domain, optionally a second peptidic linker, and a second part of the binding domain, wherein the first part of the binding domain and the second part of the binding domain form a functional binding site that specifically binds to a target,
comprising the knob-mutation if the first polypeptide comprises the hole-mutations, or the hole-mutations if the first polypeptide comprises the knob-mutation, and
as third polypeptide a polypeptide comprising a light chain variable domain and a light chain constant domain,
wherein the third polypeptide is covalently bound to the first polypeptide by a disulfide bond,
wherein i) the CH3 domain of the first polypeptide of the first heterotrimer comprises the knob-mutation and the CH3 domain of the second polypeptide of the first heterotrimer comprises the hole-mutations, or ii) the CH3 domain of the first polypeptide of the first heterotrimer comprises the hole-mutations and the CH3 domain of the second polypeptide of the first heterotrimer comprises the knob-mutation, whereby i) in case the first polypeptide of the first heterotrimer comprises the hole-mutations the second polypeptide of the second heterotrimer polypeptide comprises the knob-mutation, or ii) in case the first polypeptide of the first heterotrimer comprises the knob-mutation the second polypeptide of the second heterotrimer polypeptide comprises the hole-mutations,
wherein the second polypeptide of the first heterotrimer and the first polypeptide of the second heterotrimer polypeptide comprise perturbing mutations at different positions.

17. A pharmaceutical formulations comprising a multimeric polypeptide according to any one of embodiments 1 to 15, or comprising a composition according to embodiment 16, and optionally a pharmaceutically acceptable excipient.

18. A pharmaceutical formulations comprising
a first heterotrimeric polypeptide, which comprises a first, a second, and a third monomeric polypeptide, and
a second heterotrimeric polypeptide, which comprises a fourth, a fifth, and a sixth monomeric polypeptide,
wherein first, second, fourth and fifth monomeric polypeptide each comprises in N- to C-terminal direction
(i) the amino acid sequence DKTHTSPPS (SEQ ID NO: 66),
(ii) a first antibody variable domain, and
(iii) a human immunoglobulin (IgG1) CH3 domain,
wherein (i), (ii) and (iii) are independently of each other either directly or via a peptidic linker conjugated to each other, wherein the first antibody variable domain of i) the first and the second monomeric polypeptide, and ii) the first and the fourth monomeric polypeptide, iii) the second and the fifth monomeric polypeptide, and iv) the fourth and the fifth monomeric polypeptide are each a VH/VL pair,
wherein the CH3 domain of i) the first and the fourth monomeric polypeptide, and ii) the first and the second monomeric polypeptide, iii) the second and the fifth monomeric polypeptide, and iv) the fourth and the fifth monomeric polypeptide are each a knob-into-hole pair,
wherein the first monomeric polypeptide and the fourth monomeric polypeptide each comprise independently of each other at one or both of their N- and C-terminus independently of each other a scFv, or a scFab, or a Fab,
wherein the second and the fifth monomeric polypeptide each comprise in the CH3 domain at least one perturbing mutation, whereby the first monomeric polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation of the second monomeric polypeptide, whereby the fourth monomeric polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation of the fifth monomeric polypeptide, whereby the perturbing mutation in the second monomeric polypeptide is not at the same position in the amino acid sequence as the perturbing mutation in the fifth monomeric polypeptide, whereby the perturbing mutation in the second monomeric polypeptide and the perturbing mutation in the fifth monomeric polypeptide result in an attractive (charge) interaction when the second monomeric polypeptide and the fifth monomeric polypeptide form a heterodimer, whereby the perturbing mutations in the second and fifth monomeric polypeptide result in repulsive (charge) interactions when the second monomeric polypeptide forms a heterodimer with the first monomeric polypeptide and the fifth monomeric polypeptide forms a heterodimer with the fourth monomeric polypeptide, respectively,
wherein the first and the second monomeric polypeptide are a non-covalent dimer, the fourth and the fifth monomeric polypeptide are a non-covalent dimer, the third and the first monomeric polypeptide are a disulfide-linked dimer, and the sixth and the fourth monomeric polypeptide are a disulfide-linked dimer,
wherein the third and the sixth monomeric polypeptide are antibody light chains.

19. The pharmaceutical formulation according to embodiment 18, wherein the first polypeptide is selected from the group of polypeptides comprising in N- to C-terminal direction
i) a second heavy chain variable domain, a human IgG1 CH1 domain, a hinge region of SEQ ID NO: 66, a first heavy or light chain variable domain, and a CH3 domain derived from a human IgG1 CH3 domain,
ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain,
iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain,
iv) a scFv, optionally a peptidic linker, a hinge region of SEQ ID NO: 66, a heavy or light chain variable domain, and a CH3 domain derived from a human IgG1 CH3 domain,
v) a scFab, optionally a peptidic linker, a hinge region of SEQ ID NO: 66, a heavy or light chain variable domain, and a CH3 domain derived from a human IgG1 CH3 domain,
vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain, ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain, x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain, xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain, xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain, and the third polypeptide is a polypeptide comprising a further light chain variable domain and a light chain constant domain, wherein the third polypeptide is covalently bound to the first polypeptide by a disulfide bond.

20. The pharmaceutical formulation according to any one of embodiments 18 and 19, wherein the second polypeptide is selected from the group of polypeptides comprising in N- to C-terminal direction a hinge region of SEQ ID NO: 66, a heavy or light chain variable domain, a CH3 domain derived from a human IgG1 CH3 domain, wherein i) the variable domain of the second polypeptide is a heavy chain variable domain if the variable domain of the first polypeptide is a light chain variable domain, or ii) the variable domain of the second polypeptide is a light chain variable domain if the variable domain of the first polypeptide is a heavy chain variable domain, wherein the CH3 domain comprises the knob-mutation if the first polypeptide comprises the hole-mutations, or the hole-mutations if the first polypeptide comprises the knob-mutation, wherein the CH3 domain comprises a perturbing mutation selected from the group of mutations consisting of D356K, E357K, K370E, and K439E, whereby the first polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation.

21. The pharmaceutical formulation according to any one of embodiments 18 to 21, wherein the fifth polypeptide is selected from the group of polypeptide comprising in N- to C-terminal direction a hinge region of SEQ ID NO: 66, a first heavy or light chain variable domain, and a CH3 domain derived from a human IgG1 CH3 domain, wherein the CH3 domain comprises the knob-mutation if the second polypeptide of the first heterotrimer comprises the hole-mutations, or the hole-mutations if the second polypeptide of the first heterotrimer comprises the knob-mutation, wherein the CH3 domain comprising a second perturbing mutation selected from the group of mutations consisting of D356K, E357K, K370E, and K439E, whereby the fifth polypeptide comprises the human immunoglobulin wild-type amino acid residue(s) in its (CH3 domain) amino acid sequence at the amino acid position(s) interacting in a wild-type immunoglobulin with the amino acid residue at the perturbing mutation, whereby the perturbing mutation in the fifth polypeptide is at a different position as the perturbing mutation in the second polypeptide.

22. The pharmaceutical formulation according to any one of embodiments 18 to 21, wherein the fourth polypeptide is selected from the group of polypeptides comprising in N- to C-terminal direction i) a second heavy chain variable domain, a human IgG1 CH1 domain, a hinge region of SEQ ID NO: 66, a first heavy or light chain variable domain, and a CH3 domain derived from a human IgG1 CH3 domain, ii) a hinge region of SEQ ID NO: 66, a first heavy or light chain variable domain, a CH3 domain derived from a human IgG1 CH3 domain, optionally a peptidic linker, a second heavy chain variable domain, and a human IgG1 CH1 domain, iii) a hinge region of SEQ ID NO: 66, a first heavy or light chain variable domain, a CH3 domain derived from a human IgG1 CH3 domain, optionally a peptidic linker, a human IgG1 CH1 domain, and a second heavy chain variable domain, iv) a scFv, optionally a peptidic linker, a hinge region of SEQ ID NO: 66, a heavy or light chain variable domain, and a CH3 domain derived from a human IgG1 CH3 domain, v) a scFab, optionally a peptidic linker, a hinge region of SEQ ID NO: 66, a heavy or light chain variable domain, and a CH3 domain derived from a human IgG1 CH3 domain, vi) a hinge region of SEQ ID NO: 66, a heavy or light chain variable domain, a CH3 domain derived from a human IgG1 CH3 domain, optionally a peptidic linker, and a scFv, vii) a hinge region of SEQ ID NO: 66, a heavy or light chain variable domain, a CH3 domain derived from a human IgG1 CH3 domain, optionally a peptidic linker, and a scFab, viii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a second human IgG1 CH1 domain, ix) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a third heavy chain variable domain, x) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFv, xi) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, and a scFab, xii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second human IgG1 CH1 domain, and a second light chain variable domain, xiii) a second heavy chain variable domain, a first human IgG1 CH1 domain, a hinge region of SEQ ID NO: 66, a first heavy or light chain variable domain, a CH3 domain derived from a human IgG1 CH3 domain, optionally a peptidic linker, a second light chain variable domain, and a second human IgG1 CH1 domain, xiv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a third heavy chain variable domain, and a human kappa or lambda light chain constant domain, and xv) a second heavy chain variable domain, a human IgG1 CH1 domain, a hinge region of SEQ ID NO: 66, a first heavy or light chain variable domain, a CH3 domain derived from a human IgG1 CH3 domain, optionally a peptidic linker, a human kappa or lambda light chain constant domain, and a third heavy chain variable domain, comprising the knob-mutation if the first polypeptide comprises the hole-mutations, or the hole-mutations if the first polypeptide comprises the knob-mutation, wherein i) the first variable domain of the fourth polypeptide is a heavy chain variable domain if the first variable domain of the first polypeptide is a light chain variable domain, or ii) the first variable domain of the fourth polypeptide is a light chain variable domain if the first variable domain of the first polypeptide is a heavy chain variable domain, and the sixth polypeptide is a polypeptide comprising a further light chain variable domain and a light chain constant domain, wherein the sixth polypeptide is covalently bound to the fourth polypeptide by a disulfide bond.

23. The pharmaceutical formulation according to any one of embodiments 18 to 22, wherein the first variable domain of the first polypeptide and the first variable domain of the fourth polypeptide form a functional binding site, and the first variable domain of the second polypeptide and the first variable domain of the fifth polypeptide form a non-functional pair of variable domains.

The following examples, sequences and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 3A: with D356K (hole); FIG. 3B: with K370E (knob); FIG. 3C: with E357K (hole); FIG. 3D: with K439E (knob).

FIG. 7A: Scheme of the exchange reaction; FIG. 7B: SDS-page of the NiNTA-purification; NiNTA-bound (upper panel) represents proteins eluted from NiNTA, NiNTA flow through (lower panel) are proteins that do not contain a His-6 (SEQ ID NO: 67) or His-8 (SEQ ID NO: 68) Tag; n.r.=non-reduced, r.=reduced; M=marker.

FIG. 13: Matrix for the generation and characterization of bsAb diversity via exchange reaction according to the current invention using a miniaturized high-throughput- and automation-compatible approach.

FIG. 19A: KappaSelect;
FIG. 19B: SEC
profiles are exemplarily shown for LeY-proDig (knob)-MHCFcRP(hole).

FIG. 20A: LeY-proDig (knob)-MHCFcRP (hole), LeY-proDig (hole)-MHCFcRP (knob), MSLN-proDig (hole)-MHCFcRP (knob); FIG. 20B: LeY-proCD3 (knob)-MHCFcRP (hole), LeY-proCD3 (hole)-MHCFcRP (knob), LeY-proCD-AG-2 (knob)-MHCFcRP (hole), LeY-proCD-AG-2 (hole)-MHCFcRP (knob).

FIG. 26: Principle of on-cell conversion of different antigen targeting 2/3-BiFab prodrugs to fully functional cell bound activated tri-specific TriFabs.

FIG. 30A: PBMCs of Donor 1; FIG. 30B: PBMCs of Donor 2.

FIG. 31A: Co-culture of PBMCs and A431 cells with anti-EGFR-proCD3 2/3-BiFabs. FIG. 31B: Co-culture of PBMCs and HELA cells with anti-AG-4-proCD3 2/3-BiFabs. LDH release serves as indicator for cell-mediated killing of the targeted tumor cells.

FIGS. 32A, 32B, 32C, 32D and 32E: Cytokine amounts in supernatant after co-culture of PBMCs and HELA with anti-AG-4-proCD3 2/3-BiFabs at molar concentrations of 4 nM. FIG. 32A: IL-2 amounts; FIG. 32B: IFNγ amounts; FIG. 32C: Granzyme B amounts; FIG. 32D: TNFα amounts; FIG. 32E: legend.

FIGS. 36A and 36B: FACS analysis of dye binding on cell surface upon TriFab derivative conversion. FIG. 36A: Dig-Cy5; FIG. 36B: Bio-488.

FIGS. 46A and 46B: FACS analysis of Dig-Cy5 binding on cell surface upon application of CH2-containing 2/3-BiFabs. A Dig binding site is just converted upon application of both respective BiFabs. Top to bottom: MCF-7+Dig-Cy5; knob-educt; hole-educt; on-cell shuffling/exchange reaction; product control.

FIG. 46A: variable domains at the C-terminus of the Fc-region;

FIG. 46B: variable domains between Fc-region and targeting Fab.

FIG. 47: The molecular setup of a CH2-containing BiFab for on cell generation of a functional CD3 binding site.

FIGS. 49A, 49B and 49C: Negative Stain Transmission Electron Microscopy (NS-TEM) analysis reveals molecular shape and flexibility of 2/3-BiFabs. FIG. 49A: anti-AG-4-proCD3 (hole)-MHCFcRP (knob); FIG. 49B: AG-3-proCD3 (knob)-MHCFcRP (hole); FIG. 49C: anti-AG-4/CD3/AG-3-antibody.

EXAMPLES

Example 1

Design and Modular Composition of 2/3-IgGs
General Remarks

Figure 1:
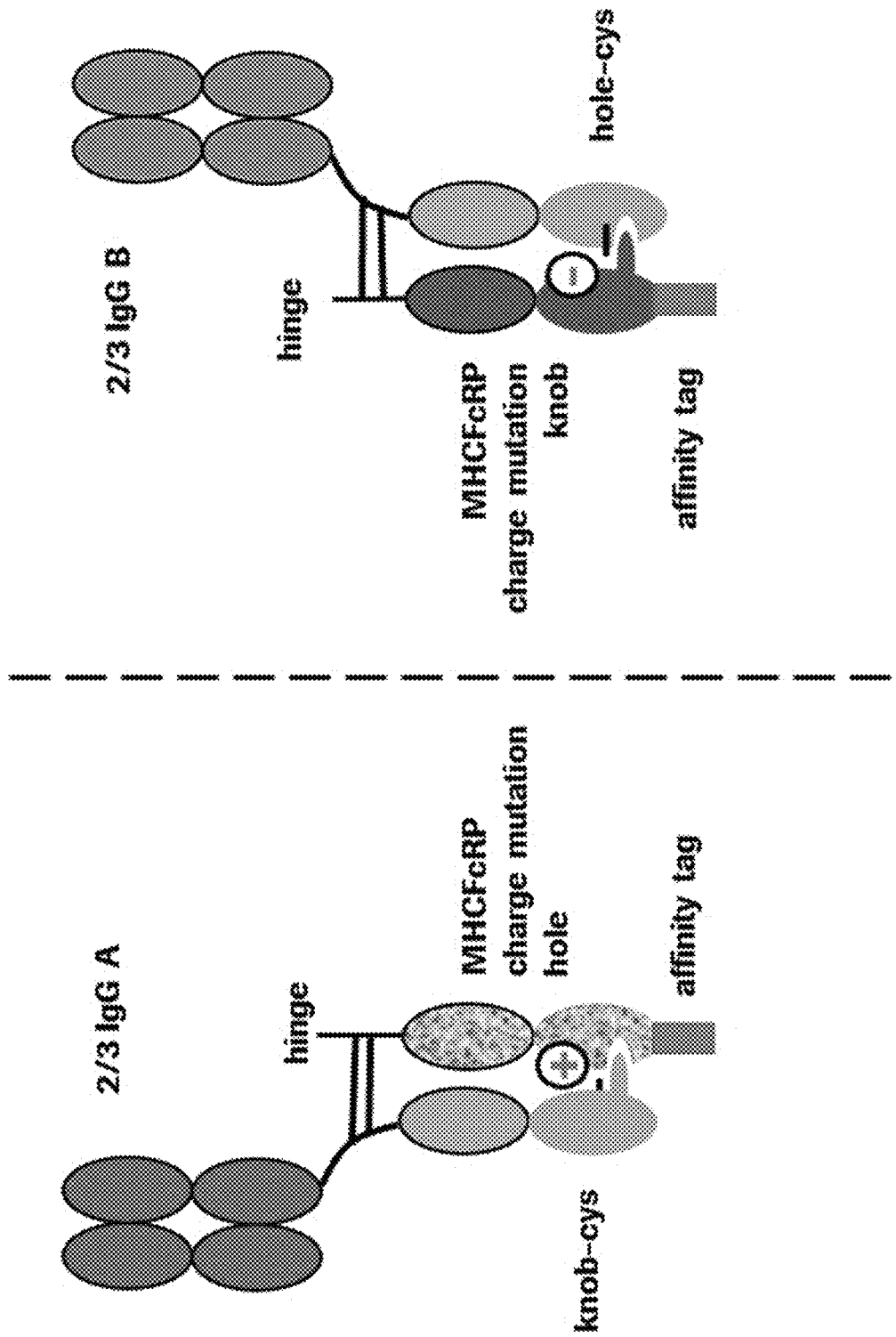
FIG. 1: Design and modular composition of exemplary 2/3-IgGs that can be used in the method according to the current invention.
Figure 2:
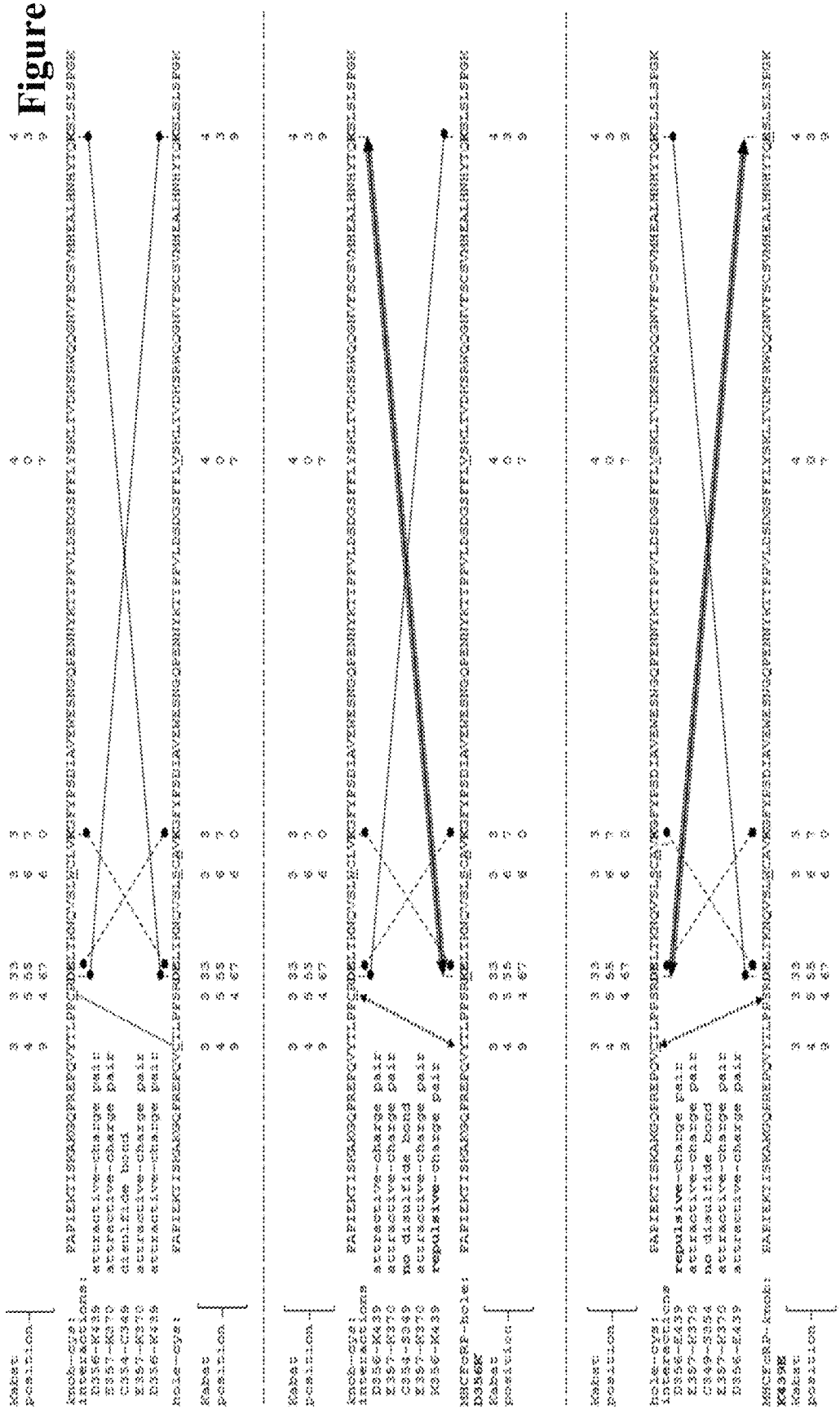
FIG. 2: Interactions between knob-cys and hole-cys heavy chains (upper part) and knob-cys heavy chain and MHCFcRP (middle and lower part). The covalent disulfide bond is indicated with a dashed line, attractive interaction pairs are depicted with line between full spheres, repulsive interactions or resulting steric hindrance are indicated with double arrows lines. Figure discloses SEQ ID NOS 101-102, 101, 103, 102 and 104, respectively, in order of appearance.
Figure 3A:
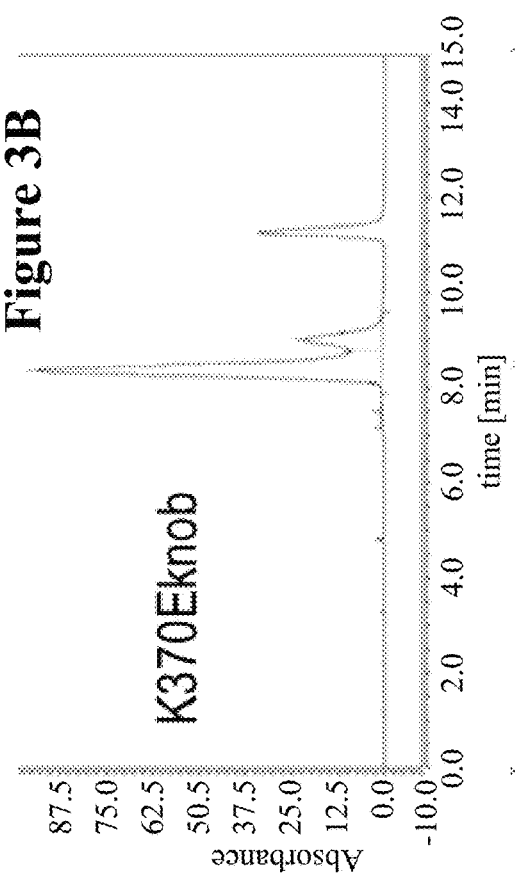
FIGS. 3A, 3B, 3C and 3D: SEC chromatograms of the purified 2/3-IgGs with different MHCFcRPs: shown are SEC profiles of 2/3-IgG preparations following protein A extraction from cell culture supernatants; the main peak of each profile represent the 2/3-IgG; with fluorescein (fluos; anti-fluos) or biotin (bio; anti-bio) binding site/specificities (see Example 2).
Figure 3B:
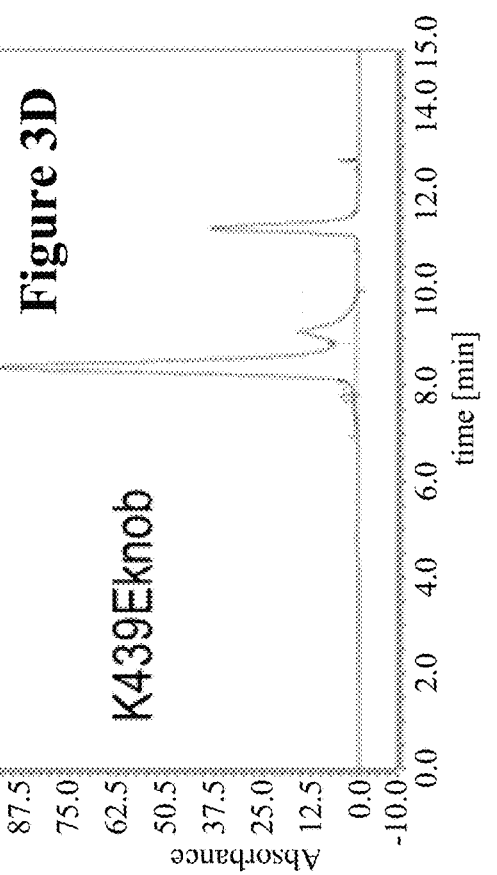
Figure 3C:
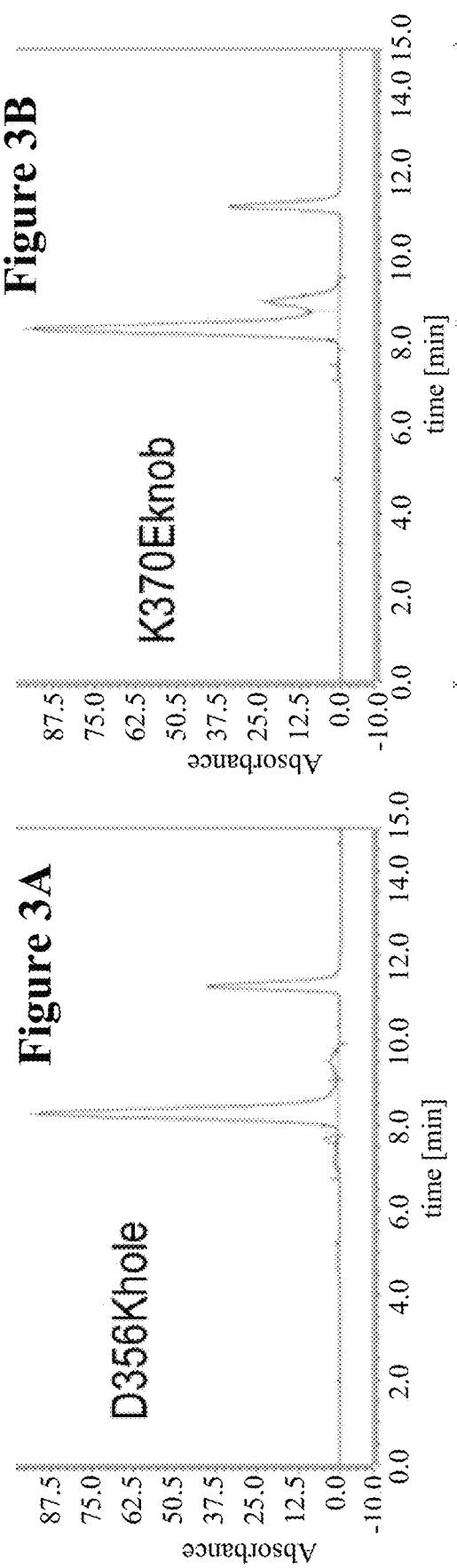
Figure 3D:
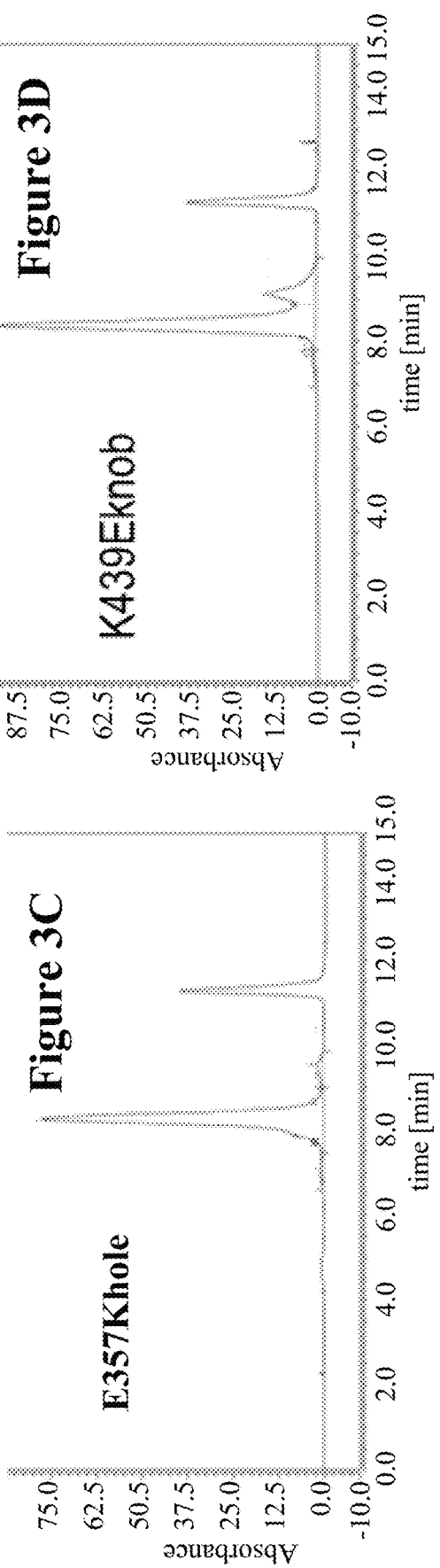

FIG. 1 shows the design and modular composition of the 2/3-IgGs used in the methods according to the current invention. These 2/3-IgGs are composed of three individual chains: one light chain (normally a full length light chain comprising a light chain variable domain and a light chain constant domain), one heavy chain (normally a full length heavy chain comprising a heavy chain variable domain and all heavy chain constant domains including a hinge region) and one heavy chain Fc-region polypeptide (normally a heavy chain Fc-region fragment comprising hinge-CH2-CH3). The variable domains of the light chain and the heavy chain form a functional binding site. The heavy chain (normally derived from the human IgG1 subclass) contains either the knob-cys-mutations or the hole-cys-mutations (the mutations T366W and S354C in the CH3 domain of an antibody heavy chain is denoted as "knob-cys-mutations" and the mutations T366S, L368A, Y407V, Y349C in the CH3 domain of an antibody heavy chain are denoted as "hole-cys-mutations" (numbering according to Kabat EU index)) in CH3 to enable the formation of knob-into-hole Fc-region dimers. The heavy chain Fc-region polypeptide is a so called 'dummy-Fc'/MHCFcRP (see below), i.e. an IgG1 derivative that lacks VH and CH1, starts at the N-terminus with at least part of the hinge region sequence and harbors a His6 tag (SEQ ID NO: 67) at its C-terminus. In addition, the heavy chain Fc-region polypeptide of the 2/3-IgG contains in its CH3 domains either the knob-mutation or the hole-mutations (the mutation T366W in the CH3 domain of an antibody heavy chain is denoted as "knob-mutation" and the mutations T366S, L368A, Y407V in the CH3 domain of an antibody heavy chain are denoted as "hole-mutations" (numbering according to Kabat EU index)). In addition to the knob- or hole-mutation(s) the heavy chain Fc-region polypeptide comprises a destabilizing mutation introducing one (i.e. a single additional) repulsive charge with respect to the wild-type sequence: D356K or E357K or K370E or K439E; SEQ ID NO: 35 to 38; this mutated heavy chain Fc-region polypeptide is denoted as MHCFcRP in the following.

The heavy chain and the MHCFcRP can form two types of heterodimers depending on the distribution of the knob-into-hole-mutations therein:
  i) heavy chain-knob:: MHCFcRP-hole, and
  ii) heavy chain-hole:: MHCFcRP-knob.

Those heterodimers are, however, somewhat 'flawed' as the complementary Fc-region lacks the additional CH3 cysteine necessary to form inter-chain disulfides to the heavy chain, and also these contain charge mutations without matching heavy chain counterparts.

Example 2

Expression and Purification of 2/3-IgGs

Expression of 2/3-IgGs was achieved by co-transfection of plasmids encoding light chain, heavy chain (with knob or hole-mutations) and matching MHCFcRP (hole or knob) into mammalian cells (e.g. HEK293) via state of the art technologies.

In more detail, for example, for the production of the 2/3-IgGs by transient transfection (e.g. in HEK293 cells) expression plasmids based either on a cDNA organization with or without a CMV-Intron A promoter or on a genomic organization with a CMV promoter were applied.

Beside the antibody expression cassettes, the plasmids contained:
- I an origin of replication, which allows replication of this plasmid in *E. coli*,
- a ß-lactamase gene, which confers ampicillin resistance in *E. coli.*, and
- the dihydrofolate reductase gene from *Mus musculus* as a selectable marker in eukaryotic cells.

The transcription unit of each antibody gene was composed of the following elements:
- unique restriction site(s) at the 5'-end
- the immediate early enhancer and promoter from the human cytomegalovirus,
- followed by the Intron A sequence in the case of the cDNA organization,
- a 5'-untranslated region of a human antibody gene,
- an immunoglobulin heavy chain signal sequence,
- the antibody chain either as cDNA or in genomic organization (the immunoglobulin exon-intron organization is maintained),
- a 3'-non-translated region with a polyadenylation signal sequence, and
- unique restriction site(s) at the 3'-end.

The fusion genes comprising the antibody chains were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The 2/3-IgGs were generated by transient transfection with the respective plasmid using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with the respective expression plasmid and 293fectin™ or fectin (Invitrogen). For 2 L shake flask (Corning) HEK293-F cells were seeded at a density of 1*10$^6$ cells/mL in 600 mL and incubated at 120 rpm, 8% $CO_2$. The day after the cells were transfected at a cell density of approx. 1.5*10$^6$ cells/mL with ca. 42 mL mix of A) 20 mL Opti-MEM (Invitrogen) with 600 µg total plasmid DNA (1 µg/mL) and B) 20 ml Opti-MEM+1.2 mL 293 fectin or fectin (2 µL/mL). According to the glucose consumption glucose solution was added during the course of the fermentation. Correctly assembled 2/3-IgGs were secreted into culture supernatants like standard IgGs. The supernatant containing the secreted 2/3-IgG was harvested after 5-10 days and 2/3-IgGs were either directly purified from the supernatant or the supernatant was frozen and stored.

Because 2/3-IgGs contain an Fc-region they were purified by applying standard protein A affinity chromatography: The 2/3-IgGs were purified from cell culture supernatants by affinity chromatography using MabSelectSure-Sepharose™ (GE Healthcare, Sweden) and Superdex 200 size exclusion (GE Healthcare, Sweden) chromatography.

Briefly, sterile filtered cell culture supernatants were captured on a MabSelectSuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted antibody fractions were pooled and neutralized with 2 M Tris, pH 9.0. The antibody pools were further purified by size exclusion chromatography using a Superdex 200 26/60 GL (GE Healthcare, Sweden) column equilibrated with 20 mM histidine, 140 mM NaCl, pH 6.0. The 2/3-IgG containing fractions were pooled, concentrated to the required concentration using Vivaspin ultrafiltration devices (Sartorius Stedim Biotech S.A., France) and stored at −80° C.

Purity and integrity were analyzed after each purification step by CE-SDS using microfluidic Labchip technology (Caliper Life Science, USA). Protein solution (5 µl) was prepared for CE-SDS analysis using the HT Protein Express Reagent Kit according manufacturer's instructions and analyzed on LabChip GXII system using a HT Protein Express Chip. Data were analyzed using LabChip GX Software.

For example, the following 2/3-IgGs have been produced by co-expression of corresponding L-chain, H-chain and MHCFcRP encoding plasmids:

|  |  | anti-fluorescein-2/3-IgG-knob-cys+ | | anti-biocytinamid-2/3-IgG-hole-cys+ | |
|---|---|---|---|---|---|
|  | MHCFcRP | D356K-hole | E357K-hole | K370E-knob | K439E-knob |
| HEK293 | protein A [mg/L] | 122 | 94 | 129 | 117 |
|  | SEC [% yield] | >70 | >50 | >70 | >70 |
| Expi-system | protein A [mg/L] | >200 | >200 | >200 | >200 |
|  | SEC [% yield] | >90 | >90 | >80 | >80 |

The corresponding SEC chromatograms are shown in FIG. 3.

Example 3

Generation of Bispecific Antibodies (bsAbs) by 2/3-IgG-Exchange Reaction

Figure 4:
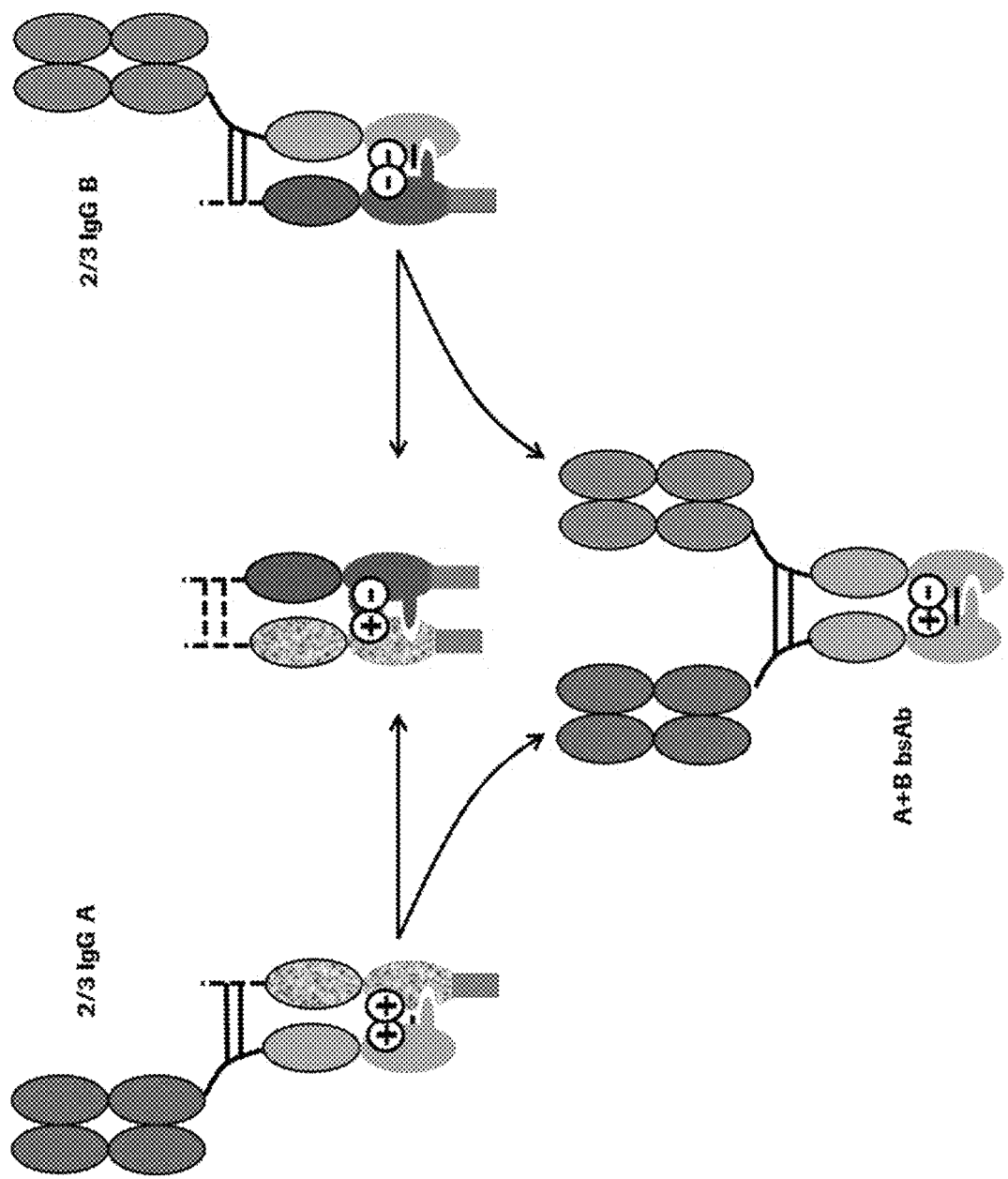
FIG. 4: Generation of bsAbs (bispecific antibodies) by exchange reaction according to the current invention exemplified with 2/3-IgGs.

The 2/3-IgGs that contain a light chain, a heavy chain and MHCFcRP have been generated in two types of KiH heterodimers: full length heavy chain-knob:: MHCFcRP-hole and full length heavy chain-hole:: MHCFcRP-knob. Both types of 2/3-IgGs are somewhat 'flawed' as the MHCFcRP lacks the additional CH3 cysteine necessary to form interchain disulfides to the heavy chain, and the MHCFcRP contains charge mutations without matching counterpart in the full length heavy chain. The modules that make up those flawed heterodimers, however, are capable to rearrange to bispecific heterodimers with matching charges as shown in FIG. 4. The full length heavy chain (knob-cys) of 2/3-IgG A and the full length heavy chain (hole-cys) from 2/3-IgG B form a matching heterodimer. Matching heterodimers are also formed when MHCFcRP (hole-charge) interacts with MHCFcRP (knob-charge). Thus, exchange reactions based on temporary separation of starting heterodimers of two different 2/3-IgGs resulted in products that contain preferentially (charge) matching heterodimers. Exchange reactions therefore converted two monospecific 2/3-IgGs to one bispecific IgG and one MHCFcRP heterodimer:

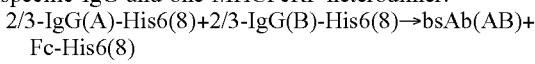

2/3-IgG(A)-His6(8)+2/3-IgG(B)-His6(8)→bsAb(AB)+ Fc-His6(8)

The exchange reaction was initiated by a reduction step (e.g. by applying 2-MEA or TCEP at various concentrations) to break especially the hinge-region inter-chain disulfide bonds. Chain rearrangement occurred spontaneously thereafter.

Therefore, anti-fluorescein-2/3-IgG and anti-biocytinamid-2/3-IgG input molecules were mixed in equimolar amounts at a protein concentration of 100 μg/ml in a total volume of 40 μl 1×PBS+0.05% Tween 20 with the indicated TCEP concentrations on a 384 well REMP® plate (Brooks, #1800030). After centrifugation, plates were sealed and incubated for one hour at 27° C.

A biotin-fluorescein bridging ELISA was subsequently used to quantify bispecific antibody. Therefore, white Nunc® MaxiSorp™ 384 well plates were coated with 1 μg/ml albumin-fluorescein isothiocyanate conjugate (FITC, Sigma, #A9771) and incubated overnight at 4° C. After washing 3 times with 90 μl PBST-buffer (PBST, bidest water, 10×PBS+0.05% Tween 20) blocking buffer (1×PBS, 2% gelatin, 0.1% Tween-20) was added 90 μl/well and incubated for one hour at room temperature. After washing 3 times with 90 μl PBST-buffer, 25 μl of a 1:10 dilution of each exchange reaction was added to each well. After incubation for one hour at room temperature, plates were again washed 3 times with 90 μl PBST-buffer. 25 μl/well biotin-Cy5 conjugate in 0.5% BSA, 0.025% Tween-20, 1×PBS was added to a final concentration of 0.1 μg/ml and plates were incubated for one hour at room temperature. After washing 6 times with 90 μl PBST-buffer, 25 μl 1×PBS were added to each well. Cy5 fluorescence was measured at an emission wavelength of 670 nm (excitation at 649 nm) on a Tecan Safire 2 Reader.

Figure 5:
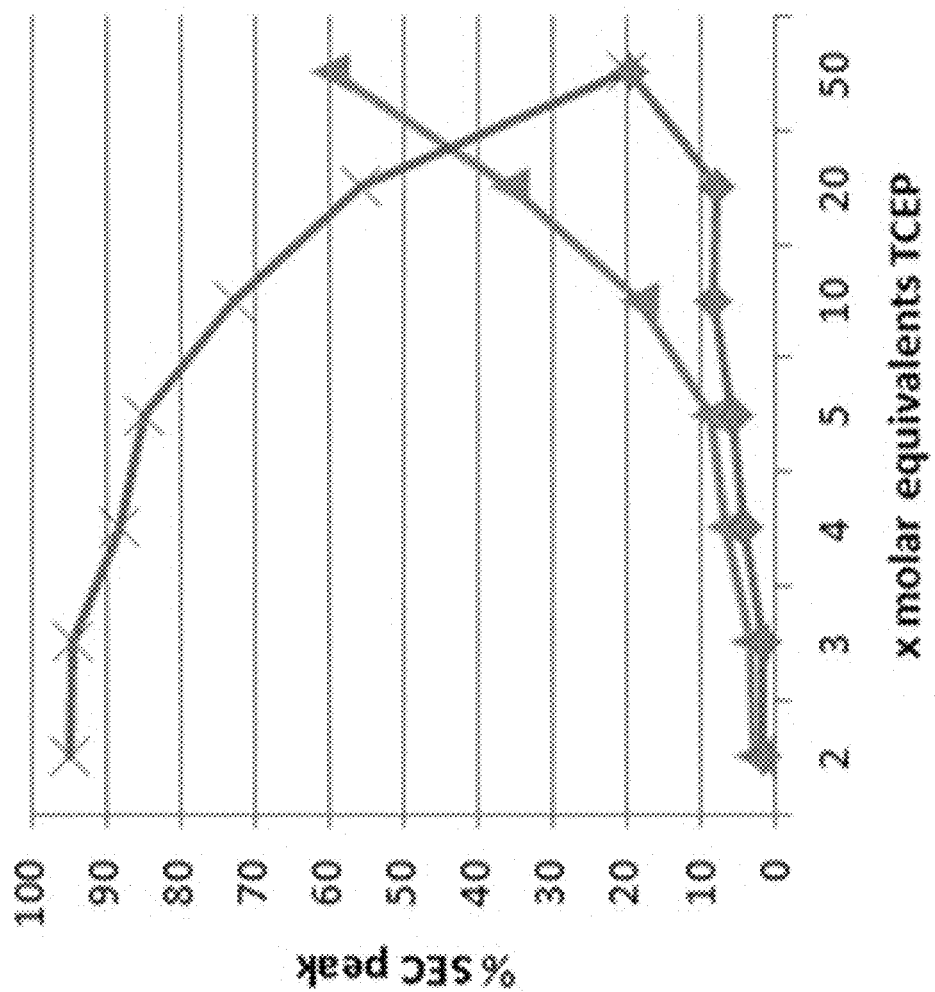
FIG. 5: TCEP (x molar equivalents in relation to 2/3 input IgGs) is applied to (partially) reduce the hinge-disulfide bonds. SEC differentiates 2/3-IgG starting molecule, generated bsAb and dimeric MHCFcRP. All reactions at different TCEP concentrations were stopped after the same incubation time (triangle: bsAb; cross: 2/3-IgG, diamond: dimeric MHCFcRP).

FIG. 5 shows the results of analyses of the redox conditions for generation of bsAbs by 2/3-IgG-exchange. TCEP is applied to (partially) reduce the hinge-disulfide bonds between the heavy chain Fc-region polypeptides, i.e. between the full length half-IgG and the MHCFcRP. Chain exchange can be identified by SEC which differentiates 2/3-IgG input, bsAb output and MHCFcRP by-product. The yield of the exchange reactions depending on the ratio between 2/3-IgG and TCEP are shown in FIG. 5 (for comparison all reactions were analyzed after the same reaction time).

Figure 6:
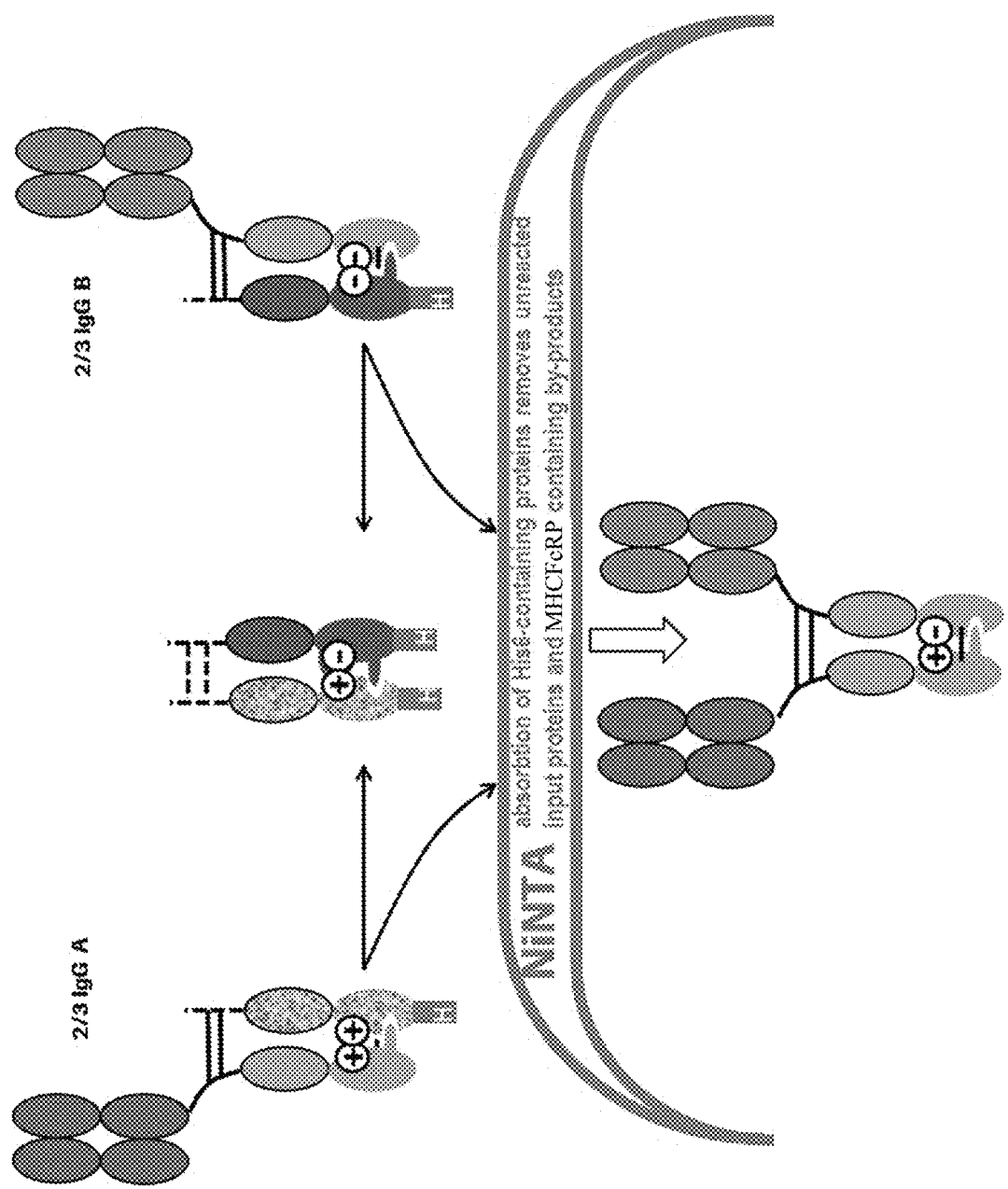
FIG. 6: Scheme of removal of undesired non-reacted input molecules and by-products from desired bsAb products if reaction is performed in vitro. Figure discloses "His6" as SEQ ID NO: 67.
Figure 7B:
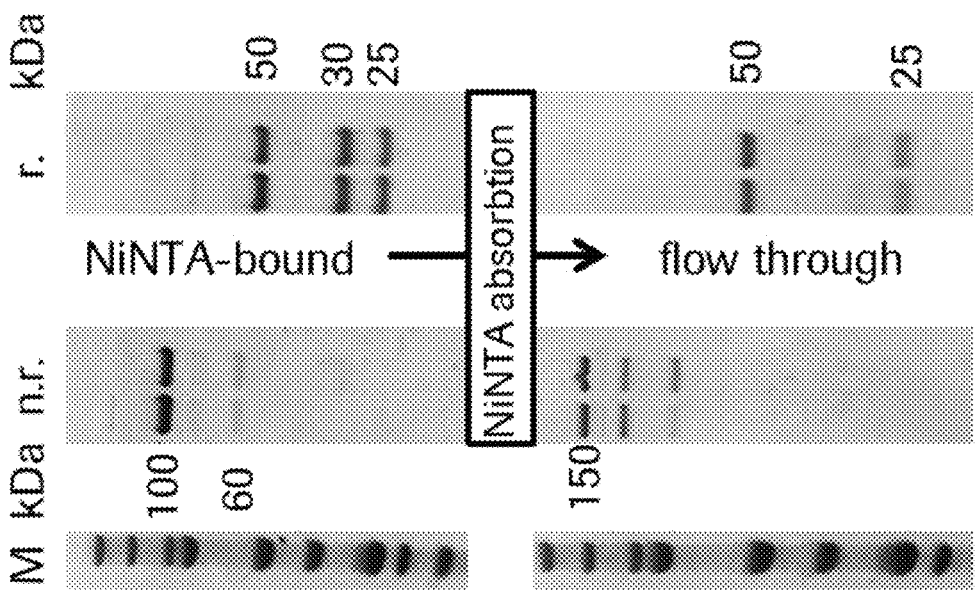
FIGS. 7A and 7B.
Figure 7A:
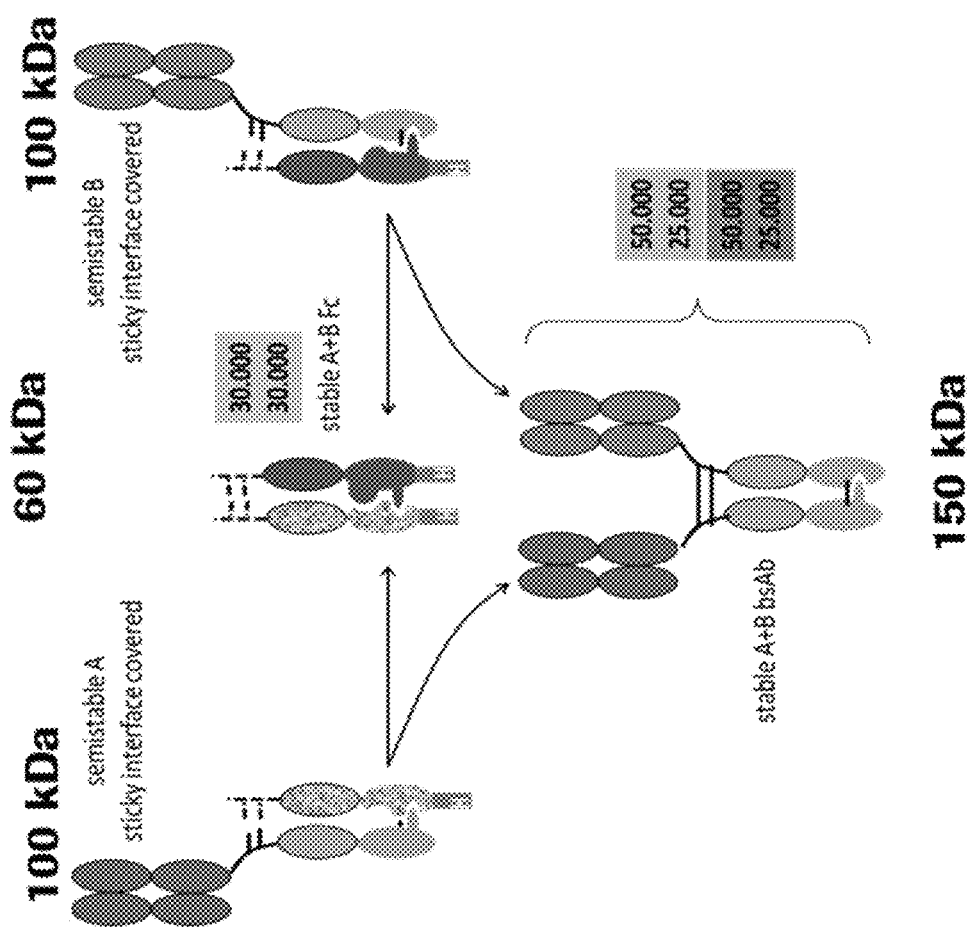

All 2/3-IgG starting molecules, all non-wanted by-products, as well as all aggregates that were potentially generated during the exchange reaction harbor affinity tags (His6 (SEQ ID NO: 67) or His8 (SEQ ID NO: 68)). The desired bsAb produced in the exchange reaction is the only molecule that does not carry a His-tag. Therefore, a simple NiNTA absorption step was applied to remove all undesired molecules (see FIGS. 6 and 7). The remaining bsAbs (not depleted by NiNTA absorption) were directly applied to screening procedures and analyzed to identify bsAbs with desired functionalities.

Example 4

Figure 8:
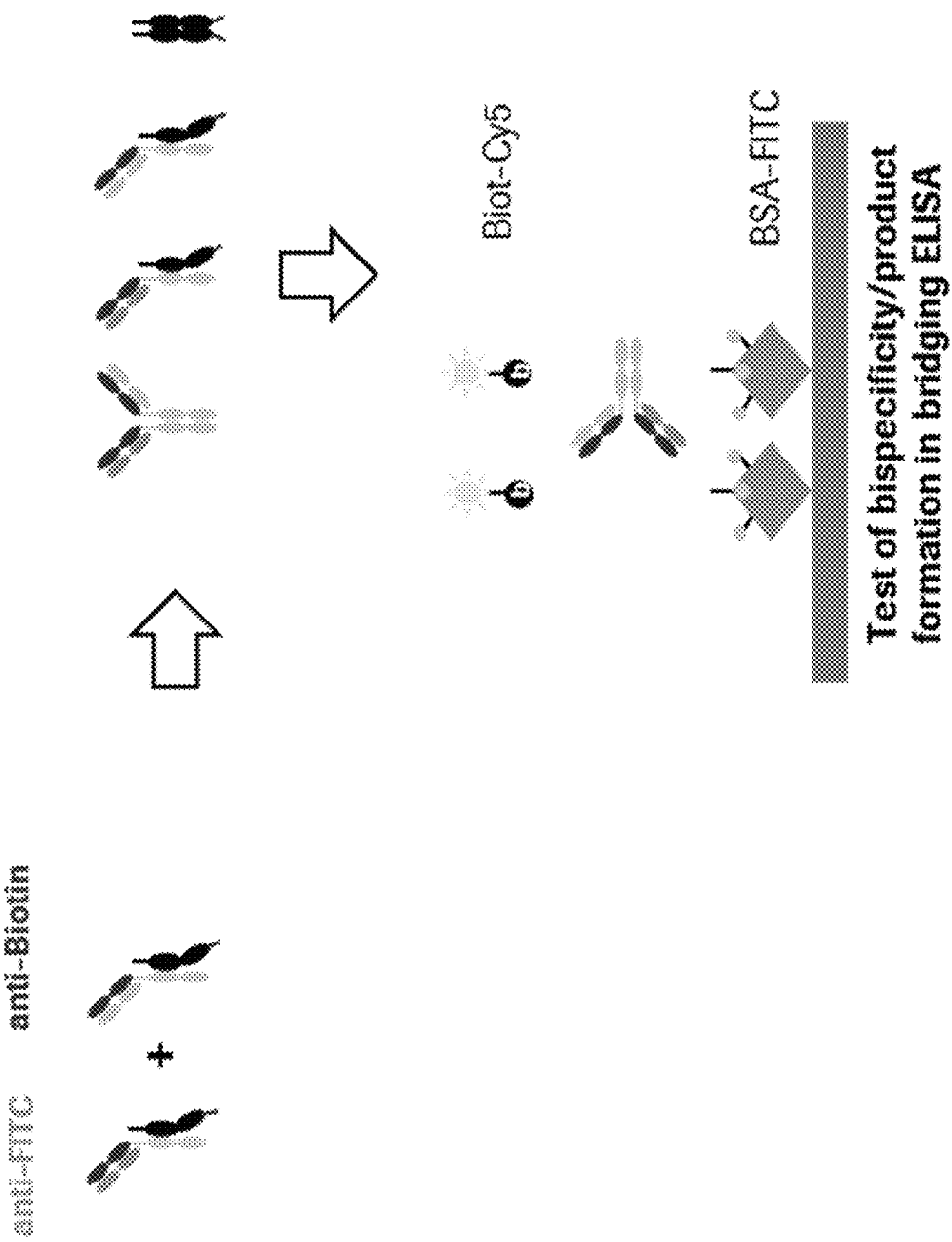
FIG. 8: Bispecific functionality of bsAbs generated by exchange reaction according to the invention. Functionality was assessed by a bridging ELISA that enables detection of simultaneous binding of binding sites of a bispecific antibody. Antigen A coated to the ELISA plate was fluorescein (fluos-BSA, FITC-BSA) and antigen B was biotin (bio-Cy5), which becomes detected by its fluorescence.

Functional Assessment of Bispecific Antibodies (bsAbs) Generated by 2/3-IgG-Exchange Reaction Bispecific functionality of bsAbs that were generated as products of 2/3-IgG-exchange reactions was evaluated by bridging-ELISA assays. FIG. 8 shows as an example the binding result for an anti-fluorescein/biocytinamid bispecific antibody generated by an exchange reaction as reported herein. In the reaction biocytinamid (bio)-binding 2/3-IgG and a fluorescein (fluos)-binding 2/3-IgG as starting molecules were employed. The fluos-binding arm of anti-fluos/bio bispecific antibodies bind to fluos-BSA coated ELISA plates. Subsequent exposure to bio-Cy5 generates signals only upon bsAb-mediated capture of bio-Cy5 via the bio-binding arm of the bsAb. Because bridging-mediated signals occur only with bsAbs but not with either monospecific Fluos or Bio binders, no signals were observed when using only 2/3-IgGs in the assay. Because of that and because the exchange reaction does not force molecule aggregation, such bridging ELISA can be performed directly on exchange reaction mixes, without requiring prior NiNTA-mediated depletion of non-bsAb molecules. Signals observed when applying the reaction mix indicated successful generation and presence of functional bsAbs. Signal generation via bridging ELISA was dependent on the amount of input entities used in the exchange reaction.

Example 5

The Exchange Reaction is Functional Independent of Binding Specificities or V-Region Composition of Starting 2/3-IgGs A variety of 2/3-IgGs was produced to evaluate if 2/3-IgG production as well as exchange reactions work for different antibodies independent of their binding specificities and V-region composition, as well as for different antibody combinations. Therefore, 2/3-IgGs with binding specificities for biocytinamid (bio), digoxigenin (dig), fluorescein (fluos), LeY-carbohydrate (LeY), VEGF and PDGF were used. These were produced by co-transfection of expression plasmids encoding full length light chains, knob- or hole-full length heavy chains and mutated heavy chain Fc-region polypeptides as described above.

| Chain MHCFcRPs | SEQ ID NO: |
|---|---|
| hole-D356K-His8 | 35 |
| hole-E357K-His8 | 36 |
| knob-K370E-His8 | 37 |
| knob-K439E-His8 | 38 |
| anti-bio antibody full length light chain | 39 |
| anti-bio antibody full length heavy chain-knob-cys | 40 |
| anti-bio antibody full length heavy chain-hole-cys | 41 |
| anti-fluos antibody full length light chain | 42 |
| anti-fluos antibody full length heavy chain-knob-cys | 43 |
| anti-fluos antibody full length heavy chain-hole-cys | 44 |
| anti-dig antibody full length light chain | 45 |
| anti-LeY antibody full length light chain | 46 |
| anti-PDGF antibody full length light chain | 47 |
| anti-VEGF antibody full length light chain | 48 |
| anti-dig antibody VH-CH1 fragment | 49 |
| anti-LeY antibody VH-CH1 fragment | 50 |
| anti-PDGF antibody VH-CH1 fragment | 51 |
| anti-VEGF antibody VH-CH1 fragment | 52 |

SEQ ID NO: 49-52 describe the VH-CH1 region of 2/3-IgGs with specificities for dig, VEGF, PDGF and LeY. Those were fused to the hinge-CH2-CH3 regions (i.e. replace the bio VH-CH1 regions) of SEQ ID NO: 40 and 41 to generate complete H-chains with desired specificity. The MHCFcRPs applied for generating these molecules are listed as SEQ ID NO: 35-38.

All of these 2/3-IgGs could be produced and purified to similar yields as for standard IgGs under comparable conditions (see Example 2). Examples for expression of these 2/3-IgGs with different binding specificities are shown in the following Table.

| 2/3-IgG = 1/2-IgG-hole-cys + MHCFcRP-knob-E357K | | | | |
|---|---|---|---|---|
| | anti-dig | anti-VEGF | anti-PDGF | anti-LeY | anti-fluos |
| Protein A [mg/L] | 76 | 76 | 96 | 81 | 94 |
| SEC [% yield] | 40-60 | >70 | >90 | >95 | >50 |

In the exchange-matrix, which was applied to generate bsAbs of different specificity, combinations of 2/3-IgGs with binding specificities for fluorescein, biocytinamid, VEGF, PDGF and digoxigenin in all combinations as shown in the following Table were employed.

| exchange reaction between | MHCFcRP-knob-E357K | | | | |
|---|---|---|---|---|---|
| | | bio | fluos | Dig | VEGF | PDGF |
| MHCFcRP-hole-K370E | bio | — | bio fluos | bio dig | bio VEGF | bio PDGF |
| | fluos | fluos bio | — | fluos dig | fluos VEGF | fluos PDGF |
| | dig | dig bio | dig fluos | — | dig VEGF | dig PDGF |
| | VEGF | VEGF bio | VEGF fluos | VEGF Dig | — | VEGF PDGF |
| | PDGF | PDGF bio | PDGF fluos | PDGF Dig | PDGF VEGF | — |

The chain exchange of starting 2/3-IgGs and generation of bsAbs with desired specificity combinations was monitored by bridging ELISA (see Example 4), wherein plate-coated antigens and signal-generating antigen-conjugates/complexes were applied that match the different bsAb specificity combinations.

The results of the bridging ELISA applied to assess the functionalities of different bsAb combinations are shown in the following Tables. Only bsAbs that recognize their cognate pair of antigens present as capturing or detection antigen generate signals in the bridging ELISA. Other bsAbs generated in the matrix are negative due to absence of at least one specificity.

TABLE

Bridging ELISA confirms the functionality of bsAbs generated. Shown are the relative signal intensities within one assay at the input molecule concentration 1.3 μM. The highest value is set to 100% as a reference.

| assay capture detection exchange reaction between | biocytinamid-fluorescein fluorescein-albumin biocytinamid-Cy5 MHCFcRP-hole-K370E |
|---|---|

| | | bio | fluos | dig | VEGF3 | PDGF |
|---|---|---|---|---|---|---|
| MHCFcRP-knob-E357K | bio | — | 100% | 2.5% | 2.5% | 1.9% |
| | fluos | 97.6% | — | 2.5% | 1.9% | n.a. |
| | dig | 2.2% | 2.5% | — | 2.2% | 2.2% |
| | VEGF | 1.9% | 2.2% | 2.3% | — | 2.3% |
| | PDGF | 1.8% | n.a. | 2.3% | 1.9% | — |

N.a. = not available.

| assay capture detection exchange reaction between | digoxigenin-fluorescein fluorescein-albumin digoxygenin-Cy5 MHCFcRP-hole-K370E |
|---|---|

| | | bio | fluos | dig | VEGF | PD1GF |
|---|---|---|---|---|---|---|
| MHCFcRP-knob-E357K | bio | — | 1.9% | 1.6% | 1.4% | 1.3% |
| | fluos | 2.4% | — | 100% | 2.8% | n.a. |
| | dig | 2.0% | 52.5% | — | 2.0% | 1.5% |
| | VEGF | 1.5% | 1.5% | 1.5% | — | 1.5% |
| | PDGF | 1.5% | n.a. | 1.8% | 2.8% | — |

| assay capture detection exchange reaction between | VEGF-biocytinamid VEGF biocytinamid-Cy5 MHCFcRP-hole-K370E |
|---|---|

| | | bio | fluos | dig | VEGF | PDGF |
|---|---|---|---|---|---|---|
| MHCFcRP-knob-E357K | bio | — | 9.0% | 9.3% | 100% | 10.1% |
| | fluos | 10.2% | — | 9.4% | 9.9% | n.a. |
| | dig | 9.0% | 9.1% | — | 8.7% | 9.9% |
| | VEGF | 78.3% | 9.2% | 9.3% | — | 9.5% |
| | PDGF | 10.5% | n.a. | 9.2% | 10.9% | — |

| assay capture detection exchange reaction between | PDGF-biocytinamid PDGF biocytinamid-Cy5 MHCFcRP-hole-K370E |
|---|---|

| | | bio | fluos | dig | VEGF | PDGF |
|---|---|---|---|---|---|---|
| MHCFcRP-knob-E357K | bio | — | 3.0% | 4.1% | 4.4% | 81.8% |
| | fluos | 3.2% | — | 3.1% | 3.3% | n.a. |
| | dig | 3.3% | 3.2% | — | 3.3% | 3.4% |
| | VEGF | 4.0% | 3.1% | 3.1% | — | 3.2% |
| | PDGF | 100% | n.a. | 3.9% | 3.2% | — |

| assay capture detection exchange reaction between | digoxigenin-VEGF VEGF digoxygenin-Cy5 MHCFcRP-hole-K370E |
|---|---|

| | | bio | fluos | dig | VEGF | PDGF |
|---|---|---|---|---|---|---|
| MHCFcRP-knob-E357K | bio | — | 7.2% | 6.2% | 6.4% | 6.1% |
| | fluos | 6.5% | — | 6.3% | 6.5% | n.a. |
| | dig | 6.2% | 6.7% | — | 59.7% | 7.0% |
| | VEGF | 6.1% | 6.6% | 100% | — | 7.0% |
| | PDGF | 6.0% | n.a. | 5.9% | 6.5% | — |

| assay capture detection exchange reaction between | digoxigenin-PDGF PDGF digoxygenin-Cy5 MHCFcRP-hole-K370E |
|---|---|

| | | bio | fluos | dig | VEGF | PDGF |
|---|---|---|---|---|---|---|
| MHCFcRP-knob-E357K | bio | — | 3.0% | 2.9% | 2.9% | 3.0% |
| | fluos | 3.7% | — | 3.2% | 2.8% | n.a. |
| | dig | 2.9% | 3.1% | — | 3.5% | 62.3% |
| | VEGF | 3.1% | 3.3% | 3.0% | — | 2.9% |
| | PDGF | 3.7% | n.a. | 100% | 3.8% | — |

For the VEGF containing bispecific antibodies the same assays have been performed. These also showed only signals above background levels for the respective combinations.

It can be seen that the exchange reaction according to the current invention is a generally applicable method: exchange reactions lead to functional bsAb independent of binding specificities or V-region composition of the starting molecules.

Example 6

Design, Composition and Generation of Format Variants

The 2/3-IgG-exchange reaction of Example 4 was expanded to starting molecules that have either one binding site at the C-terminus of the heavy chain, or heavy chains with binding sites at N- as well as C-terminus. For generation of the exchanged bsAbs the exchange driving principle (conversion of flawed input heterodimers to matching output-heterodimers) was kept unaltered. The composition of the MHCFcRPs was also retained as described above.

Figure 9:
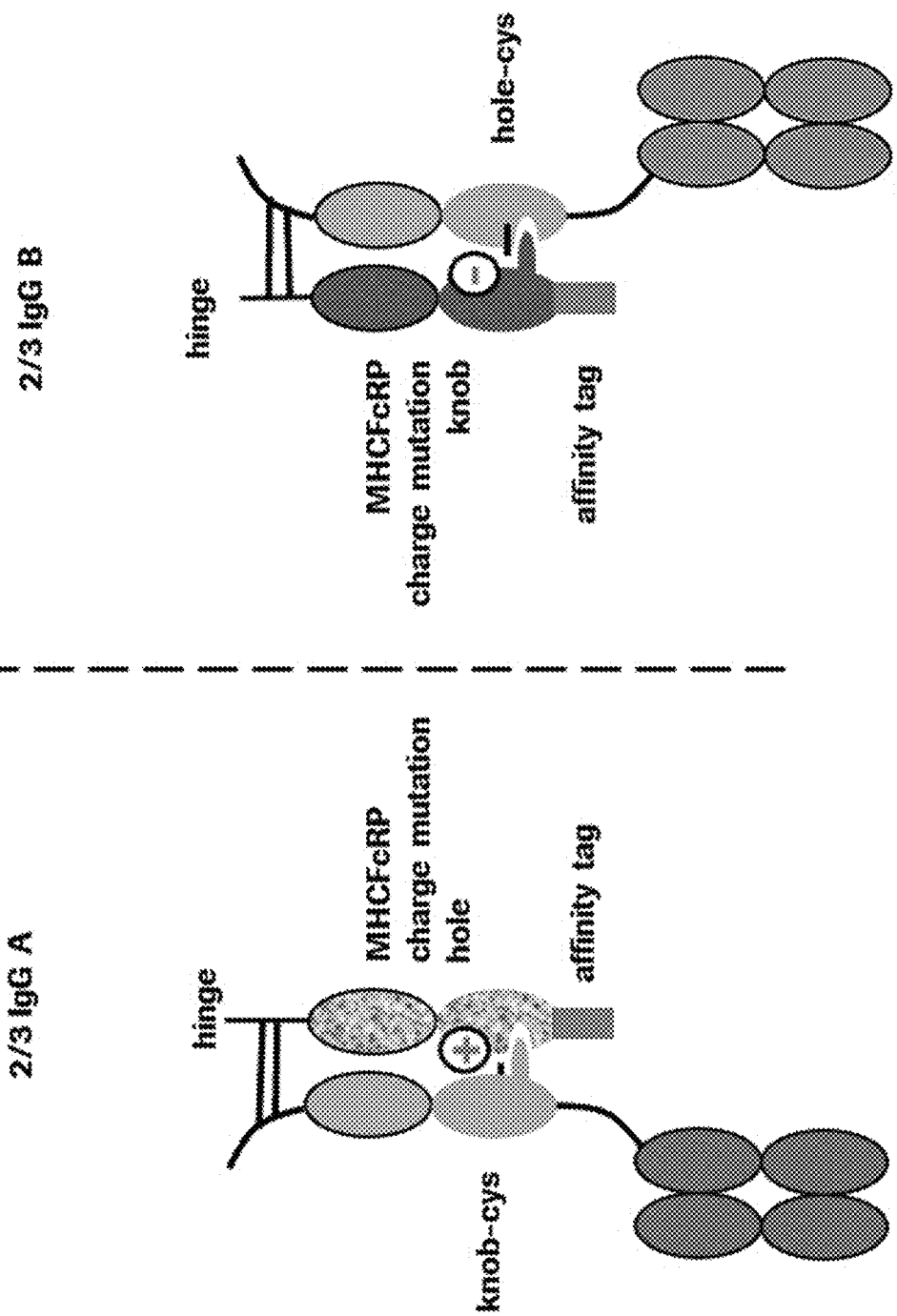
FIG. 9: Exemplary 2/3-IgGs for 2/3-IgG-exchange reaction with binding sites at the C-terminus of the heavy chain.
Figure 10:
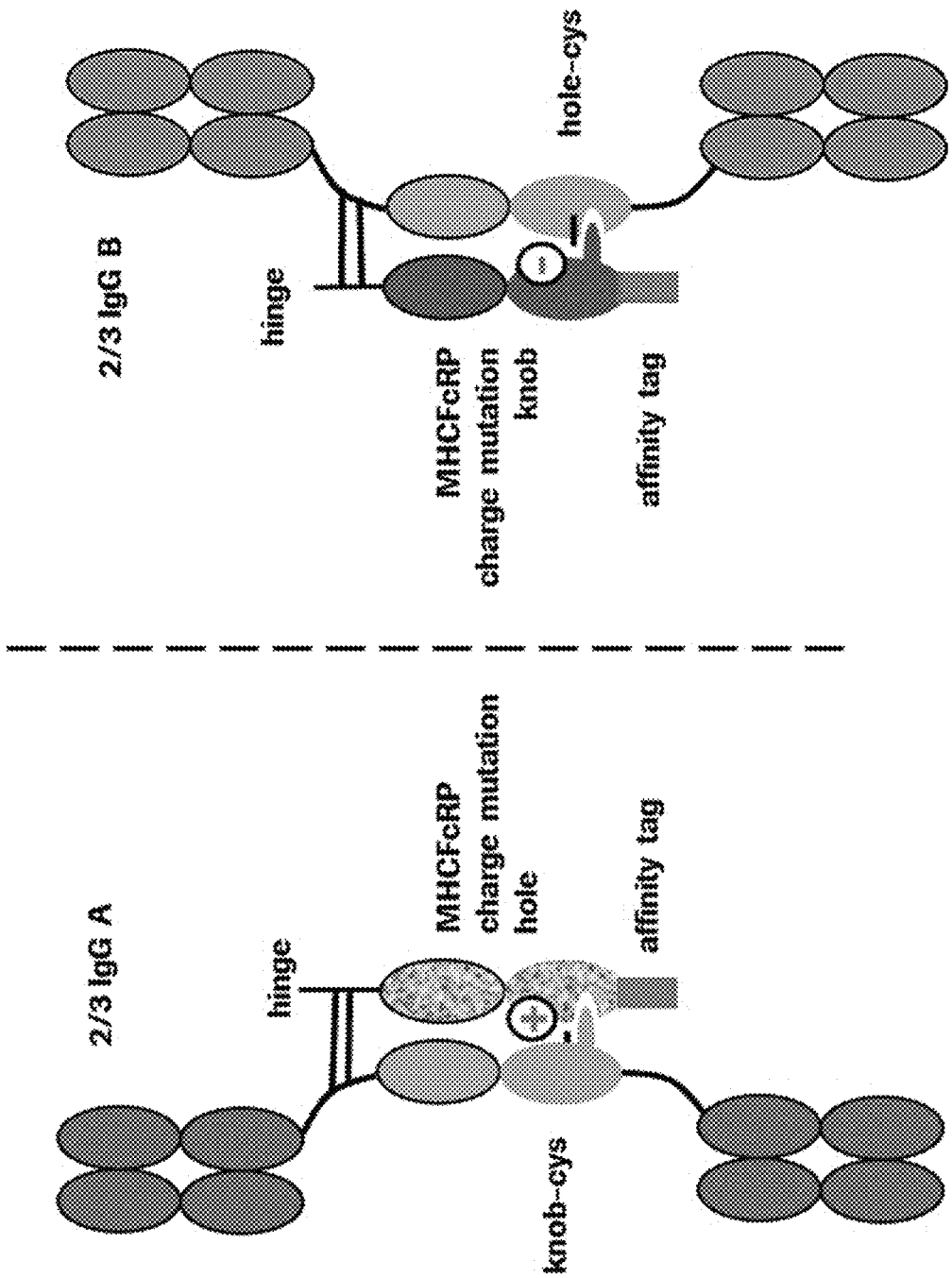
FIG. 10: Exemplary 2/3-IgGs for 2/3-IgG-exchange reaction with binding sites at the N-terminus as well as at the C-terminus of the heavy chain.

FIGS. 1, 9 and 10 show the modular composition of the three 2/3-IgG formats that were applied to generate different bsAb formats. One of the 2/3-IgGs has one Fab arm at the N-terminal position. Another of the 2/3-IgGs has the Fab arm attached via a flexible linker to the C-terminus of the heavy chain (i.e. it starts at the N-terminus with the hinge-region). The third 2/3-IgG has the C-terminal Fab arm as well as the N-terminal Fab arm.

Expression of these 2/3-IgG variants was achieved by co-transfection of plasmids encoding light chain, heavy chain (knob or hole) and corresponding MHCFcRP (hole or knob) into mammalian cells (e.g. HEK293) (see Example 2).

Sequences of the full length heavy chains modified used for the generation of the different bsAb formats are as follows:

| chain<br>MHCFcRPs | SEQ ID NO: |
|---|---|
| hole-D356K-His8 | 35 |
| hole-E357K-His8 | 36 |
| knob-K370E-His8 | 37 |
| knob-K439E-His8 | 38 |
| anti-bio antibody full length heavy chain-hole-cys with C-terminal fusion | 53 |
| anti-bio antibody full length heavy chain-hole-cys with N- and C-terminal fusion | 54 |
| anti-fluos antibody full length heavy chain-hole-cys with C-terminal fusion | 55 |
| anti-fluos antibody full length heavy chain-hole-cys with N- and C-terminal fusion | 56 |

The 2/3-IgGs are secreted into culture supernatants like standard IgGs and were purified by standard protein A affinity chromatography (see Example 2). Size-exclusion and mass-spec analytics revealed correct assembly of purified 2/3-IgG variants as well as absence of undesired dimers and aggregates. Expression yields of 2/3-IgGs were similar to those observed with standard IgGs in the same expression systems. The respective data is presented in the following Table.

|  | anti-fluorescein antibody-knob-cys + MHCFcRP-hole-E357K | | | anti-biocytinamid antibody - hole-cys + MHCFcRP-knob-K370E | | |
|---|---|---|---|---|---|---|
| SEQ ID NO: | 43 + 36 (N-Fc) | 55 + 36 (C-Fc) | 56 + 36 (NC-Fc) | 41 + 37 (N-Fc) | 53 + 37 (C-Fc) | 54 + 37 (NC-Fc) |
| protein A [mg/L] | 94 | 94 | 75 | 129 | 87 | 75 |
| SEC [% yield] | 55 | 90 | 87 | 40-80 | 61 | 63 |

Example 7

Characterization of bsAbs with Combined Binding Functionalities in Different Valencies, Stoichiometries and Geometries Three different starting molecules (2/3-IgG with N-terminal, C-terminal, N- and C-terminal binding site(s)) can be combined with each other in the method according to the current invention to result in nine different bsAb formats. These differ in valencies, geometries and positions of the individual binding sites. The exchange reaction to generate these different bsAbs was performed under the same conditions as outlined in Example 3.

All types of input formats are 'flawed' as the MHCFcRP lacks the additional CH3 cysteine necessary to form interchain disulfides to the heavy chain and as it contains a repulsive charge mutation (i.e. a charge without matching full length heavy chain counterpart). The heavy chains that make up those "flawed" heterodimers rearrange to form (charge and disulfide) matching heterodimers in the method according to the current invention. The different types of full length heavy chains (knob-cys with hole-cys) form matching heterodimers. Matching heterodimers are also formed from the MHCFcRP (hole-charge with knob-charge).

Without being bound by this theory it is assumed that exchange reactions based on temporary separation of flawed heterodimers of two different 2/3-IgGs results in products that contain preferentially perfectly matching heterodimers with matching charges and, if present, cysteine residues for the formation of disulfide bonds. Exchanges therefore convert the monospecific 2/3-IgGs to bispecific IgGs (in different formats), as well as corresponding (variable region free, i.e. non-target binding competent) Fc-region heterodimer.

For the description of the exchange reactions, the input molecules are termed:
 'nA or nB' for molecules having the Fab arm at the normal N-terminus of the full length heavy chain (H-chain)
 'cA or cB' for molecules having the Fab arm at the C-terminus of the H-chain
 'ncA or ncB' for molecules with Fab at N- as well as C-terminus of the H-chain The different format-exchange reactions are as follows:
 2/3-IgG(nA)-His-tag+2/3-IgG(nB)-His-tag→bsAb (nAnB)+Fc-His-tag
 2/3-IgG(nA)-His-tag+2/3-IgG(cB)-His-tag→bsAb (nAcB)+Fc-His-tag
 2/3-IgG(nA)-His-tag+2/3-IgG(ncB)-His-tag→bsAb (nAncB)+Fc-His-tag
 2/3-IgG(cA)-His-tag+2/3-IgG(cB)-His-tag→bsAb (cAcB)+Fc-His-tag
 2/3-IgG(cA)-His-tag+2/3-IgG(nB)-His-tag→bsAb (cAnB)+Fc-His-tag
 2/3-IgG(cA)-His-tag+2/3-IgG(ncB)-His-tag→bsAb (cAncB)+Fc-His-tag 2/3-IgG(ncA)-His-tag+2/3-IgG(nB)-His-tag→bsAb
(ncAnB)+Fc-His-tag 2/3-IgG(ncA)-His-tag+2/3-IgG(cB)-His-tag→bsAb
(ncAcB)+Fc-His-tag 2/3-IgG(ncA)-His-tag+2/3-IgG(ncB)-His-tag→bsAb
(ncAncB)+Fc-His-tag Exchange reactions are initiated by a reduction step to break the inter-chain (hinge-region) disulfide bonds, chain rearrangement occurs spontaneously thereafter. All input molecules, all by-products, as well as all aggregates that may potentially form during the exchange reaction harbor affinity tags (e.g. a His6-(SEQ ID NO: 67) or His8-tag (SEQ ID NO: 68)). The bsAb products of the exchange reaction, however, do not carry the affinity tag and can therefore be separated via affinity (e.g. NiNTA) absorption chromatography. The bsAbs (in different formats) can directly be applied to screening procedures and analyses to identify and to rank the different bsAbs formats with optimal functionality.

The bispecific formats were generated by exchanging the above described input 2/3-IgGs in a 384 well MTP format followed by bridging ELISA to assess functional assembly. Therefore, the exchange partners (2/3-IgG molecule 1 consisting of a full length heavy chain containing the hole-cys-mutations and an MHCFcRP-knob-K370E;

2/3-IgG molecule 2 consisting of a full length heavy chain containing the knob-cys-mutations and a MHCFcRP-hole-E357K) were mixed in equimolar amounts (4 µM) in a total volume of 100 µl 1×PBS+0.05% Tween 20. Protein solutions were diluted in 11 times 1:2 in a 384-deep well plate (Greiner 384 masterblock®). 20 µl of each sample from the dilution series were mixed with 20 µl of a 0.5 mM TCEP solution to a final protein concentration of 200-0.2 µg/ml and 0.25 mM TCEP on a 384 well REMP® plate (Brooks, #1800030). After centrifugation, plates were sealed and incubated for one hour at 37° C.

As control examples, bsAbs containing bio-binding functionality on one side and fluorescein-binding functionality on the other side were used. Functionality of the resulting bsAbs was assessed by biotin-fluorescein bridging ELISA. Therefore, white Nunc® MaxiSorp™ 384 well plates were coated with 1 µg/ml albumin-fluorescein isothiocyanate conjugate (Sigma, #A9771) and incubated overnight at 4° C. After washing 3 times with 90 µl PBST-buffer (PBST, double distilled water, 10×PBS Roche #11666789001+ 0.05% Tween 20), 90 µl/well blocking buffer (1×PBS, 2% BSA, 0.1% Tween 20) was added and incubated for one hour at room temperature. After washing 3 times with 90 µl PBST-buffer 25 µl of a 1:4 dilution of each exchange reaction was added to each well. After incubation for one hour at room temperature, plates were again washed 3 times with 90 µl PBST-buffer. 25 µl per well biotin-Cy5 conjugate in 0.5% BSA, 0.025% Tween 20, 1×PBS was added to a final concentration of 0.1 µg/ml and plates were incubated for one hour at room temperature. After washing 6 times with 90 µl PBST-buffer, 25 µl 1×PBS were added to each well. Cy5 fluorescence was measured at an emission wavelength of 670 nm (excitation at 649 nm) on a Tecan Safire 2 Reader.

Figure 11:
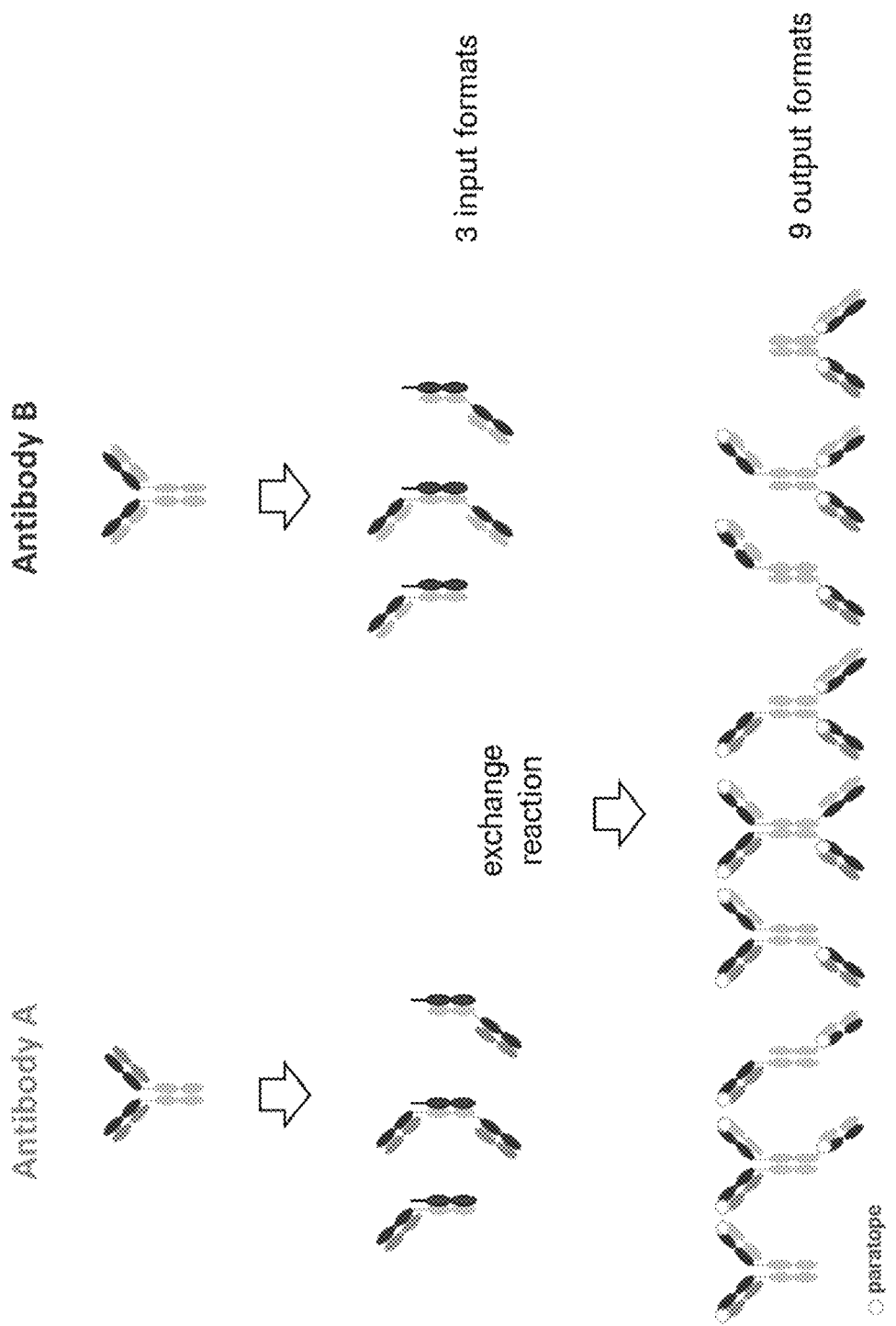
FIG. 11: General applicability of the method according to the invention shown by IgG-exchange reaction using starting materials of different binding specificities and formats, exemplified with 2/3-IgGs.

Different bsAb formats via exchange of 2/3-IgGs of different formats were generated with one fluorescein binding entity and one biocytinamid binding entity. Input molecules and exchange-derived output molecules are shown in FIG. 11.

Figure 12:
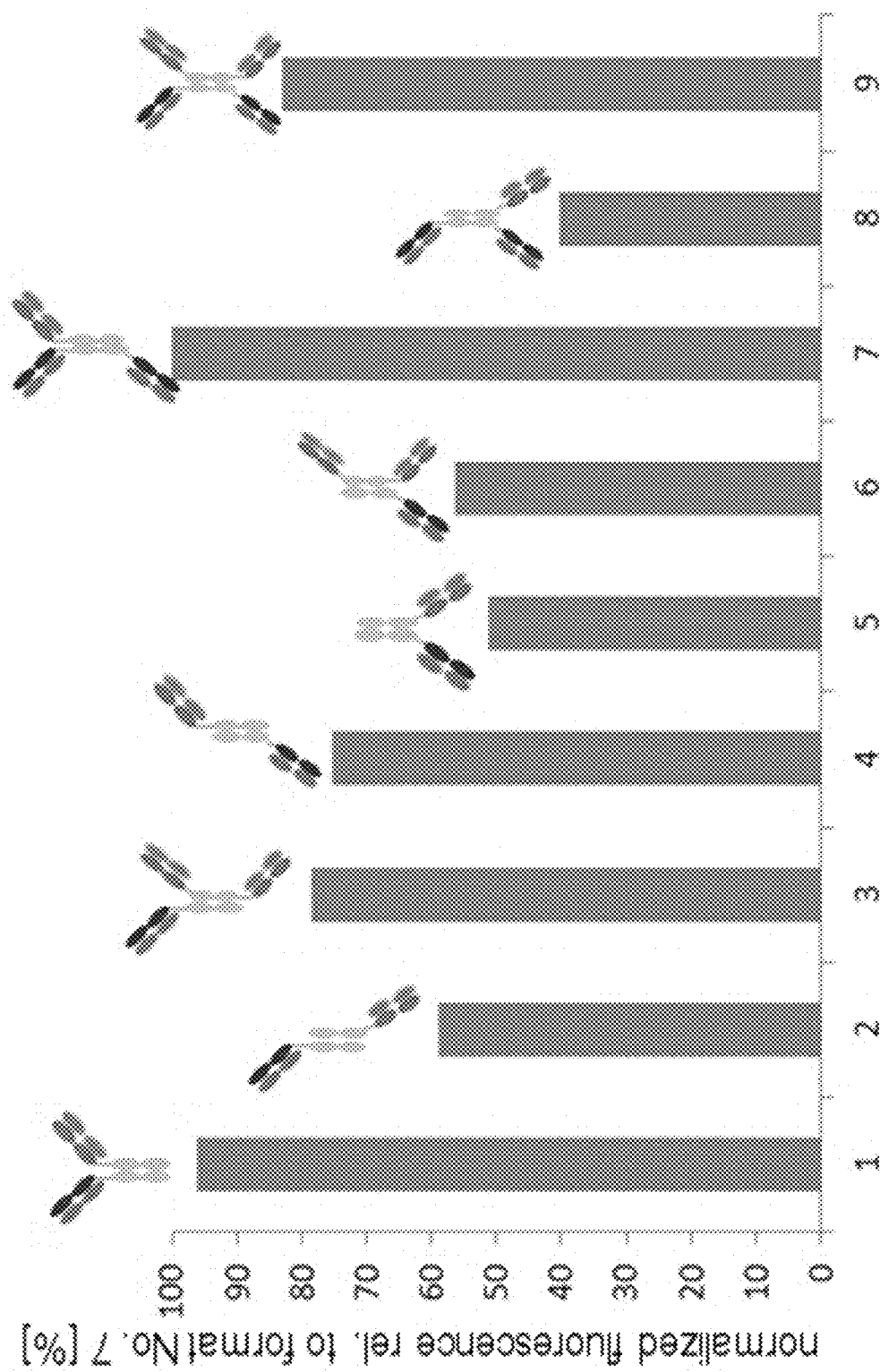
FIG. 12: Different bsAb format matrix generated via exchange reaction according to the current invention using exemplary 2/3-IgG. The matrix was generated with a fluorescein binding entity and a biocytinamid binding entity. Input molecules and exchange-derived output molecules are shown in FIG. 11. Functionality of generated bsAbs was assessed by bridging ELISA using fluos-BSA as capture antigen and bio-Cy5 to detect bispecific binding functionality. Signals derived from bridging ELISA shows that all formats have bispecific binding efficacy.

Functionality of generated bsAbs was assessed by bridging ELISA as shown in FIG. 12, using fluos-BSA as capture antigen and bio-Cy5 to detect bispecific bridging binding functionality. All different formats result in a bridging ELISA signal.

These results show the feasibility to generate different formats using a method according to the current invention via chain exchange reactions in a robust and high-throughput compatible manner.

Example 8

Generation of Functional bsAbs by 2/3-IgG-Exchange and Screening/Identification of bsAbs with Desired Functionality is Compatible with Miniaturization and High-Throughput as Well as Automation Technologies Application of high-throughput and automation technologies is desired and in many instance necessary to handle large numbers of different bsAbs-differing in binding site sequence and/or format. It has therefore been analyzed if bsAb generation via the 2/3-IgG exchange method according to the current invention, as well as analysis/screening of the functionality, i.e. bispecific binding, of the thereby generated bispecific antibodies, can be miniaturized in order to be compatible with high throughput and automation technologies.

Therefore, 2/3-IgG exchange reactions were performed and the reaction products were analyzed in miniaturized scale in 348 well plates.

A matrix screen was set up in 384 well MTP format as follows: The exchange partners (2/3-IgG molecule 1 consisting of a full length heavy chain containing the hole-cys-mutations and an MHCFcRP-knob-K370E; 2/3-IgG molecule 2 consisting of a full length heavy chain containing the knob-cys-mutations and a MHCFcRP-hole-E357K) were mixed in equimolar amounts (4 µM) in a total volume of 30 µl 1×PBS+0.05% Tween 20. Protein solutions were diluted four times 1:3 in a 384-deep well plate (Greiner 384 masterblock®). 20 µl of each sample from the dilution series were mixed with 20 µl of a 0.5 mM TCEP solution to a final protein concentration of 2 µM-0.025 UM and 0.25 mM TCEP on a 384 well REMP® plate (Brooks, #1800030). After centrifugation, plates were sealed and incubated for one hour at 37° C.

Figure 13:
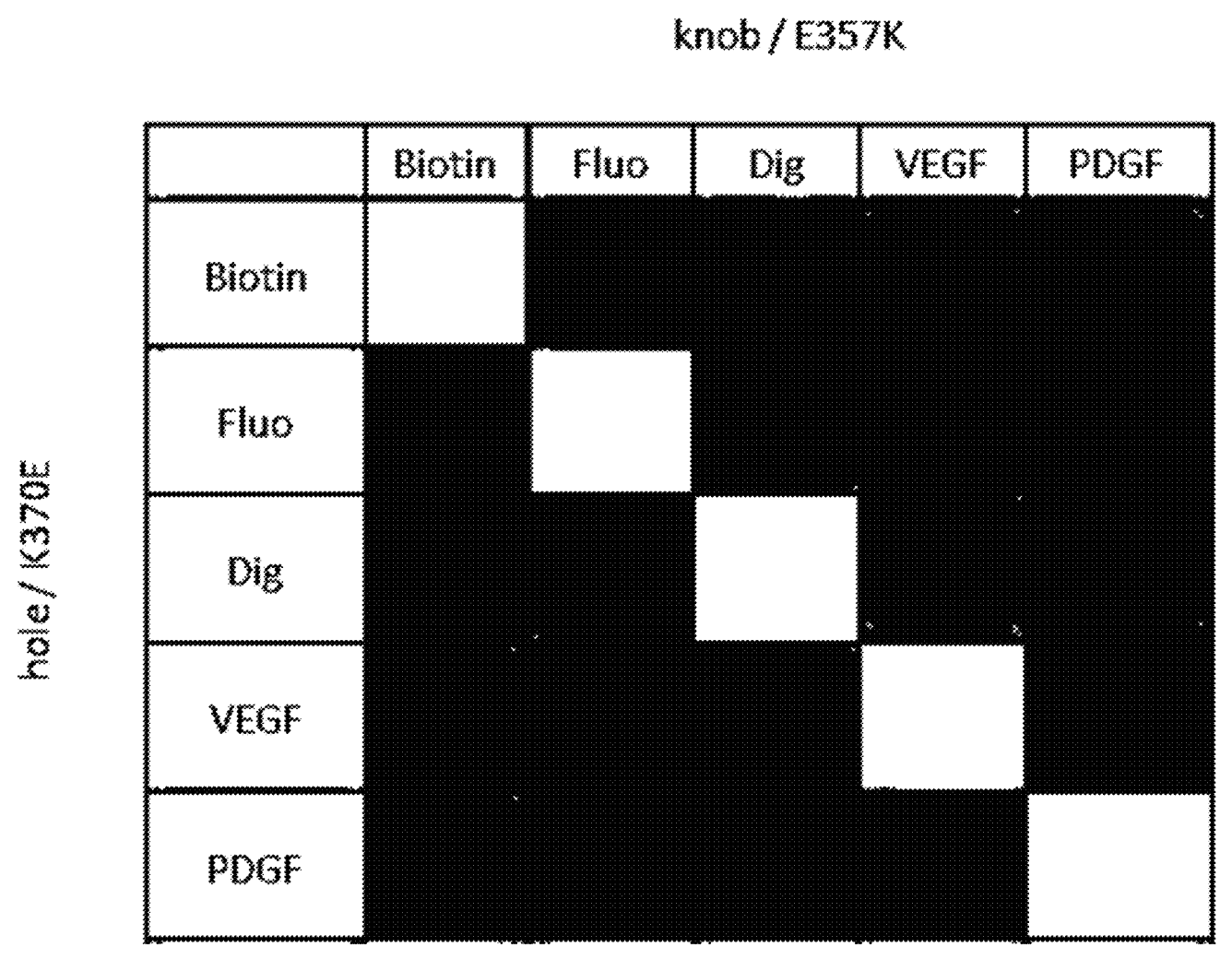
Figure 14:
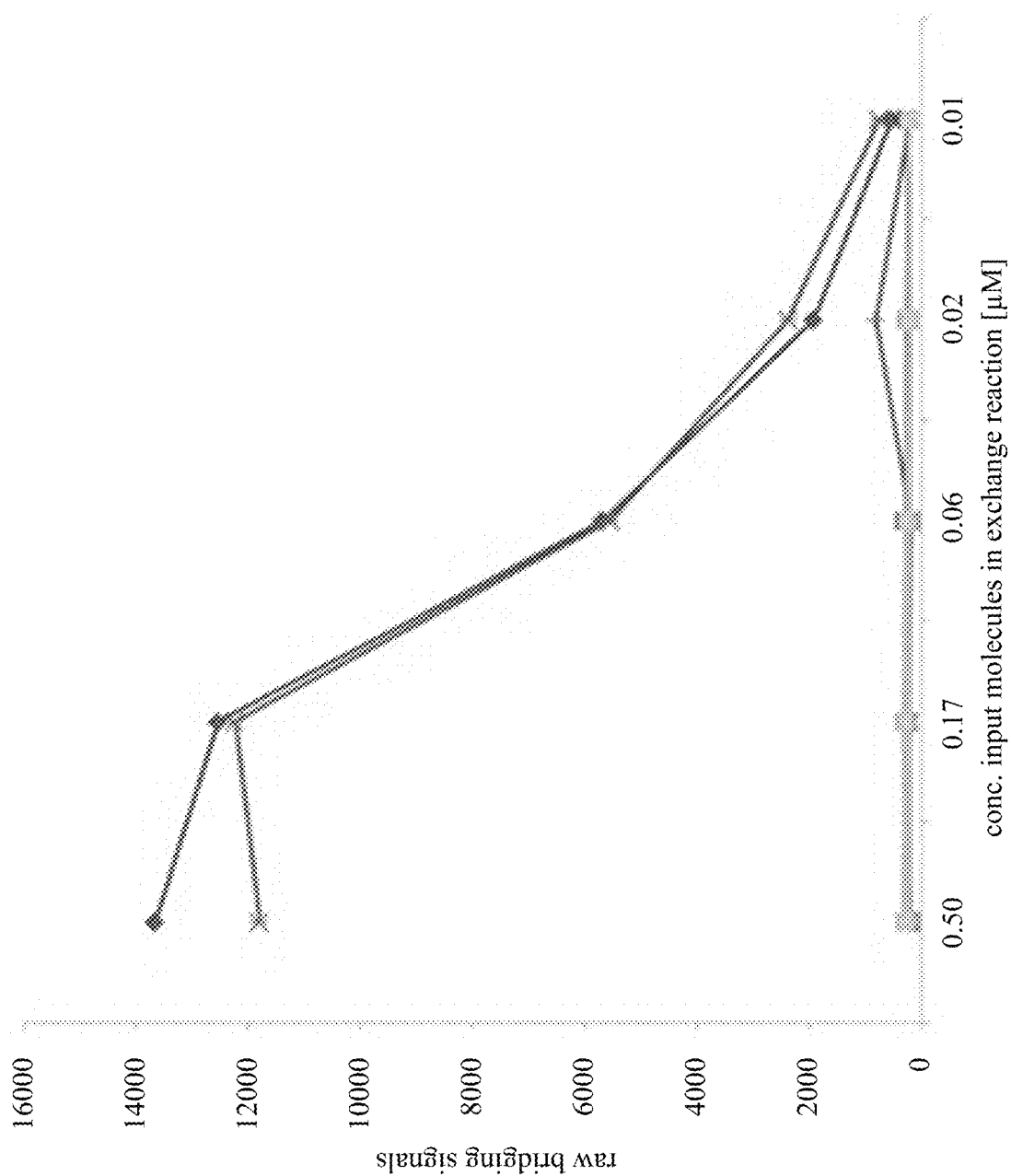
FIG. 14: Bispecific antibody formation via exchange reaction according to the method of the current invention with HTS technology. Shown is the signal of an exemplary bridging ELISA showing concentration dependent fluorescence signals that are indicative for bispecific antibody formation. Fluos-bio bridging ELISA, cross: fluos [hole/K370E]+bio [knob/E357K], diamond: bio [hole/K370E]+fluos [knob/E357K]. All other curves: 2/3-IgG input molecules without cognate exchange partners (these do not show bridging signal as only one binding site is present).

The functionality of the thereby generated bsAbs was subsequently assessed via bridging ELISA (see above) in a miniaturized high-throughput format: White Nunc® MaxiSorp™ 384 well plates were coated with 1 µg/ml albumin-fluorescein isothiocyanate conjugate (Sigma, #A9771), 1 µg/ml PDGF (CST, #8912) or 1 µg/ml VEGF121 and incubated overnight at 4° C. After washing 3 times with 90 µl PBST-buffer (PBST, double distilled water, 10×PBS+ 0.05% Tween 20) blocking buffer (1×PBS, 2% BSA, 0.1% Tween 20) was added 90 µl/well and incubated for one hour at room temperature. After washing 3 times with 90 µl PBST-buffer 25 µl of a 1:4 dilution of each exchange reaction was added to each well. After incubation for 1 h at room temperature, plates were again washed 3 times with 90 µl PBST-buffer. 25 µl per well biotin-Cy5 conjugate or dig-Cy5 conjugate in 0.5% BSA, 0.025% Tween 20, 1×PBS was added to a final concentration of 0.1 µg/ml and plates were incubated for one hour at room temperature. After washing 6 times with 90 µl PBST-buffer, 25 µl 1×PBS were added to each well. Cy5 fluorescence was measured at an emission wavelength of 670 nm (excitation at 649 nm) on a Tecan Safire 2 Reader. The details of the exchange reactions and bridging ELISAs these analyses with 2/3-IgG modules that bind either VEGF or PDGF or dig or bio or fluos are shown in FIG. 13. The results of one exemplary these analysis is shown in FIG. 14 and demonstrates that 2/3-IgG-exchange reactions and subsequent functional analyses can be performed and are compatible with high-throughput and automation technologies.

Example 9

Generation of bsAbs with Three Binding Sites that Target a First Antigen with One Binding Site and a Further Antigen with the Two Other Binding Sites The method according to the current invention can be used for the generation of T-cell bispecific antibodies (TCBs). These can have a format as described before (see e.g. WO 2013/026831). For the TCB-exchange approach, one H-chain (either with knob-cys or with hole-cys as described above) contains a CD3-binding CrossFab-derived entity N-terminal of its hinge, further being extended at the N-terminus by another antibody-derived targeting entity. The exchange reaction is carried out under the same conditions described above and results in a TCB harboring a CD3 binding entity and two additional binding entities. These can bind to a target cell antigen. Those molecules can simultaneously bind to CD3 on T-cells and to an antigen on a target (e.g. tumor) cell and thereby induce killing of target cells.

Example 10

Figure 15:
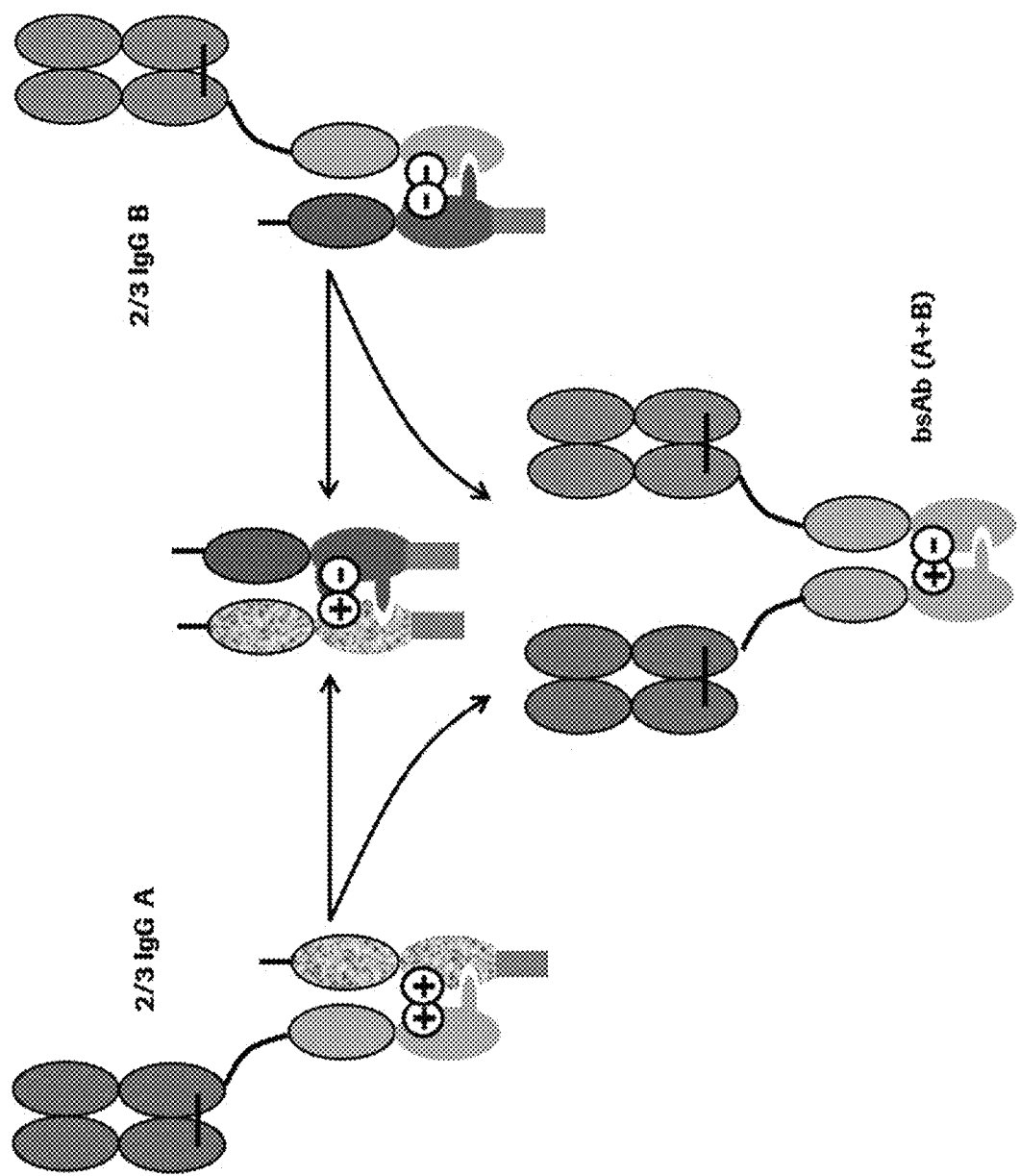
FIG. 15: Scheme of the exchange reaction according to the current invention exemplified with 2/3-IgGs without hinge-region and CH3 domain inter-chain disulfide bonds. This enables chain-exchange reaction in the method according to the current invention without the need to add a reducing agent.

Design and Generation of 2/3-IgGs without Fc-Region Inter-Chain Disulfide Bonds (in Hinge Region as Well as in CH3 Domain) According to the Current Invention Chain exchange with Fc-region (hinge region) disulfide containing 2/3-IgGs requires reduction as initial step to enable chain separation and subsequent assembly of desired bsAbs. To avoid the reduction step and the associated need to remove the reducing agent 2/3-IgGs without hinge region disulfide bonds were generated. The principle is shown in FIG. 15. The cysteine residues in the hinge region responsible for hinge-disulfide formation were removed by mutation to serine. Also the CH3-cysteine at position 354 or 349 that forms the KiH associated disulfide bond has been omitted. The respective amino acid sequences are:

| Chain | SEQ ID NO: |
|---|---|
| anti-bio antibody full length heavy chain-knob without hinge-region cysteine residues | 57 |
| anti-bio antibody full length heavy chain-hole without hinge-cysteine residues | 58 |
| anti-fluos antibody full length heavy chain-knob without hinge-cysteine residues | 59 |
| anti-fluos antibody full length heavy chain-hole without hinge-cysteine residues | 60 |
| MHCFcRP | |
| hole-D356K-His8 without hinge-cysteine residues | 61 |
| hole-E357K-His8 without hinge-cysteine residues | 62 |
| knob-K370E-His8 without hinge-cysteine residues | 63 |
| knob-K439E-His8 without hinge-cysteine residues | 64 |

Figure 16:
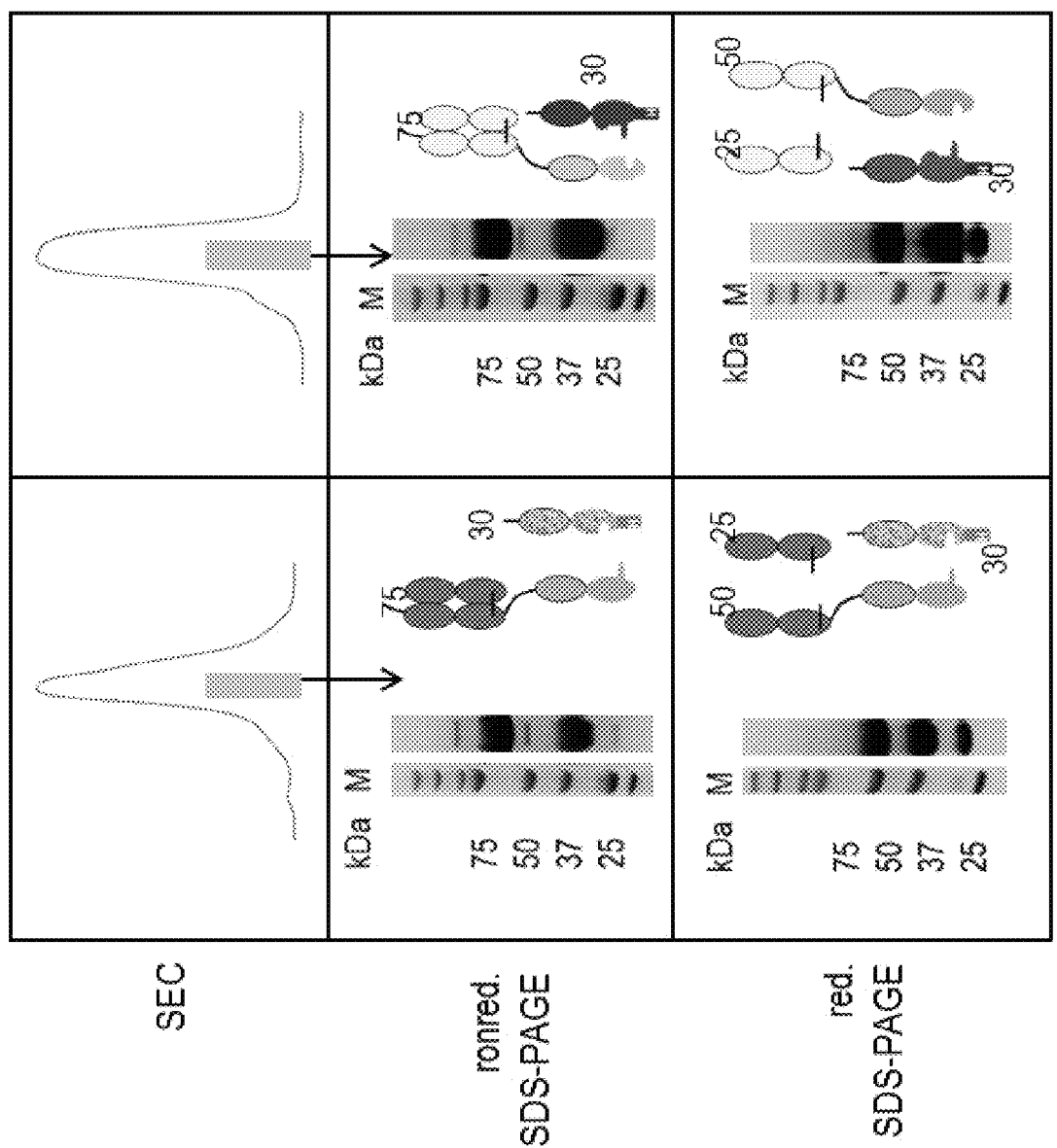
FIG. 16: The 2/3-IgGs without inter-chain disulfide bridges are secreted into culture supernatants like standard IgGs, purified by standard protein A affinity and size exclusion chromatography, and analyzed by SDS-PAGE confirming the desired 100 kDa 2/3-IgG as expression product. This proves correct assembly of the purified 2/3-IgG-derivatives without inter-chain disulfide bridges as well as absence of undesired dimers and aggregates. Purification of i) anti-bio antibody light chain (SEQ ID NO: 39)+anti-bio antibody heavy chain-knob without hinge region cysteine residues (SEQ ID NO: 57)+MHCFcRP-hole-E357K without hinge regions cysteine residues (SEQ ID NO: 62) (shown on the left) and ii) anti-fluos antibody light chain (SEQ ID NO: 42)+anti-fluos antibody full length heavy chain-hole without hinge region disulfide bonds (SEQ ID NO: 60)+MHCFcRP-knob-K370E without hinge region cysteine residues (SEQ ID NO: 63) (shown on the right).

Expression of the above 2/3-IgGs was achieved by co-transfection of plasmids encoding light chain, full length heavy chain (knob or hole) and corresponding MHCFcRP (hole or knob) into mammalian cells (e.g. HEK293) (see Example 2). The 2/3-IgGs were secreted into culture supernatants like standard IgGs and were thereafter purified by standard protein A affinity and size exclusion chromatography (see Example 2). Subsequent analytics via size exclusion chromatography and SDS-PAGE the desired 100 kDa 2/3-IgG expression product (FIG. 16). This proves correct assembly of the 2/3-IgG as well as absence of undesired dimers and aggregates. This is surprising as such molecules are not stabilized by disulfides between the Fc-regions (neither hinge region nor CH3 domain). The purification yield of anti-fluos- and anti-bio-2/3-IgGs without Fc-region inter-chain disulfide bonds are presented in the following Table

| | anti-bio antibody light chain (SEQ ID NO: 39) + anti-bio antibody heavy chain-knob without hinge region cysteine residues (SEQ ID NO: 57) + MHCFcRP-hole-E357K without hinge regions cysteine residues (SEQ ID NO: 62) | anti-fluos antibody light chain (SEQ ID NO: 42) + anti-fluos antibody full length heavy chain-hole without hinge region disulfide bonds (SEQ ID NO: 60) + MHCFcRP-knob-K370E without hinge region cysteine residues (SEQ ID NO: 63) |
|---|---|---|
| protein A [mg/L] | >100 | >100 |
| SEC yield [mg/L 100 kDa] | >50 | >50 |

Example 11

Figure 17:
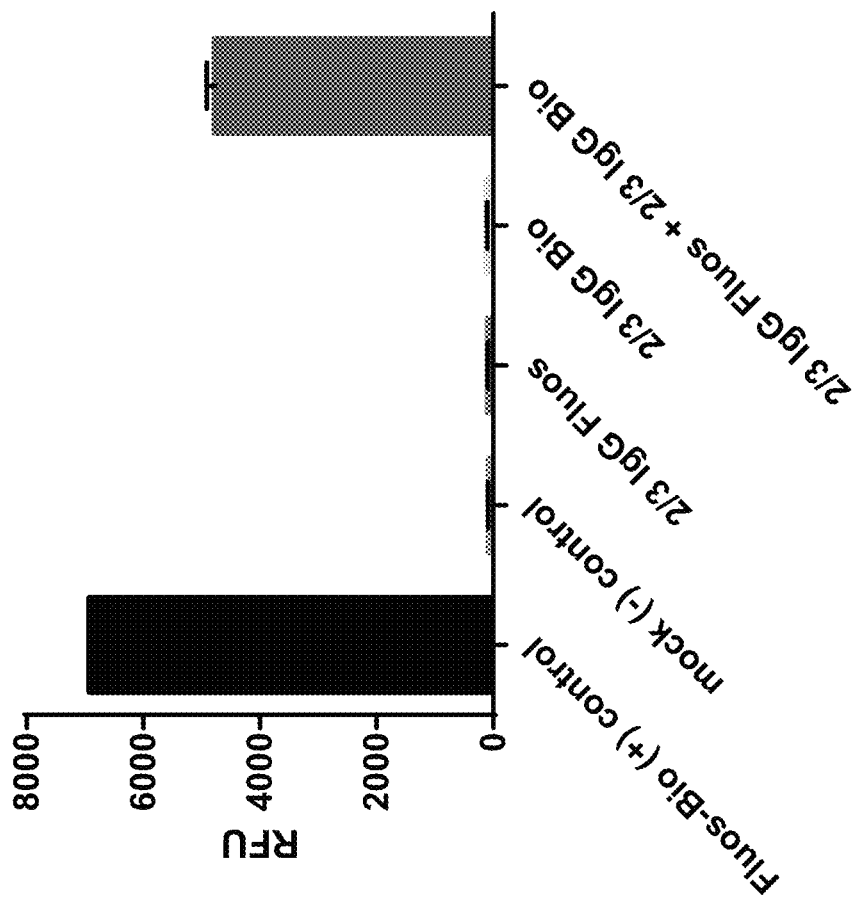
FIG. 17: Results of the exchange reaction according to the current invention with starting materials without hinge-region disulfide bonds: 2.5 μM concentration of input molecules with purified bsAb as positive control demonstrate successful bsAb generation via chain exchange with monospecific 2/3-IgG input molecules without Fc-region inter-chain disulfide bonds.

Generation of Functional bsAbs by 2/3-IgG-Exchange Reaction without Reduction in the Method According to the Invention The 2/3-IgGs that do not contain Fc-region inter-chain disulfide bonds were subjected to chain exchange reactions as described above (see Example 3), except for omitting the initial reduction step. The 2/3-IgGs either contained fluos- or bio-binding sites and Fc-regions without inter-chain disulfide bonds between the full length heavy chain and MHCFcRP. Composition and production of these 2/3-IgGs was described in Example 10. Following exchange reactions without initiating reduction, a bridging ELISA was performed to demonstrate bispecific functionality of bsAbs. The bridging ELISA comprised the addition of exchange reaction products to immobilized fluos-BSA, followed by wash steps and subsequent addition of bio-Cy5 to probe for presence of the $2^{nd}$ binding arm of the bsAb (see previous examples for details of the bridging ELISA). Only correct assembled functional bsAbs can bind by their fluos-binding site to the assay plate, are retained and generate signals by capturing and retaining bio-Cy5. Molecules without bispecificity do not generate signals as they either do not bind to the plate (bio-only binder) or cannot capture the signal generating bio-Cy5 (fluos-only binder). The results of these analyses (performing the exchange reaction in this example at 2.5 μM concentration of input molecules with purified bsAb as positive control) are shown in FIG. 17. The results demonstrate successful bsAb generation via chain exchange with monospecific 2/3-IgG input molecules without Fc-region inter-chain disulfide bonds. Productive chain exchange took place without requirement of initial reduction. Thus, removal of inter Fc-region polypeptide disulfide bonds eliminated the necessity of an initial reduction step. The resulting bsAbs are held together by non-covalent Fc-Fc interactions. Elimination of Fc-Fc inter-chain disulfides thus allows for corresponding Fc-region mismatch driven exchange reactions without the need for reduction and thereby allowing in vivo application.

Example 12

Chain Exchange Reactions are Driven by Partially De-Stabilized Full Length Heavy Chain-MHCFcRP Interfaces

The driver for conversion of 2/3-IgGs to bsAbs is a designed 'flawed' interface between the full length heavy chain and the MHCFcRP. This artificial repulsive interface is the result of mutations introduced into the knob- or hole-CH3 domains of the MHCFcRP. The MHCFcRP still associate with the corresponding ("normal") knob- or hole-partners during expression of 2/3-IgGs (see examples above). Those molecules have sufficient stability to present 2/3-IgGs as well behaved molecules without undesired aggregation tendencies.

Without being bound by this theory, the exchange reaction according to the current invention leading to bsAbs occurs when two complementary 2/3-IgGs come into close distance and the full length antibody heavy chain:: MHCFcRP pairs are partially released next to each other. Re-assembly of the matching, i.e. not charged repulsed, knob-hole full length heavy chains should be favored under such conditions because the full length antibody heavy chain (CH3) interfaces are perfect. Thus, the full length heavy chains of the formed bsAb remain associated with preference over re-formation of the partially imperfect (charge mismatched) 2/3-IgG molecules. Thus, a designed partially de-stabilized (charge repulsed) CH3 interface is a key parameter for successful directed chain exchange reactions.

Partial de-stabilization of the Fc interface, especially the CH3-CH3 interface, can be achieved by mutating CH3 residues of the MHCFcRP while maintain the interacting residues on the full length antibody heavy chain.

Exemplary mutations that can be introduced into the CH3 domain of the MHCFcRP affecting the full length antibody heavy chain:: MHCFcRP interface are provided in the following Table.

| position (EU numbering) | perturbing mutation(s) |
|---|---|
| 345E | R |
| 347Q | K |
| 349Y | W or E |
| 351L | F or Y |
| 354S | E or V |
| 356D | S or A or K |
| 357E | S or A or L or F or K |
| 360K | S or E |
| 362Q | E |
| 364S | V or L |
| 366T | I |
| 368L | F or V |
| 370K | E |
| 390N | E |
| 392K | E or D |
| 394T | I |
| 397V | Y |
| 399D | A or K |
| 400S | K |
| 401D | R |
| 405F | W |
| 407Y | W or L or I |
| 409K | D or E or I |
| 439K | E |
| 441L | Y |

Some of the mutations include exchanges that place altered charges into the interface. Charge mutations either weaken or break previously existing stabilizing charge pairs or result in repulsion effects, or in both.

Similarly, amino acids with differently sized side chains can be introduced to generate steric repulsion effects. Such mutations either weaken or interfere with existing hydrophobic interface interactions or generate steric hindrances, or combine both.

Mutations that partially de-stabilize via charge and/or steric effects can also be combined with each other.

Furthermore, a first 2/3-IgG that contains charge and/or steric alterations introduced into its MHCFcRP can be combined with a second 2/3-IgG that contains different charge and/or steric alterations introduced into its MHCFcRP which match those of the MHCFcRP from the first 2/3-IgG.

The 2/3-IgGs as well as the resulting bsAbs assemble in a manner in which paired CH3 domains harbor knob-mutations on one side and hole-mutations on the other. Therefore, 'back-mutation' to wild-type composition of corresponding knob- or hole-residues of the MHCFcRP generate also interface disturbances. Such combinations of knob- or hole-CH3-domains with wild-type domains are listed in the following Table.

| | perturbing backmutation |
|---|---|
| CH3 hole | |
| position (EU numbering) | |
| 349C* | Y |
| 366S | T |
| 368A | L |
| 407V | Y |
| CH3 knob | |
| Fc position (EU numbering) | |
| 354C* | S |
| 366W | T |

These backmutations can be applied to partially destabilize the CH3-CH3-interface.

These backmutations can also be applied in combination with other perturbing mutations incl. those described in the previous Table.

All partially perturbing individual mutations or combination of mutations as described above can also be chosen in a manner that they partially destabilize the 2/3-IgG, yet stabilize a knob-MHCFcRP:: hole-MHCFcRP heterodimer as the 2nd product of the exchange reaction and thereby shifting the reaction equilibrium further to the product side (exchange reaction).

Example 13

On-Cell Conversion of Monovalent 2/3-IgG Derivatives to Bivalent bsAbs According to the Current Invention

2/3-IgG derivatives without inter-chain disulfide bonds between the heavy chain and the MHCFcRP do not require reduction to initiate the exchange reaction. It is therefore possible that exchange may also be achieved under physiological conditions, possibly even when individual 2/3-IgGs are bound to cell surfaces. If the functional Fab arms of 2/3-IgGs bind to cell surfaces, they accumulate on target cells. If two complementary 2/3-IgGs bind to the surface of the same cell, the chain exchange can occur while being bound directly on the surface of said cells. This exchange generates a fully functional bsAb with dual specificity directly on the cell surface.

To demonstrate this in situ on-cell chain exchange, two complementary 2/3-IgGs that bind either the antigens LeY or Her1 are applied to cells that display either high levels of LeY, high levels of Her1, or high levels of both. It can be shown in FACS analyses that individually applied 2/3-BiFabs bind to cells with express their cognate antigen. Co-application (simultaneously or consecutive) of both 2/3-BiFabs results in increased binding only to cells that express both antigens. This indicates successful generation of functional bivalent bsAb products (with avidity-mediated improved binding) by on-cell exchange reactions of monovalent 2/3-BiFabs (prodrugs).

Example 14

Figure 18:
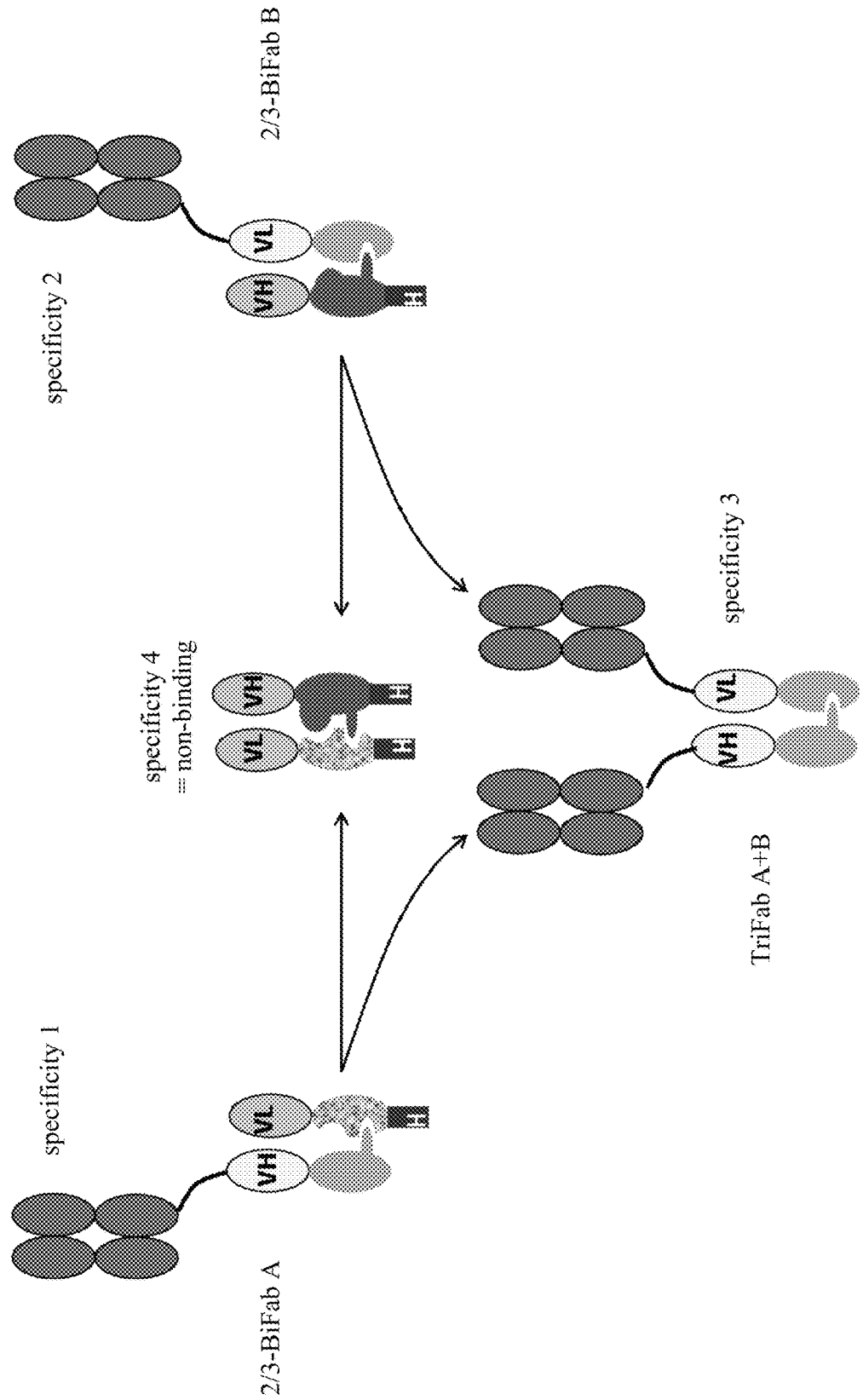
FIG. 18: Design and composition and chain exchange principle of BiFabs to TriFabs.

Design & Composition and Functionality of 2/3-BiFabs without Heavy Chain: MHCFcRP Disulfide Bonds According to the Current Invention TriFabs are antibody derivatives that harbor bispecific functionalities due to an exchange of the IgG CH2 domains to VH and VL, respectively. The Fc-like 'stem-region' of such molecules is held together by intact KiH CH3 domains. This enables the generation of MHCFcRP containing BiFab analogues with potentially exchange-enabling features. FIG. 18 shows the design and composition of MHCFcRP containing 2/3-IgG-BiFab derivatives. Applying the same general principles as for 2/3-IgGs, engineered 2/3-BiFab analogues are composed of a KiH heavy chain and a MHCFcRP entity harboring a complementary VL or VH domain of an irrelevant antibody instead of the CH2 domain as well as a matching CH3 KiH domain. Thus, the CH2 domains of heavy chain and MHCFcRP in 2/3-IgGs becomes replaced by either a VH or a VL domain. In addition, and as a further difference to the 2/3-IgGs described in Example 1, the heavy chain as well as the MHCFcRP-stem of these 2/3-BiFab derivatives do not harbor cysteines that promote heavy chain: MHCFcRP covalent connections (analogous to 2/3-IgG derivative of Example 10). Because 2/3-BiFabs harbor exchange modules, i.e. CH3 domains, based on the same principle as 2/3-IgGs (without inter-chain-disulfides), exchange reactions can occur in the same manner as described and shown for 2/3-IgGs. The general principle of the 2/3-BiFab associated exchange reaction is shown in FIG. 18. The sequences of the light chains, knob- or hole-heavy-chains, and MHCFcRP hole- or knob-chains applied to produce 2/3-BiFabs are as follows:

| Chain | SEQ ID NO: |
|---|---|
| anti-LeY antibody light chain | 83 |
| anti-LeY-antibody heavy chain with anti-dig antibody variable domain as CH2 domain-knob | 84 |
| anti-LeY-antibody heavy chain with anti-dig antibody variable domain as CH2 domain-hole | 85 |
| anti-MSLN-antibody heavy chain with anti-dig antibody variable domain as CH2 domain-hole | 86 |
| anti-MSLN antibody light chain (MSLN = mesothelin) | 87 |
| anti-LeY-antibody heavy chain with anti-CD3 antibody variable domain as CH2 domain-knob | 88 |
| anti-LeY-antibody heavy chain with anti-CD3 antibody variable domain as CH2 domain-hole | 89 |
| anti-LeY-antibody heavy chain with anti-CD-AG-2 antibody variable domain as CH2 domain-knob | — |
| anti-LeY-antibody heavy chain with anti-CD-AG-2 antibody variable domain as CH2 domain-hole MHCFcRP | — |
| with non-binding variable domain as CH2 domain-hole | 90 |
| with non-binding variable domain as CH2 domain-knob | 91 |

Example 15

Expression & Purification of 2/3-BiFabs According to the Invention

Figure 19A:
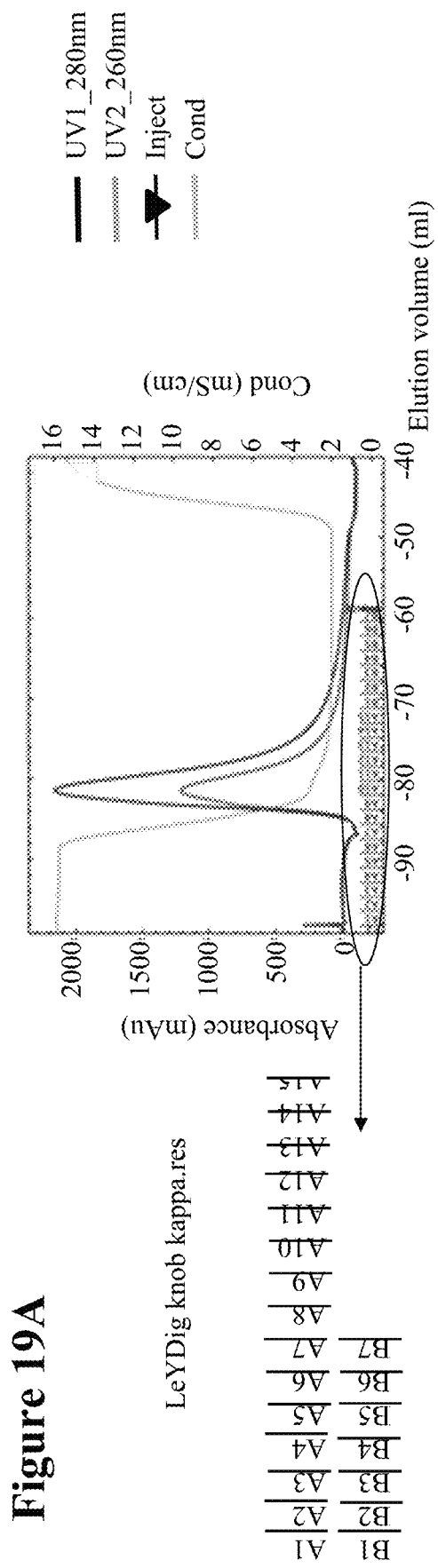
FIGS. 19A and 19B: Expression and purification of 2/3-BiFabs.
Figure 19B:
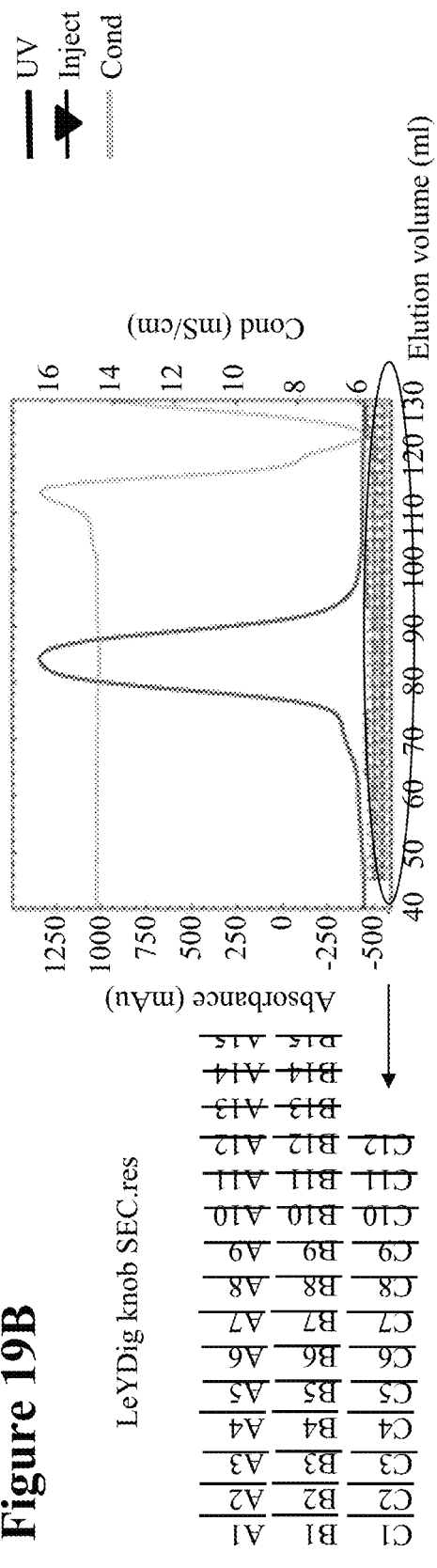
Figure 20A:
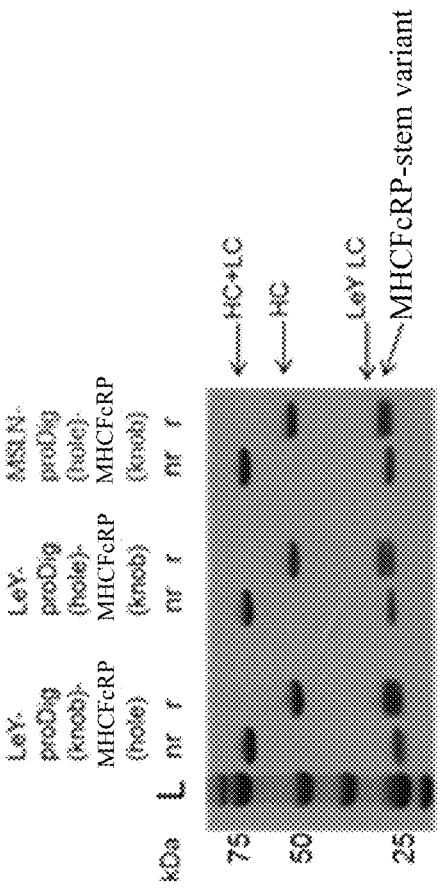
FIGS. 20A and 20B: Expression and purification of 2/3-BiFabs: SDS-Page; n.r=non-reduced; r=reduced; L=molecular weight marker.
Figure 20B:
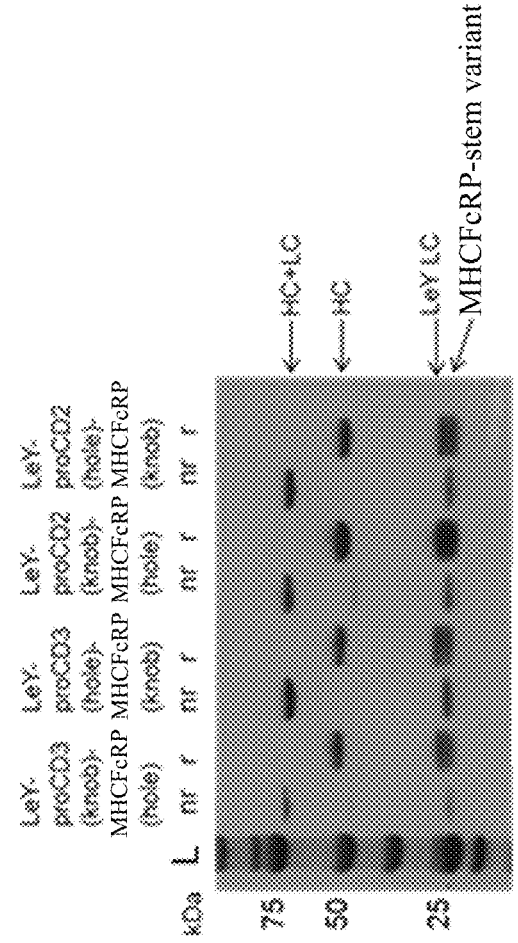

Expression of 2/3-BiFabs was achieved by co-transfection of plasmids encoding the light chain, modified stem-heavy chain (knob or hole) and matching MHCFcRP-stem (hole or knob) into mammalian cells (e.g. HEK293) via state of the art technologies previously described (WO 2016/087416). The 2/3-BiFabs are secreted into culture supernatants like standard IgGs. Due to absence of a functional Fc-region as they lack CH2 domains, 2/3-BiFabs were purified by standard protein L (KappaSelect) affinity chromatography as shown in FIGS. 19 and 20. It is surprising that 2/3-BiFabs can be produced and purified in an effective manner even though they do not possess a functional V region in the stem region (as that is composed of non-matching VH and VL), and though they do not contain inter-chain disulfides for covalent connection of the chains. Size-exclusion and native mass-spec analytics showed correct assembly of purified 2/3-BiFab-derivatives as well as absence of undesired dimers and aggregates. The expression yields of 2/3-BiFabs under non-optimized transient expression conditions are listed in the following Table.

| 2/3 TriFabs | | LeY-proDig (knob)-MHCFcRP (hole) | LeY-proDig (hole)-MHCFcRP-knob | MSLN-proDig (hole)-MHCFcRP (knob): | LeY-proCD3 (knob)-MHCFcRP (hole): | LeY-proCD3 (hole)-MHCFcRP (knob) | LeY-proCD-AG-2 (knob)-MHCFcRP (hole) | LeY-proCD-AG-2 (hole)-MHCFcRP (knob): |
|---|---|---|---|---|---|---|---|---|
| HighTrap Kappa Select | yield [mg/L] | 130 | 190 | 135 | 68 | 86 | 70 | 120 |
| | 2/3-BiFab [mg] | 100 | 150 | 110 | 35 | 75 | 50 | 100 |
| | by-products [mg] | 30 | 40 | 25 | 23 | 11 | 20 | 20 |
| SEC | purified 2/3-BiFab [mg/L] | 90 | 150 | 110 | 35 | 70 | 50 | 100 |

Example 16

Generation of Functional TriFabs by Reduction-Free Chain Exchange According to the Invention Elimination of Fc-Fc inter-chain disulfides as shown above for 2/3-IgGs enables MHCFcRP driven exchange reactions without the need for controlled reduction and re-oxidation, i.e. under physiological conditions. It is, thus, possible to "shuffle" such molecules under physiological conditions, potentially even when already bound to target cell surfaces.

Figure 21:
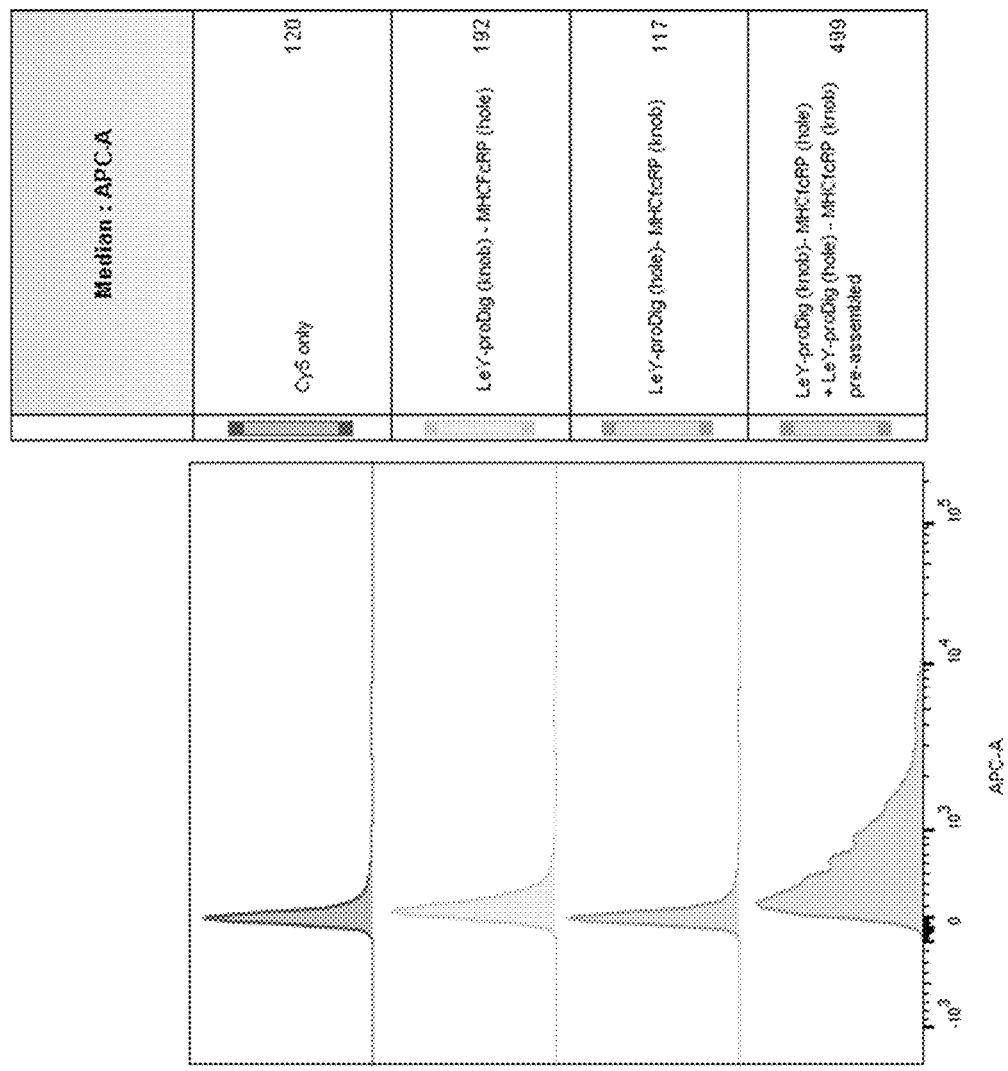
FIG. 21: FACS analysis of cells exposed to the starting molecules and the molecule obtained by exchange reaction according to the current invention.

Therefore, 2/3-BiFab exchange reactions were performed without reduction as initial trigger of the exchange reaction. Input molecules into these exchange reactions were the LeY-binding 2/3-BiFabs with functional LeY binding arms and 'split' Dig-binding stem region (proDig) as described above. Depletion of unreacted 2/3-BiFabs and MHCFcRP by-products was subsequently achieved via absorption of undesired His8-containing proteins ("His8" disclosed as SEQ ID NO: 68) on NiNTA resin. FACS analyses were subsequently applied to assess the binding functionality of the generated TriFab in comparison to the 2/3-BiFab precursor molecules. Therefore, LeY-antigen expressing MCF7 cells were exposed to either individual LeY-binding 2/3-BiFabs or to the TriFab of the exchange reaction. Dig-Cy5 was subsequently added and fluorescence of the cells was assessed. FIG. 21 shows low Dig-Cy5 associated signals with cells that were exposed to either 2/3-BiFabs even though both entities possess intact Fab arms which recognize the cell surface carbohydrate LeY.

The reason for inability of 2/3-BiFabs to bind the digoxigenylated payload is that they do not harbor a functional Dig-binding Fv in their stem region. The TriFab product of the chain exchange reaction, however, unambiguously displayed Dig-Cy5 associated signals, i.e. Dig-binding functionality. This demonstrates that 2/3-BiFab precursor molecules with inactivated binding functionality of their 'stem-Fv' become converted via chain exchange to fully functional TriFabs.

Example 17

Figure 22:
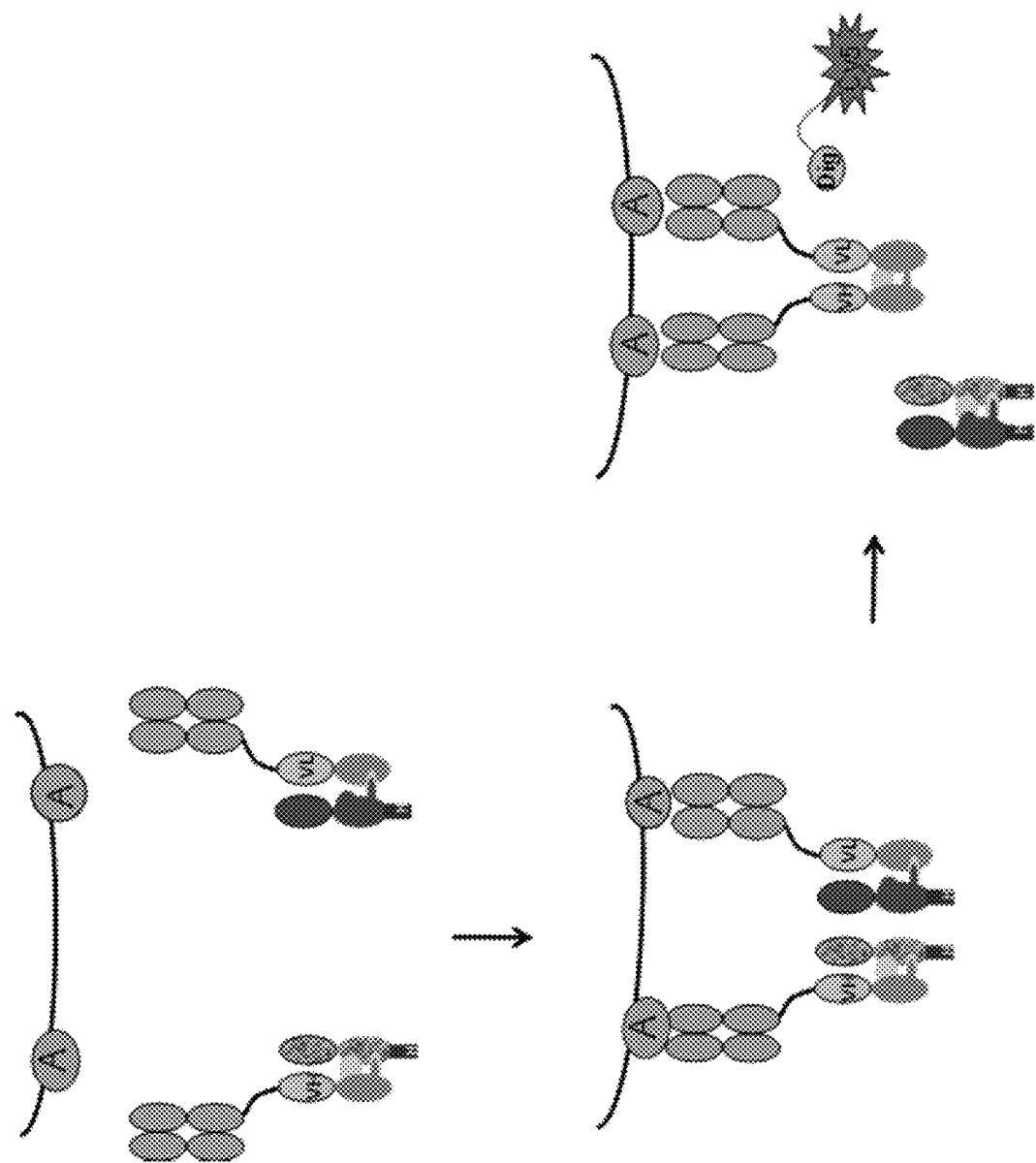
FIG. 22: 2/3-BiFab exchange reaction on the cell surface re-arranges and thereby activates the 3rd binding site (Fv) in the stem-region.

On-Cell Conversion of 2/3-BiFabs Prodrugs to Fully Functional Cell Bound Activated Bi- or Tri-Specific TriFabs According to the Invention 2/3-BiFabs are only partially non-binding competent as they comprise one fully functional Fab arm. Only the Fv at the tip of the stem region is non-functional as it is composed of non-complementary VH and VL domains (of different antibodies or containing mutations that interfere with binding to cognate antigens, precursor inactive pro-form of the binding site). If the functional Fab arm binds to cell surfaces, 2/3-BiFabs accumulate on target cells. If two complementary 2/3-BiFabs (both carrying inactivated yet each other complementing stem-Fvs) bind to the surface of the same cell, chain exchange reactions can occur while being bound directly on the surface of said cell. This exchange then generates a fully functional TriFab with at least dual specificity directly on the cell surface (FIG. 22).

Figure 23:
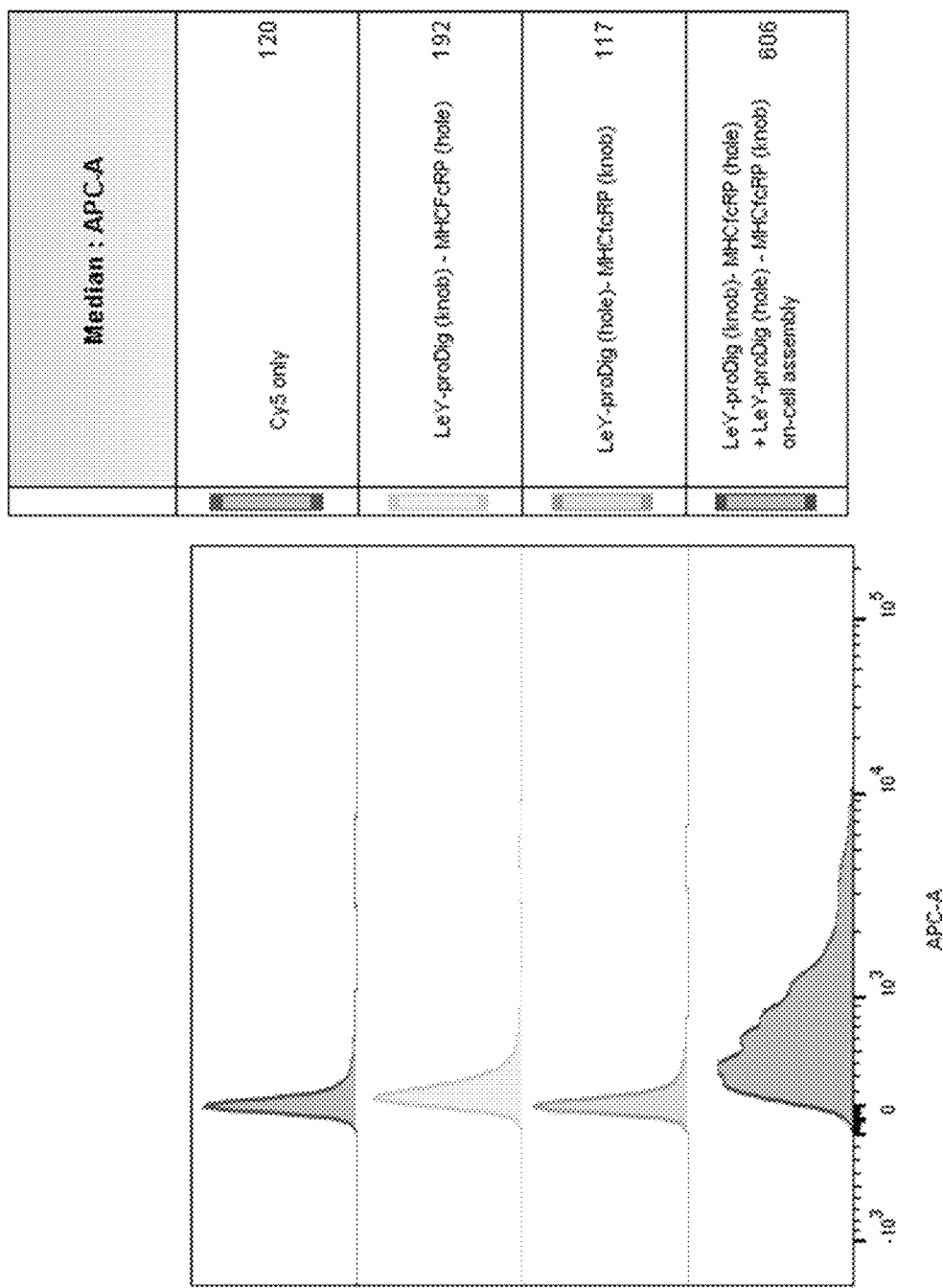
FIG. 23: On-cell conversion of different antigen targeting and different stem-Fv containing TriFab-like prodrugs to cell bound tri-specific TriFabs.

To experimentally demonstrate in situ on-cell chain exchange, we applied the individual 2/3-BiFab modules as well as those that were subjected to biochemical chain shuffling (described in examples above) to MCF7 cells followed by FACS analyses. MCF7 cells carry the LeY antigen on their cell surface and hence bind the individual 2/3-BiFabs with their functional Fab arms. FIG. 23 shows that individually applied 2/3-BiFabs bind to MCF7 cells, but are not capable to capture the 2nd target Dig-Cy5 (FIG. 23, rows 2 and 3). This reflects absence of functional stem-Fv in the 2/3-BiFab and hence on cells that bind only one 2/3-BiFab. Simultaneous application of both (complementary) 2/3-BiFabs however, enables to capture and retain Dig-Cy5 on the surface of MCF7 cells (FIG. 23, row 4). This indicates successful chain rearrangement/exchange and generation of functional TriFabs with Dig-binding functionality of the stem-Fv. Successful chain exchange of the stem region and recovery of the functional stem-Fv (Dig-Cy5 associated targeted FACS signals) was also observed upon consecutive application of the complementary 2/3-BiFabs. Application of the first entity to enable cell binding followed by extensive washing to remove unbound molecules and subsequent application of the 2nd entity also generates FACS signals on antigen positive cells. This confirms that successful exchange reaction (either by simultaneous or sequential application) can occur under physiological conditions on the surface of target cells.

Example 18

On-Cell Chain Conversion of Targeted Anti-CD3-Prodrug 2/3-BiFabs to Fully Functional Bispecific Antibodies According to the Invention To demonstrate that on-cell conversion of 2/3-BiFab prodrugs is a general principle that can be applied for different binding specificities, 2/3-BiFabs were generated that contain VH or VL domains of CD3-binding antibodies. T-cell bispecific antibodies (also termed T-cell recruiters) are proteins that combine binding entities that recognize antigen on the surface of tumor cells with CD3-binding functionalities. Such molecules bind to tumor cells via their tumor-antigen-binding entities as well as to T-cells (via CD3-binding functionality). That in turn generates (activation) signals and processes which ultimately results in tumor cell lysis/death mediated by the antibody binding-induced T-cell attack.

2/3-BiFabs with anti-CD3-prodrug functionality, i.e. the CD3 binding site is located in the stem region and, thus, not binding competent in the 2/3-BiFab educts, were designed as described above (see Examples 14 and 15). The light chains, knob- or hole-heavy chains and matching MHCFcRPs were co-expressed to generate the 2/3-BiFab LeY-proCD3(hole)-MHCFcRP(knob) and the 2/3-BiFab LeY-proCD3(knob)-MHCFcRP(hole). 2/3-BiFabs were purified as described above (see Table in Example 15) and subjected to on-cell chain exchange reaction.

Figure 24:
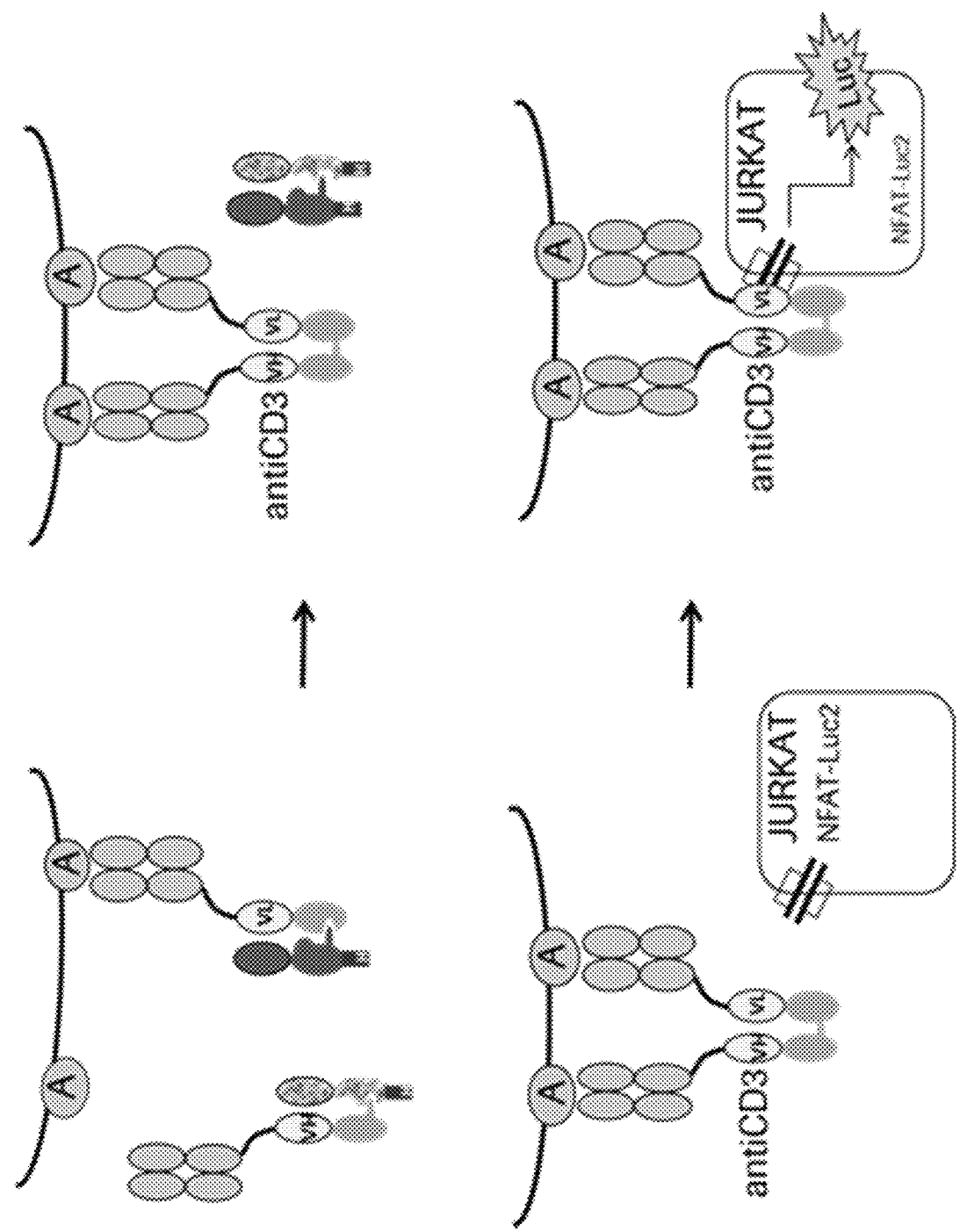
FIG. 24: Principle of detecting on-cell activation of CD3 binding functionality by CD3-signaling reporter assay.

To experimentally demonstrate on-cell chain exchange of 2/3-BiFabs with anti-CD3-prodrug functionality, these were then applied to MCF7 cells. Presence or absence of CD3-binding functionality was subsequently determined via cell-based reporter assays that generate signals upon CD3-receptor binding (Promega T-cell Activation Bioassay (NFAT), cat. #J1621, FIG. 24).

Figure 25:
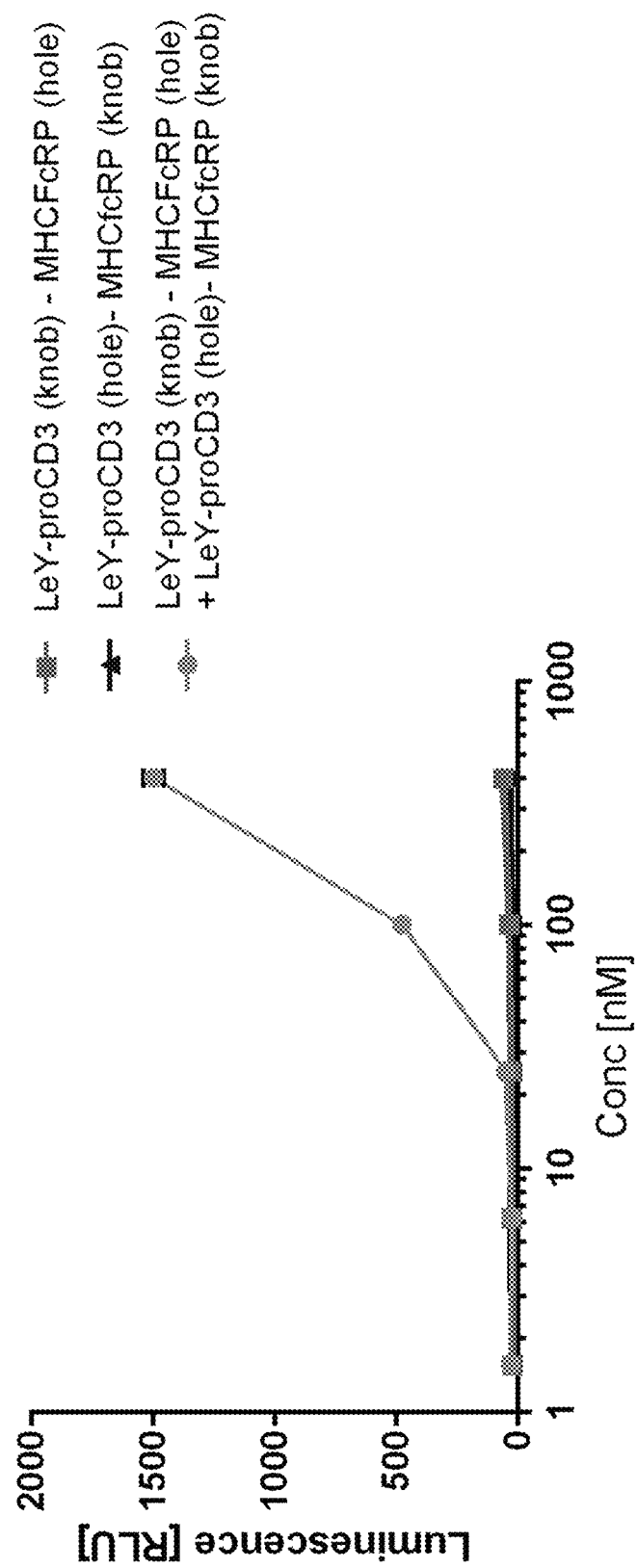
FIG. 25: Activation of CD3 binding functionality by 2/3-BiFab exchange on target cells.

MCF7 cells carry the LeY antigen on their cell surface and hence the individual 2/3-BiFabs can bind with their functional Fab arms. In FIG. 25 it can be seen that individually applied 2/3-BiFabs bind to MCF7 cells but generate no/low CD3 reporter signals. This reflects absence of CD3-binding functionality in these molecules. Simultaneous application of both (complementary) 2/3-BiFabs however generated significant signals that reflect efficient CD3-binding. This indicates successful on-cell/in vivo chain rearrangement/exchange and generation of functional TriFabs with CD3-binding functionality on the cells.

Successful chain exchange of the stem region and recovery of the functional stem-Fv (CD3-signals) was also observed upon consecutive application of the complementary 2/3-BiFabs. Application of the first entity to enable cell binding followed by extensive washing to remove unbound molecules and subsequent application of the 2nd entity also generated signals on antigen positive cells. This confirmed that successful exchange and activation of targeted anti-CD3 prodrug molecules reaction can occur under physiological conditions on the surface of target cells.

Example 19

On-Cell Conversion of Different Antigen Targeting 2/3-BiFab Prodrugs to Fully Functional Cell Bound Activated Tri-Specific TriFabs According to the Invention 2/3-BiFab mediated chain exchange and subsequent activation of prodrug-like antibody derivatives can be combined with dual antigen binding principles. This enhances the prodrug-activation specificity as depicted in FIG. 26: pairs of 2/3-BiFabs that upon chain exchange generate functional TriFabs can be generated which comprise stem-Fv complementing functionalities of the same specificity (e.g. CD3 (=CD-antigen 1) or CD-AG-2 (=CD-antigen 2) or other binders that benefit from targeted prodrug approaches), but comprise cell surface binding Fab arms of differing specificities. Thereby, productive chain exchange and recovery of stem-Fv functionality occurs only on cells that express both antigens. In such settings, exchange reaction generates on the cell surface trispecific TriFabs with one Fab arm derived from each 2/3-BiFab and the stem-Fv recovered from complementing VH and VL from both. High specificity of prodrug-activation is provided because the stem-Fv functionality is absent in the individual 2/3-BiFab or on cells that bind only one 2/3-BiFab. Only cells that carry target antigens for both complementary 2/3-BiFabs (in sufficient density) enable chain exchange and thereby re-creation of the functional stem-Fv region. On-cell generation of the bispecific binding functionality also contributes to avidity as it converts monovalent to bivalent cell surface binders. Thus, it increases and stabilizes the binding of the TriFab derivative on the surface of the target cell (avidity-mediated improvement as shown also for disulfide-lacking 2/3-IgGs).

Thus, cell surface concentration is higher and thereby additional specificity is gained.

Figure 27:
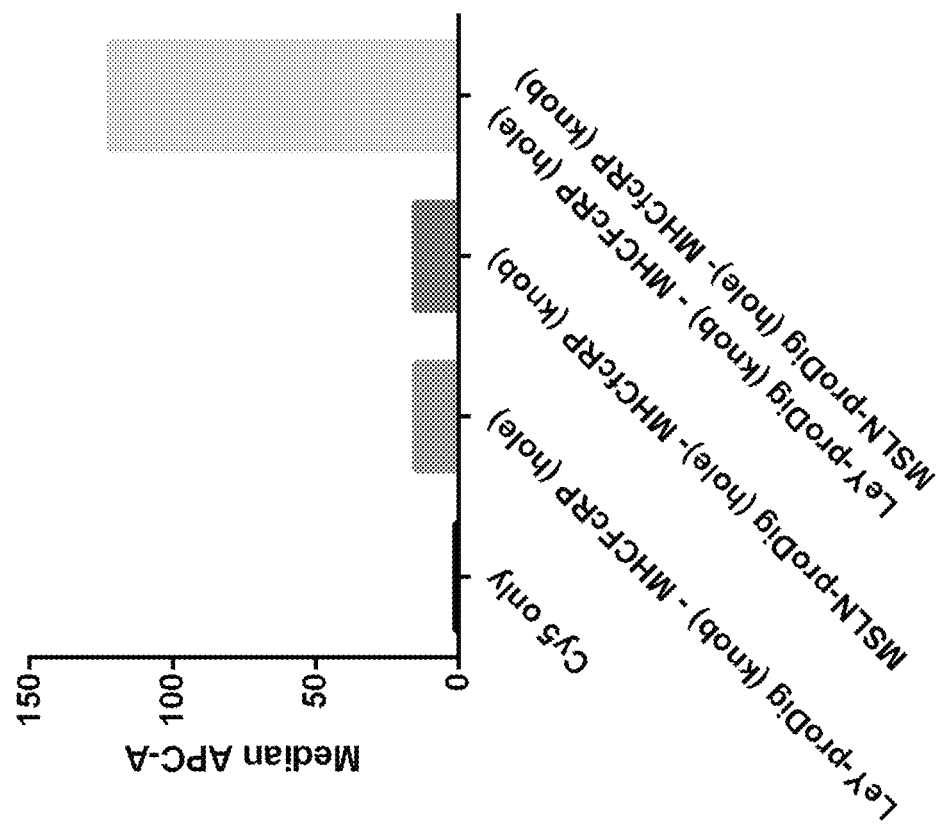
FIG. 27: On-cell conversion of different antigen targeting 2/3-BiFab prodrugs. LeY and MSLN targeting antibodies on A431-H9 cells. Incubation for six hours at 37° C.

FIG. 27 shows the experimental results for on-cell conversion of different antigen targeting 2/3-BiFab prodrugs to fully functional, cell bound, activated, tri-specific TriFabs. Complementary 2/3-BiFabs binding either the cell surface antigen LeY or the cell surface antigen mesothelin (MSLN) were produced and combined for 6 hours on a cell line that simultaneously express both antigens. The (inactivated) stem-Fv of both constructs harbored VH or VL of a Dig-binding antibody. FACS analyses indicated lack of relevant Dig-binding activity upon application of only the LeY-binding or only the mesothelin-binding 2/3-BiFab (FIG. 27, columns 2 and 3). Co-application of both, however, lead to generation of Dig-binding cell surface associated functionalities as indicated by increased fluorescence of these cells (FIG. 27, column 4).

Example 20

Figure 28:
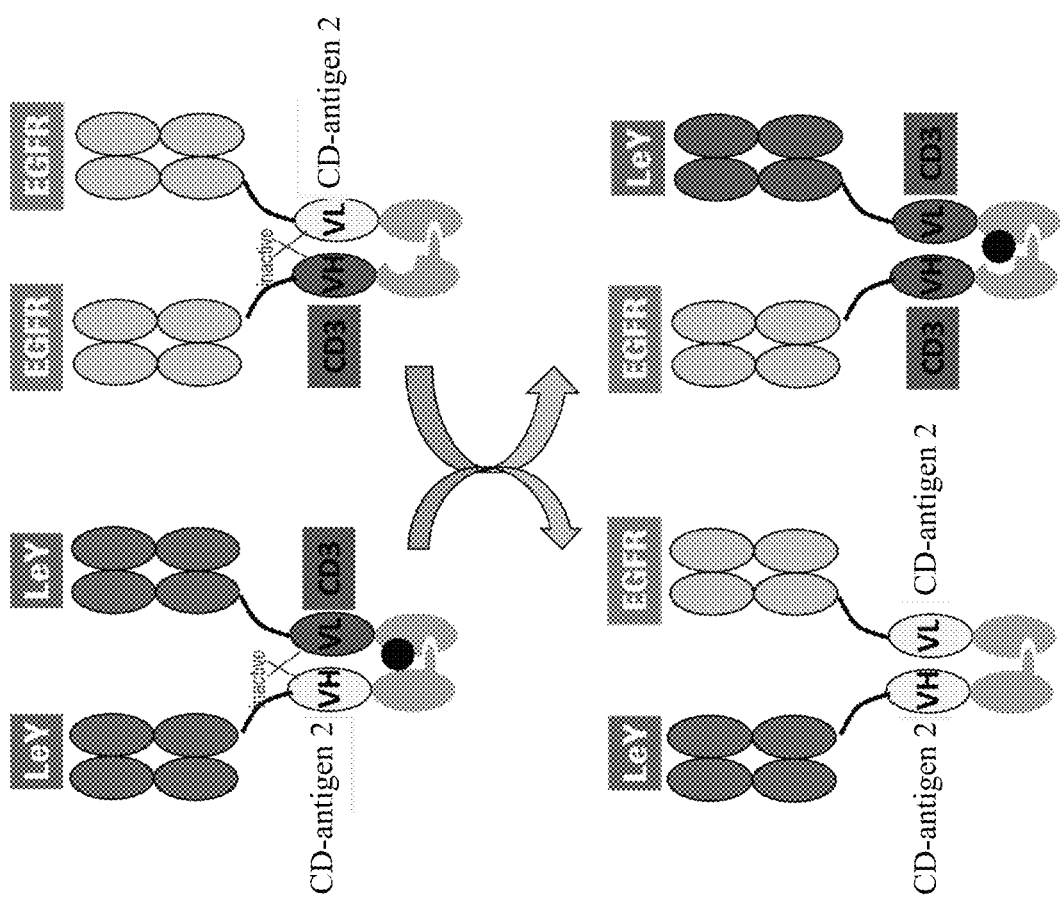
FIG. 28: TriFab derivatives containing prodrug exchange modules that can rearrange to fully functional trispecific entities.

On-Cell Conversion of Different Antigen Targeting TriFab Prodrugs to Tri-Specific TriFabs According to the Invention 2/3-BiFab derivatives as starting molecules comprise as MHCFcRP a modified stem-Fv region without Fab arm at their N-terminus. Attachment of Fab arms to these entities and expression thereof in combination with heavy chains generates exchange-enabled 2/3-TriFab-derivatives as shown in FIG. 28. Those molecules have their MHCFcRPs altered to potentially antigen-binding competent chains which-upon finding their corresponding partner-exchange to functional trispecific TriFabs.

Thus, 2/3-TriFab derivatives with cell surface target binding specificity 'A' can be generated that harbor a non-functional stem-Fv composed of VH with specificity 'X' and VL of specificity 'Y'. Correspondingly, complementary 2/3-TriFab derivatives can be generated with cell surface target binding specificity 'B' harbor a non-functional stem-Fv composed of VH with specificity 'Y' and VL of specificity 'X'. On-cell chain exchange of such molecules generates two types of trispecific TriFabs both carrying (avidity-enhanced) bispecific cell binding Fab arms (both A+B). One of those TriFabs harbors fully active stem-Fv functionality of the first specificity, the other TriFab contains the second stem Fv functionality (either fully active 'X' TriFab or fully active 'Y' TriFab). Applying such TriFab-prodrug pairs, for example, should enable the simultaneous conversion of inactive to active CD3 as well as CD-AG-2 binders (or of other binder pairs that benefit from avidity-enhanced specific prodrug activation) selectively on only those cells that simultaneously express two defined (cancer) surface antigens in sufficient density.

Example 21

Tri- or Tetraspecific 2/3-BiFab Prodrug Derivatives According to the Invention

Figure 29:
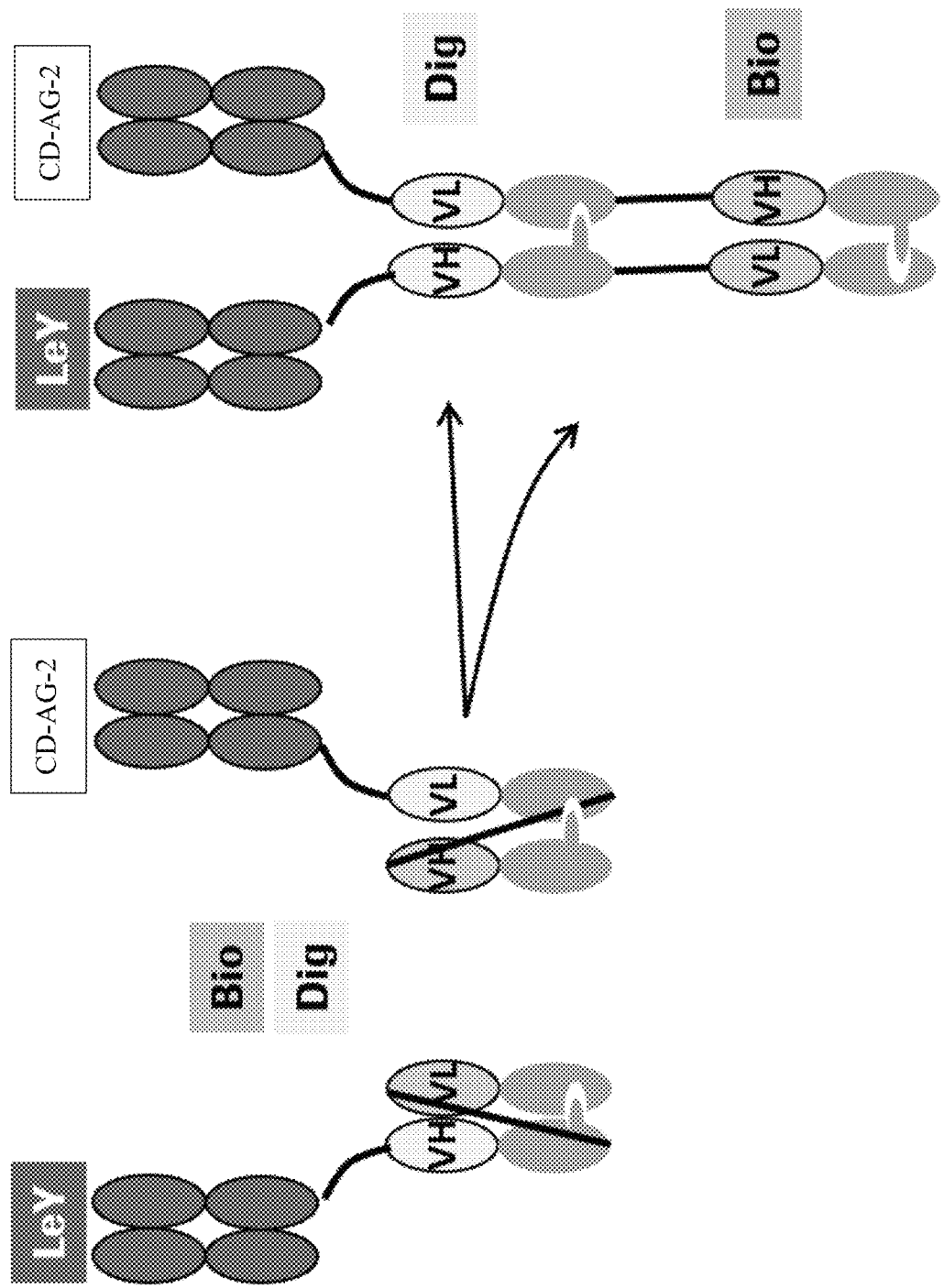
FIG. 29: 2/3-BiFab derivatives containing single-chain prodrug exchange modules that can rearrange to fully functional tetraspecific entities.

2/3-BiFab derivatives were designed and can be generated as starting molecules for the exchange reaction as reported herein, wherein the MHCFcRPs are covalently conjugated to the C-terminus of the heavy chain via a peptidic linker, such as e.g. a (G4S)6 linker (SEQ ID NO: 100). This generates a 'non-functional' entity resembling a single-chain stem-module of TriFabs as shown in FIG. 29. Attachment of Fab arms to these single-chain stem modules generates exchange-enabled TriFab-derivatives. Two of these can exchange to functional tri- or tetraspecific antibody derivatives as shown in FIG. 29.

| Chain | SEQ ID NO: |
|---|---|
| single chain anti-LeY-Dig TriFab heavy chain (knob) - Bio VL (hole) | 92 |
| single chain anti-LeY-Dig TriFab heavy chain (hole) - Bio VH (knob) | 93 |

The LeY binding region can be exchanged with sequences that enable binding to other antigens to generates antibody-prodrugs that bind different antigens on cells and rearrange in the same manner as described in FIG. 28.

Example 22

On-Cell Chain Conversion of Targeted Anti-CD3-Prodrug 2/3-BiFabs According to the Invention Enables Effective T-Cell-Mediated Killing of Tumor Cells This example demonstrates that on-cell conversion of 2/3-BiFab prodrugs to CD3-binding TriFabs enables T-cell mediated killing of the targeted tumor cells: LeY-tumor antigen binding 2/3-BiFabs were generated that contain either VH or VL domains of CD3-binding antibodies. Design and generation of those 2/3-BiFab prodrugs is described in the previous examples. The VH and VL sequences of the CD3-binder of these 2/3-BiFab prodrugs are described in US 2015/0166661 A1.

To demonstrate that those molecules induce cell-mediated killing upon simultaneous binding, they were applied at different concentrations to LeY positive MCF7 cells. Therefore, MCF7 cells were seeded out in 96 well plates and incubated overnight, followed by exposing those cells to 2/3-BiFab anti-LeY-proCD3 (knob)-MHCFcRP (hole) and 2/3-BiFab anti-LeY-proCD3 (hole)-MHCFcRP (knob). These components were either added individually/sequentially or in combination. To assess T-cell mediated killing, PBMCs from whole blood of healthy donors (isolated via state-of-the-art Ficoll purification) were added in a 5:1 ratio. Cultures were then maintained at 37° C. 5% $CO_2$ for 48 hours, followed by assessment of the degree of tumor cell lysis (applying state-of-the art LDH release assays).

Figure 30A:
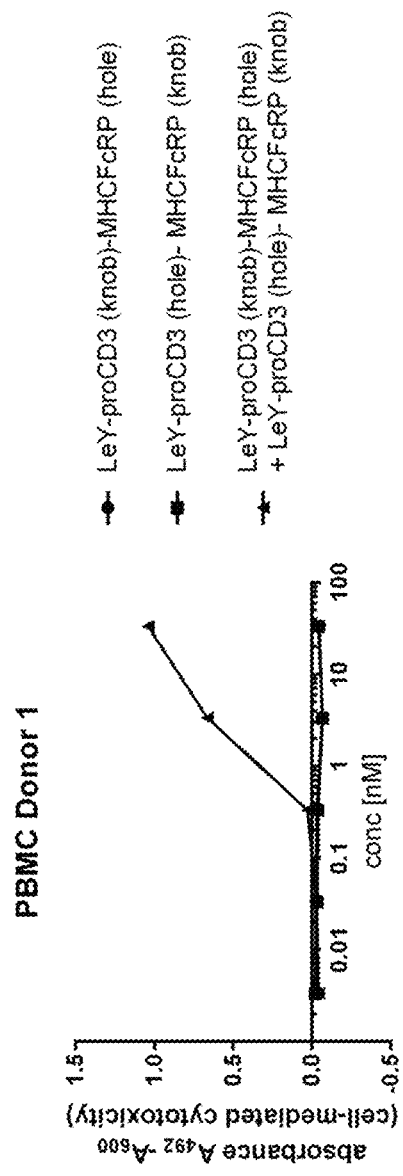
FIGS. 30A and 30B: Co-culture of PBMCs from two different donors and MCF7 with anti-LeY-proCD3 2/3-BiFabs. LDH release serves as indicator for cell-mediated killing of the targeted tumor cells.
Figure 30B:
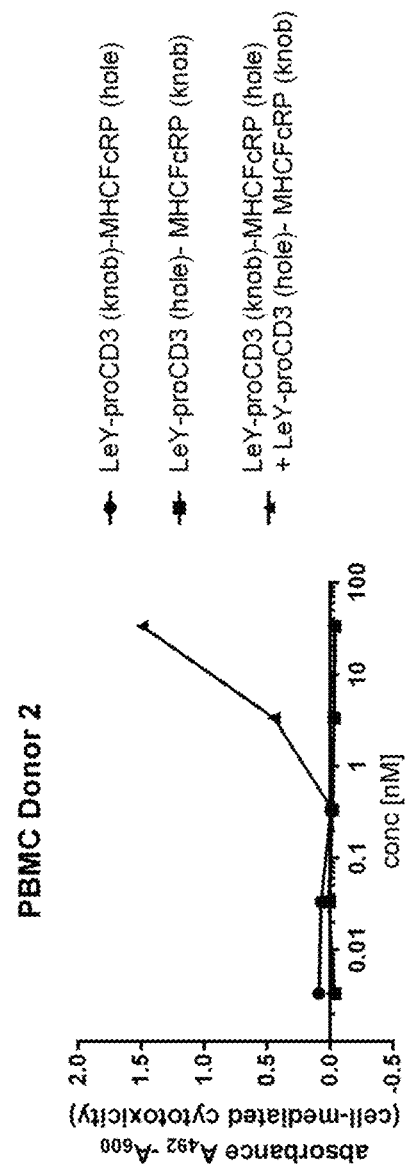

The results of these assays are shown in FIG. 30.

MCF7 cells carry the LeY antigen on their cell surface and hence the individual 2/3-BiFabs can bind with their functional Fab arms. Individually applied 2/3-BiFab, i.e. administration of either anti-LeY-proCD3 (knob)-MHCFcRP (hole) or 2/3-BiFab anti-LeY-proCD3 (hole)-MHCFcRP (knob) does not result in relevant T-cell-mediated killing (no release of LDH) even at high molar concentrations. This reflects absence of CD3-binding functionality (required for T-cell mediated cell lysis) of these molecules.

In contrast, simultaneous application of both (complementary) 2/3-BiFabs resulted in significant LDH release. This reflects significant tumor cell lysis already at quite low concentrations. The reason for this is successful chain rearrangement/exchange on tumor cell surfaces and generation of functional TriFabs with CD3-binding functionality. Those functional CD3-binding TriFabs then recruit and engage T-cells which—in turn—leads to targeted tumor cell lysis.

Example 23

On-Cell Chain Conversion of AG-4 and EGFR-Targeted Anti-CD3-Prodrug 2/3-BiFabs According to the Invention Enables Effective T-Cell-Mediated Killing of Tumor Cells and Strong Cytokine Release Analogously to the experimental setup described in Example 22, AG-4 expressing HELA cells and EGFR expressing A431 cells were targeted with respective 2/3-BiFabs.

Administration of either anti-AG-4-proCD3 (knob)-MHCFcRP (hole) or 2/3-BiFab anti-AG-4-proCD3 (hole)-MHCFcRP (knob) to HELA cells does not result in relevant cell-mediated killing (no release of LDH). This reflects absence of CD3-binding functionality (required for T-cell mediated cell lysis) of these molecules.

Additionally, administration of either anti-EGFR-proCD3 (knob)-MHCFcRP (hole) or 2/3-BiFab anti-EGFR-proCD3 (hole)-MHCFcRP (knob) to A431 cells does not result in relevant cell-mediated killing (no release of LDH).

Figure 31A:
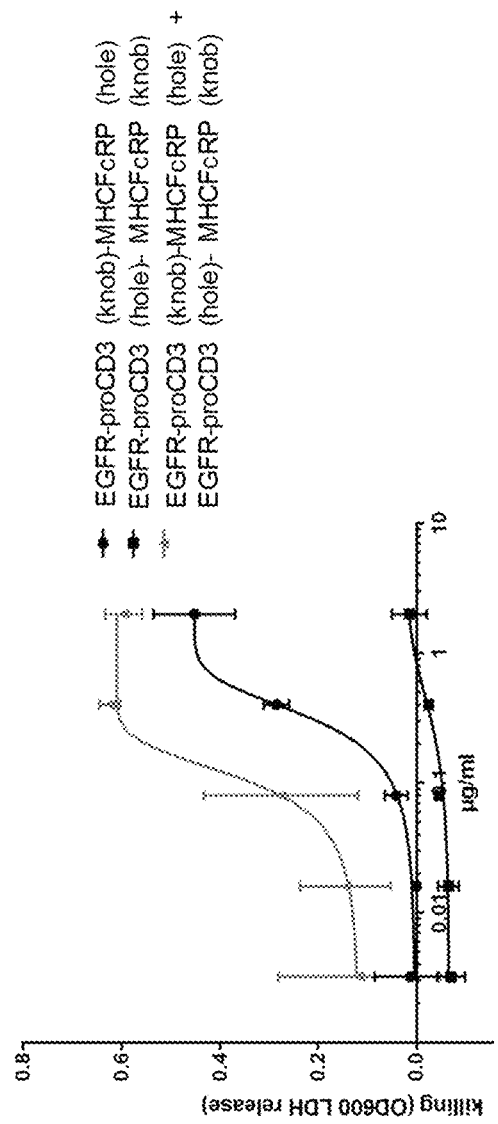
FIGS. 31A and 31B.
Figure 31B:
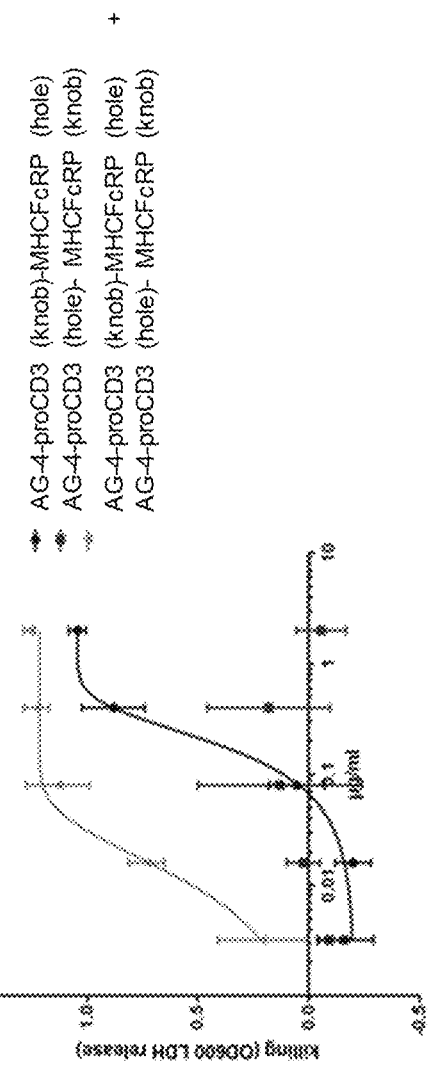

In contrast, simultaneous application of both (complementary) 2/3-BiFabs resulted in significant LDH release in both target cell setups. This reflects significant tumor cell lysis already at quite low concentrations (FIG. 31). The reason for this is successful chain exchange between the 2/3-BiFabs on tumor cell surfaces and generation of functional TriFabs with CD3-binding functionality.

Moreover, FIG. 32 shows the amounts of secreted cytokines at concentrations of 4 nM for AG-4 targeting on HELA cells. Significant more amounts of IL-2, IFN-γ, Granzyme B and TNFα are present in the setting where both anti-AG-4-proCD3 (knob)-MHCFcRP (hole) and 2/3-BiFab anti-AG-4-proCD3 (hole)-MHCFcRP (knob) were applied reflecting a strong immune response also on cytokine level (FIG. 32).

Example 24

Dual Targeting of EGFR and AG-4 on HELA Cells Enables On-Cell Chain Conversion of Anti-CD3-Prodrug 2/3-BiFabs According to the Invention and Effective T-Cell Activation Dual targeting was evaluated in a functional assay using reporter cell line that generates signals upon CD3-receptor binding (Promega T-cell Activation Bioassay (NFAT), cat. #J1621).

Figure 33:
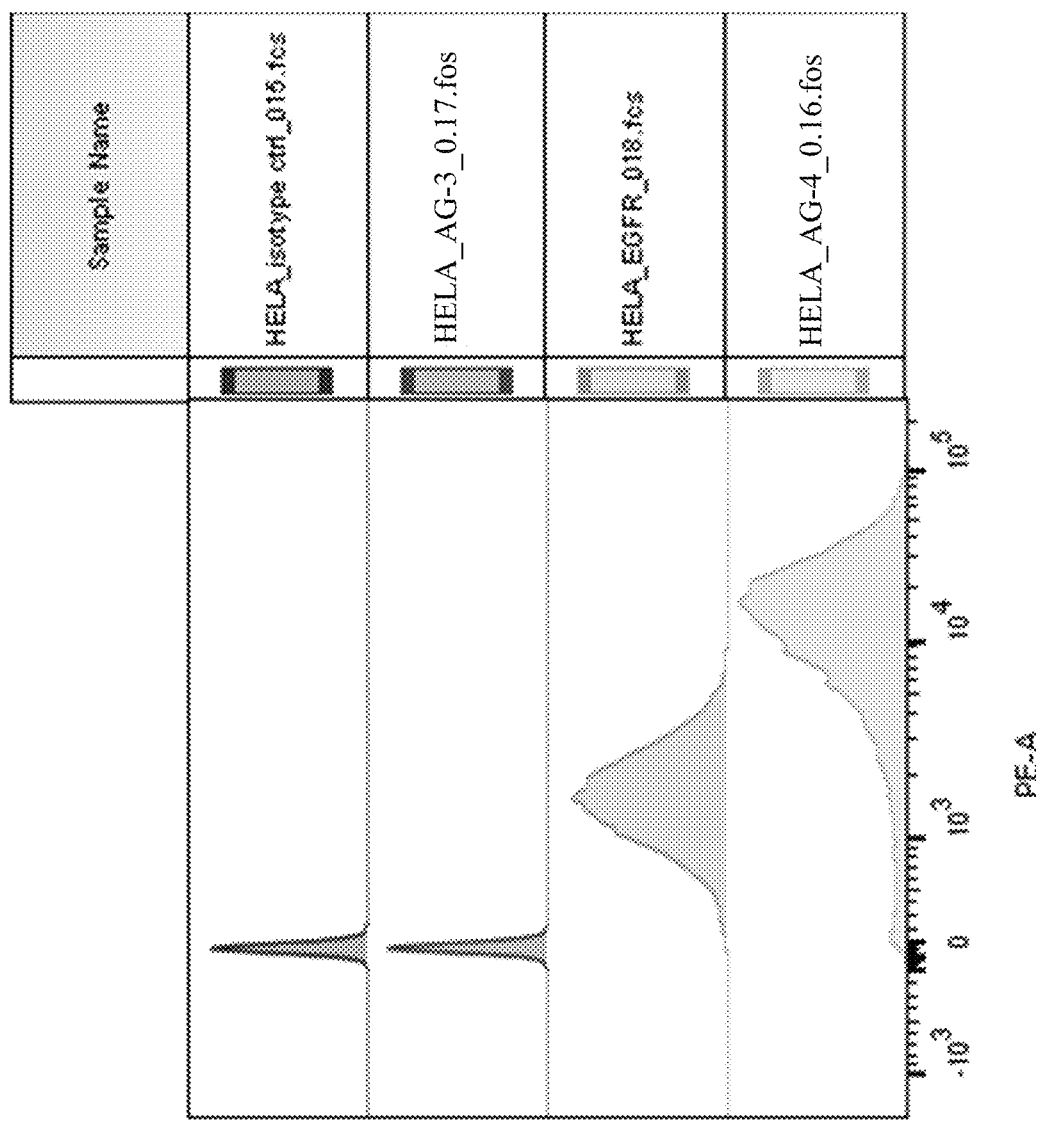
FIG. 33: Expression level of surface antigens AG-4 and EGFR on HELA cells
Figure 34:
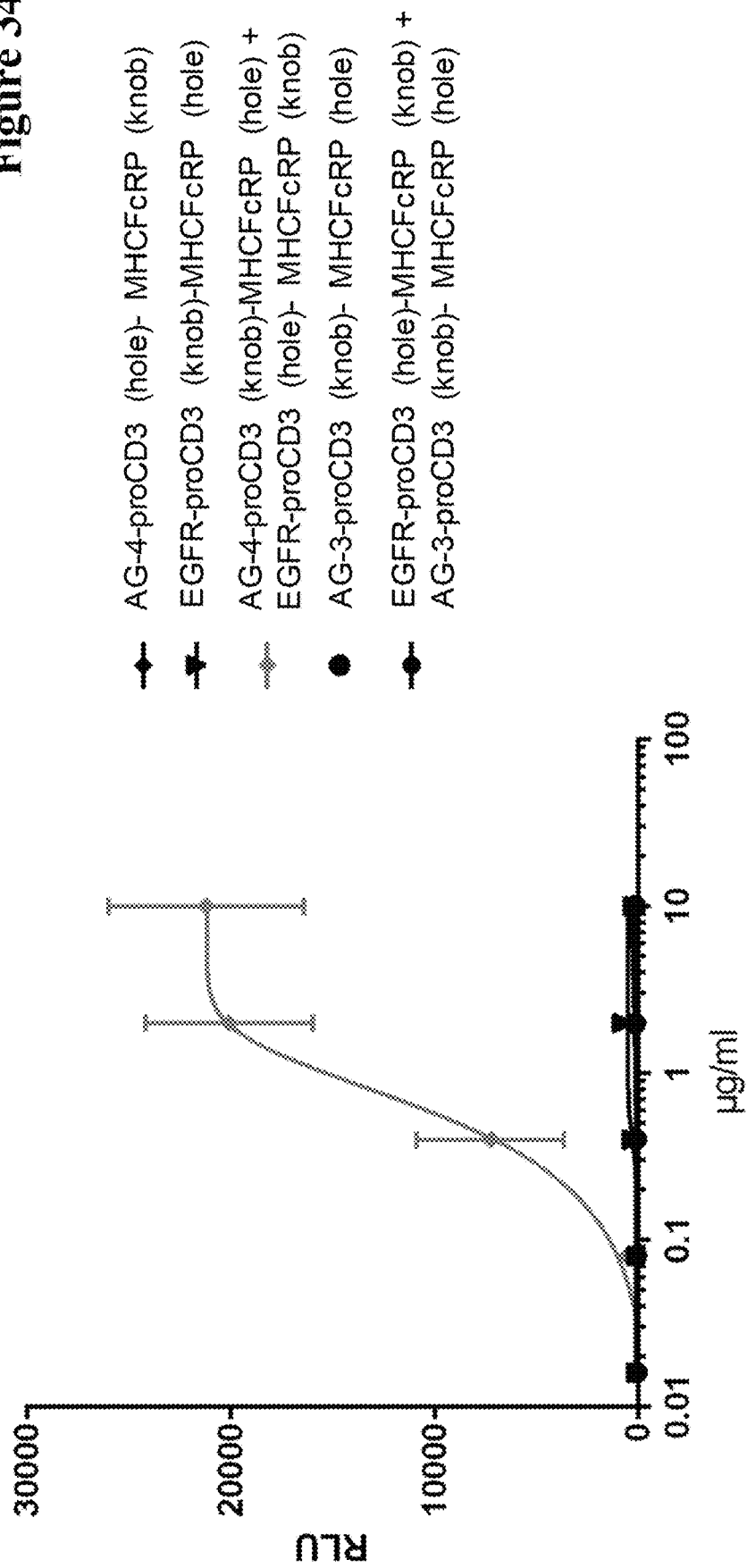
FIG. 34: Dual targeting of AG-4 and EGFR with respective proCD3 2/3-BiFabs and resulting T-cell activation in Jurkat reporter assay.

HELA cells that express both cell surface antigen 4 (AG-4) and epidermal growth factor (EGFR) (FIG. 33) were treated with either 2/3-BiFab targeting AG-4 or EGFR. The (inactivated) stem-Fv of both constructs harbored VH or VL of a CD3-binding antibody. The results indicated lack of relevant CD3-binding activity upon application of only the EGFR-proCD3 (knob)-MHCFcRP (hole) or only the AG-4-proCD3 (hole)-MHCFcRP (knob). Co-application of both, however, leads to significant binding to CD3 and activation of the reporter cell line (FIG. 34). As control EGFR-proCD3 (hole)-MHCFcRP (knob) and AG-3-proCD3 (knob)-MHCFcRP (hole) molecules were analyzed. In regard to antigen expression HELA cells are AG-3 negative, hence only the EGFR targeted 2/3-BiFabs are able to bind. This control serves as another prove that the shuffling reaction takes place on the cell surface and only when both 2/3-BiFabs are bound to the cell surface. In case the conversion would have been efficient even at low concentrations in media, the conversion product EGFR/AG-3/CD3 TriFab would have been able to bind the cell surface via the EGFR-binding entity and, thus, induce a CD3-mediated activation-which was not detected.

Example 25

Trispecific 2/3 Fab Prodrug Derivatives with Single-Chain Stem Motive Undergo On-Cell Conversion According to the Invention, Thereby Generate Two Additional Binding Sites and Strongly Activate T-Cells 2/3-BiFab derivatives were designed and were generated as starting molecules for the exchange reaction as reported herein, wherein the MHCFcRPs were covalently conjugated to the C-terminus of the heavy chain via a peptidic linker, such as e.g. a (G4S)6 linker (SEQ ID NO: 100). This generated a 'non-functional' entity resembling a single-chain stem-module of TriFabs as shown in FIG. 29. Attachment of Fab arms to these single-chain stem modules generated exchange-enabled TriFab-derivatives. Two of these were shown to exchange to functional tri-specific antibody derivatives as shown in FIG. 29.

| Chain | SEQ ID NO: |
| --- | --- |
| single chain anti-LeY-Dig TriFab heavy chain (knob) - Bio VL (hole) | 92 |
| single chain anti-LeY-Dig TriFab heavy chain (hole) - Bio VH (knob) | 93 |

Figure 35:
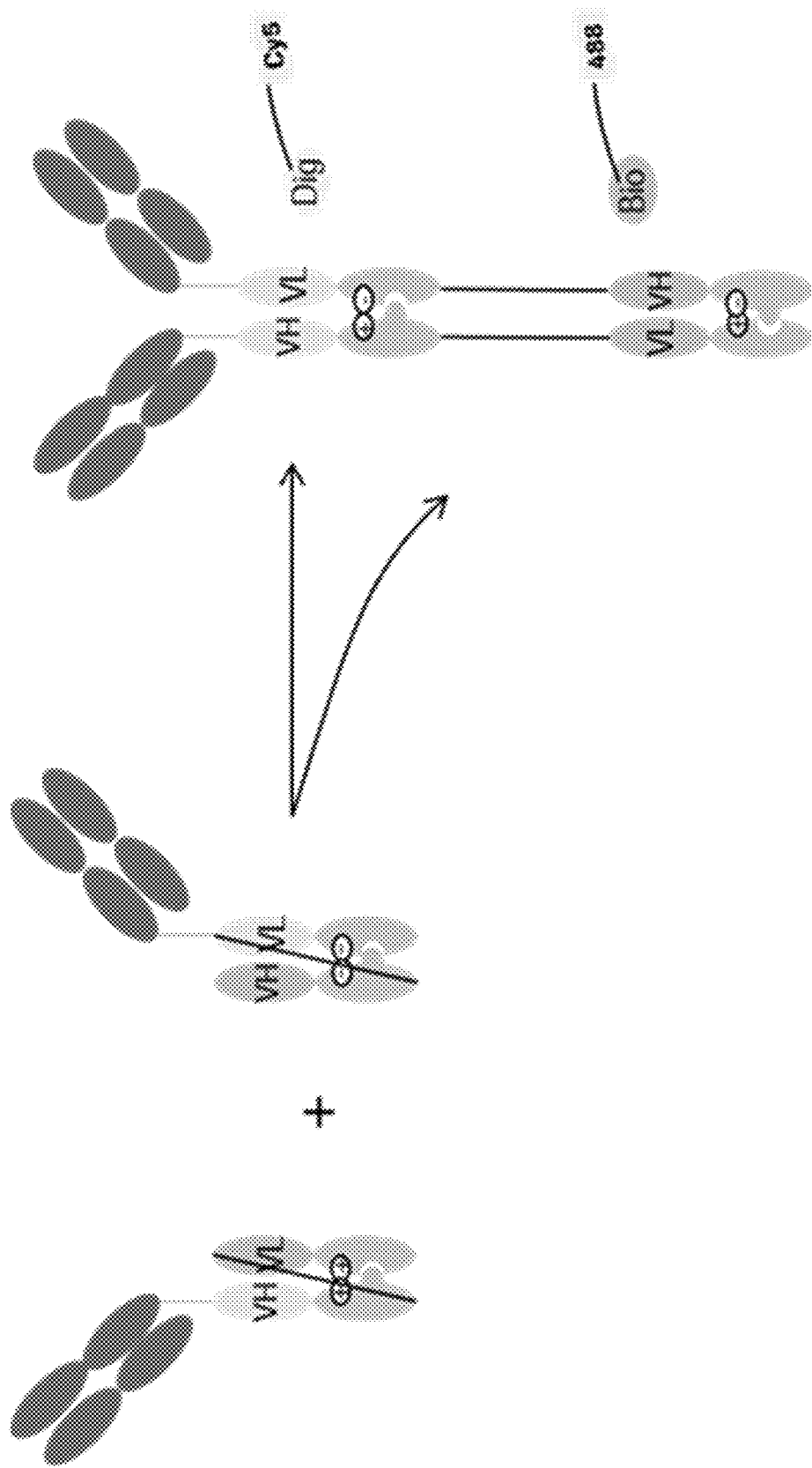
FIG. 35: 2/3-BiFab derivatives containing single-chain prodrug exchange modules that can rearrange to fully functional Digoxigenin and Biotin binding entities and can be analyzed by FACS by Dig-Cy5 and Bio-488 binding.

FIG. 35 depicts the setup for the binding studies via flow cytometry. The obtained results are shown in FIG. 36. Whereas, either of the constructs alone did not lead to binding of Dig-Cy5 or Bio-488 (FIG. 36A: row 2 and 3; FIG. 36B: row 2 and 3), the co-application of both, however, lead to generation of Dig and Bio-binding cell surface associated functionalities as indicated by increased fluorescence of these cells (FIG. 36A: row 4; FIG. 36B: row 4).

Figure 37:
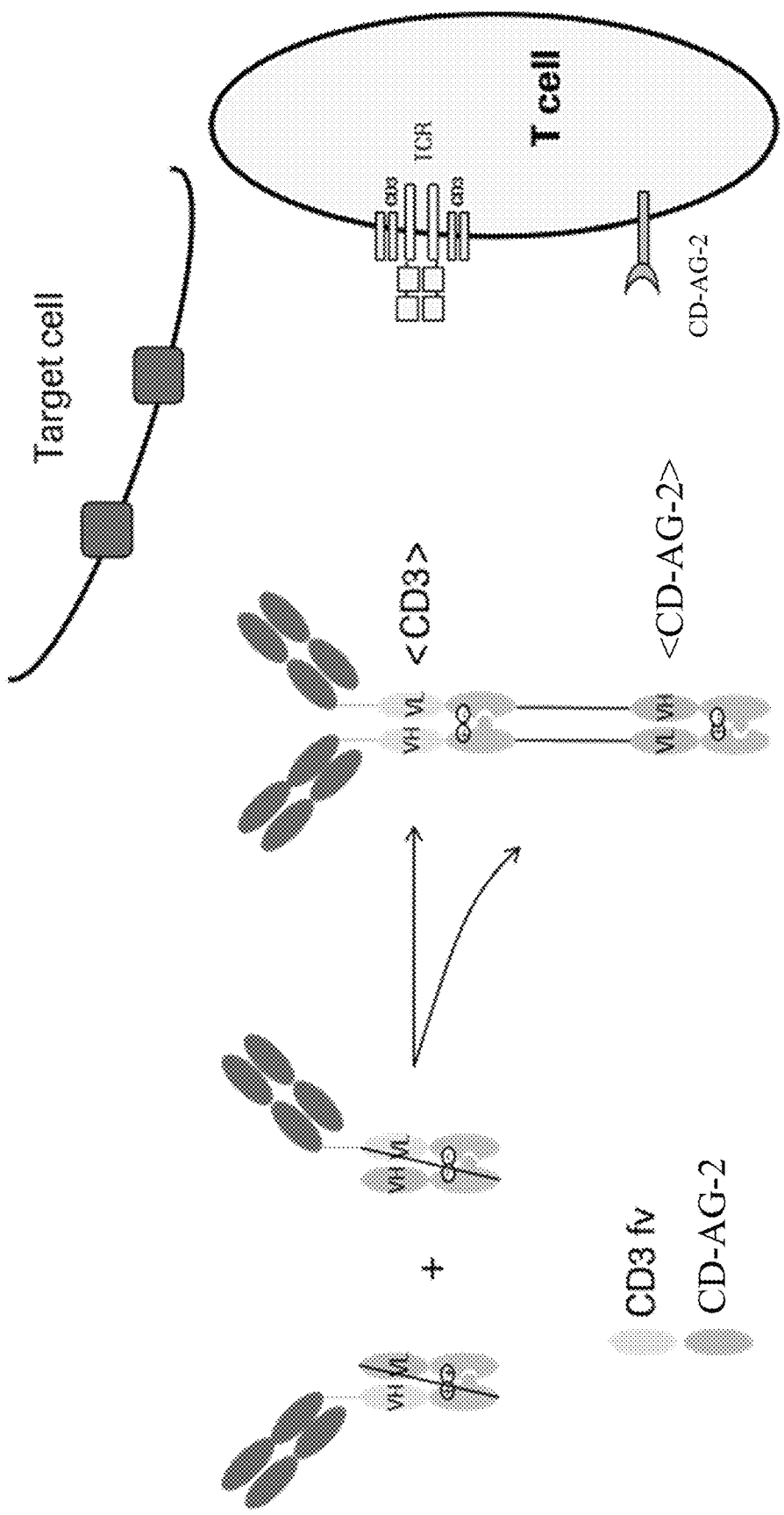
FIG. 37: 2/3-BiFab derivatives containing single-chain prodrug exchange modules that can rearrange to fully functional CD3 and CD-AG-2 binders.
Figure 38:
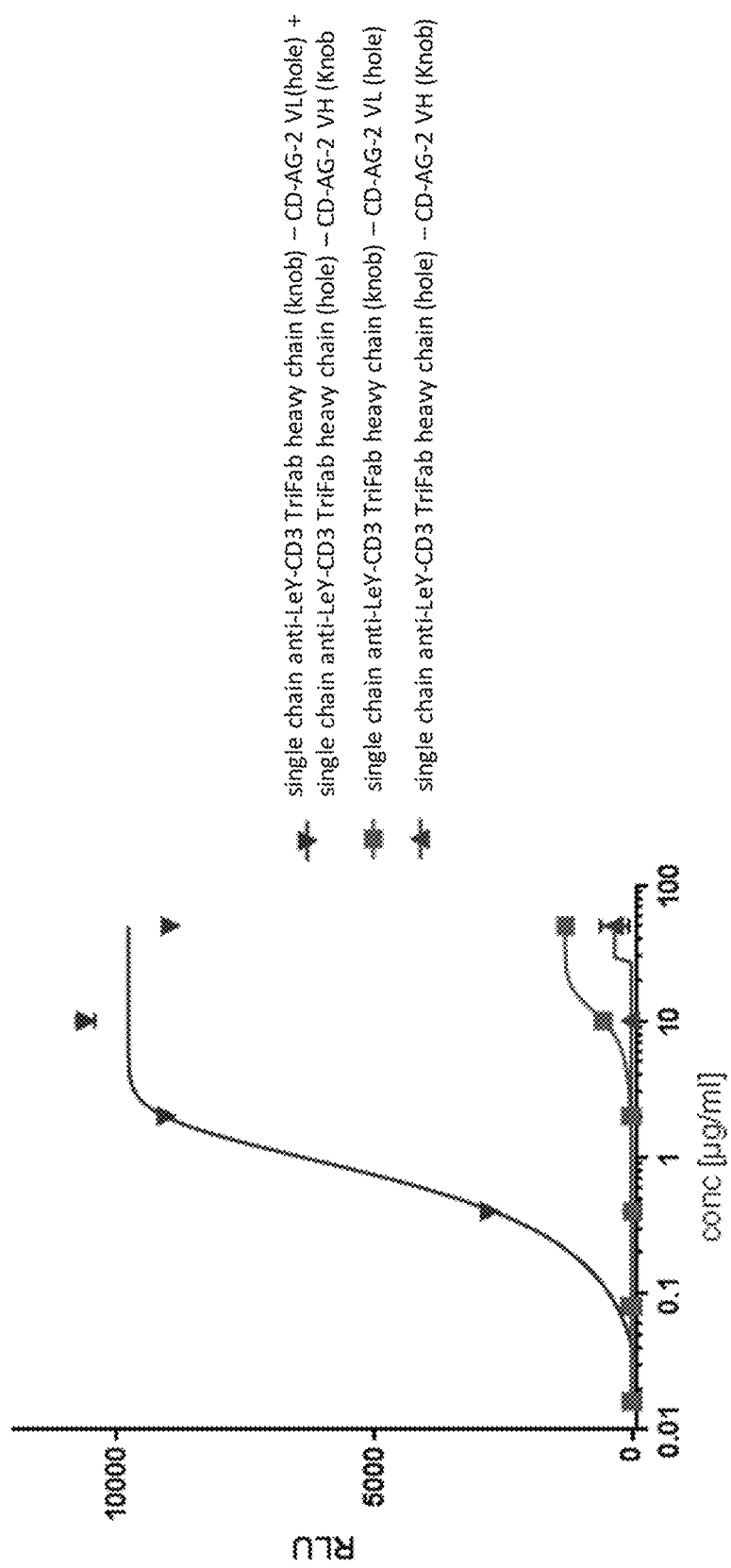
FIG. 38: 2/3-BiFab derivatives containing single-chain prodrug exchange modules that can rearrange to fully functional CD3 and CD-AG-2 binders activate T-cells in a CD3 signaling reporter assay.

Accordingly, trispecific antibodies were generated with CD3 and CD-AG-2 binding entities by combining single chain anti-LeY-CD3-TriFab heavy chain (knob)-CD-AG-2-VL (hole) and single chain anti-LeY-CD3-TriFab heavy chain (hole)-CD-AG-2-VH (knob) (FIG. 37). The ability of these molecules to activate T-cells was proven by using (Promega T-cell Activation Bioassay (NFAT), cat. #J1621) and is shown in FIG. 38.

Example 26

Figure 39:
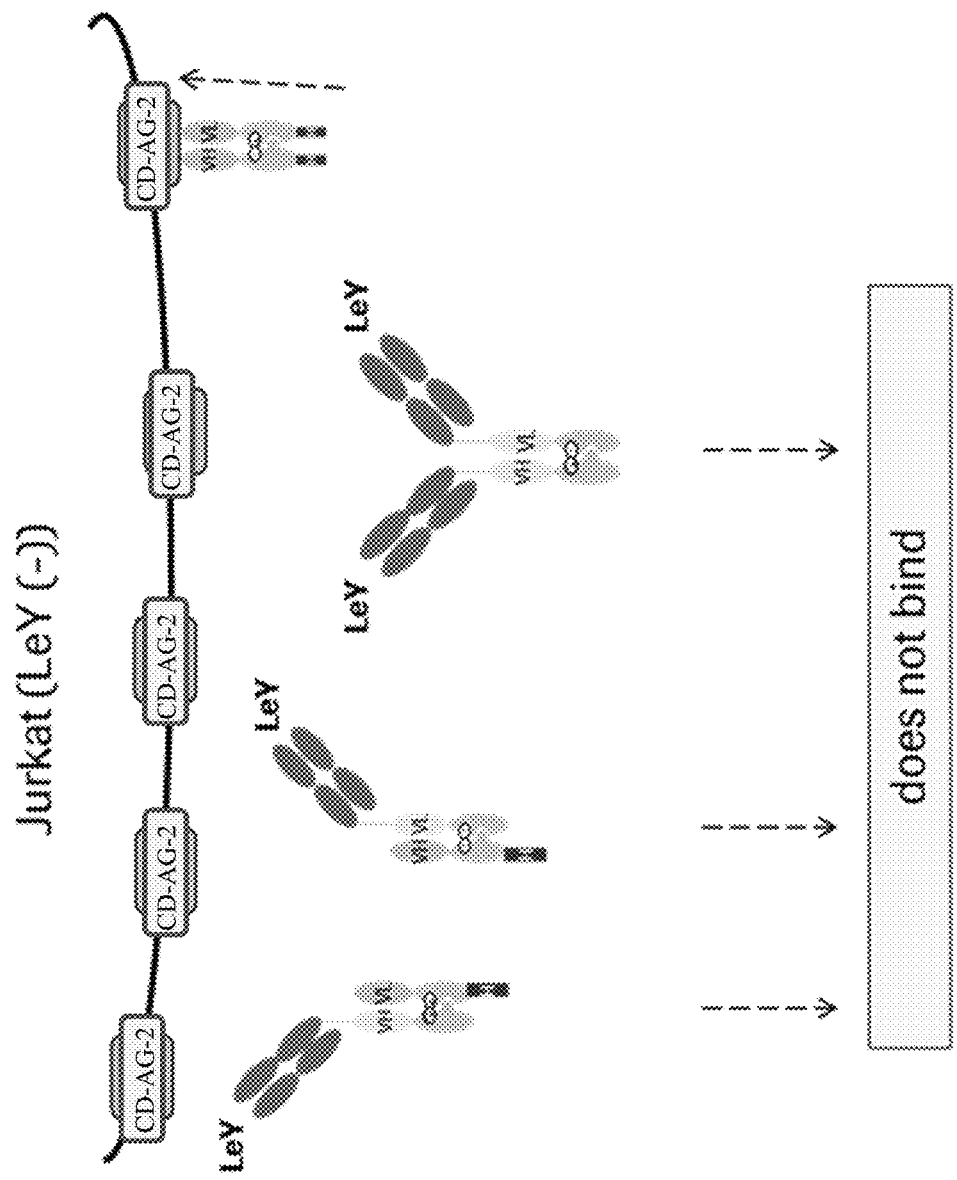
FIG. 39: MHCFcRP can be equipped with a variable fragment (VH or VL) and generate upon 2/3-BiFab conversion a CD-AG-2 binding Fab molecule as by-product.
Figure 40:
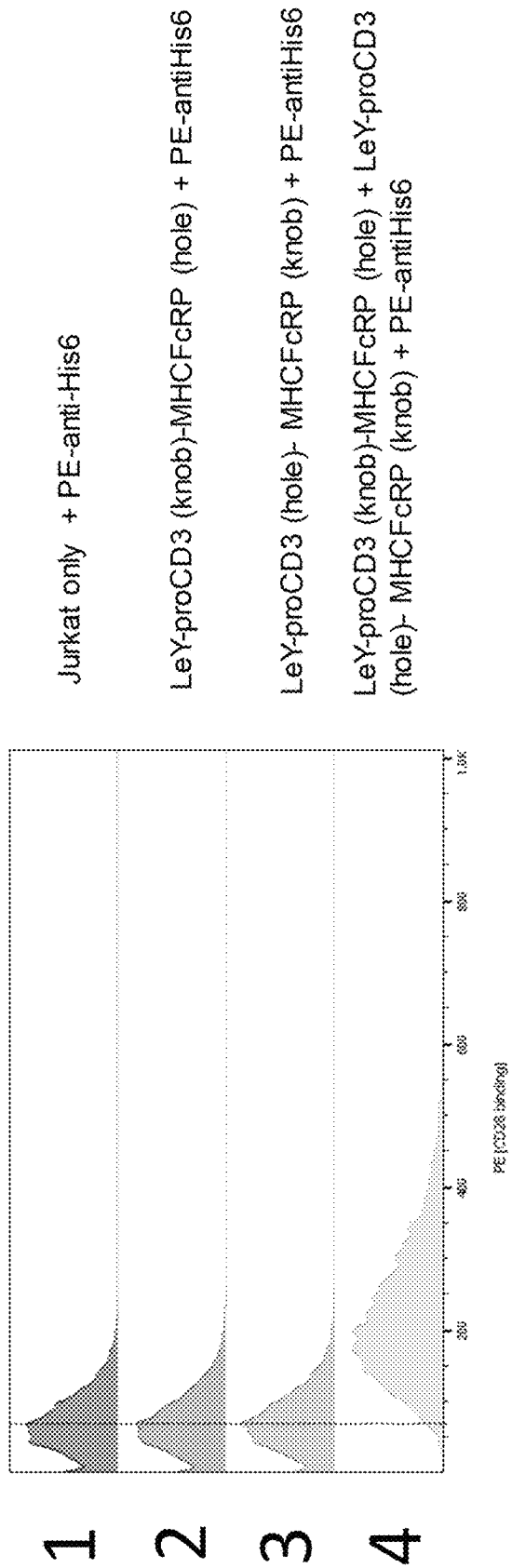
FIG. 40: FACS analysis CD-AG-2-MHCFcRP by product binding to Jurkat cell surface.

Fab-Shaped MHCFcRP Dimers with an Additional Binding Site as by-Products of the On-Cell Chain Conversion of Targeted Anti-CD3-Prodrug 2/3-BiFabs According to the Invention As depicted in FIG. 18, the MHCFcRP by-products with specificity 4 can be non-binding. However, by adding VH or the respective VL of a functional binding entity into the MHCFcRP, a functional, i.e. binding competent, Fab molecule was generated during the exchange reaction. To show the binding functionality of the MHCFcRP by-products, LeY-targeting 2/3-BiFabs pairs carrying CD-AG-2 MHCFcRP were added either alone or in combination to media. In addition, LeY-negative Jurkat cells that express CD-AG-2 were added. The whole setup is shown in FIG. 39. The MHCFcRP by-products were detected with PE-anti His6 antibody. 2/3-BiFabs (FIG. 40, row 2 and 3) alone did not lead to a His6 binding ("His6" disclosed as SEQ ID NO: 67) of the detection antibody due to the fact that the Jurkat cells are LeY negative and the 2/3-BiFab could not bind the cell surface. Combining the two 2/3-BiFabs lead to the generation of MHCFcRP by-products which were able to bind to CD-AG-2 and could be detected via an anti-His6 antibody by flow cytometry (see FIG. 40, row 4). Non-reacted 2/3-BiFabs were not able to bind the cell, because of absent LeY expression.

Example 27

Figure 41:
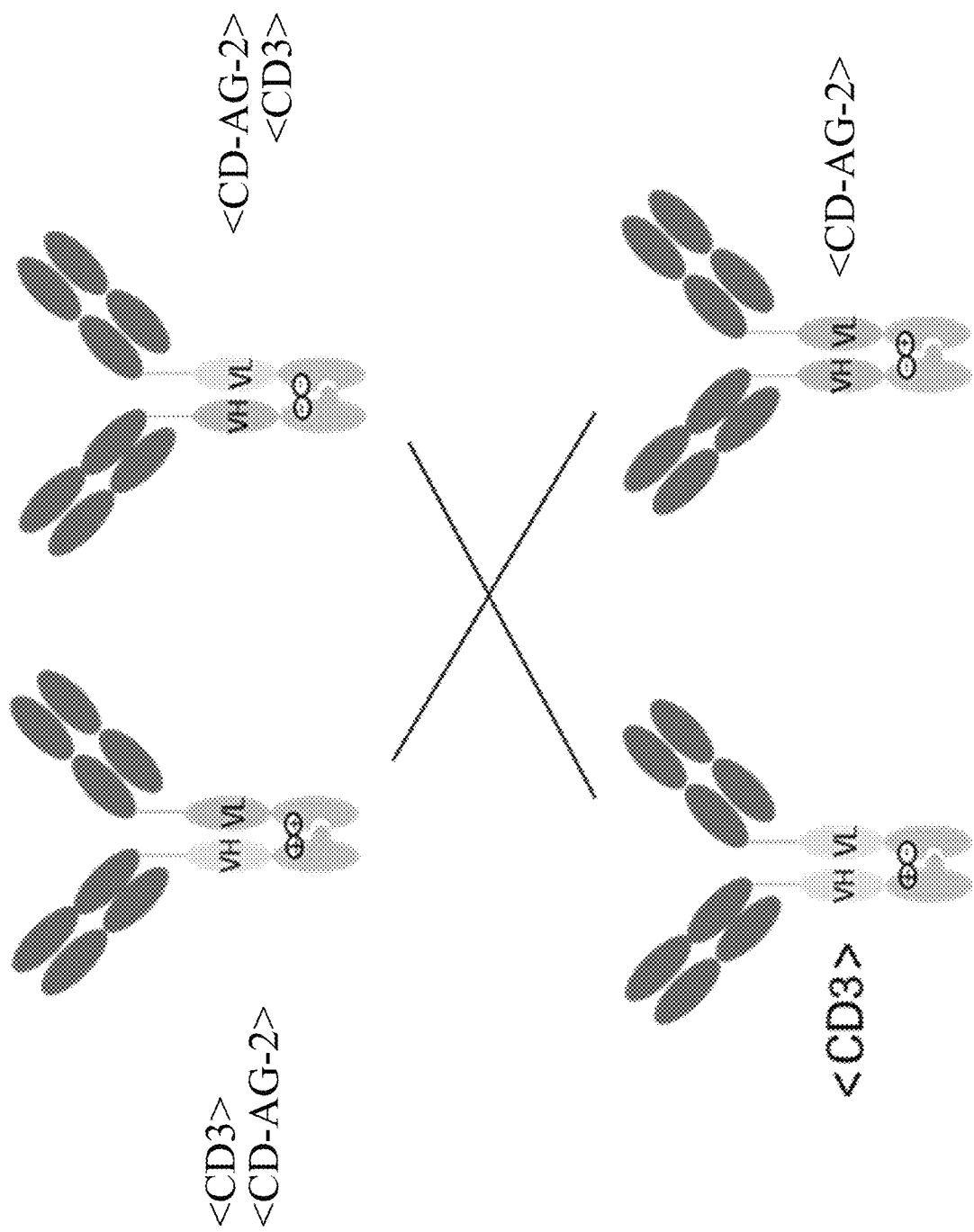
FIG. 41: N-terminal addition of a targeting Fab entity to MHCFcRP in combination with two proCD3/proCD-AG-2 variable regions within MHCFcRP leads to on cell assembly of two types of trispecific TriFabs that enable CD3 as well as CD-AG-2 binding.

MHCFcRP with an Additional N-Terminal Fused Fab as Targeting Entity Allow Bivalent Cell Targeting, Mediate On-Cell Conversion and the Production of Trivalent MHCFcRP by-Products According to the Invention 2/3-BiFab derivatives as starting molecules comprise as MHCFcRP a modified stem-Fv region without Fab arm at their N-terminus. Attachment of Fab arms to these entities and expression thereof in combination with heavy chains generates exchange-enabled 2/3-TriFab-derivatives as shown in FIG. 41. Those molecules have their MHCFcRPs altered to LeY-binding competent chains which-upon finding their corresponding partner-exchange to functional trispecific TriFabs.

Thus, 2/3-TriFab derivatives with LeY target binding specificity can be generated that harbor a non-functional stem-Fv composed of VH with CD3 specificity and VL of CD-AG-2 specificity, or vice versa. On-cell chain exchange of such molecules generates two types of trispecific TriFabs both carrying (avidity-enhanced) bispecific LeY Fab arms. One of those TriFabs harbors fully active stem-Fv functionality of the CD3 specificity, the other TriFab contains the CD-AG-2 stem Fv functionality. Applying such TriFab-prodrug pairs to LeY-expressing MCF7 cells, for example, enable the simultaneous conversion of inactive to active CD3 as well as CD-AG-2 binders.

Figure 42:
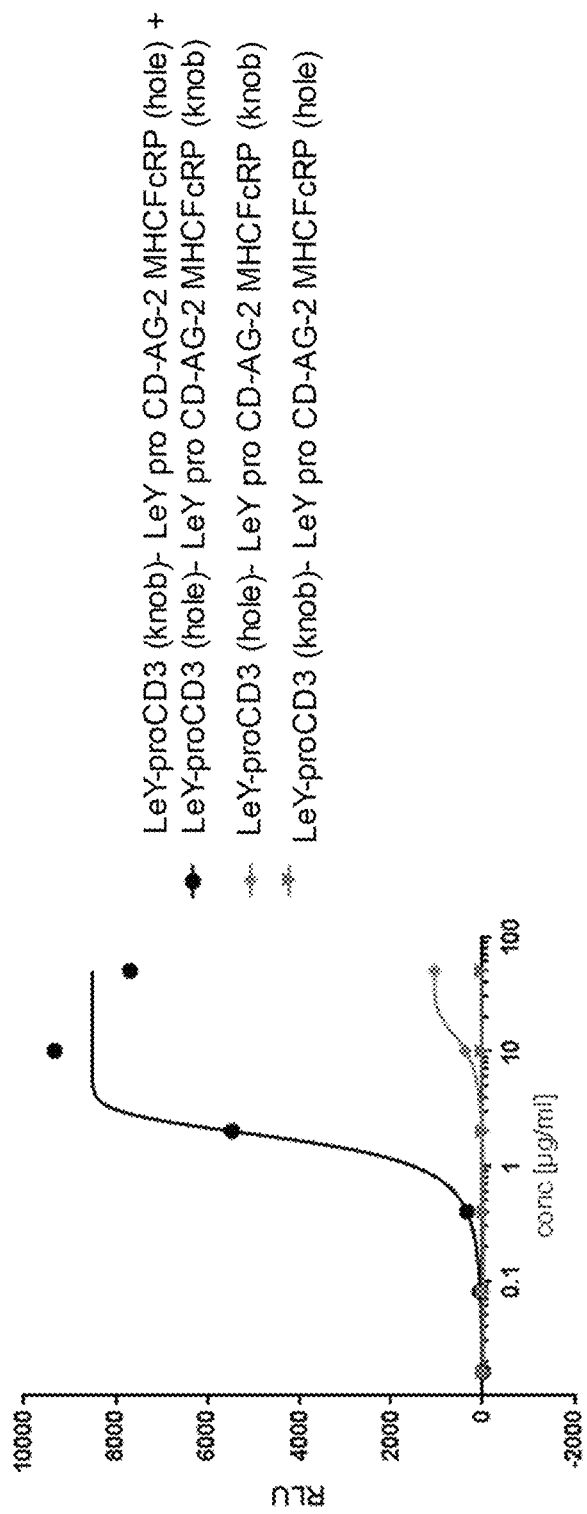
FIG. 42: T-cell activation capability of trispecific TriFab in a CD3 signaling assay.

Results are depicted in FIG. 42. The results indicated lack of relevant T-cell activating entities upon application of only the LeY-proCD3 (knob)-LeY-proCD-AG-2-MHCFcRP (hole) or LeY-proCD3 (hole)-LeY-proCD-AG-2-MHCFcRP (knob). Co-application of both, however, leads to a significant T-cell activation.

Example 28

Figure 43:
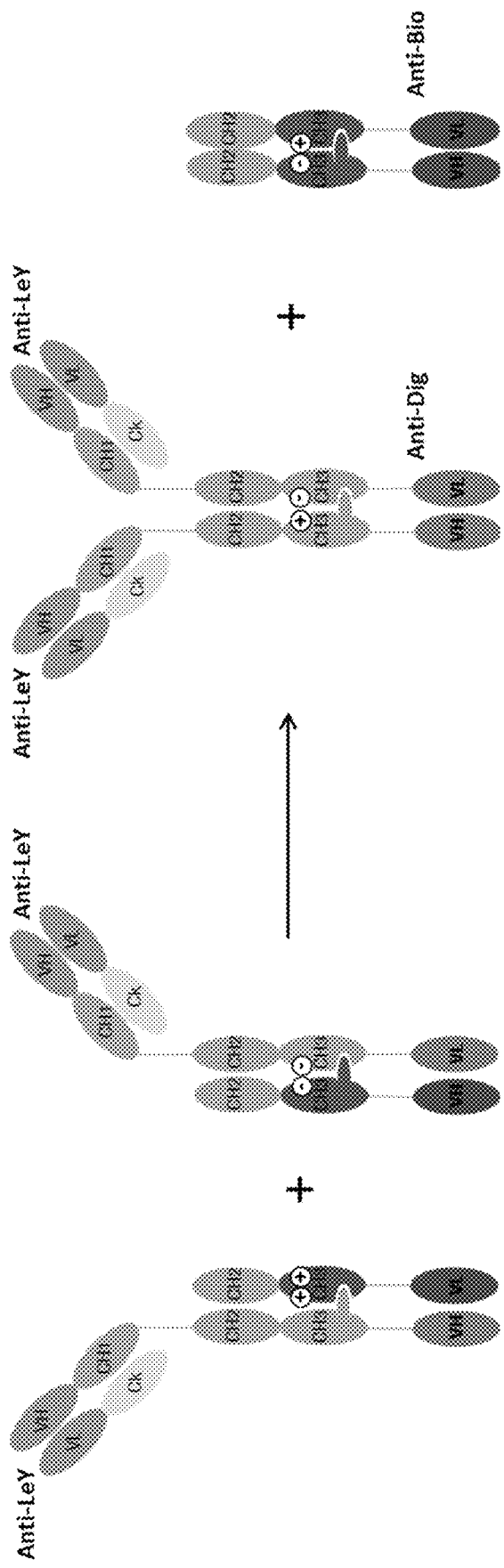
FIG. 43: An alternative 2/3-BiFab format that contains a CH2 domain and thereby an effector function competent Fc-region; the variable domains are each at the C-terminal end of the Fc-region.
Figure 44:
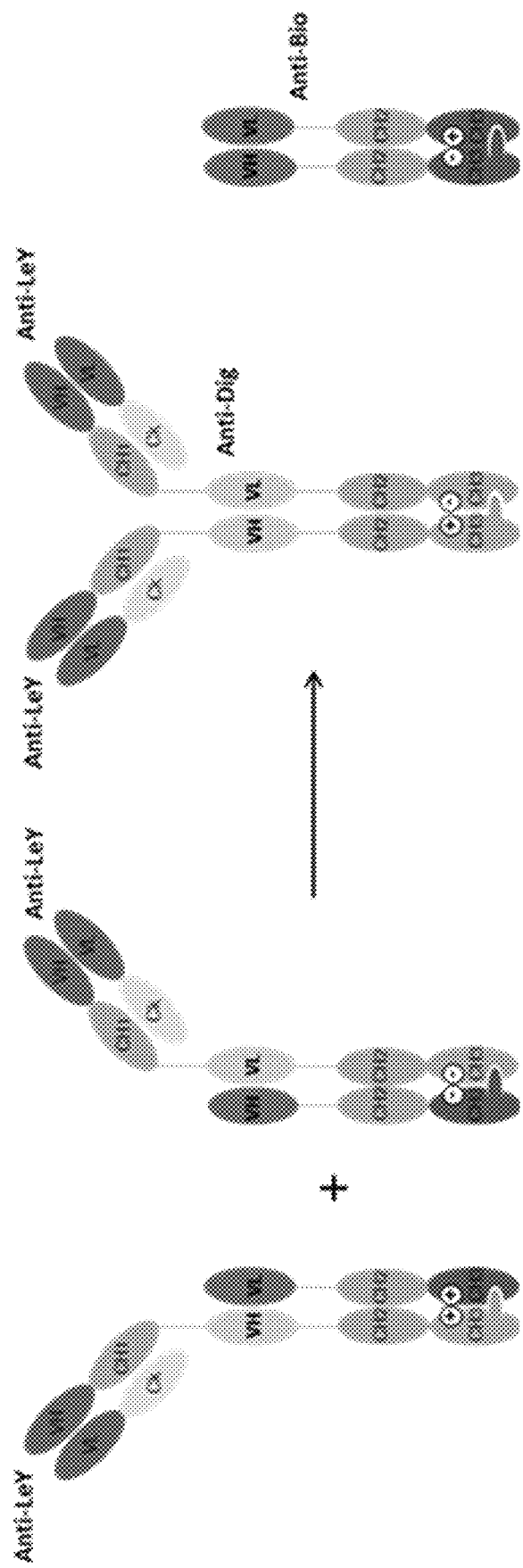
FIG. 44: An alternative 2/3-BiFab format that contains an additional CH2 domain and thereby an effector function competent Fc-region; the variable domain is in between the Fc-region and the targeting Fab or at the N-terminus, respectively.
Figure 45:
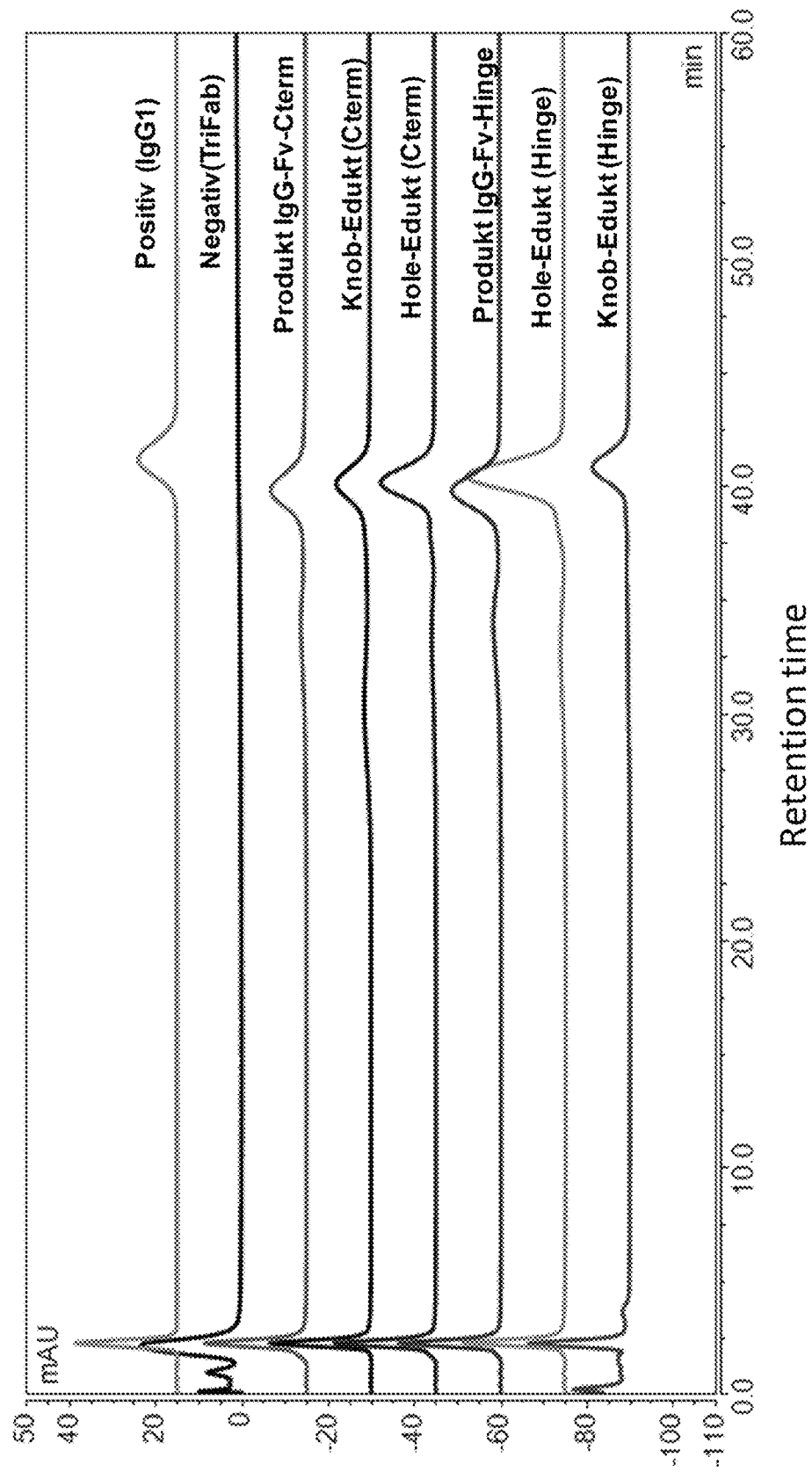
FIG. 45: Analytical FcRn affinity chromatography was performed to prove the CH2-dependent binding of the CH2 competent 2/3-BiFab molecules.

Alternative 2/3-BiFab Derivatives Remain CH2-Dependent FcRn Binding Intact and Show On-Cell Chain Conversion According to the Invention 2/3-BiFab derivatives as starting molecules comprise as MHCFcRP a modified stem-Fv region. To keep the CH2 domain from conventional IgG and hence the ability to bind FcRn for prolonged half-life, the variable fragment can be attached at the C-terminal end of a CH2-CH3 dimer as depicted in FIG. 43. The partially destabilizing mutations in the CH3 domain are the same as in 2/3-BiFabs. Alternatively, the variable fragment can be introduced in-between the Fc-part (CH2+CH3) and the Fab part as shown in FIG. 44. All antibodies were expressed as described earlier in good yields (72 mg/L to 161 mg/L). FIG. 45 confirms the ability of the CH2 containing formats to display a higher binding to FcRn revealing an extended serum half-life compared to initial 2/3-BiFabs (the analytical FcRn affinity chromatography was performed as described in Schlothauer, T., et al., MAbs 5 (2013) 576-586).

The ability of CH2 containing 2/3-BiFabs to confer on-cell chain conversion was analyzed by flow cytometry as described above. Two educt molecules were sequentially applied (with two times wash in-between) to MCF7 cells. Upon chain exchange a functional anti digoxigenin binding site was assembled and hence able to bind digoxigenylated Cy5 on the cell surface, which was detected by FACS. Both molecule classes according to FIGS. 43 and 44, successfully underwent chain exchange reaction according to the invention as depicted in FIG. 46.

Example 29

Figure 48:
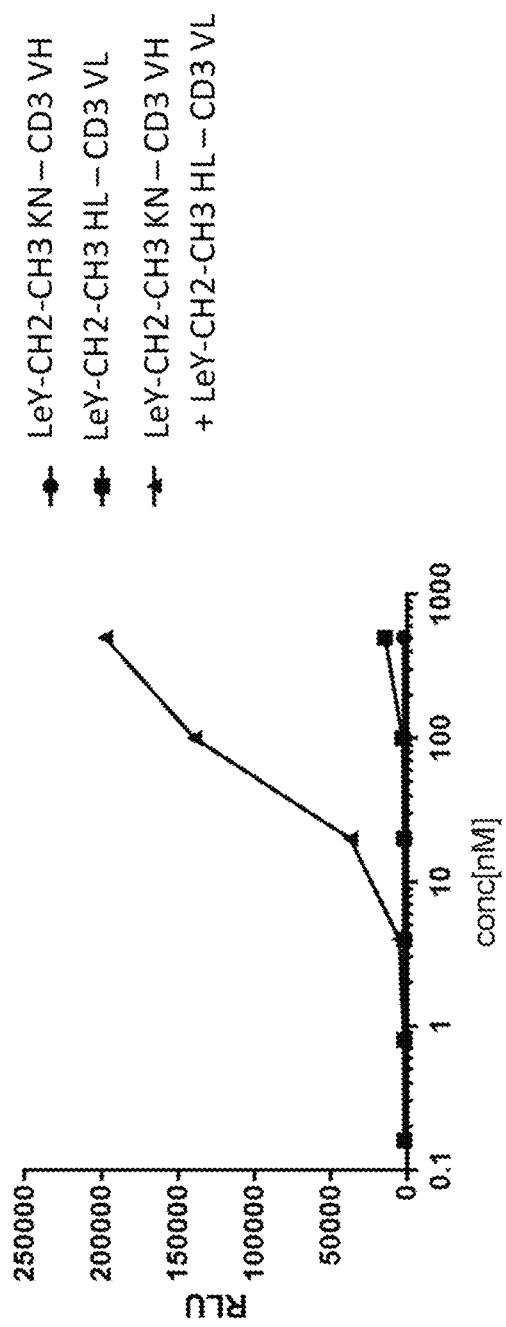
FIG. 48: A T-cell reporter assay reveals the ability of CH2-containing 2/3-BiFabs to induce a T-cell activation. KN=knob; HL=hole.

CH2 Domain Containing 2/3-BiFabs are Able to Convert into Functional CD3-Binding Sites in a Method According to the Invention and Thereby Mediate T-Cell Activation CH2-containing 2/3-BiFabs with the variable fragment attached at the C-terminal end (FIG. 47) were analyzed for their ability to generate a functional CD3 binder using the Jurkat activation assay as outlined above. MCF7 cells served as target cells, LeY as target antigen. Whereas the 2/3-BiFabs did not induce a significant Jurkat activation, the combination of both resulted in a dose-dependent activation and light emission in the reporter system (RLU) (FIG. 48).

Example 30

Transmission Electron Microscopy Confirms the Proposed Structure of 2/3-BiFabs and the Corresponding Product and Reveals them as being Highly Flexible To analyze the shape and structure of the 2/3-BiFabs and the respective chain exchange product obtained in a method according to the invention Negative Stain Transmission Electron Microscopy (NS-TEM) was performed. Results (FIG. 49) reveal a rigid intradomain character but high interdomain flexibility.

Grid Preparation: Freshly thawed samples are diluted in D-PBS to a concentration of about 5 mg/ml. 4 µl of the diluted sample was adsorbed to glow discharged 400 mesh carbon coated parlodion copper grids, washed with 3 drops of water, incubated with 3 µl of TMV containing solution, further washed with 2 drops of water and finally stained with 2 drops of uranyl acetate 2%.

Transmission electron microscopy: Samples were imaged using a Tecnai 12 transmission electron microscope (FEI, Eindhoven, The Netherlands) operating at 120 kV. Electron micrographs were recorded on a 2048×2048 pixel charge-coupled device camera (Veleta Gloor Instruments) at a nominal magnification of 195,000× yielding a final pixel size of 0.296 nm on the specimen level. Alternatively, samples were imaged using a FEI Tecnai G2 Spirit TEM (FEI, Eindhoven, The Netherlands) operating at 80 kV. Electron micrographs were then recorded on a 2048×2048 pixel charge-coupled device camera (Veleta Soft Imaging Systems) at a nominal magnification of 135,000× yielding a final pixel size of 0.33 nm on the specimen level.

Image processing: Reference-free alignment was performed on manually selected particles from recorded images using the EMAN2 image processing package (see e.g. G. Tang, L., et al., J. Struct. Biol. 157 (2007) 38-46). The extracted particles were aligned and classified by multivariate statistical analysis yielding 2D class averages. Additionally, when class averaging was not possible, raw images of particles were also manually stained for clarity using Photoshop.

Example 31

Figure 50:
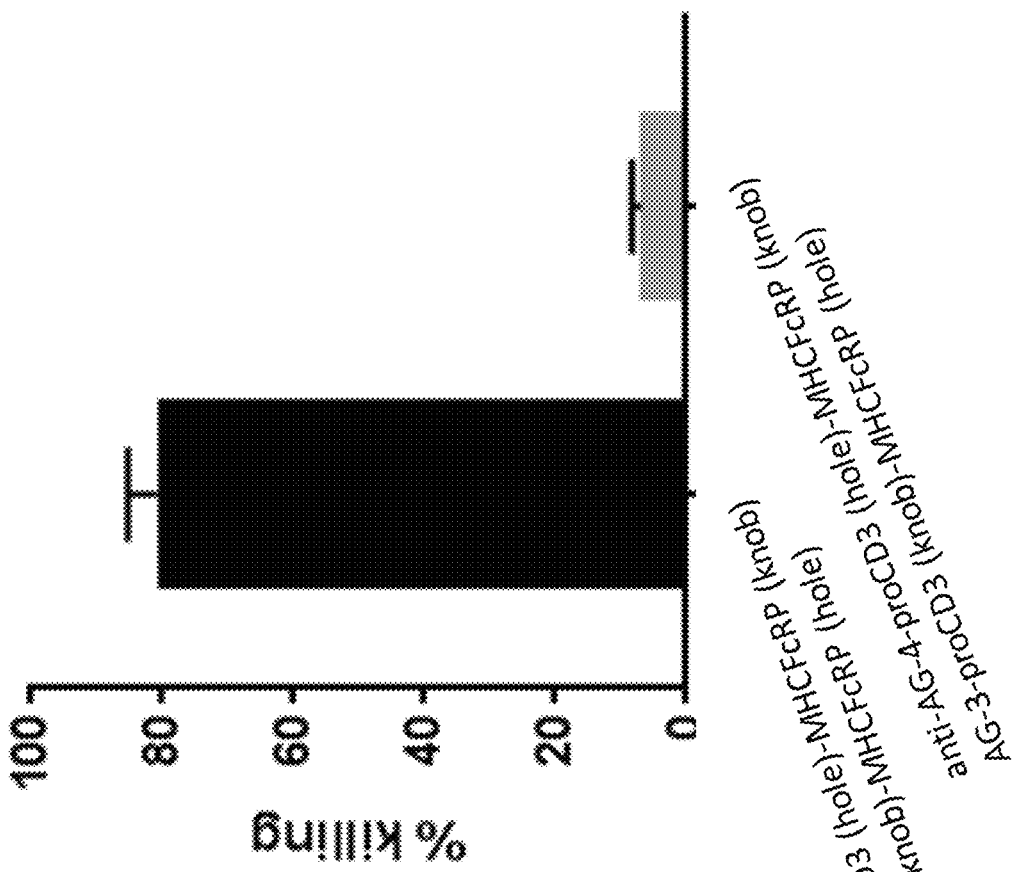
FIG. 50: Target-independent shuffling occurs at a low level only at high concentrations (300 nM).
Figure 51:
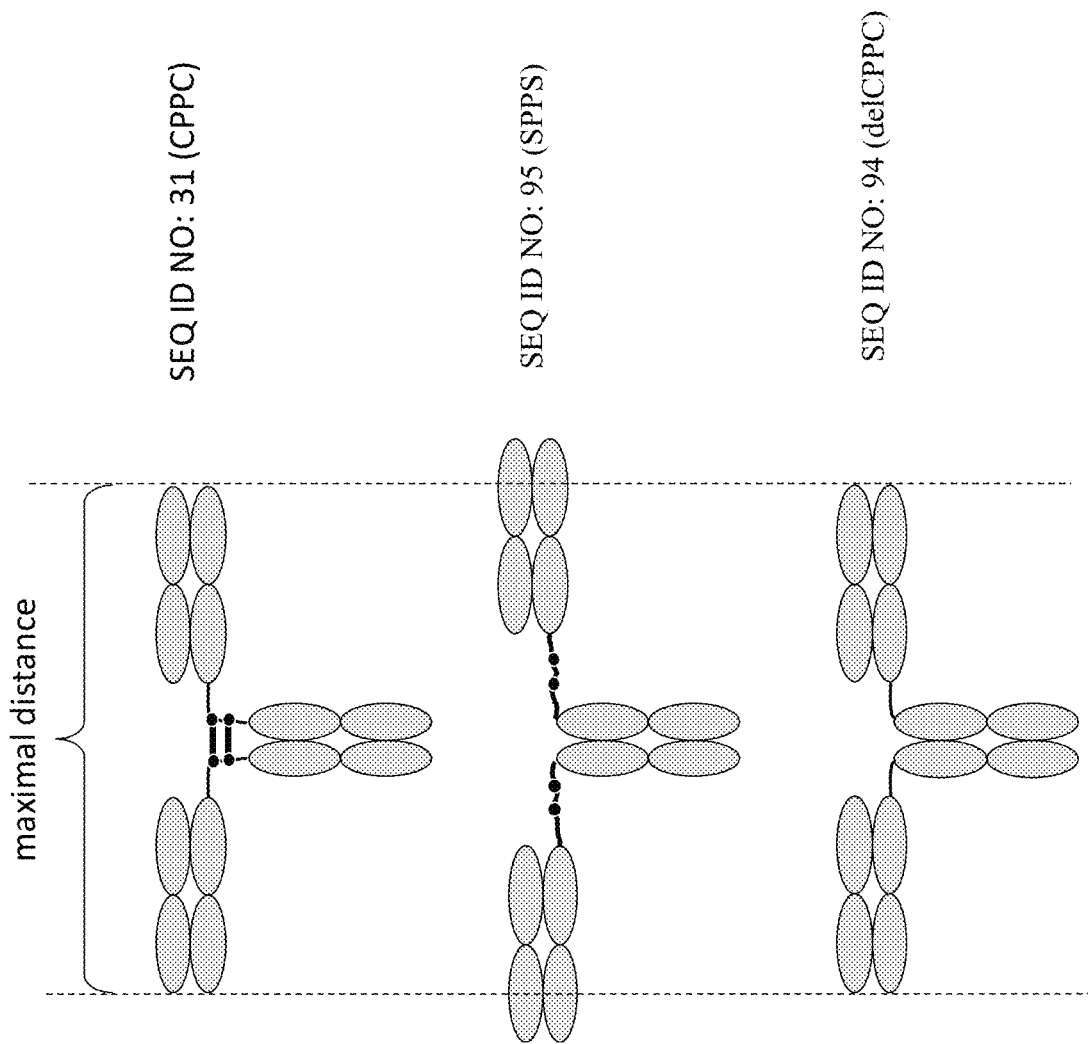
FIG. 51: By modification of the IgG1 hinge region, i.e. by removal of the disulfide bonds or by shortening the hinge region, different distances between the individual binding sites can be engineered.

Target-Unrelated Chain Conversion Occurs Inefficiently Only at High Concentrations To address whether chain conversion also occurs at high concentrations in media, 2/3-BiFabs were applied to HELA cells co-cultured with PBMC. In the first setup, anti-AG-4-proCD3(hole)-MHCFcRP(knob) and EGFR-proCD3(knob)-MHCFcRP(hole) were applied (on-cell conversion takes place since both targets are expressed on HELA cells). In the second setup anti-AG-4-proCD3(hole)-MHCFcRP (knob) and AG-3-proCD3(knob)-MHCFcRP(hole) were applied (AG-3 is not expressed on HELA cells, thus on-cell conversion should not be possible). However, the percentage of killing at concentrations of 300 nM reveals, that conversion in media and monovalent binding to the HELA cell surface via the AG-4 binding site is rarely occurring and mediating killing of target cells only to a low percentage (FIG. 50).

The invention claimed is:

1. A multimeric polypeptide comprising
a first polypeptide comprising
  i) in N- to C-terminal direction a) a first antibody variable domain selected from a pair of an antibody light and heavy chain variable domain specifically binding to a first target, and b) a first human immunoglobulin G CH3 domain, and
  ii) a pair of an antibody light and heavy chain variable domain specifically binding to a second target either N-terminal to the first antibody variable domain or C-terminal to the first CH3 domain, and
a second polypeptide comprising
  in N- to C-terminal direction a) a second antibody variable domain selected from a pair of an antibody light and heavy chain variable domain specifically binding to a third target, and b) a second human immunoglobulin G CH3 domain, wherein the second polypeptide lacks a pair of an antibody light and heavy chain variable domain specifically binding to a target,
    wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
and
  wherein the second CH3 domain comprises a perturbing mutation selected from the group of mutations consisting of D356K, E357K, K370E and K439E, wherein the first CH3 domain comprises
    a) the amino acid residue K at position 439 if the perturbing mutation is D356K, or
    b) the amino acid residue K at position 370 if the perturbing mutation is E357K, or
    c) the amino acid residue E at position 357 if the perturbing mutation is K370E, or
    d) the amino acid residue D at position 356 if the perturbing mutation is K439E,
wherein all numbering is according to Kabat EU index.

2. A multimeric polypeptide comprising
a first polypeptide comprising
  i) in N- to C-terminal direction a) a first human immunoglobulin G CH3 domain, and b) a first antibody variable domain selected from a pair of an antibody light and heavy chain variable domain specifically binding to a first target, ii) a pair of an antibody light and heavy chain variable domain specifically binding to a second target either N-terminal to the first CH3 domain or C-terminal to the first variable domain, a second polypeptide comprising
  in N- to C-terminal direction a) a second human immunoglobulin G CH3 domain and b) a second antibody variable domain selected from a pair of an antibody light and heavy chain variable domain specifically binding to a third target,
  wherein the second antibody variable domain is an antibody light chain variable domain if the first antibody variable domain is an antibody heavy chain variable domain; or the second antibody variable domain is an antibody heavy chain variable domain if the first antibody variable domain is an antibody light chain variable domain,
  and
  wherein the second CH3 domain comprises a perturbing mutation selected from the group of mutations consisting of D356K, E357K, K370E and K439E, whereby the first CH3 domain comprises
    a) the amino acid residue K at position 439 if the perturbing mutations is D356K, or
    b) the amino acid residue K at position 370 if the perturbing mutations is E357K, or
    c) the amino acid residue E at position 357 if the perturbing mutations is K370E, or
    d) the amino acid residue D at position 356 if the perturbing mutations is K439E,
  wherein all numbering is according to Kabat EU index.

3. The multimeric polypeptide according to claim 1, wherein the first CH3 domain and the second CH3 domain comprise further mutations to foster heterodimer formation between said first CH3 domain and said second CH3 domain and that are different from the perturbing mutation.

4. The multimeric polypeptide according to claim 1, wherein
  the first CH3 domain comprises
    a) the mutation T366W, or
    b) the mutations T366S/L368A/Y407V,
  and
  the second CH3 domain comprises
    a) the mutations T366S/L368A/Y407V if the first CH3 domain comprises the mutation T366W, or
    b) the mutation T366W if the first CH3 domain comprises the mutations T366S/L368A/Y407V,
  wherein all numbering is according to Kabat EU index.

5. The multimeric polypeptide according to claim 1, wherein the first polypeptide and the second polypeptide are a non-covalent dimer.

6. The multimeric polypeptide according to claim 1, wherein the first variable domain and the second variable domain form a non-functional binding site.

7. The multimeric polypeptide according to claim 1, wherein the first and the second polypeptide each comprise the amino acid sequence DKTHTSPPS (SEQ ID NO: 66) or DKTHT (SEQ ID NO: 94) or GGGS (SEQ ID NO: 69) or DKTHGGGGS (SEQ ID NO: 97) N-terminal to each of the first and second variable domains.

8. The multimeric polypeptide according to claim 1, wherein
  i) the first CH3 domain comprises the mutation T366W and the amino acid residue K at position 439, and the second CH3 domain comprises the perturbing mutation D356K and the mutations T366S/L368A/Y407V, or
  ii) the first CH3 domain comprises the mutation T366W and the amino acid residue K at position 370, and the second CH3 domain comprises the perturbing mutation E357K and the mutations T366S/L368A/Y407V, or
  iii) the first CH3 domain comprises the mutations T366S/L368A/Y407V and the amino acid residue E at position 357, and the second CH3 domain comprises the perturbing mutation K370E and the mutation T366W, or
  iv) the first CH3 domain comprises the mutations T366S/L368A/Y407V and the amino acid residue D at position 356, and the second CH3 domain comprises the perturbing mutation K439E and the mutation T366W,
  wherein all numbering is according to Kabat EU index.

9. The multimeric polypeptide according to claim 1, wherein the first, second and third target are different.

10. The multimeric polypeptide according to claim 1, wherein the first target and/or the third target is human CD3.

11. The multimeric polypeptide according to claim 1, wherein the pair of an antibody light and heavy chain variable domain specifically binding to the second target is an Fv, scFv, Fab, scFab, dsscFab, CrossFab, or bispecific Fab.

12. The multimeric polypeptide according to claim 1, wherein each of the first and the second polypeptide further comprises an immunoglobulin G CH2 domain directly N-terminal to the CH3 domain.

13. The multimeric polypeptide according to claim 1, wherein the human immunoglobulin G is human IgG1 or human IgG2 or human IgG3 or human IgG4.

14. A composition comprising a first multimeric polypeptide and a second multimeric polypeptide according to claim 1, wherein
  the second CH3 domain of the first multimeric polypeptide comprises the mutation D356K and the second CH3 domain of the second multimeric polypeptide comprises the mutation K439E,
  or
  the second CH3 domain of the first multimeric polypeptide comprises the mutation E357K and the second CH3 domain of the second multimeric polypeptide comprises the mutation K370E,
  and
  the first antibody variable domain of the first multimeric polypeptide and the first variable domain of the second multimeric polypeptide are a pair of an antibody light chain variable domain and an antibody heavy chain variable domain that specifically bind to the first target,
  and
  the second antibody variable domain of the first multimeric polypeptide and the second variable domain of the second multimeric polypeptide are a pair of an antibody light chain variable domain and an antibody heavy chain variable domain that specifically bind to the third target,
  wherein all numbering is according to Kabat EU index.

15. The composition according to claim 14, wherein for each of the first multimeric polypeptide and second multimeric polypeptide,
  the first CH3 domain of the first polypeptide comprises
    a) the mutation T366W, or
    b) the mutations T366S/L368A/Y407V,
  and
  the second CH3 domain of the second polypeptide comprises
    a) the mutations T366S/L368A/Y407V if the first CH3 domain comprises the mutation T366W, or b) the mutation T366W if the first CH3 domain comprises the mutations T366S/L368A/Y407V, wherein all numbering is according to Kabat EU index.

16. The composition according to claim 14, wherein the first CH3 domain of the first multimeric polypeptide and the second CH3 domain of the second multimeric polypeptide comprise the mutation T366W or the mutations T366S/L368A/Y407V, and the second CH3 domain of the first multimeric polypeptide comprises the mutation D356K and the second CH3 domain of the second multimeric polypeptide comprises the mutation K439E, or the second CH3 domain of the first multimeric polypeptide comprises the mutation E357K and the second CH3 domain of the second multimeric polypeptide comprises the mutation K370E, and the first antibody variable domain of the first multimeric polypeptide and the first variable domain of the second multimeric polypeptide are a pair of an antibody light chain variable domain and an antibody heavy chain variable domain that specifically bind to the first target, and the second antibody variable domain of the first multimeric polypeptide and the second variable domain of the second multimeric polypeptide are a pair of an antibody light chain variable domain and an antibody heavy chain variable domain that specifically bind to the third target, wherein all numbering is according to Kabat EU index.

17. The composition according to claim 14, wherein the first and/or the third target is human CD3.

18. The composition according to claim 14, wherein the composition is a pharmaceutical composition and optionally further comprises a pharmaceutically acceptable excipient.

* * * * *